US010495645B2

(12) United States Patent
Wong et al.

(10) Patent No.: US 10,495,645 B2
(45) Date of Patent: Dec. 3, 2019

(54) CANCER MARKERS AND METHODS OF USE THEREOF

(71) Applicant: Academia Sinica, Taipei (TW)

(72) Inventors: Chi-Huey Wong, Rancho Santa Fe, CA (US); Chung-Yi Wu, New Taipei (TW); Sarah K. C. Cheung, Taipei (TW); Po-Kai Chuang, Taipei (TW); Tsui-Ling Hsu, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 15/005,930

(22) Filed: Jan. 25, 2016

(65) Prior Publication Data

US 2016/0274121 A1   Sep. 22, 2016

Related U.S. Application Data

(63) Continuation-in-part of application No. 14/599,174, filed on Jan. 16, 2015.

(60) Provisional application No. 62/107,378, filed on Jan. 24, 2015, provisional application No. 62/266,514, filed on Dec. 11, 2015.

(51) Int. Cl.
*G01N 33/574* (2006.01)
*C07K 16/18* (2006.01)
*C07K 16/30* (2006.01)
*G01N 33/50* (2006.01)
*A61K 39/00* (2006.01)

(52) U.S. Cl.
CPC ....... *G01N 33/57492* (2013.01); *C07K 16/18* (2013.01); *C07K 16/3053* (2013.01); *G01N 33/5073* (2013.01); *G01N 33/57407* (2013.01); *A61K 2039/505* (2013.01); *C07K 2317/21* (2013.01); *C07K 2317/24* (2013.01); *C07K 2317/622* (2013.01); *C07K 2317/734* (2013.01); *C07K 2317/92* (2013.01); *G01N 2333/70585* (2013.01); *G01N 2333/70596* (2013.01); *G01N 2405/10* (2013.01); *G01N 2500/04* (2013.01); *G01N 2500/10* (2013.01); *G01N 2800/52* (2013.01)

(58) Field of Classification Search
CPC ......... G01N 33/57492; G01N 33/5073; G01N 33/57407
USPC ...................................... 424/133.1
See application file for complete search history.

(56) References Cited

U.S. PATENT DOCUMENTS

| 3,773,919 A | 11/1973 | Boswell et al. |
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,270,537 A | 6/1981 | Romaine |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,376,110 A | 3/1983 | David et al. |

(Continued)

FOREIGN PATENT DOCUMENTS

| CN | 101855339 A | 10/2010 |
| CN | 101868534 A | 10/2010 |

(Continued)

OTHER PUBLICATIONS

Chang et al. PNAS Aug. 19, 2008 vol. 105 (No. 33): 11667-11672.*

(Continued)

*Primary Examiner* — Lynn A Bristol

(74) *Attorney, Agent, or Firm* — Duane Morris LLP

(57) ABSTRACT

The present disclosure relates to methods and compositions which can modulate the globoseries glycosphingolipid synthesis. Particularly, the present disclosure is directed to glycoenzyme inhibitor compound and compositions and methods of use thereof that can modulate the synthesis of globoseries glycosphingolipid SSEA-3/SSEA-4/GloboH in the biosynthetic pathway; particularly, the glycoenzyme inhibitors target the alpha-4GalT; beta-4GalNAcT-I; or beta-3GalT-V enzymes in the globoseries synthetic pathway. Additionally, the present disclosure is also directed to vaccines, antibodies, and/or immunogenic conjugate compositions targeting the SSEA-3/SSEA-4/GLOBO H associated epitopes (natural and modified) which elicit antibodies and/or binding fragment production useful for modulating the globoseries glycosphingolipid synthesis. Moreover, the present disclosure is also directed to the method of using the compositions described herein for the treatment or detection of hyperproliferative diseases and/or conditions. Furthermore, the instant disclosure also relates to cancer stem cell biomarkers for disgnostic and therapeutic uses.

3 Claims, 36 Drawing Sheets

Specification includes a Sequence Listing.

(56) References Cited

U.S. PATENT DOCUMENTS

| | | |
|---|---|---|
| 4,419,446 A | 12/1983 | Howley et al. |
| 4,424,219 A | 1/1984 | Hashimoto et al. |
| 4,450,254 A | 5/1984 | Isley et al. |
| 4,560,655 A | 12/1985 | Baker |
| 4,596,556 A | 6/1986 | Morrow et al. |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,601,978 A | 7/1986 | Karin |
| 4,657,866 A | 4/1987 | Kumar |
| 4,676,980 A | 6/1987 | Segal et al. |
| 4,741,900 A | 5/1988 | Alvarez et al. |
| 4,767,704 A | 8/1988 | Cleveland et al. |
| 4,790,824 A | 12/1988 | Morrow et al. |
| 4,816,567 A | 3/1989 | Cabilly et al. |
| 4,849,222 A | 7/1989 | Broaddus |
| 4,886,499 A | 12/1989 | Cirelli et al. |
| 4,927,762 A | 5/1990 | Darfler |
| 4,940,460 A | 7/1990 | Casey et al. |
| 4,941,880 A | 7/1990 | Burns |
| 4,965,199 A | 10/1990 | Capon et al. |
| 4,970,198 A | 11/1990 | Lee et al. |
| 4,975,278 A | 12/1990 | Senter et al. |
| 5,004,697 A | 4/1991 | Pardridge |
| 5,015,235 A | 5/1991 | Crossman |
| 5,053,394 A | 10/1991 | Ellestad et al. |
| 5,061,620 A | 10/1991 | Tsukamoto et al. |
| 5,064,413 A | 11/1991 | McKinnon et al. |
| 5,075,109 A | 12/1991 | Tice et al. |
| 5,079,233 A | 1/1992 | Lee |
| 5,100,669 A | 3/1992 | Hyon et al. |
| 5,112,596 A | 5/1992 | Malfroy-Camine |
| 5,122,469 A | 6/1992 | Mather et al. |
| 5,141,496 A | 8/1992 | Dalto et al. |
| 5,190,521 A | 3/1993 | Hubbard et al. |
| 5,208,020 A | 5/1993 | Chari et al. |
| 5,229,275 A | 7/1993 | Goroff |
| 5,264,365 A | 11/1993 | Georgiou et al. |
| 5,268,164 A | 12/1993 | Kozarich et al. |
| 5,312,335 A | 5/1994 | McKinnon et al. |
| 5,326,856 A | 7/1994 | Coughlin et al. |
| 5,328,483 A | 7/1994 | Jacoby |
| 5,334,144 A | 8/1994 | Alchas et al. |
| 5,339,163 A | 8/1994 | Homma et al. |
| 5,362,852 A | 11/1994 | Geoghegan |
| 5,369,017 A | 11/1994 | Wong et al. |
| 5,374,541 A | 12/1994 | Wong et al. |
| 5,383,851 A | 1/1995 | McKinnon, Jr. et al. |
| 5,395,541 A | 3/1995 | Carpenter et al. |
| 5,416,064 A | 5/1995 | Chari et al. |
| 5,417,662 A | 5/1995 | Hjertman et al. |
| 5,466,220 A | 11/1995 | Brenneman |
| 5,480,381 A | 1/1996 | Weston |
| 5,500,362 A | 3/1996 | Robinson et al. |
| 5,503,627 A | 4/1996 | McKinnon et al. |
| 5,506,206 A | 4/1996 | Kozarich et al. |
| 5,508,192 A | 4/1996 | Georgiou et al. |
| 5,518,725 A | 5/1996 | Daynes et al. |
| 5,520,639 A | 5/1996 | Peterson et al. |
| 5,527,288 A | 6/1996 | Gross et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,189 A | 10/1996 | Parsons |
| 5,569,825 A | 10/1996 | Lonberg et al. |
| 5,571,894 A | 11/1996 | Wels et al. |
| 5,580,717 A | 12/1996 | Dower et al. |
| 5,585,089 A | 12/1996 | Queen et al. |
| 5,587,458 A | 12/1996 | King et al. |
| 5,591,669 A | 1/1997 | Krimpenfort et al. |
| 5,591,828 A | 1/1997 | Bosslet et al. |
| 5,599,302 A | 2/1997 | Lilley et al. |
| 5,606,040 A | 2/1997 | McGahren et al. |
| 5,624,821 A | 4/1997 | Winter et al. |
| 5,625,126 A | 4/1997 | Lonberg et al. |
| 5,633,425 A | 5/1997 | Lonberg et al. |
| 5,635,483 A | 6/1997 | Pettit et al. |
| 5,639,635 A | 6/1997 | Joly et al. |
| 5,641,870 A | 6/1997 | Rinderknecht et al. |
| 5,643,577 A | 7/1997 | Pang et al. |
| 5,648,237 A | 7/1997 | Carter |
| 5,648,260 A | 7/1997 | Winter et al. |
| 5,649,912 A | 7/1997 | Peterson |
| 5,661,016 A | 8/1997 | Lonberg et al. |
| 5,663,149 A | 9/1997 | Pettit et al. |
| 5,674,988 A | 10/1997 | Sabesan |
| 5,677,180 A | 10/1997 | Robinson et al. |
| 5,686,416 A | 11/1997 | Kozarich et al. |
| 5,690,938 A | 11/1997 | Ermak et al. |
| 5,693,762 A | 12/1997 | Queen et al. |
| 5,704,911 A | 1/1998 | Parsons |
| 5,712,374 A | 1/1998 | Kuntsman et al. |
| 5,714,374 A | 2/1998 | Arnold et al. |
| 5,714,586 A | 2/1998 | Kunstman et al. |
| 5,731,168 A | 3/1998 | Cater et al. |
| 5,733,743 A | 3/1998 | Johnson et al. |
| 5,736,137 A | 4/1998 | Anderson et al. |
| 5,739,116 A | 4/1998 | Hamann et al. |
| 5,767,285 A | 6/1998 | Hamann et al. |
| 5,770,701 A | 6/1998 | McGahren et al. |
| 5,773,001 A | 6/1998 | Hamann et al. |
| 5,780,588 A | 7/1998 | Pettit et al. |
| 5,814,344 A | 9/1998 | Tice et al. |
| 5,820,883 A | 10/1998 | Tice et al. |
| 5,821,337 A | 10/1998 | Carter et al. |
| 5,837,234 A | 11/1998 | Gentile et al. |
| 5,840,523 A | 11/1998 | Simmons et al. |
| 5,849,716 A | 12/1998 | Akimoto |
| 5,853,763 A | 12/1998 | Tice et al. |
| 5,869,046 A | 2/1999 | Presta et al. |
| 5,877,296 A | 3/1999 | Hamann et al. |
| 5,893,397 A | 4/1999 | Peterson et al. |
| 5,993,412 A | 11/1999 | Deily et al. |
| 6,004,940 A | 12/1999 | Marasco et al. |
| 6,027,888 A | 2/2000 | Georgiou et al. |
| 6,083,715 A | 7/2000 | Georgiou et al. |
| 6,111,132 A | 8/2000 | Kim et al. |
| 6,143,724 A | 11/2000 | Ohira et al. |
| 6,210,670 B1 | 4/2001 | Berg |
| 6,265,150 B1 | 7/2001 | Terstappen et al. |
| 6,329,173 B1 | 12/2001 | Marasco et al. |
| 6,340,702 B1 | 1/2002 | Honda et al. |
| 6,399,071 B1 | 6/2002 | Duthaler |
| 6,455,571 B1 | 9/2002 | Maring et al. |
| 6,506,564 B1 | 1/2003 | Mirkin et al. |
| 6,528,286 B1 | 3/2003 | Ryll |
| 6,548,476 B1 | 4/2003 | Wu et al. |
| 6,680,054 B1 | 1/2004 | Reece et al. |
| 6,696,304 B1 | 2/2004 | Davies |
| 6,703,019 B1 | 3/2004 | Malfroy-Camine |
| 6,824,780 B1 | 11/2004 | Devaux et al. |
| 6,855,551 B2 | 2/2005 | Bawendi et al. |
| 6,873,914 B2 | 3/2005 | Winfield et al. |
| 6,984,630 B1 | 1/2006 | Descamps et al. |
| 6,994,966 B2 | 2/2006 | Dukler |
| 7,019,288 B2 | 3/2006 | Becker |
| 7,090,973 B1 | 8/2006 | Breton |
| 7,151,164 B2 | 12/2006 | Hansen et al. |
| 7,157,433 B2 | 1/2007 | Mercep et al. |
| 7,205,333 B2 | 4/2007 | Wu et al. |
| 7,488,491 B2 | 2/2009 | Tsjui et al. |
| 7,498,298 B2 | 3/2009 | Doronina et al. |
| 7,592,004 B2 | 9/2009 | Kaisheva et al. |
| 7,854,934 B2 | 12/2010 | Danishefsky |
| 7,888,337 B2 | 2/2011 | Wong et al. |
| 7,923,013 B2 | 4/2011 | Tsuji et al. |
| 7,928,077 B2 | 4/2011 | Wong et al. |
| 7,943,330 B2 | 5/2011 | Wong et al. |
| 7,960,139 B2 | 6/2011 | Sawa et al. |
| 7,977,097 B1 | 7/2011 | Gay et al. |
| 8,022,043 B2 | 9/2011 | Porcelli |
| 8,088,387 B2 | 1/2012 | Steeves et al. |

(56) References Cited

U.S. PATENT DOCUMENTS

| | | |
|---|---|---|
| 8,101,179 B2 | 1/2012 | Numazaki et al. |
| 8,163,290 B2 | 4/2012 | Tsuji et al. |
| 8,268,969 B2 | 9/2012 | Wong et al. |
| 8,383,554 B2 | 2/2013 | Wong et al. |
| 8,507,660 B2 | 8/2013 | Wong et al. |
| 8,680,020 B2 | 3/2014 | Wong et al. |
| 8,715,963 B2 | 5/2014 | Sethuraman |
| 8,716,465 B2 * | 5/2014 | Rossi .................... C12N 15/111 435/455 |
| 8,765,390 B2 | 7/2014 | Ailles et al. |
| 8,802,438 B2 * | 8/2014 | Rossi .................... C12N 15/111 435/325 |
| 8,815,941 B2 | 8/2014 | Withers |
| 8,883,506 B2 * | 11/2014 | Rossi .................... C12N 15/111 435/455 |
| 8,906,832 B2 | 12/2014 | Wong et al. |
| 8,907,111 B2 | 12/2014 | Withers |
| 9,187,552 B2 | 11/2015 | Stadheim |
| 9,221,859 B2 | 12/2015 | Withers |
| 9,382,284 B2 | 7/2016 | Withers |
| 9,434,786 B2 | 9/2016 | Wang |
| 9,547,009 B2 | 1/2017 | Wong et al. |
| 9,566,282 B2 * | 2/2017 | Bhatia ................ A61K 31/5415 |
| 9,759,726 B2 | 9/2017 | Wong et al. |
| 9,782,476 B2 | 10/2017 | Wong et al. |
| 9,803,177 B2 * | 10/2017 | Rossi .................... C12N 15/111 |
| 9,874,562 B2 | 1/2018 | Wong et al. |
| 9,879,042 B2 | 1/2018 | Wong et al. |
| 9,914,956 B2 | 3/2018 | Wong et al. |
| 9,975,965 B2 * | 5/2018 | Wong .................... C07K 16/44 |
| 9,981,030 B2 | 5/2018 | Wong et al. |
| 9,982,041 B2 * | 5/2018 | Wong .................... C07K 16/18 |
| 10,005,847 B2 | 6/2018 | Wong |
| 10,023,892 B2 | 7/2018 | Wong |
| 10,086,054 B2 | 10/2018 | Wong et al. |
| 10,087,236 B2 | 10/2018 | Wong et al. |
| 10,111,951 B2 | 10/2018 | Wong et al. |
| 10,118,969 B2 * | 11/2018 | Wong .................... C07K 16/30 |
| 10,119,972 B2 | 11/2018 | Wong et al. |
| 10,130,714 B2 | 11/2018 | Wong et al. |
| 10,150,818 B2 * | 12/2018 | Wong .................... C07K 16/18 |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0118592 A1 | 6/2003 | Ledbetter et al. |
| 2003/0129186 A1 | 7/2003 | Beliveau et al. |
| 2003/0162695 A1 | 8/2003 | Schatzberg et al. |
| 2003/0175884 A1 | 9/2003 | Umana et al. |
| 2003/0219433 A1 | 11/2003 | Hansen et al. |
| 2004/0072290 A1 | 4/2004 | Umana et al. |
| 2004/0086423 A1 | 5/2004 | Wohlstadter |
| 2004/0131692 A1 | 7/2004 | Kreuter et al. |
| 2004/0137557 A1 | 7/2004 | DeFrees et al. |
| 2004/0204354 A1 | 10/2004 | Nelson et al. |
| 2004/0259142 A1 | 12/2004 | Chai et al. |
| 2005/0085413 A1 | 4/2005 | Jin et al. |
| 2005/0089473 A1 | 4/2005 | Black et al. |
| 2005/0106108 A1 | 5/2005 | Hansen et al. |
| 2005/0123546 A1 | 6/2005 | Umana et al. |
| 2005/0124533 A1 | 6/2005 | Schatzberg et al. |
| 2005/0221337 A1 | 10/2005 | Seeberger et al. |
| 2005/0255491 A1 | 11/2005 | Lee |
| 2006/0019256 A1 | 1/2006 | Clarke et al. |
| 2006/0073122 A1 | 4/2006 | Koezuka et al. |
| 2006/0073161 A1 | 4/2006 | Breton |
| 2006/0211856 A1 | 9/2006 | Tsuji et al. |
| 2006/0286140 A1 | 12/2006 | Wickstrom et al. |
| 2006/0286637 A1 | 12/2006 | Hamilton |
| 2007/0059769 A1 | 3/2007 | Blixt et al. |
| 2007/0065949 A1 | 3/2007 | Hutchens |
| 2007/0207090 A1 | 9/2007 | Giudice |
| 2007/0213278 A1 | 9/2007 | Wong et al. |
| 2007/0213297 A1 | 9/2007 | Wong et al. |
| 2007/0219351 A1 | 9/2007 | Fiume et al. |
| 2007/0224189 A1 | 9/2007 | Lazar et al. |
| 2007/0238871 A1 | 10/2007 | Tsuji et al. |
| 2008/0070324 A1 | 3/2008 | Floyd |
| 2008/0145838 A1 | 6/2008 | Suda et al. |
| 2008/0175870 A1 | 7/2008 | Mather et al. |
| 2008/0220988 A1 | 9/2008 | Zhou |
| 2008/0260774 A1 | 10/2008 | Wong et al. |
| 2009/0035179 A1 | 2/2009 | Rakow et al. |
| 2009/0060921 A1 | 3/2009 | Dickey et al. |
| 2009/0081255 A1 | 3/2009 | Bublot et al. |
| 2009/0123439 A1 | 5/2009 | Yun et al. |
| 2009/0285837 A1 | 11/2009 | Kao et al. |
| 2009/0298797 A1 | 12/2009 | Zheng et al. |
| 2009/0317837 A1 | 12/2009 | Wong et al. |
| 2010/0003674 A1 * | 1/2010 | Cope .................... C12Q 1/6881 435/6.14 |
| 2010/0009339 A1 | 1/2010 | Bovin et al. |
| 2010/0022026 A1 | 1/2010 | Rump et al. |
| 2010/0047827 A1 | 2/2010 | Laine et al. |
| 2010/0047828 A1 | 2/2010 | Sorenson et al. |
| 2010/0068806 A1 | 3/2010 | Laine et al. |
| 2010/0112195 A1 | 5/2010 | Kodas et al. |
| 2010/0113397 A1 | 5/2010 | Wong et al. |
| 2010/0136009 A1 | 6/2010 | Papkoff et al. |
| 2010/0136042 A1 | 6/2010 | Wong et al. |
| 2010/0173323 A1 | 7/2010 | Strome |
| 2010/0275280 A1 | 10/2010 | Clevers et al. |
| 2011/0086408 A1 | 4/2011 | Powers |
| 2011/0104188 A1 | 5/2011 | Tashiro et al. |
| 2011/0124116 A1 | 5/2011 | Wohlstadter et al. |
| 2011/0137570 A1 | 6/2011 | Lapadula et al. |
| 2011/0237459 A1 | 9/2011 | Nova et al. |
| 2011/0262358 A1 | 10/2011 | Torigoe et al. |
| 2011/0263828 A1 | 10/2011 | Wong et al. |
| 2012/0046346 A1 * | 2/2012 | Rossi .................... C12N 15/111 514/44 R |
| 2012/0171201 A1 | 7/2012 | Sapra |
| 2012/0178705 A1 | 7/2012 | Liang et al. |
| 2012/0178802 A1 | 7/2012 | Withers et al. |
| 2012/0226024 A1 | 9/2012 | Wang et al. |
| 2012/0270826 A1 * | 10/2012 | Cope .................... C12Q 1/6881 514/43 |
| 2012/0294859 A1 | 11/2012 | Goletz et al. |
| 2012/0322864 A1 * | 12/2012 | Rossi .................... C12N 15/111 514/44 R |
| 2012/0322865 A1 * | 12/2012 | Rossi .................... C12N 15/111 514/44 R |
| 2012/0328646 A1 | 12/2012 | Wong et al. |
| 2013/0065887 A1 * | 3/2013 | Bhatia ................ A61K 31/5415 514/225.5 |
| 2013/0071390 A1 | 3/2013 | Stadheim et al. |
| 2013/0189258 A1 | 7/2013 | Rother et al. |
| 2013/0196356 A1 | 8/2013 | Jackson et al. |
| 2013/0230886 A1 | 9/2013 | Votsmeier et al. |
| 2013/0295104 A1 | 11/2013 | Deckert et al. |
| 2013/0331381 A1 * | 12/2013 | Bhatia ................ A61K 31/5415 514/225.5 |
| 2013/0337018 A1 | 12/2013 | Fox |
| 2013/0345289 A1 * | 12/2013 | Cope .................... C12Q 1/6881 514/44 A |
| 2014/0051127 A1 | 2/2014 | Wong et al. |
| 2014/0086916 A1 | 3/2014 | Zha |
| 2014/0127241 A1 | 5/2014 | Leuschner et al. |
| 2014/0178365 A1 | 6/2014 | Ghaderi et al. |
| 2014/0227290 A1 | 8/2014 | Sethuraman |
| 2014/0302028 A1 | 10/2014 | Zha |
| 2014/0308746 A1 * | 10/2014 | Rossi .................... C12N 15/111 435/377 |
| 2015/0087814 A1 | 3/2015 | Wang |
| 2015/0094237 A1 | 4/2015 | Liang et al. |
| 2015/0160217 A1 | 6/2015 | Wong et al. |
| 2015/0225766 A1 | 8/2015 | Wong et al. |
| 2015/0309041 A1 | 10/2015 | Wong et al. |
| 2015/0344544 A1 | 12/2015 | Wong et al. |
| 2015/0344551 A1 * | 12/2015 | Wong .................... C07K 16/18 424/133.1 |

(56) References Cited

U.S. PATENT DOCUMENTS

| | | |
|---|---|---|
| 2015/0344559 A1 | 12/2015 | Wong et al. |
| 2015/0344585 A1 | 12/2015 | Wong et al. |
| 2015/0344587 A1 | 12/2015 | Wong et al. |
| 2016/0009803 A1 | 1/2016 | Rother et al. |
| 2016/0017390 A1 | 1/2016 | Wong et al. |
| 2016/0058886 A1* | 3/2016 | Fonseca ............ A61K 47/48815 424/450 |
| 2016/0102151 A1* | 4/2016 | Wong ...................... C07K 16/18 424/135.1 |
| 2016/0213763 A1 | 7/2016 | Wong et al. |
| 2016/0215061 A1 | 7/2016 | Shaeen |
| 2016/0274121 A1 | 9/2016 | Wong et al. |
| 2016/0280794 A1* | 9/2016 | Wong ...................... C07K 16/30 |
| 2016/0289340 A1* | 10/2016 | Wong ...................... C07K 16/44 |
| 2017/0038378 A1 | 2/2017 | Wong et al. |
| 2017/0275389 A1 | 9/2017 | Wong et al. |
| 2017/0283878 A1* | 10/2017 | Wong ................ C07K 16/3053 |
| 2017/0362265 A1 | 12/2017 | Wong et al. |
| 2017/0362330 A1 | 12/2017 | Liu |
| 2018/0106780 A1 | 4/2018 | Wong et al. |
| 2018/0155761 A1 | 6/2018 | Wong et al. |
| 2018/0265590 A1 | 9/2018 | Wong et al. |
| 2018/0291109 A1 | 10/2018 | Lin et al. |
| 2018/0362662 A1 | 12/2018 | Wong et al. |
| 2019/0085062 A1* | 3/2019 | Wong ...................... C07K 16/18 |
| 2019/0177435 A1* | 6/2019 | Wong ...................... C07K 16/18 |

FOREIGN PATENT DOCUMENTS

| | | |
|---|---|---|
| CN | 102203290 A | 9/2011 |
| CN | 103436627 A | 12/2013 |
| CN | 104225616 A | 12/2014 |
| EP | 0404097 A2 | 12/1990 |
| EP | 0341735 B1 | 9/1992 |
| EP | 0425235 B1 | 9/1996 |
| EP | 1208909 A2 | 5/2002 |
| EP | 1391213 A1 | 2/2004 |
| EP | 2123271 | 11/2009 |
| EP | 2187217 A1 | 5/2010 |
| JP | 05-222085 | 8/1993 |
| JP | 05-507068 | 10/1993 |
| JP | 05-339283 A | 12/1993 |
| JP | 11-343295 A | 12/1999 |
| JP | 2005-06008 | 5/2000 |
| JP | 2002-371087 A | 12/2002 |
| JP | 2008-025989 A | 2/2008 |
| WO | WO 87/00195 A1 | 1/1987 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 92/006691 | 4/1992 |
| WO | WO 92/09690 A2 | 6/1992 |
| WO | WO 93/01161 A1 | 1/1993 |
| WO | WO 93/06213 A1 | 4/1993 |
| WO | WO 93/07861 A1 | 4/1993 |
| WO | WO 93/08829 A1 | 5/1993 |
| WO | WO 93/09764 | 5/1993 |
| WO | WO 93/16185 A2 | 8/1993 |
| WO | WO 93/021232 A1 | 10/1993 |
| WO | WO 94/04690 A1 | 3/1994 |
| WO | WO 94/11026 | 5/1994 |
| WO | WO 94/29351 | 12/1994 |
| WO | WO 95/11010 A1 | 4/1995 |
| WO | WO 96/07754 A1 | 3/1996 |
| WO | WO 96/16673 A1 | 6/1996 |
| WO | WO 96/33735 A1 | 10/1996 |
| WO | WO 96/34096 A1 | 10/1996 |
| WO | WO 97/05267 A2 | 2/1997 |
| WO | WO 97/013537 | 4/1997 |
| WO | WO 97/17852 A1 | 5/1997 |
| WO | WO 97/037705 | 10/1997 |
| WO | WO 98/00558 A1 | 1/1998 |
| WO | WO 98/02463 A1 | 1/1998 |
| WO | WO 98/24893 A2 | 6/1998 |
| WO | WO 99/034850 | 7/1999 |
| WO | WO 99/49019 A2 | 9/1999 |
| WO | WO 99/051642 | 10/1999 |
| WO | WO 99/057134 A1 | 11/1999 |
| WO | WO 01/42505 A2 | 6/2001 |
| WO | WO 01/86001 A1 | 11/2001 |
| WO | WO 02/088172 | 11/2002 |
| WO | WO 03/040104 A1 | 5/2003 |
| WO | WO 03/68821 A2 | 8/2003 |
| WO | WO 03/077945 A1 | 9/2003 |
| WO | WO 2004/035607 A2 | 4/2004 |
| WO | WO 2004/056312 A2 | 7/2004 |
| WO | WO 2004/063351 | 7/2004 |
| WO | WO 2004/103404 A1 | 12/2004 |
| WO | WO 2005/030258 A2 | 4/2005 |
| WO | WO 2005/044859 | 5/2005 |
| WO | WO 2005/088310 A2 | 9/2005 |
| WO | WO 2005/103081 A2 | 11/2005 |
| WO | WO 2006/055925 A2 | 5/2006 |
| WO | WO 2006/064983 A1 | 6/2006 |
| WO | WO 2006/106959 | 10/2006 |
| WO | WO 2006/126069 A2 | 11/2006 |
| WO | WO 2006/130458 A2 | 12/2006 |
| WO | WO 2007/053648 A2 | 5/2007 |
| WO | WO 2007/078873 A1 | 7/2007 |
| WO | WO 2007/133855 | 11/2007 |
| WO | WO 2007/146847 A2 | 12/2007 |
| WO | WO 2008-020596 A2 | 2/2008 |
| WO | WO 2008/087260 A1 | 7/2008 |
| WO | WO 2008/118013 | 10/2008 |
| WO | WO 2008/133801 A1 | 11/2008 |
| WO | WO 2008/133857 A1 | 11/2008 |
| WO | WO 2009/029888 A3 | 3/2009 |
| WO | WO 2009/126735 A1 | 10/2009 |
| WO | WO 2010/006315 A2 | 1/2010 |
| WO | WO 2010/009271 A1 | 1/2010 |
| WO | WO 2010/011703 | 1/2010 |
| WO | WO2010/029302 A2 | 3/2010 |
| WO | WO 2011/005756 A1 | 1/2011 |
| WO | WO 2011/006237 A1 | 1/2011 |
| WO | WO 2011/031236 A1 | 3/2011 |
| WO | WO 2011/074621 A1 | 6/2011 |
| WO | WO 2011/089004 A1 | 7/2011 |
| WO | WO 2011/130332 | 10/2011 |
| WO | WO 2011/143262 A2 | 11/2011 |
| WO | WO 2011/145957 A1 | 11/2011 |
| WO | WO 2012/082635 A1 | 6/2012 |
| WO | WO 2012/094540 A2 | 7/2012 |
| WO | WO 2013/011347 A1 | 1/2013 |
| WO | WO 2013/024895 A1 | 2/2013 |
| WO | WO 2013/088395 A1 | 6/2013 |
| WO | WO 2013/106937 A1 | 7/2013 |
| WO | WO 2013/120066 A1 | 8/2013 |
| WO | WO 2013/126993 A1 | 9/2013 |
| WO | WO 2013/130603 A1 | 9/2013 |
| WO | WO 2013/152034 A1 | 10/2013 |
| WO | WO 2013/155375 A1 | 10/2013 |
| WO | WO 2013/181585 A2 | 12/2013 |
| WO | WO 2014/031498 | 2/2014 |
| WO | WO 2014/078373 A1 | 5/2014 |
| WO | WO 2014/210397 A1 | 12/2014 |
| WO | WO 2014/210564 | 12/2014 |
| WO | WO 2015/026484 A1 | 2/2015 |
| WO | WO 2015/035337 A1 | 3/2015 |
| WO | WO 2015/038963 A1 | 3/2015 |
| WO | WO 2015/184008 | 12/2015 |
| WO | WO 2016/040369 A2 | 3/2016 |
| WO | WO 2016-118090 A1 | 7/2016 |
| WO | WO 2014/031762 A1 | 2/2017 |

OTHER PUBLICATIONS

Hung et al. J. Am. Chem. Soc. 2013, 135, 5934-5937.*
Shevinsky et al. Cell vol. 30, Issue 3, Oct. 1982, pp. 697-705.*
Frank et al. J. Clin. Invest. 120:41-50 (2010).*
Cheung et al. (Glycoconjugate Journal, (Jul. 2015) vol. 32, No. 5, pp. 323. Abstract No. 338, Meeting Info: 23rd International Sym-

(56) References Cited

OTHER PUBLICATIONS posium on Glycoconjugates, GLYCO 23. Split, Croatia. Sep. 15, 2015-Sep. 20, 2015).*
Cheung et al. (Glycoconjugate Journal, (Jul. 2015) vol. 32, No. 5, pp. 323. Abstract: 338; Meeting Info: 23rd International Symposium on Glycoconjugates, GLYCO 23; Split, Croatia. Sep. 15, 2015-Sep. 20, 2015).*
Cheung et al. (PNAS (2016), 113(4), 960-965).*
Sun et al. (Translational Oncology (2017) 10, 976-987).*
Bacteroides Fragilis NCTC 9343, Complete Genome., Mar. 3, 2005, XP002775523, Database Accession No. CR626927, 2 Pages.
Bacteroides Thetaiotaomicron VPI-5482, Section 8 of 21 of the Complete Genome, XP002775522, Jan. 6, 2006, Database Accession No. AE016933, 2 Pages.
Berg, Jan-Olof et al., Purification of Glycoside Hydrolases From Bacteroides Fragilis, Applied and Environmental Microbiology, vol. 40, No. 1, Jul. 1980, p. 40-47.
Dicker, Martina et al., Using Glyco-Engineering to Produce Therapeutic Proteins, Expert Opinion on Biological Therapy, vol. 15, Jan. 1, 2015, pp. 1501-1516.
Extended European Search Report, App. No. 15799789.1, dated Nov. 28, 2017, 10 Pages.
Extended European Search Report, App. No. 158001917, dated Nov. 28, 2017, 12 Pages.
Extended European Search Report, App. No. 15799981.4, dated Nov. 29, 2017, 9 Pages.
Huang, Wei et al., Chemoenzymatic Glycoengineering of Intact lgG Antibodies for Gain of Functions, Journal American Chemical Socirty, vol. 134, No. 9, Jul. 25, 2012, pp. 12308-12318.
Liao, Shih-Fen et al., Immunization of Fucose-Containing Polysaccharides From Reishi Mushroom Induces Antibodies to Tumor-Associated Globo H-Series Epitopes, Proceedings National Academy of Sciences PNAS, vol. 110, No. 34, Aug. 1, 2013, pp. 13809-13814.
Lin, Chin-Wei et al., A Common Glycan Structure on Immunoglobulin G for Enhancement of Effector Functions, vol. 112, No. 34, Aug. 7, 2015, pp. 10611-10616.
Sakurama, Haruko et al., Differences in the Substrate Specificities and Active-Site Structures of Two α-L-Fucosidases (Glycoside Hydrolase Family 29) From Bacteroides Thetaiotaomicron, Bioscience Biotechnology Biochemistry, vol. 76, No. 5, May 23, 2012, pp. 1022-1024.
Tsai, Tsung-I et al., An Effective Bacterial Ducosidase for Glycoprotein Remodeling, ACS Chemical Biology, vol. 12, No. 1, Jan. 20, 2017, pp. 63-72.
Greene, Theodora et al., Protective Groups in Organic Synthesis, pp. 42-51 and 96-100, 1991.
Schelhaas, Michael et al., Protecting Group Strategies in Organic Synthesis, Angew. Chem. Int. Ed. Engl. 1996, 35, 2056-2083.
Unverzagt, Carlo et al., A Double Regio- and Stereoselective Glycosylation Strategy for the Synthesis of N-Glycans, Chem. Eur. J., 2008, 14, 1304-1311.
International Search Report and Written Opinion in International Application No. PCT/US2017/048074, dated Dec. 26, 2017, 17 pages.
Lei, Jianqing et al., Potential antitumor applications of a monoclonal antibody specifically targeting human papilloma virus 16 E749-57 peptide, Microbiology and Immunology, 2012, vol. 56, pp. 456-462.
Tsai, Charng-Sheng et al., Cell-Permeable Probe for Identification and Imaging of Sialidases, PNAS, vol. 110, No. 7, 2013, 2466-2471.
European Application 14817316.4, Communication pursuant to Article 94(3), dated Apr. 16, 2018, 5 pages.
Al-Hajj, Muhammad, et al. "Prospective identification of tumorigenic breast cancer cells." Proceedings of the National Academy of Sciences 100.7 (2003): 3983-3988.
Almagro, Juan C., and Johan Fransson. "Humanization of antibodies." Front Biosci 13.1 (2008): 1619-1633.
Beck, Benjamin, and Cédric Blanpain. "Unravelling cancer stem cell potential." Nature Reviews Cancer 13.10 (2013): 727.
Bomken, S., et al. "Understanding the cancer stem cell." British journal of cancer 103.4 (2010): 439-445.
Casset, Florence, et al. "A peptide mimetic of an anti-CD4 monoclonal antibody by rational design." Biochemical and biophysical research communications 307.1 (2003): 198-205.
Clarke, Michael F., and Andrew T. Hass. "Cancer stem cells." Reviews in Cancer Res. (2006) 66(19):9339-9344.
De Genst, Erwin, et al. "Antibody repertoire development in camelids." Developmental & Comparative Immunology 30.1-2 (2006): 187-198.
De Leoz, Maria Lorna A., et al. "High-mannose glycans are elevated during breast cancer progression." Molecular & Cellular Proteomics 10.1 (2011): M110-002717, 9 pages; https://doi.org/10.1074/mcp.M110.002717.
Danishefsky, Samuel J., et al. "Development of Globo-H cancer vaccine," *Accounts of chemical research* 48.3 (2015): 643-652.
De Pascalis, Roberto, et al. "Grafting of "abbreviated" complementarity-determining regions containing specificity-determining residues essential for ligand contact to engineer a less immunogenic humanized monoclonal antibody." The Journal of Immunology 169.6 (2002): 3076-3084.
Dorner, Brigitte G., et al. "MIP-1a, MIP-1 β, RANTES, and ATAC/lymphotactin function together with IFN-? as type 1 cytokines." Proceedings of the National Academy of Sciences 99.9 (2002): 6181-6186.
Fuster, Mark M., and Jeffrey D. Esko. "The sweet and sour of cancer: glycans as novel therapeutic targets." Nature Reviews Cancer 5.7 (2005): 526-542.
Gao, Jingqing, Dianjun Liu, and Zhenxin Wang. "Microarray-based study of carbohydrate-protein binding by gold nanoparticle probes." Analytical chemistry 80.22 (2008): 8822-8827.
Ginestier, Christophe, et al. "ALDH1 is a marker of normal and malignant human mammary stem cells and a predictor of poor clinical outcome." Cell stem cell 1.5 (2007): 555-567.
Hakomori, S., and W. W. Young Jr. "Tumor-associated glycolipid antigens and modified blood group antigens." Scandinavian Journal of Immunology 7 (1978): 97-117.
Hakomori, Sen-itiroh. "Aberrant glycosylation in cancer cell membranes as focused on glycolipids: overview and perspectives." Cancer research 45.6 (1985): 2405-2414.
Harvey, David J. "Matrix-assisted laser desorption/ionization mass spectrometry of sphingo- and glycosphingo-lipids." Journal of Mass Spectrometry 30.9 (1995): 1311-1324.
Hwang-Verslues, Wendy W., et al. "Multiple lineages of human breast cancer stem/progenitor cells identified by profiling with stem cell markers." PloS one 4.12 (2009): e8377.
Jordan, et al. "Cancer stem cells." N Engl J Med 355.12 (2006): 1253-1261.
Lamminmäki, Urpo, and Jussi A. Kankare. "Crystal structure of a recombinant anti-estradiol Fab fragment in complex with 17β-estradiol." Journal of Biological Chemistry 276.39 (2001): 36687-36694.
Liang, Chi-Hui, et al. "Effects of neighboring glycans on antibody-carbohydrate interaction." Angewandte Chemie International Edition 50.7 (2011): 1608-1612.
Lingwood, Daniel, et al. "Cholesterol modulates glycolipid conformation and receptor activity." Nature chemical biology 7.5 (2011): 260-262.
Lloyd et al "Modelling the human immune response: performance of a 1011 human antibody repertoire against a broad panel of therapeutically relevant antigens" Protein Eng Des Sel. Mar. 2009;22(3):159-68. doi: 10.1093/protein/gzn058. Epub Oct. 29, 2008.
MacCallum, Robert M., et al. "Antibody-antigen interactions: contact analysis and binding site topography." Journal of molecular biology 262.5 (1996): 732-745.
Novak, Anton, et al. "Cholesterol masks membrane glycosphingolipid tumor-associated antigens to reduce their immunodetection in human cancer biopsies." Glycobiology 23.11 (2013): 1230-1239.
Office Action dated Oct. 26, 2018, from corresponding Chinese Patent Application No. 201680006858.6, 13 total pages.

(56) References Cited

OTHER PUBLICATIONS

Padlan, Eduardo A., et al. "Structure of an antibody-antigen complex: crystal structure of the HyHEL-10 Fab-lysozyme complex." Proceedings of the National Academy of Sciences 86.15 (1989): 5938-5942.
Partial European Search Report dated Jun. 13, 2018 in EP application 16740906.9, 14 pages.
Pece, Salvatore, et al. "Biological and molecular heterogeneity of breast cancers correlates with their cancer stem cell content." Cell 140.1 (2010): 62-73.
Rajan, Valanila P., et al. "A cloned human DNA restriction fragment determines expression of a GDP-L-fucose: beta-D-galactoside 2-alpha-L-fucosyltransferase in transfected cells. Evidence for isolation and transfer of the human H blood group locus." Journal of Biological Chemistry 264.19 (1989): 11158-11167.
Rouquier, Sylvie, et al. "Molecular cloning of a human genomic region containing the H blood group a (1, 2) fucosyltransferase gene and two H locus-related DNA restriction fragments isolation of a candidate for the human secretor blood group locus." Journal of Biological Chemistry 270.9 (1995): 4632-4639.
Rudikoff, Stuart, et al. "Single amino acid substitution altering antigen-binding specificity." Proceedings of the National Academy of Sciences 79.6 (1982): 1979-1983.
Shaw, Frances L., et al. "A detailed mammosphere assay protocol for the quantification of breast stem cell activity." Journal of mammary gland biology and neoplasia 17.2 (2012): 111-117.
Stanley, Pamela, and Richard D. Cummings. "Chapter 13. Structures common to different glycans." Essentials of Glycobiology [Internet]. 2nd edition. Cold Spring Harbor Laboratory Press (NY), 2009; NCBI Bookshelf, retrieved from the internet on Aug. 17, 2017, 40, pages.
Tripp, Ralph A., et al. "Bioconjugated nanoparticle detection of respiratory syncytial virus infection." International Journal of Nanomedicine 2(1) (2007): 117-124.
Vajdos, Felix F., et al. "Comprehensive functional maps of the antigen-binding site of an anti-ErbB2 antibody obtained with shotgun scanning mutagenesis." Journal of molecular biology 320.2 (2002): 415-428.
Wright, Mollie H., et al. "Brca1 breast tumors contain distinct CD44+/CD24- and CD133+ cells with cancer stem cell characteristics." Breast Cancer Research 10.1 (2008): R10.
Wu, Herren, et al. "Humanization of a murine monoclonal antibody by simultaneous optimization of framework and CDR residues." Journal of Molecular Biology 294.1 (1999): 151-162.
Zhou, Dapeng, et al. "The β1, 3-galactosyltransferase β3GalT-V is a stage-specific embryonic antigen-3 (SSEA-3) synthase." Journal of Biological Chemistry 275.30 (2000): 22631-22634.
Herter et al "Glycoengineering of therapeutic monoclonal antibodies enhances monocyte/macrophage-mediated phagocytosis and cytotoxicity" J Immunol. Mar. 1, 2014, vol. 192 No. 5, pp. 2252-2260.
Jez et al "Significant Impact of Single N-Glycan Residues on the Biological Activity of Fc-based Antibody-like Fragments" Journal of Biological Chemistry Jul. 13, 2012, vol. 287 No. 29, pp. 24313-24319.
Junttila et al "Superior in vivo efficacy of afucosylated trastuzumab in the treatment of HER2-amplified breast cancer" Cancer Res. 2010, vol. 70 No. 11, pp. 4481-4489.
Komarova et al "Plant-Made Trastuzumab (Herceptin) Inhibits HER2/Neu+ Cell Proliferation and Retards Tumor Growth" PLOS ONE 2011, vol. 6 No. 3, p. e17541.
McConville, Malcolm J., and M. A. Ferguson. "The structure, biosynthesis and function of glycosylated phosphatidylinositols in the parasitic protozoa and higher eukaryotes." Biochemical Journal 294.Pt 2 (1993): 305.
Ochiai et al "Expeditious Chemoenzymatic Synthesis of Homogeneous N-Glycoproteins Carrying Defined Oligosaccharide Ligands" J. Am. Chem. Soc. 2008, vol. 130 No. 41, pp. 13790-13803.
Office Action dated Aug. 29, 2017, from corresponding Japanese Patent Application No. 2016-169045, 5 total pages.
Tebbey et al "Importance of manufacturing consistency of the glycosylated monoclonal antibody adalimumab (Humira®) and potential impact on the clinical use of biosimilars" GABI Journal 2016, vol. 5 Issue 2, pp. 70-73.
Wiseman, Gregory A., et al. "Radiation dosimetry results and safety correlations from (90) Y-ibritumomab tiuxetan radioimmunotherapy for relapsed or refractory non-Hodgkin's lymphoma: Combined data from 4 clinical trials" The Journal of Nuclear Medicine 44.3 (2003): 465-474.
Zhang et al "Glycoengineered Pichia produced anti-HER2 is comparable to trastuzumab in preclinical study" mAbs May-Jun. 2011, vol. 3 No. 3, pp. 289-298.
Hodoniczky J, Zheng YZ, James DC. "Control of recombinant monoclonal antibody effector functions by Fc N-glycan remodeling in vitro" Biotechnology Progress. 2005;21(6):1644-1652.
Komarova TV, et al. "Trastuzumab and pertuzumab plant biosimilars: Modification of Asn297-linked glycan of the mAbs produced in a plant with fucosyltransferase and xylosyltransferase gene knockouts" Biochemistry (Moscow). Apr. 1, 2017;82(4):510-520.
Liu L. "Antibody glycosylation and its impact on the pharmacokinetics and pharmacodynamics of monoclonal antibodies and Fc-fusion proteins" Journal of Pharmaceutical Sciences. Jun. 2015;104(6):1866-1884.
Raju TS. "Terminal sugars of Fc glycans influence antibody effector functions of IgGs" Current Opinion in Immunology. Aug. 1, 2008;20(4):471-478.
Zhou Q, et al. "Site-specific antibody—drug conjugation through glycoengineering" Bioconjugate Chemistry. Feb. 28, 2014;25(3):510-520.
Dissertation, ChongQing Medical University, "Characterization and Culture of Microspheres Isolated Directly From Tumor Tissues of Breast Cancer Patients Received Neoadjuvant Chemotherapy" May 2011, 120 pages; English translation of Abstract provided.
U.S. Appl. No. 15/005,930, filed Jan. 25, 2016, Wong et al.
U.S. Appl. No. 15/011,543, filed Jan. 30, 2016, Wong et al.
U.S. Appl. No. 15/011,544, filed Jan. 30, 2016, Wong et al.
U.S. Appl. No. 15/173,496, filed Jun. 3, 2016, Wong et al.
Abbas et al., "Functional diversity of helper T lymphocytes," Nature, Oct. 31, 1996, 383(6603):787-793.
Abrahmsén et al, "Analysis of signals for secretion in the staphylococcal protein A gene," EMBO J., Dec. 30, 1985, 4(13B):3901-3906.
Achtman, M., Epidemic Spread and Antigenic Variability of Neisseria Meningitidis, Trends Microbial 1995, 3, 186-192.
Adam et al., "Proteomic profiling of mechanistically distinct enzyme classes using a common chemotype," Nat. Biotechnol., Aug. 2002, 20(8):805-809.
Agard, N. et al., A Strain-Promoted [3+2]Azide-Alkyne Cycloaddition for Covalent Modification of Biomolecules in Living Systems, J. Am. Chem. Soc. 2004, 126, 15046-15047.
Ahmadi, T. S. et al., Shape-Controlled Synthesis of Colloidal Platinum Nanoparticles, Science, 272, 1924 (1996).
Ahmed et al.,Structural Characterization of Anti-Inflammatory Immunoglobulin G Fc Proteins, K Mol Biol (2014) 426, 3166-3179.
Altevogt, Peter et al., Different Patterns of Lectin Binding and Cell Surface Sialylation Detected on Related High- and Low-Metastatic Tumor Lines, Cancer Res. 43, 5138-5144, 1983.
Altschul SF et al., "Basic local alignment search tool", J Mol Biol. Oct. 5, 1990;215(3):403-10.
Altschul SF, et al., "Gapped BLAST and PSI-BLAST: a new generation of protein database search programs", Nucleic Acids Res. Sep. 1, 1997;25(17):3389-402.
Amin, M. N. et al. Synthetic glycopeptides reveal the glycan specificity of HIV-neutralizing antibodies. Nat. Chem. Biol. 9, 521-526, (2013).
Anderson et al., "Stimulation of Natural Killer T Cells by Glycolipids", Molecules, May 2013, 18(12), 15662-15688.
Andrews et al., Synthesis and influenza virus sialidase inhibitory activity of analogues of 4-Guanidino-Neu5Ac2en (Zanamivir modified in the glycerol side-chain. Eur J Med Chem Jul.-Aug. 1999;34(7-8):563-74.

(56) References Cited

OTHER PUBLICATIONS

Angata et al., "Chemical diversity in the sialic acids and related α-keto acids: an evolutionary perspective," Chem. Rev., Feb. 2002, 102(2):439-469.
Anthony, Robert et al., Recapitulation of IVIG Anti-Inflammatory Activity with a Recombinant IgG Fc, Science Apr. 18, 2008. 320:373-376.
Arase et al., "NK1.1$^+$ CD4$^+$ CD8$^-$ thymocytes with specific lymphokine secretion," Eur. J. Immunol., Jan. 1993, 23(1):307-310.
Arié et al., "Chaperone function of FkpA, a heat shock prolyl isomerase, in the periplasm of Escherichia coli," Mol. Microbiol., Jan. 2001, 39(1):199-210.
Aspeslagh et al., "Galactose-modified iNKT cell agonists stabilized by an induced fit of CD1d prevent tumour metastasis," EMBO J., Jun. 1, 2011, 30(11):2294-2305.
Astronomo, R. D. & Burton, D.R. Carbohydrate vaccines: developing sweet solutions to sticky situations? Nat. Rev. Drug. Discov. 9, 308-324, (2010).
Bachmann, Cellular and Molecular Biology, vol. 2, Chapter 72: Derivations and Genotypes of Some Mutant Derivatives of Escherichia coli K-12, Neidhardt et al., eds., 1987, pp. 1190-1219, American Society for Microbiology, Washington, D.C.
Bacilieri, Magdalena et al., Ligand-Based Drug Design Methodologies in Drug Discovery Process: An Overview, Current Drug Discovery Technologies, vol. 3 (3), Sep. 2006, p. 155-165.
Bai, Dan et al., Exploring Forster Electronic Energy Transfer in a Decoupled Anthracenyl-based Borondipyrromethene (Bodipy) Dyad, Physical Chemistry Chemical Physics (2012), 14(13), 4447-4456.
Bailey, Ryan et al., Real-Time Multicolor DNA Detection with Chemoresponsive Diffraction Gratings and Nanoparticle Probes, J. Am Chem. Soc., 2003, 125, 13541-13547.
Baldwin et al., "Monoclonal antibodies in cancer treatment," Lancet, Mar. 15, 1986, 327(8481):603-605.
Banchereau et al., "Dendritic cells and the control of immunity," Nature, Mar. 19, 1998, 392(6673):245-252.
Barbas et al., "Assembly of combinatorial antibody libraries on phage surfaces: the gene III site," Proc. Natl. Acad. Sci. U.S.A., Sep. 15, 1991, 88(18):7978-7982.
Barbas et al., "In vitro evolution of a neutralizing human antibody to human immunodeficiency virus type 1 to enhance affinity and broaden strain cross-reactivity," Proc. Nat. Acad. Sci. U.S.A., Apr. 26, 1994, 91(9):3809-3813.
Barbas et al., "Semisynthetic combinatorial antibody libraries: a chemical solution to the diversity problem," Proc. Natl. Acad. Sci. U.S.A., May 15, 1992, 89(10):4457-4461.
Bardotti, Angela et al., Size Determination of Bacterial Capsular Oligosaccharides Used to Prepare Conjugated Vaccines Against Neisseria Meningitidis Groups Y and W135, Vaccine 2005, 23, 1887-1899.
Barnes et al., "Methods for growth of cultured cells in serum-free medium," Anal. Biochem., Mar. 1, 1980, 102(2):255-270.
Barouch, D. H. Challenges in the development of an HIV-I vaccine. Nature 455, 613-619, (2008).
Barry, C.S. et al., 'Naked' and Hydrated Confirmers of the Conserved Core Pentasaccharide of N-Linked Glycoproteins and Its Building Blocks, Journal of the American Chemical Society, 2013, vol. 135(45), p. 16895-16903.
Basak et al., In Vitro Elucidation of Substrate Specificity and Bioassay of Proprotein Convertase 4 Using Intramolecularly Quenched Fluorogenic Peptides, Biochem. J. Jun. 1, 2004, 380(pt 2): 505-514.
Baselga J, et al., "Phase II study of weekly intravenous recombinant humanized anti-p185HER2 monoclonal antibody in patients with HER2/neu-overexpressing metastatic breast cancer", J Clin Oncol. Mar. 1996;14(3):737-44.
Baskin, J.M.; Amacher, S. L.; Bertozzi, C.R. "In vivo imaging of membraneassociated glycans in developing zebrafish." Science 2008, 320, 664-667.
Bass et al., "Hormone phage: an enrichment method for variant proteins with altered binding properties," Proteins, 1990, 8(4):309-314.
Bassell, G.J. et al., Single mRNAs Visualized by Ultrastructural in Situ Hybridization are Principally Localized at Actin Filament Intersections in Fibroblasts, J. Cell Biol., 126, 863-876 (1994.
Baz et al., Emergence of oseltamivir-resistant pandemic H1N1 virus during prophylaxis. N Engl J Med. Dec. 3, 2009;361(23):2296-7. doi: 10.1056/NEJMc0910060. Epub Nov. 11, 2009.
Beck A., "Biosimilar, biobetter and next generation therapeutic antibodies" MAbs. Mar.-Apr. 2011;3(2):107-10. Epub Mar. 1, 2011.
Beckman et al., Antibody constructs in cancer therapy: protein engineering strategies to improve exposure in solid tumors, cancer, 109(2): 170-179 (2007).
Bendayan, Moise, Possibilities of False Immunocytochemical Results Generated by the Use of Momoclonal Antibodies: The Example of the Anti-Proinsulin Antibody, J. Histochem. Cytochem, 43: 881-886, (1995).
Bennett, Clay et al., Chemoenzymatic Approaches to Glycoprotein Synthesis, Chem. Soc. Rev. 2007, 36:1227-1238.
Berge, Steven et al. J. Pharmaceutical Sciences (1977) 66: 1-19.
Berra et al., "Correlation between ganglioside distribution and histological grading of human astrocytomas," Int. J. Cancer, Sep. 15, 1985, 36(3):363-366.
Best, M. D. "Click chemistry and bioorthogonal reactions: unprecedented selectivity in the labeling of biological molecules." Biochemistry 2009, 48, 6571-6584.
Bertozzi, CR et al., Glycans in Cancer and Inflammation—Potential for Therapeutics and Diagnostics, Nat Rev Drug Discovery, 2005, 4, 477-488.
Bigi et al., "Human sialidase NEU4 long and short are extrinsic proteins bound to outer mitochondrial membrane and the endoplasmic reticulum, respectively," Glycobiology, Feb. 2010, 20(2):148-157.
Birklé et al., "Role of tumor-associated gangliosides in cancer progression," Biochimie, Mar.-Apr. 2003, 85(3-4):455-463.
Blixt, O. et al. Printed covalent glycan array for ligand profiling of diverse glycan binding proteins. Proc. Natl. Acad. Sci. U.S.A. 101, 17033-17038, (2004.
Bobo et al., "Convection-enhanced delivery of macromolecules in the brain," Proc. Natl. Acad. Sci. U.S.A., Mar. 15, 1994, 91(6) 2076-2080.
Boens, N. et al., "Fluorescent indicators based on BODIPY." Chem. Soc. Rev. 2012, 41, 1130-1172.
Boerner et al., "Production of antigen-specific human monoclonal antibodies from in vitro-primed human splenocytes," J. Immunol., Jul. 1, 1991, 147(1):86-95.
Borg et al., "CD1d-lipid-antigen recognition by the semi-invariant NKT T-cell receptor," Nature, Jul. 5, 2007, 448(7149):44-49.
Bosmann et al., "Enzyme activity in invasive tumors of human breast and colon," Proc. Natl. Acad. Sci. USA, May 1974, 71(5):1833-1837.
Bost, Kenneth et al., Antibodies Against a Peptide Sequence Within the HIV Envelope Protein Crossreacts With Human Interleukin-2, Immunol. Invest., 17: 577-586 (1988).
Bothmann et al., "The periplasmic Escherichia coli peptidylprolyl cis,trans-isomerase FkpA. I. Increased functional expression of antibody fragments with and without cis-prolines," J. Biol. Chem., Jun. 2, 2000, 275(22):17100-17105.
Boyer, David et al., Photothermal Imaging of Nanometer-Sized Metal Particles Among Scatterers, Science, 2002, 297, 1160-116 3.
Braun-Howland et al., Development of a Rapid Method for Detecting Bacterial Cell In Situ Using 16S rRNA-Targeted Probes, Biotechniques, 13, 928-931 (1992).
Brennan et al., "Preparation of bispecific antibodies by chemical recombination of monoclonal immunoglobulin G$_1$ fragments," Science, Jul. 5, 1985, 229(4708):81-83.
Bricard et al., "Enrichment of human CD4$^+$ Vα24/Vβ11 invariant NKT cells in intrahepatic malignant tumors," J. Immunol., Apr. 15, 2009, 182(2):5140-5151.
Brimble et al., "The cell surface glycosphingolipids SSEA-3 and SSEA-4 are not essential for human ESC pluripotency," Stem Cells, Jan. 2007, 25(1):54-62.

(56) References Cited

OTHER PUBLICATIONS

Brodeur et al., *Monoclonal Antibody Production Techniques and Applications*, Chapter 4: Mouse-Human Myeloma Partners for the Production of Heterohybridomas, Schook, ed., 1987, pp. 51-63, Marcel Dekker, Inc., New York.
Bruchez, Marcel et al. Semiconductor Nanocrystals as Fluorescent Biological Labels, Science 281:2013-2016, 1998.
Brüggemann et al., "Designer mice: the production of human antibody repertoires in transgenic animals," *Year in Immunol.*, 1993, 7:33-40.
Buchini et al., "Towards a new generation of specific *Trypanosoma cruzi* trans-sialidase inhibitors," *Angew. Chem. Int. Ed. Engl.*, 2008, 47(14):2700-2703.
Burton, D.R., Mascola, J. R. Antibody responses to envelope glycoproteins in HIV-I infection. Nature Immunol. 16, 571-6, (2015).
Calarese, D. A. et al. Antibody domain exchange is an immunological solution to carbohydrate cluster recognition. Science 300, 2065-2071, (2003).
Cao, Y. C. et al., Nanoparticles with Raman Spectroscopic Fingerprints for DNA and RNA Detection, Science, 2002, 289, 1757-60.
Capel PJ et al., "Heterogeneity of human IgG Fc receptors" *Immunomethods*. Feb. 1994;4(1):25-34.
Carlsson, Jan et al., Protein Thiolation and Reversible Protein-Protein Conjugation, Biochem J 173: 723-737 (1978).
Carter et al., "High level *Escherichia coli* expression and production of a bivalent humanized antibody fragment," *Nature Biotechnology*, Feb. 1992, 10(2):163-167.
Carter et al., "Humanization of an anti-p185$^{HER2}$ antibody for human cancer therapy," *Proc. Natl. Acad. Sci. U.S.A.*, May 15, 1992, 89(10):4285-4289.
Carter PJ. "Potent antibody therapeutics by design" *Nat Rev Immunol.* May 2006;6(5):343-357.
Carter, A rationale for using steroids in the treatment of severe cases of H5N1 avian influenza. J Med Microbiol. Jul. 2007;56(Pt 7):875-83.
Centers for Disease Control and Prevention (CDC), "Influenza activity—United States and worldwide, 2007-08 season" *MMWR*, Jun. 27, 2008, 57(25):692-697.
Cespedes et al., Mouse models in oncogenesis and cancer therapy, Clin Transl Oncl., 8(5): 318-329 (2006).
Chan, Warren et al., Quantum Dot Bioconjugates for Ultrasensitive Nonisotopic Detection, Science 281:2016-2018 (1998).
Chandler et al., Synthesis of the potent influenza neuraminidase inhibitor 5-guanidino Neu5Ac2en. X-Ray molecular structure of 5-acetaminido-4amino-2,6-anahydro-3,4,5-tryoxy-D-erythoro-L-gluco-nononic acid. J Chem Soc Perkin Trans 1. 1995; 1173-1180.
Chang et al., "Expression of Globo H and SSEA3 in breast cancer stem cells and the involvement of fucosyl transferases 1 and 2 in Globo H synthesis," *Proc. Natl. Acad. Sci. U.S.A.*, Aug. 19, 2008, 105(33):11667-11672.
Chang, S. H. et al. Glycan array on aluminum oxide-coated glass slides through phosphonate chemistry. J. Am. Chem. Soc. 132, 13371-13380, (2010).
Chang et al., "Potent immune-modulating and anticancer effects of NKT cell stimulatory glycolipids," *Proc. Natl. Acad. Sci. USA*, Jun. 19, 2007, 104(25):10299-10304.
Chao, W.; Fang, X.; Nisaraporn, S.; Jian, S.; Qian, W. "Tuning the optical properties of BODIPY dye through Cu(I) catalyzed azide-alkyne cycloaddition (CuAAC) reaction." Sci. China Chemistry 2012, 55, 125-130.
Chari, Ravi et al., Immunoconjuates Containing Novel Maytansinoids: Promising Anticancer Drugs Cancer Research 52: 127-131 (1992).
Chauhan, D. P.; Saha, T.; Lahiri, M.; Talukdar, P. "BODIPY based 'click on' fluorogenic dyes: application in live cell imaging." Tetrahedron Lett. 2014, 55, 244-247.
Chen et al., "Chaperone activity of DsbC," *J. Bio. Chem.*, Jul. 9, 1999, 274(28):19601-19605.

Chen et al., "Selection and analysis of an optimized anti-VEGF antibody: crystal structure of an affinity-matured Fab in complex with antigen," *J. Mol. Biol.*, Nov. 5, 1999, 293(4):865-881.
Chen et al., "Selective killing of transformed cells by cyclin/cyclin-dependent kinase 2 antagonists," *Proc. Natl. Acad. Sci. U.S.A.*, Apr. 13, 1999, 96(8):4325-4329.
Cheng, Peter et al., Oseltamivir- and Amandtadine-resistant Influenza Viruses A (H1N1), Emerg. Infect. Dis., Jun. 2009, 15(6): 966-968.
Cheung et al., Stage-specific embryonic antigen-3 (SSEA-3) and beta3GalT5 are cancer specific and significant markers for breast cancer stem cells, PNAS, Jan. 26, 2016, vol. 113, No. 4, pp. 960-965.
Chiang et al., Ethyl caffeate suppresses NF-kappaB activation and its downstream inflammatory mediators, iNOS, COX-2, and PGE2 in vitro or in mouse skin. Br J Pharmacol. Oct. 2005; 146(3):352-63.
Chiari, M. et al., Advanced Polymers for Molecular Recognition and Sensing at the Interface. J Chromatography B, Apr. 15, 2008, 866(1-2):89-103.
Childs et al., Receptor-Binding Specificity of Pandemic Influenza A (H1N1) 2009 Virus Determined by Carbohydrate Microarray. Nat. Biotechnol. 2009, 27(9): 797-799.
Cho, Se-Heon et al., Sialyl-Tn Antigen Expression Occurs Early During Human Mammary Carcinogenesis and Is Associated with High Nuclear Grade and Aneuploidy, Cancer Res. 54, 6302-6305, 1994.
Chong et al., Influenza Virus Sialidase: Effect of Calcium on Steady-State Kinetic Parameters, Biochim. Biophys. Acta, Mar. 8, 1991, 1077(1): 65-71.
Chothia et al., "Canonical structures for the hypervariable regions of immunoglobulins," *J. Mol. Biol.*, Aug. 20, 1987, 196(4):901-917.
Chothia et al., "Domain association in immunoglobulin molecules. The packing of variable domains," *J. Mol. Biol.*, Dec. 5, 1985, 186(3):651-663.
Chu, Kuo-Chinget al., Efficient and Stereoselective Synthesis of [alpha](2->9) Oligosialic Acids: From Monomers to Dodecamers, Angewandte Chemie International Edition, vol. 50, No. 40, Sep. 2011, 9391-9395.
Clackson et al., "Making antibody fragments using phage display libraries," *Nature*, Aug. 15, 1991, 352(6336):624-628.
Clark EA et al., "Structure, function, and genetics of human B cell-associated surface molecules" *Adv Cancer Res.* 1989;52:81-149.
Clynes R, et al., "Fc receptors are required in passive and active immunity to melanoma" *Proc Natl Acad Sci U S A.* Jan. 20, 1998;95(2):652-6.
Codelli, J. A. et al., Second-Generation Difluorinated Cyclooctynes for Copper-Free Click Chemistry, J. Am. Chem. Soc. 2008, 130, 11486-11493.
Cohen-Daniel et al., Emergance of Oseltamivir-Resistant Influenza A/H3N2 Virus with Altered Hemagglutination Pattern in Hematopoietic Stem Cell Transplant Recipient, J Clin Virol., Feb. 2009, 44(2):138-140.
Coligan et al., Current Protocols in Immunology, sections 2.5.1-2.6.7, 1991.
Collins et al., Crystal Structures of Oseltamivir-Resistant Influenza Virus Neuraminidase Mutants, Nature, Jun. 26, 2008, 453(7199):1258-1261.
Connor, Robert et al., Receptor Specifcity in Human, Avian, and Equine H2 and H3 Influenza Virus Isolates, Virology, 205: 17, 1994.
Cox et al., New Options for the Prevention of Influenza, N. Engl. J. Med. Oct. 28, 1999, 341(18): 1387-1388.
Cragg, M.S. et al., Complement-Mediated Lysis by Anti-CD20 mAb Correlates with Segregation into Lipid Rafts, Blood 101 (2003) 1045-1052.
Cragg, M.S. et al., Antibody Specificity Controls in Vivo Effector Mechanism of Anti-CD20 Reagents, Blood, 103 (2004) 2738-2743.
Craigo, J. K., Montelaro, R. C. Lessons in AIDS vaccine development learned from studies of equine infectious, anemia virus infection and immunity. Viruses 5, 2963-76, (2013).
Crispin et al., "Carbohydrate and domain architecture of an immature antibody glycoform exhibiting enhanced effector functions," J. Mol. Biol., Apr. 17, 2009, 387(5):1061-1066.

(56) References Cited

OTHER PUBLICATIONS

Cunningham et al., "High-resolution epitope mapping of hGH-receptor interactions by alanine-scanning mutagenesis," *Science*, Jun. 2, 1989, 244(4908):1081-1085.
Cyranoski, Threat of Pandemic Brings Flu Drug Back to Life, Nat. Med. Sep. 2005, 11(9): 909.
Daëron, "Fc receptor biology," *Annu. Rev. Immunol.*, 1997, 15:203-234.
Davies, JW et al., Streamlining Lead Discovery by Aligning in Silico and High-Throughput Screening, Curr Opin Chem Biol. Aug. 2006; 10(4):343-51.
Davodeau et al., "Close phenotypic and functional similarities between human and murine αβ T cells expressing invariant TCR alpha-chains," *J. Immunol.*, Jun. 15, 1997, 158(12):5603-5611.
De Almeida et al., "Thiacycloalkynes for copper-free click chemistry," *Angew. Chem. Int. Ed. Engl.*, Mar. 5, 2012, 51(10):2443-2447.
Debets, M. F. et al., Bioconjugation with Strained Alkenes and Alkynes, Acc. Chem. Res. 2011, 44, 805-815.
De Haas et al., "Fcγ receptors of phagocytes," *J. Lab. Clin. Med.*, Oct. 1995, 126(4):330-341.
Dejong et al., Fatal outcome of human influenza A (H5N1) is associated with high viral load and hypercytokinemia. Nat Med Oct. 2006;12(10):1203-7. Epub Sep. 10, 2006.
Delente, Jacqubs, Glycosylation Revisited, Trends in Biotechnology 3, letters to editor, No. 9 (1985).
Dellabona et al., "An invariant Vα24-JαQ/Vβ11 T cell receptor is expressed in all individuals by clonally expanded CD4⁻8⁻ T cells," *J. Exp. Med.*, Sep. 1, 1994, 180(3):1171-1176.
Demchenko, A.V., Ed., Hanbook of Chemical Glycosylation: Advances in Stereoselectivity and Therapeutic Relevance (2008) WILEY-VCH. Chapter 1. General Aspects of the Glycosidic Bond Formation, in 28 pages.
Dennis, Carina, Cancer: Off by a whisker, Nature 442: 739-741 (2006).
De Paz, J. L., Horlacher, T. & Seeberger, P.H. Oligosaccharide microarrays to map interactions of carbohydrates in biological systems. Methods Enzymol. 415, 269-292, (2006).
Dhodapkar et al., "α-Galactosyl ceramide-loaded dendritic cells for expansion of natural killer T cells" CAPLUS 145:354715 (2006).
Dhodapkar et al., "A reversible defect in natural killer T cell function characterizes the progression of premalignant to malignant multiple myeloma," *J. Exp. Med.*, Jun. 16, 2003, 197(12):1667-1676.
Dohi, Taeko et al., Fucosyltransferase-Producing Sialyl Lea and Sialyl Lex Carbohydrate Antigen in Benign and Malignant Gastrointestinal Mucosa, Cancer 73, 1552, 1994.
Dohi, H. et al., Stereoselective Glycal Fluorophosphorlation: Synthesis of ADP-2-Fluoroheptose, an Inhibitor of the LPS Biosynthesis, Chem-Eur J 2008, 14, 9530-9539.
Dommerholt, Jan, Readily Accessible Bicyclononynes for Bioorthogonal Labeling and Three-Dimensional Imaging of Living Cells, Angew. Chem. Int. Ed. 2010, 49, 9422-9425.
Doores KJ, et al. A nonself sugar mimic of the HIV glycan shield shows enhanced antigenicity. Proc. Natl. Acad Sci. US.A. 107(40), 17107-17112, (2010).
Doores, K. J. & Burton, D.R. Variable Loop Glycan Dependency of the Broad and Potent HIV-I-Neutralizing Antibodies PG9 and PG16. J. Virol. 84, 10510-10521, (2010).
Doores, K. J. et al. Envelope glycans of immunodeficiency virions are almost entirely oligomannose antigens. Proc. Natl. Acad. Sci. U. S. A 107, 13800-13805, (2010).
Doronina, Svetlana et al., Development of Potent Monoclonal Antibody Auristatin Conjugates for Cancer Therapy, Nat Biotechnol 21(7): 778-784 (2003).
Dougan, Michael et al., Immune Therapy for Cancer, Annual Review of Immunology, 2009, 27, pp. 83-117.
Drugs of the future 25(7): 686 (2000).
Dubertret. Benoit et al., In Vivo Imaging of Quantum Dots Encapsulated in Phospholipid Micelles, Science 298:759-1762, 2002.
Duncan, AR; Winter, G, The binding Site for C1q on IgG, Nature 322:738-40 (1988).
Dunn et al., Zanamivir: A Review of Its Use in Influenza, Drugs, Oct. 1999, 58(4):761-784.
Durrant et al., "Immunology in the clinic review series; focus on cancer: glycolipids as targets for tumour immunotherapy," *Clin. Exp. Immunol.*, Feb. 2012, 167(2):206-215.
Eberl et al., "Selective bystander proliferation of memory CD4⁺ and CD8⁺ T cells upon NK T or T cell activation," *J. Immunol.*, Oct. 15, 2000, 165(8):4305-4311.
Eberl et al., "Selective induction of NK cell proliferation and cytotoxicity by activated NKT cells," *Eur. J. Immunol.*, Apr. 2000, 30(4):985-992.
Eggink, D. et al. Lack of complex N-glycans on HIV-I envelope glycoproteins preserves protein conformation and entry function. Virology 401, 236-247, (2010).
Eisen, Michael et al., Binding of the Influenza A Virus to Cell-Surface Receptors: Structures of Five Hemagglutinin-Sialyloligosaccharide Complexes Determined by X-Ray Crystallography, Virology, 232:19, 1997.
Ellis J., et al., Evaluation of Four Real-Time PCR Assays for Detection of Influenza A9H1N1)v Viruses, Euro Surveill. 2009; 14(22), p. 1-3.
Embleton et al., "In-cell PCR from mRNA: amplifying and linking the rearranged immunoglobulin heavy and light chain V-genes within single cells," *Nucl. Acids Res.*, Aug. 11, 1992, 20(15):3831-3837.
Engels et al., "Gene synthesis [new synthetic methods (77)]," *Angew. Chem. Int. Ed. Engl.*, Jun. 1989, 28(6):716-734.
European Search Report issued in connection with corresponding European Patent Application No. 15181446.4, dated Dec. 7, 2015, 10 pages.
Evans, Michael et al., "Mechanism-based profiling of enzyme families," *Chem. Rev.*, Aug. 2006, 106(8):3279-3301.
Evans, "The rise of azide-alkyne 1,3-dipolar 'click' cycloaddition and its application to polymer science and surface modification," *Australian J. Chem.*, Jun. 2007, 60(6):384-395.
Extended European Search Report dated Jan. 5, 2016 in European Patent Application No. 13830785.5, in 10 pages.
Falkowska, E. et al. Broadly neutralizing HIV antibodies define a glycan-dependent epitope on the prefusion conformation of gp41 on cleaved envelope trimers. Immunity 40, 657-68, 2014.
Fan, Shu-Quan et al., Remarkable Transglycosylation Activity of Glycosynthase Mutants of Endo-D, an Endo-β-N-acetylglucosaminidase from *Streptococcus pneumoniae*, JBC vol. 287, No. 14, pp. 11272-11281, Mar. 30, 2012.
Fazio, F. et al., Synthesis of sugar arrays in microtiter plate. J. Am. Chem. Soc. 124, 14397-14402, (2002).
FDA Guidance for Industry for Container Closure Systems for Packaging Human Drugs and Biologics, May 1999.
Fedson, Confronting the next influenza pandemic with anti-inflammatory and immunomodulatory agents: why they are needed and how they might work. Influenza Other Respi Virusts. Jul. 2009;3(4):129-42.
Feizi, Ten, Carbohydrate Differentiation Antigens: Probable Ligands for Cell Adhesion Molecules,Trends Biochem. Sci. 16, 84-86.
Fellouse et al., "Synthetic antibodies from a four-amino-acid code: a dominant role for tyrosine in antigen recognition," *Proc. Natl. Acad. Sci. U.S.A.*, Aug. 24, 2004, 101(34):12467-12472.
Fernandez-Tejada, Alberto et al., Designing synthetic vaccines for HIV. Expert Rev. Vaccines 14, 815-31, 2015.
Fernandez-Megia et al., A Click Approach to Unprotected Glycodendrimers. Macromolecules 2006, vol. 39, pp. 2113-2120.
Fessner et al., Enzymes in Organic Synthesis, Short Enzymatic Synthesis of L-Fucose Analogs. Eur. J. Org. Chem 2000, p. 125-132.
Fiehn, Oliver, Combining Genomics, Metabolome Analysis, and Biochemical Modelling to Understand Metabolic Networks, Comparative and Functional Genomics 2:155-168, 2001.
Fishwild et al., "High-avidity human IgGκ monoclonal antibodies from a novel strain of minilocus transgenic mice," *Nature Biotechnol.*, Jul. 1996, 14(7):845-851.

(56) References Cited

OTHER PUBLICATIONS

Fraker, PJ et al., Protein and Cell Membrane Iodinations with a Sparingly Soluble Chloroamide, 1,3,4,6-tetrachloro-3a,6a-diphrenylglycoluril, Biochem. Biophys. Res. Commun. 80: 49-57 (1978).
Frank, Natasha et al., The Therapeutic Promise of the Cancer Stem Cell Concept, Journal of Clinical Investigation, 120(1) 41-50, Jan. 2010.
Fredman et al., "Expression of gangliosides GD3 and 3'-isoLM1 in autopsy brains from patients with malignant tumors," *J. Neurochem.*, Jan. 1993, 60(1):99-105.
Fredman et al., "Potential ganglioside antigens associated with human gliomas," *Neurol. Res.*, Jun. 1986, 8(2):123-126.
Fredman et al., "Sialyllactotetraosylceramide, a ganglioside marker for human malignant gliomas," *J. Neurochem.*, Mar. 1988, 50(3):912-919.
Friscourt, F. et al., A Fluorogenic Probe for the Catalyst-Free Detection of Azide-Tagged Molecules, J. Am. Chem. Soc. 2012, 134, 18809-18815.
Friscourt et al., "Polar Dibenzocyclooctynes for Selective Labeling of Extracellular Glycoconjugates of Living Cells," *J. Am. Chem. Soc.*, Mar. 21, 2012, 134(11):5381-5389.
Fujimore, Kenji et al., A Modeling Analysis of Monoclonal Antibody Percolation Through Tumors: A Binding-Site Barrier, J Nuc Med. 31: 1191-1198 (1990).
Fujio, M. et al. "Structure-Based Discovery of Glycolipids for CD1d-Mediated NKT Cell Activation: Turning the Adjuvant versus Immunosuppression Activity." CAPLUS 145:240945 (2006).
Fujio, M. et al. "Structure-Based Discovery of Glycolipids for CD1d-Mediated NKT Cell Activation: Turning the Adjuvant versus Immunosuppression Activity." J. Am. Chem. Soc. (2006), vol. 128, pp. 9022-9023.
Fujita M et al., "A novel disaccharide substrate having 1,2-oxazoline moiety for detection of transglycosylating activity of endoglycosidases" *Biochim Biophys Acta.* Sep. 3, 2001;1528(1):9-14.
Fukui, S et al., Oligosaccharide microarrays for high-throughput detection and specificity assignments of carbohydrate-protein interactions. Nat. Biotechnol. 20, 1011-1017, (2002).
Gabius, HJ. Tumor Lectinology: at the intersection of carbohydrate chemistry, biochemistry, cell biology and oncology. Angew. Chem. Int. Ed. Engl. 27, 1267-1276.
Galfrè et al., "Preparation of monoclonal antibodies: strategies and procedures," *Methods Enzymol.*, 1981, 73(Pt B):3-46.
Gamblin, SJ et al., The Structure and Receptor Binding Properties of the 1918 Influenza Hemagglutinin, Science, 303:1838, 2004.
Garces, F. et al. Structural evolution of glycan recognition by a family of potent HIV antibodies. Cell 159, 69-79, (2014).
Gaschen, B. et al. AIDS—Diversity Considerations in HIV-I vaccine selection. Science 296, 2354-2360, (2002).
Gazzano-Santoro et al., "A non-radioactive complement-dependent cytotoxicity assay for anti-CD20 nonclonal antibody," *J. Immunol. Methods*, Mar. 28, 1997, 202(2):163-171.
Geiler et al., Comparison of pro-inflammatory cytokine expression and cellular signal transduction in human macrophages infected with different influenza A viruses. Med Microbiol Immunol. Feb. 2011;200(1):53-60.
GenBank accession No. AAA24922.1, "endoglycosidase F [Elizabethkingia meningoseptica]," May 27, 2008.
GenBank accession No. AAA24923.1, "endoglycosidase, partial [Elizabethkingia meningoseptica]," Jun. 8, 1993.
GenBank accession No. AAA24924.1.1, "endoglycosidase, partial [Elizabethkingia meningoseptica]," Jun. 7, 1993.
GenBank accession No. AAA26738.1, "endo-beta-N-acetylglucosaminidase H [Streptomyces plicatus]," Apr. 26, 1993.
GenBank accession No. J05449.1, "F.meningosepticum peptide-N-4-(N-acetyl-beta-D-glucosaminyl) asparagine amidase (PNGase F) mRNA, complete cds," Jan. 16, 1996.
GenBank accession No. YP_212855.1, "Putative exported alpha-L-fucosidase protein [Bacteroides fragilis NCTC 9343]," Mar. 2, 2014.
GenBank accession No. WP_0080769537.1, published May 10, 2013.
GenBank accession No. WP_008767711.1, published May 10, 2013.
Geoghegan, Kieran et al., Site-Directed Conjugation of Nonpeptide Groups to Peptides and Proteins via Periodate Oxidation of a 2-amino Alcohol. Applications to Modification at N-Terminal Serine, Bioconjugate chem. 3:138-146 (1992).
Gerson et al., "ESR. Spectra and Structures of Radical Anions in the Dibenzo[a, e]cyclooxtene Series," *Helvetica Chinica Acta*, Jan. 1, 1976, 59(6): 2038-2048.
Giaccone, Giuseppe et al., "A phase I study of the natural killer T-cell ligand α-galactosylceramide (KRN7000) in patients with solid tumors," *Clin. Cancer Res.*, Dec. 2002, 8(12):3702-3709.
Gill et al., "Direct brain infusion of glial cell line-derived neurotrophic factor in Parkinson disease," *Nature Med.*, May 2003, 9(5):589-595 and Addendum from Apr. 2006, 12(4):479.
Go, E. P. et al. Characterization of glycosylation profiles of HIV-I transmitted/founder envelopes by mass spectrometry. J. Virol. 85, 8270-8284, (2011).
Go, E. P. et al. Comparative Analysis of the Glycosylation Profiles of Membrane-Anchored HIV-I Envelope Glycoprotein Trimers and Soluble gp140. J. Virol. 89, 8245-57, (2015).
Godefroy, S. et al., Effect of Skin Barrier Disruption on Immune Responses to Topically Applied Cross-Reacting Material, CRM197 of Diphtheria Toxin, Infect. Immun. 2005, 73, 4803.
Goding, *Monoclonal Antibodies: Principles and Practice* $2^{nd}$ ed., Chapter 3: Production of Monoclonal Antibodies, 1986, pp. 59-103, Academic Press, London.
Goldenthal et al., "Safety Evaluation of Vaccine Adjuvants: National Cooperative Vaccine Development Working Group," *AIDS Res. Hum. Retroviruses*, 1993, 9(Supp.1):S47-S51.
Golkowski et al., "Strategy for catch and release of azide-tagged biomolecules utilizing a photolabile strained alkyne construct," *Organic and Biomolecular Chemistry*, Jan. 1, 2012, 10(23):4496.
Goochee CF et al., "The oligosaccharides of glycoproteins: bioprocess factors affecting oligosaccharide structure and their effect on glycoprotein properties", *Biotechnology* (N Y). Dec. 1991;9(12):1347-55.
Gordon et al., "Reactivity of biarylazacyclooctynones in copper-free click chemistry," *J. Am. Chem. Soc.*, Jun. 6, 2012, 134(22): 9199-9208.
Gottschling et al., "Stage-specific embryonic antigen-4 is expressed in basaloid lung cancer and associated with poor prognosis," *Eur. Respir. J.*, Mar. 2013, 41(3):656-663.
Govorkova et al, Combination chemotherapy for influenza. Viruses. Aug. 2010;2(8):1510-29.
Graham et al., "Characteristics of a human cell line transformed by DNA from human adenovirus type 5," *J. Gen. Virol.*, Jul. 1977, 36(1):59-72.
Graham, Duncan et al., Surface-Enhanced Resonance Raman Scattering as a Novel Method of DNA Discrimination, Angew. Chem., 2000, 112(6), 1103-1105.
Gram et al., "In vitro selection and affinity maturation of antibodies from a naive combinatorial immunoglobulin library," *Proc. Natl. Acad. Sci. U.S.A.*, Apr. 15, 1992, 89(8):3576-3580.
Grandjean, C. et al., On the Preparation of Carbohydrate-Protein Conjugates Using the Traceless Staudinger Ligation, J Org Chem 2005, 70, 7123-7132.
Green, "Targeting targeted therapy," *N. Engl. J. Med.*, May 20, 2004, 350(21):2191-2193.
Greenbaum et al., "Chemical approaches for functionally probing the proteome," *Mol. Cell. Proteomics*, 2002, 1:60-68.
Griffiths et al., "Human anti-self antibodies with high specificity from phage display libraries," *EMBO J.*, Feb. 1993, 12(2):725-734.
Gruber et al., "Efficient tumor cell lysis mediated by a bispecific single chain antibody expressed in *Escherichia coli*," *J. Immunol.*, Jun. 1, 1994, 152(11):5368-5374.

(56) References Cited

OTHER PUBLICATIONS

Grubisha, D. S. et al., Femtomolar Detection of Prostate-Specific Antigen: An Immunoassay Based on Surface-Enhanced Raman Scattering and Immunogold labels, Anal. Chem. (2003), 75, 5936-5943.

Gulati et al., Deletions of Neuraminidase and Resistance to Oseltamivir May Be a Consequence of Restricted Receptor Specificity in Recent H3N2 Influenza Viruses. Virol. J. 2009, 6(22)L 1-15.

Gulland, Fire Cases of Spread of Oseltamivir Resistant Swine Flu Between Patients are Reported in Wales, BMJ, Nov. 23, 2009:339:b4975.

Guss et al., "Structure of the IgG-binding regions of streptococcal protein G," *EMBO J.*, Jul. 1986, 5(7):1567-1575.

Guyer et al., "Immunoglobulin binding by mouse intestinal epithelial cell receptors," *J. Immunol.*, Aug. 1976, 117(2):587-593.

Ha, Ya et al., X-Ray Structures of H5 Avian and H9 Swine Influenza Virus Hemagglutinins Bound to Avian and Human Receptor Analogs, Proc Natl Acad Sci USA, 98:11181-11186, 2001.

Ha, Ya et al., X-Ray Structure of the Hemagglutinin of a Potential H3 Avian Progenitor of the 1968 Hong Kong Pandemic Influenza Virus, Virology, 309:209-218, 2003.

Hajishengallis, "Mucosal immunization with a bacterial protein antigen genetically coupled to cholera toxin A2/B subunits," *J. Immuol.*, May 1, 1995, 154(9):4322-4332.

Hakomori et al., "Glycosphingolipid antigens and cancer therapy," *Chem. Biol.*, Feb. 1997, 4(2):97-104.

Hakomori, "Glycosylation defining cancer malignancy: new wine in an old bottle," *Proc. Natl. Acad. Sci. U.S.A.*, Aug. 6, 2002, 99(16):10231-10233.

Ham, Richard et al., Media and Growth Requirements, Meth. Enz 58, 44 (1979).

Hammerling et al., in: Monoclonal Antibodies and T-Cell Hybridomas 563-587, 1981.

Han, Junyan et al., 3- and 5-Functionalized BODIPYs via the Liebeskind-Srogl Reaction, Organic & Biomolecular Chemistry (2009), 7(1), 34-36.

Hanski, Christoph et al., Altered Glycosylation of the MUC-1 Protein Core Contributes to the Colon Carcinoma-Associated Increase of Mucin-Bound Sialyl-Lewis Expression, Cancer Res. 53, 4082-4088 (1993).

Hanski, C. et al., Characterization of the Major Sialyl-Lex-Poristive Mucins Present in Colon, Colon Carcinoma, and Sera of Patients with Colorectal Cancer, Cancer Res. 55, 928-933 (1995).

Hara et al., "Overproduction of penicillin-binding protein 7 suppresses thermosensitive growth defect at low osmolarity due to an spr mutation of *Escherichia coli,*" *Microbial Drug Resistance*, Spring 1996, 2(1):63-72.

Harris, "Production of humanized monoclonal antibodies for in vivo imaging and therapy," *Biochem. Soc. Transactions*, Nov. 1995, 23(4):1035-1038.

Hasegawa, Akira, et al., Synthesis of Sialyl Lewis X Ganglioside Analogues Containing Modified L-Fucose Residues, Carbohydr. Res. 1995, 274, 165-181.

Hata, K. et al., Limited Inhibitory Effects of Oseltamivir and Zanamivir on Human Sialidases, Antimicrobial Agents and Chemotherapy, vol. 52, No. 10, Oct. 2008, in 8 pages.

Hawkins et al., "Selection of phage antibodies by binding affinity. Mimicking affinity maturation," *J. Mol. Biol.*, 1992, 226(3):889-896.

Healthy Living, "10 Simple and Natural Ways to Boost Your Immune System," Published Jan. 31, 2014, downloaded from online, http://www.everydayhealth.com/columns/white-seeber-grogan-the-remedy-chicks/ten-simple-natural-ways-to-b . . . on Aug. 19, 2016.

Henglein, A. et al., Absorption Spectrum and Some Chemical Reactions of Colloidal Platinum in Aqueous Solution, J. Phys. Chem., 99, 14129 (1995).

Herner, A et al., A new family of bioorthogonally applicable fluorogenic labelst, Org. Biomol. Chem. 2013, 11, 3297-3306.

Hey, Thomas et al., Artificial, non-antibody binding proteins for pharmaceutical and industrial application, Trends in Biotechnology 23(10) 514-522 (2005).

Heyman, "Complement and Fc-receptors in regulation of the antibody response," *Immunol. Lett.*, Dec. 1996, 54(2-3):195-199.

Hinman et al., "Preparation and characterization of monoclonal antibody conjugates of the calicheamicins: a novel and potent family of antitumor antibiotics," *Cancer Res.*, Jul. 15, 1993, 53(14):3336-3342.

Hirabayashi, J. et al., Oligosaccharide Microarrays for Glycomics, Trends in Biotechnology 21 (4): 141-143, 2003.

Hogrefe et al., "A bacteriophage lambda vector for the cloning and expression of immunoglobulin Fab fragments on the surface of filamentous phage," *Gene*, Jun. 15, 1993, 128(1):119-126.

Holliger et al., "'Diabodies': small bivalent and bispecific antibody fragments," *Proc. Natl. Acad. Sci. U.S.A.*, Jul. 15, 1993, 90(14):6444-6448.

Holmskov, Uffe et al., Collectins: Collagenous C-Type Lectins of the Innate Immune Defense System, 1994, Immunol. Today, 15: 67.

Honda et al., Synthesis and anti-influenza virus activity of 7-0-alkylated derivatives related to zanamivir. Bioorg Med Chem Lett. Aug. 5, 2002;12(15):1925-8.

Honegger et al., "Yet another numbering scheme for immunoglobulin variable domains: an automatic modeling and analysis tool," *J. Mol. Biol.*, Jun. 8, 2001, 309:657-670.

Hoogenboom et al., "By-passing immunisation: Human antibodies from synthetic repertoires of germline $V_H$ gene segments rearranged in vitro," *J. Mol. Biol.*, Sep. 20, 1992, 227(2):381-388.

Hoogenboom et al., "Multi-subunit proteins on the surface of filamentous phage: methodologies for displaying antibody (Fab) heavy and light chains," *Nucl. Acids Res.*, Aug. 11, 1991 19(15):4133-4137.

Hotha, Srinivas et al., "Click Chemistry" Inspired Synthesis of Pseudo-Oligosaccharides and Amino Acid Glycoconjugates, J Org Chem 2006, 71, 364-367.

Horiya, S. et al., Recent strategies targeting HIV glycans in vaccine design. Nat. Chem. Biol. 10, 990-999, (2014).

Horn et al., Investigation into an Efficient Synthesis of 2,3-dehydro-N-acetyl Neuraminic Acid Leads to Three Decarboxylated Sialic Acid Dimers, Carbohdr. Res., Apr. 7, 2008, 343(5):936-940.

Howard et al., "Biological properties of interleukin 10," *Immunol. Today*, Jun. 1992, 13(6):198-200.

Hsu et al., "Alkynyl sugar analogs for the labeling and visualization of glycoconjugates in cells," *Proc. Natl. Acad. Sci. USA*, Feb. 20, 2007, 104(8), 2614-2619.

Hsu, Nien-Yeen et al., Desorption Ionization of Biomolecules on Metals, Anal. Chem., 80, 5203-5210, 2008.

Huang et al., "Carbohydrate-based vaccines with a glycolipid adjuvant for breast cancer," *Proc. Natl. Acad. Sci. U.S.A.*, Feb. 12, 2013, 110(7):2517-2522.

Huang, Lijun et al., Iterative One-Pot Syntheses of Chitotetroses, Carbohydr. Res. 2006, 341, 1669-1679.

Huang et al., Recombinant immunotherpaeutics: current state and perspectives regarding the feasibility and market, Appl Microbiol Biotechnol, 87: 401-410. 2010.

Hung et al., "Investigation of SSEA-4 binding protein in breast cancer cells," *J. Am. Chem. Soc.*, Apr. 24, 2013, 135(16):5934-5937.

Hurle et al., "Protein engineering techniques for antibody humanization," *Curr. Opin. Biotechnol.*, Aug. 1994, 5(4):428-433.

Immunogenicity, Wikipedia p. 1-3. Downloaded on Aug. 16, 2016 from https://en.wikipedia.org/wiki/Immunogenicity. (2016).

Inouye et al., "Single-step purification of F(ab')$_{2u}$ fragments of mouse monoclonal antibodies (immunoglobulins M) by hydrophobic interaction high-performance liquid chromatography using TSKgel Ether-5PW," *J. Biochem. Biophys. Methods*, Feb. 1993, 26(1):27-39.

International Search Report and Written Opinion issued for International application No. PCT/US2015/011748, dated Aug. 21, 2015, 17 pages.

International Search Report and Written Opinion issued for International application No. PCT/US2015/032737, dated Oct. 1, 2015, 13 pages.

(56) References Cited

OTHER PUBLICATIONS

International Search Report and Written Opinion issued for International application No. PCT/US2015/032738, dated Oct. 20, 2015, 15 pages.
International Search Report and Written Opinion issued for International application No. PCT/US2015/032740, dated Oct. 26, 2015, 13 pages.
International Search Report and Written Opinion issued for International application No. PCT/US2015/032744, dated Oct. 2, 2015, 12 pages.
International Search Report and Written Opinion issued for International application No. PCT/US2015/032745, dated Oct. 8, 2015, 13 pages.
International Search Report dated Jan. 13, 2012, from corresponding International Patent Application No. PCT/US2011/035982, 17 pages.
International Search Report dated Nov. 13, 2014, from corresponding International Patent Application No. PCT/US2014/054617, 10 pages.
International Search Report issued for International application No. PCT/US2015/049014, dated Dec. 14, 2015, 3 pages.
International Search Report and Written Opinion in International Application No. PCT/US16/15858, dated Jun. 27, 2016, in 8 pages.
International Search Report issued for International application No. PCT/US15/22977, dated Jun. 22, 2015, 3 pages.
International Search Report issued for International application No. PCT/US15/40199, dated Mar. 2, 2016, 6 pages.
International Search Report issued for International application No. PCT/US2009/050754, dated Feb. 24, 2010, 10 pages.
International Search Report and Written Opinion in International Application No. PCT/US2017/021454, dated Jul. 31, 2017, 8 pages.
Isshiki et al., Cloning, Expression, and Characterization of a Novel UDP-galactose:b-N-Acetylglucosamine b1,3-Galactosyltransferase (b3Gal-T5) Responsible for Synthesis of Type 1 Chain in Colorectal and Pancreatic Epithelia and Tumor Cells Derived Therefrom, The Journal of Biological Chemistry, Apr. 30, 1999, vol. 274, No. 18, pp. 12499-12507.
Ito, Akihiro et al., A Novel Ganglioside Isolated From Renal Cell Carcinoma, Biol Chem 2001, 276, 16695.
Jackson et al., "In vitro antibody maturation: Improvement of a high affinity, neutralizing antibody against IL-1β," *J. Immunol.*, Apr. 1, 1995, 154(7):3310-3319.
Jacobs et al., "Metabolic labeling of glycoproteins with chemical tags through unnatural sialic acid biosynthesis," *Methods Enzymol.*, 2000, 327:260-275.
Jakobovits et al., "Analysis of homozygous mutant chimeric mice: deletion of the immunoglobulin heavy-chain joining region blocks B-cell development and antibody production," *Proc. Natl. Acad. Sci. U.S.A.*, Mar. 15, 1993, 90(6):2551-2555.
Jakobovits et al., "Germ-line transmission and expression of a human-derived yeast artificial chromosome," *Nature*, Mar. 18, 1993, 362(6417):255-258.
Japanese Office Action dated Apr. 21, 2015, from Related Japanese Patent Application No. 2013-510261, 6 Pages.
Jayasena, Sumedha, Aptamers: An Emerging Class of Molecules That Rival Antibodies in Diagnostics, Clin. Chem. (1999), 45, 1628-1650.
Jenkins N, Curling EM., "Glycosylation of recombinant proteins: problems and prospects", *Enzyme Microb Technol.* May 1994;16(5):354-64.
Jewett, J.C.; Bertozzi, C.R., Cu-Free Click Cycloaddition Reactions in Chemical Biology, Chem. Soc. Rev. 2010, 39, 1272-1279.
Jewett, J.C.; Sletten, E. M.; Bertozzi, C.R., Rapid Cu-Free Click Chemistry with Readily Synthesized Biarylazacyclooctynones, J. Am. Chem. Soc. 2010, 132, 3688-3690.
Jewett et al., "Synthesis of a fluorogenic cyclooctyne activate by Cu-free click chemistry," *Org. Lett.*, Nov. 18, 2011, 13(22):5937-5939.
Jin, R. C. et al., Photoinduced Conversion of Silver Nanospheres to Nanoprisms, Science (2001), 294, 1901-1903.

Jobling, Michael et al., Fusion Proteins Containing the A2 Domain of Cholera Toxin Assemble With B Polypeptides of Cholera Toxin to Form Immunoreactive and Functional Holotoxin-Like Chimeras, Infect Immun., 60: 4915-24, 1992.
John, F. & Hendrickson, T. L. Synthesis of Truncated Analogues for Studying the Process of Glycosyl Phosphatidylinositol Modification. Org. Lett. 12, 2080-2083, (2010).
Jones et al., "Rapid PCR-cloning of full-length mouse immunoglobulin variable regions," *Nature Biotechnol.*, Jan. 1991, 9(1):88-89.
Jones et al., "Replacing the complementarity-determining regions in a human antibody with those from a mouse," *Nature*, May 29-Jun. 4, 1986, 321(6069):522-525.
Jones, "Analysis of polypeptides and proteins," *Adv. Drug Delivery Rev.*, Jan.-Apr. 1993, 10(1):29-90.
Jonges, M. et al., Dynamics of Antiviral-Resistant Influenza Viruses in the Netherlands, 2005-2008, Antiviral Res., Sep. 2009, 83(3): 290-297.
Jorgensen, Trond et al., Up-Regulation of the Oligosaccharide Sialyl Lewisx: A New Prognostic Parameter in Metastatic Prostate Cancer, Cancer Res. 55, 1817-1819, 1995.
Jose, Jiney et al., Energy transfer dyads based on Nile Red, Tetrahedron Letters (2009), 50(47), 6442-6445.
Joshi, Shantaran et al., Cell Surface Properties Associated with Malignancy of Metastatic Large Cell Lymphoma Cells, (1987) Cancer Res. 47, 3551-3557.
Joyce, J. G. et al. An oligosaccharide-based HIV-I 2G12 mimotope vaccine induces carbohydrate-specific antibodies that fail to neutralize HIV-I virions. Proc. Natl. Acad. Sci. U. S. A 105, 15684-15689, (2008).
Kakeji, Y. et al., Correlation Between Sialyl Tn Antigen and Lymphatic Metastasis in Patients with Borrmann Type IV Gastric Carcinoma, Brit. J. Cancer 71, 191-195, 1995.
Kale et al., Detection of intact influenza viruses using biotinylated biantennary S-sialosides. J Am Chem Soc. Jul. 2, 2008;130(26):8169-71.
Kalesh et al., "Peptide-based activity-based probes (ABPs) for target-specific profiling of protein tyrosine phosphatases (PTPs)," *Chem. Commun.*, Jan. 28, 2010, 46(4):589-591.
Kamkaew, A. et al., "BODIPY dyes in photodynamic therapy." Chem. Soc. Rev. 2013, 42, 77-88.
Kam et al., "Carbon nanotubes as multifunctional biological transporters and near-infrared agents for selective cancer cell destruction," *Proc. Natl. Acad. Sci. U.S.A.*, Aug. 16, 2005, 102(33):11600-11605.
Kaneko et al., "Anti-inflammatory activity of immunoglobulin G resulting from Fc sialylation," *Science*, Aug. 4, 2006, 313(5787):670-673.
Kawakami et al., "Critical role of Vα14$^+$ natural killer T cells in the innate phase of host protection against *Streptococcus pneumoniae* infection," *Eur. J. Immunol.*, Dec. 2003, 33(12):3322-3330.
Kawano et al., "CD1d-restricted and TCR-mediated activation of $v_\alpha 14$ NKT cells by glycosylceramides," *Science*, Nov. 28, 1997, 278(5343):1626-1629.
Kanie, Osmau et al., Orthogonal glycosylation strategy in synthesis of extended blood group B determinant. Tetrahedron Lett. 37, 4551-4554 (1996).
Kannagi et al., "New globoseries glycosphingolipids in human teratocarcinoma reactive with the monoclonal antibody directed to a developmentally regulated antigen, stage-specific embryonic antigen 3," *J. Biol. Chem.*, Jul. 25, 1983, 258(14):8934-8942.
Kannagi et al., "Stage-specific embryonic antigens (SSEA-3 and -4) are epitopes of a unique globo-series ganglioside isolated from human teratocarcinoma cells," *EMBO J.*, 1983, 2(12):2355-2361.
Kannappan, Ramaswamy et al., "Photoaffinity labeling of sialidase with a biotin-conjugated phenylaminodizairine derivative of 2,3-didehydro-2-deoxy-N-acetylneuraminic acid," *Biol. Pharm. Bull.*, Mar. 2008, 31(3):352-356.
Karlin, Samuel et al., Applications and Statistics for Multiple High-Scoring Segments in Molecular Sequences, Proc. Natl. Acad Sci. USA 90:5873-77, 1993.

(56) References Cited

OTHER PUBLICATIONS

Karlin S. et al., "Methods for assessing the statistical significance of molecular sequence features by using general scoring schemes", *Proc Natl Acad Sci USA*. Mar. 1990;87(6):2264-8.
Karmakar, M. et al., Current Trends in Research and Application of Microbial Cellulases, Research Journal of Microbiology, (2001) 6(1): 41-53.
Katagiri, Yohko et al., Laminin Binding Protein, 34/67 Laminin Receptor, Carries Stage-Specific Embryonic Antigen-4 Epitope Defined by Monoclonal Antibody Raft.2, Biochemical and Biophysical Research Communcations, 332, 1004-1011, 2005.
Kato et al., "GMab-1, a high-affinity anti-3'-isoLM1/3'6'-isoLD1 IgG monoclonal antibody, raised in lacto-series ganglioside-defective knockout mice," *Biochem. Biophys. Res. Commun.*, Jan. 1, 2010, 391(1):750-755.
Kermani, Pouneh et al., Production of ScFv Antibody Fragments Following Immunization with a Phage-Displayed Fusion Protein and Analysis of Reactivity to Surface-Exposed Epitopes of the Protein F of Pseudomonas Aeruginosa by Cytofluorometry, Hybridoma, 14(4):323-328 (1995).
Kidd et al., "Profiling serine hydrolase activities in complex proteomes," *Biochemistry*, Apr. 3, 2001, 40(13):4005-4015.
Kiick, K.L. et al., Identificationof an Expanded Set of Translationally Active Methionine Analogues in *Escherichia Coli*, tetrahedron 56:9487, 2001.
Kim et al., "Localization of the site of the murine IgG1 molecule that is involved in binding to the murine intestinal Fc receptor," *Eur. J. Immunol.*, 1994, 24:2429-2434.
Kim et al., High-Throughput Screening of Glycan-Binding Proteins Using Miniature Pig Kidney N-Glycan-Immobilized Beads, Chemistry & biology 15.3, p. 215-223 (2008).
Kim, Gap-Sue et al., AB Initio Study of Excited Electronic States and Vibronic Spectra of Phenyl Radical, Chem Phys. Lett., 2002, 3 5 2, 421.
Kimura et al., Design and Synthesis of Immobilized Tamiflu Analog on Resin for Affinity Chromatography, Tetrahedron Lett., Jul. 1, 2009, 50(26):3205-3208.
King, M. et al., New Tetramethlthiepinium (TMTI) for Copper-Free Click Chemistry, Chem. Commun. 2012, 48, 9308-9309.
Kitamura et al., "α-galactosylceramide induces early B-cell activation through IL-4 production by NKT cells," *Cell. Immunol.*, Jan. 10, 2000, 199(1):37-42.
Klein, J. et al., "Isomaltines and their N-acyl derivatives, their preparation, and use of some acyl derivatives as surfactants or for preparation of hydrophilic polymers," CAPLUS 110:95711 (1989).
Köhler et al., "Continuous cultures of fused cells secreting antibody of predefined specificity," *Nature*, Aug. 7, 1975, 256(5517):495-497.
Kolb et al., "Click chemistry: diverse chemical function from a few good reactions," *Angew. Chem. Int. Ed. Engl.*, Jun. 1, 2001, 40(11):2004-2021.
Kolb et al., "The growing impact of click chemistry on drug discovery," *Drug Discov. Today*, Dec. 15, 2003, 8(24):1128-1137.
Komba S, et al. Synthesis and Bioloical Activities of Three Sulfated Sialyl Lex Ganglioside Analogues for Clarifying the Real Carbohydrate Ligand Structure of L-Selectin, Bioorg. Med. Chem. 1996, 4, 1833-1847.
Komori, Tatsuya et al., Study on Systematizing the Synthesis of the A-Series Ganglioside Glycans GT1a, GD1a, and GM1 Using the Newly Developed N-Troc-Protected GM3 and GaIN Intermediates, Carbohydr. Res. 2009, 344, 1453.
Kong, L. et al. Expression-system-dependent modulation of HIV-I envelope glycoprotein antigenicity and immunogenicity. J. Mol. Biol. 403, 131-147, (2010).
Kontermann, "Intrabodies as therapeutic agents," *Methods*, Oct. 2004, 34(2):163-170.
Kos, "Regulation of adaptive immunity by natural killer cells," *Immunol. Res.*, 1998, 17(3):303-312.
Koshihara et al., 1984, Biochmica et biophysica acta, 792(1), pp. 92-97.
Kostelny et al., "Formation of a bispecific antibody by the use of leucine zippers," *J. Immunol.*, Mar. 1, 1992, 148(5):1547-1553.
Kotteas et al., Immunotherapy for pancreatic cancer, J cancer Res Clin Oncol, 142(8): 1795-1805, 2016.
Kozbor, "A human hybrid myeloma for production of human monoclonal antibodies," *J. Immunol.*, Dec. 1984, 133(6):3001-3005.
Kriegler M et al., "A novel form of NF/cachectin is a cell surface cytotoxic transmembrane protein: ramifications for the complex physiology of TNF" *Cell*. Apr. 8, 1988;53(1):45-53.
Krise, Jeffrey et al., Prodrugs of Phosphates, Phosphonates, and Phosphinates, Adv. Drug Deliv. Rev. 1996, 19(2), 287-310.
Kruis et al., Low dose balsalazide (1.5 g twice daily) and mesalazine (0.5 g three times daily) maintained remission of ulcerative colitis but high dose alsalazide (3.0 g twice daily) was superior in preventing relapses. Gut. Dec. 2001;49(6):783-9.
Kubin, R. F. et al., Fluorescence Quantum Yields of Some Rhodamine Dyes, Luminescence 1982, 27, 455-462.
Kubler-Kielb, J. et al., A New Method for Conjugation of Carbohydrates to Proteins Using an Aminooxy-Thiol Heterbifunctional Linker, J Org Chem 2005, 70, 6987-6990.
Kudo et al., "Up-regulation of a set of glycosyltransferase genes in human colorectal cancer," *Lab. Invest.*, Jul. 1998, 78(7):797-811.
Kwong, Peter et al., Rational Design of Vaccines to Elicit Broadly Neutralizing Antibodies to HIV-I. Cold Spring Harb.Perspect. Med. 1, 2011, 1-16.
Lantz et al., "An invariant T cell receptor α chain is used by a unique subset of major histocompatibility complex class I-specific $CD4^+$ and $CD4^-8^-$ T cells in mice and humans," *J. Exp. Med.*, Sep. 1, 1994, 180(3):1097-1106.
Lau et al., "N-Glycans in cancer progression," *Glycobiology*, Oct. 2008, 18(10):750-760.
Lau, K. et al. Highly efficient chemoenzymatic synthesis of β1-4-linked galactosides with promiscuous bacterial β1-4-galactosyltransferases. Chem. Commun. 46, 6066-6068, (2010).
Le, Mai et al., Avian flu: Isolation of Drug-Resistant H5N1 Virus, Nature, Oct. 20, 2005, 437(7062):1108.
Lebens et al., Mucosal vaccines based on the use of cholera toxin B as immunogen and antigen carrier, *Dev. Biol. Stand.*, 1994, 82:215-227.
Le Droumaguet, C. et al., Fluorogenic Click Reaction., Chem. Soc. Rev. 2010, 39, 1233-1239.
Lederman et al., A single amino acid substitution in a common African allele of the CD4 molecule ablates binding of the monoclonal antibody, OKT4, Molecular Immunology, 28, 1171-1181 (1991).
Lee et al., Analogs of Cell Surface Carbohydrates. Synthesis of D-Galactose Derivatives Having an Ethynyl, Vinyl or Epoxy Residue at c-5. Carbohydrate Research 1988, vol. 176, pp. 59-72.
Lee et al., "Bivalent antibody phage display mimics natural immunoglobulin," *J. Immunol. Methods*, Jan. 2004, 284(1-2):119-132.
Lee et al., "High-affinity human antibodies from phage-displayed synthetic Fab libraries with a single framework scaffold," *J. Mol. Biol.*, Jul. 23, 2004, 340(5):1073-1093.
Lee et al., A new Solvent System for Efficient Synthesis of 1,2,3-Triazoles, Tetrahedron Lett., Jul. 17, 2006, 47(29):5105-5109.
Lee et al., An Efficient and Practical Method for the Synthesis of Mono-N-Protected α,ω-diaminoalkanes, Tetrahedron Lett., Apr. 2, 2001, 42(14):2709-2711.
Lee, H.K. et al. Reactivity-based one-pot synthesis of oligomannoses: defining antigens recognized by 2G12, a broadly neutralizing anti-HIV-I antibody. Angew. Chem. Int. Ed. 43, 1000-1003, (2004.
Lee et al., Immunogenicity Study of Globo H Analogues with Modification at the Reducing or Nonreducing end of the tumor antigen, J Am Chem Soc, 136: 16844-16853 (2014).
Lefranc et al., "IMGT, the international ImMunoGeneTics database," *Nucleic Acids Res.*, Jan. 1, 1999, 27(1):209-212.
Lehninger, *Biochemistry: The Molecular Basis of Cell Structure and Function*, $2^{nd}$ ed., 1975, pp. 73-75, Worth Publishers, New York.
Lemieux, R. U. et al., Halide ion catalyzed glycosidation reactions. Syntheses of a-linked disaccharides. J. Am. Chem. Soc. 97(14), 4056-62, (1975).

(56) References Cited

OTHER PUBLICATIONS

Leung et al., "A method for random mutagenesis of a defined DNA segment using a modified polymerase chain reaction," Technique—A Journal of Methods in Cell and Molecular Biology, Aug. 1989, 1(1):11-15.

Lew et al., Discovery and Development of GS 4104 (oseltamivir): an Orally Active Influenza Neuraminidase Inhibitor, Curr Med Chem, Jun. 2000, 7(6):663-672.

Li et al., β-endorphin omission analogs: Dissociation of Immunoreactivity from other biological activities, Proc Natl Avad Sci USA, 77:3211-3214 (1980).

Li, Y. L. et al., Crystallization and Melting Behaviors of PPC-BS/PVA Blends, 19, 1557-1566, 2003.

Li, Henghui et al., MALDI-MS Analysis of Sialylated N-Glycan Linkage Isomers Using Solid-Phase Two Step Derivatization Method, Analytica Chimica Acta 924 (2016) 77-85.

Li et al., "Design of a potent CD1d-binding NKT cell ligand as a vaccine adjuvant," Proc. Natl. Acad. Sci. USA, Jul. 20, 2010, 107:13010-13015.

Li, J.; Hu, M.; Yao, S. Q. "Rapid synthesis, screening, and identification ofxanthone and xanthene-based fluorophores using click chemistry." Org. Lett. 2009, 11, 3008-3011.

Li, Lingling, et al., "Syntheses and spectral properties of functionalized, water-soluble BODIPY derivatives." J. Org. Chem. 2008, 73, 1963-1970.

Li, L. et al. Efficient chemoenzymatic synthesis of an N-glycan isomer library. Chem. Sci. 6, 5652-5661 (2015).

Liang, Yuh-Jin et al., Switching of the Core Structures of Glycosphingolipids From Blobo- and Lacto- to Ganglio-Series Upon Human Embryonic Stem Cell Differentiation, PNAS, 107(52), Dec. 2010, 22564-22569.

Liang et al., "Quantitative microarray analysis of intact glycolipid-CD1d interaction and correlation with cell-based cytokine production," J. Am. Chem. Soc., Sep. 17, 2008, 130(37):12348-12354.

Liang, Chi-Hui et al., Iron Oxide/Gold Core/Shell Nanoparticles for Ultrasensitive Detection of Carbohydrate-Protein Interactions, Anal. Chem. 2009; 81, 7750-7756.

Liang, P.H. et al., Quantitative Analysis of Carbohydrate-Protein Interactions Using Glycan Microarrays: Determination of Surface and Solution Dissociation Constants, J. Amer. Chem. Sci. 2007, 129, 11177-11184.

Lin et al., A common glycan structure on immunoglobulin G for enhancement of effector functions, PNAS, Aug. 25, 2015, vol. 112, No. 34, p. 10611-10616.

Lindmark et al., "Binding of immunoglobulins to protein A and immunoglobulin levels in mammalian sera," J. Immunol. Meth., Aug. 12, 1983, 62(1):1-13.

Liu C, et al., "Expansion of spleen myeloid suppressor cells represses NK cell cytotoxicity in tumor-bearing host" Blood. May 15, 2007;109(10):4336-42. Epub Jan. 23, 2007.

Liu et al., "Activity-based protein profiling: the serine hydrolases," Proc. Natl. Acad. Sci. USA, Dec. 21, 1999, 96(26):14694-14699.

Liu et al., "Eradication of large colon tumor xenografts by targeted delivery of maytansinoids," Proc. Natl., Acad. Sci. U.S.A., Aug. 6, 1996, 93(16):8618-8623.

Liu et al., Enhanced anti-influenza agents conjugated with anti-inflammatory activity. J Med Chem. Oct. 11, 2012;55(19):8493-501.

Liu et al., Intramolecular ion-pair prodrugs of znamivir nad guanidino-oseltamivir. Bioorganic & Medicinal Chemistry. Jun. 2011; 19(16):4796-4802.

Liu et al., Synthesis and anti-influenza activities of carboxyl alkoxyalkyl esters of 4-guanidino-Neu5Ac2en (zanamivir). Bioorg Med Chem Lett. Sep. 1, 2007;17(17):4851-4. Epub Jun. 20, 2007.

LoBuglio et al., "Mouse/human chimeric monoclonal antibody in man: kinetics and immune response," Proc. Natl. Acad. Sci. U.S.A., Jun. 1989, 86(11):4220-4224.

Lode et al., "Targeted therapy with a novel enediyene antibiotic calicheamicin $\Theta^I_I$ effectively suppresses growth and dissemination of liver metastases in a syngeneic model of murine neuroblastoma," Cancer Res., Jul. 15, 1998, 58(14):2925-2928.

Lonberg et al., "Antigen-specific human antibodies from mice comprising four distinct genetic modifications," Nature, Apr. 28, 1994, 368(6474):856-859.

Lonberg et al., "Human antibodies from transgenic mice," Int. Rev. Immunol., 1995, 13(1):65-93.

Lopes, J.F. et al., Simulataneous Chromatographic Separation of Enantiomers, Anomers and Structural Isomers of Some Biologically Relevant Monsaccharides. J. Chomatogr. A, (2008) 1188:34-42.

Lou, et al., Stage-specific embryonic antigent-4 as a potential therapeutic target in glioblastoma multiforms and other cancers. Proc Natl Acad Sci USA 2014, 111(7):2482-7.

Loudet, A.; Burgess, K. "BODIPY dyes and their derivatives: syntheses and spectroscopic properties." Chem. Rev. 2007, 107, 4891-4932.

Louis et al., "The 2007 WHO classification of tumours of the central nervous system," Acta. Neuropathol., Aug. 2007, 114(2):97-109.

Lu et al., "Design of a mechanism-based probe for neuraminidase to capture influenza viruses," Angew. Chem. Int. Ed. Engl., Oct. 28, 2005, 44(42):6888-6892.

Lu, Guokai et al., Reactivity-Based One-Pot Synthesis of Immunosuppressive Glycolipids From the Caribbean Sponge Plakortis Simplex, J. Chem. 2009, 27, 2217-2222.

Lu et al., "Single chain anti-c-Met antibody conjugated nanoparticles for in vivo tumor-targeted imaging and drug delivery," Biomaterials, Apr. 2011, 32(12):3265-3274.

MacBeath, G. and Schreiber, S. L., Printing Proteins as Microarrays for High-Throughput Function Determination, Science, 289, 1760-1763, 2000.

MacFarlane GT, et al., "Formation of glycoprotein degrading enzymes by Bacteroides fragilis" FEMS Microbial Lett. Jan. 15, 1991;61(2-3):289-93.

Makino et al., Predominant expression of invariant $V_\alpha 14^+$ TCR α chain in $NK1.1^+$ T cell populations, Int. Immunol., Jul. 1995, 7(7):1157-1161.

Mandler et al., "Immunoconjugates of geldanamycin and anti-HER2 monoclonal antibodies: antiproliferative activity on human breast carcinoma cell lines," J. Nat. Cancer Inst., Oct. 4, 2000, 92(19):1573-1581.

Mandler et al., "Modifications in synthesis strategy improve the yield and efficacy of geldanamycin-herceptin immunoconjugates," Bioconjugate Chem., Jul.-Aug. 2002, 13(4):786-791.

Mandler et al., "Synthesis and evaluation of antiproliferative activity of a geldanamycin-Herceptin™ immunoconjugate," Bioorganic & Med. Chem. Letters, May 15, 2000, 10(10):1025-1028.

Mandal, M., Dudkin, V. Y., Geng, X. & Danishefsky, S. J. In pursuit of carbohydrate-based HIV vaccines, part I: The total synthesis of hybrid-type gp 120 fragments. Angew. Chem. Int. Ed. 43, 2557-2561, (2004).

Månsson et al., "Characterization of new gangliosides of the lactotetraose series in murine xenografts of a human glioma cell line," FEBS Lett., May 26, 1986, 201(1):109-113.

Marasco et al., "Design, intracellular expression, and activity of a human anti-human immunodeficiency virus type 1 gp120 single-chain antibody," Proc. Natl. Acad. Sci. U.S.A., Aug. 15, 1993, 90(16):7889-7893.

Marasco, "Intrabodies: turning the humoral immune system outside in for intracellular immunization," Gene Therapy, Jan. 1997, 4(1):11-15.

Marcato et al., "Chapter 17: The Rocky Road from Cancer Stem Cell Discovery to Diagnostic Applicability," Cancer Stem Cells Theories and Practice, pp. 335-360, Mar. 22, 2011.

Marks et al., "By-passing immunization. Human antibodies from V-gene libraries displayed on phage," J. Mol. Biol., Dec. 5, 1991, 222(3):581-597.

Marks et al., "By-passing immunization: Building high affinity human antibodies by chain shuffling," Nature Biotechnology, Jul. 1992, 10(7):779-783.

Massart, R., IEEE Transactions on Magnetics, 17, 1247 (1981).

Masuko, T. et al., Thiolation of Chitosan. Attachment of Proteins via Thioether Formation, Biomacromolecules 2005, 6, 880-884.

(56) References Cited

OTHER PUBLICATIONS

Mather et al., "Culture of testicular cells in hormone-supplemented serum-free medium," *Annals N.Y. Acad. Sci.*, 1982, 383:44-68.
Mather, "Establishment and characterization of two distinct mouse testicular epithelial cell lines," *Biol. Reprod.*, Aug. 1980, 23(1):243-252.
Matrosovich M, et al., The Surface Glycoproteins of H5 Influenza Viruses Isolated From Humans, Chickens, and Wild Aquatic Birds Have Distinguishable Properties, J. Virol. 1999, 73, 1146-1155.
Matsuda et al., "Structure and physical map of 64 variable segments in the 3' 0.8-megabase region of the human immunoglobulin heavy-chain locus," *Nature Genet.*, Jan. 1993, 3(1):88-94.
Matz et al., "Fluorescent proteins from nonbioluminescent *anthozoa* species," *Nat. Biotechnol.*, Oct. 1999, 17(10):969-973.
McCafferty et al., "Phage antibodies: Filamentous phage displaying antibody variable domains," *Nature*, Dec. 6, 1990, 348:552-554.
McKimm-Breschkin et al., "Tethered neuraminidase inhibitors that bind an influenza virus: a first step towards a diagnostic method for influenza," Angew. Chem. Int. Ed Engl., Jul. 14, 2003, 42(27):3118-3121.
McKimm-Breschkin, "Resistance of influenza viruses to neuraminidase inhibitors—a review," Antiviral Res., Jul. 2000, 47(1): 1-17.
McKimm-Breschkin, J. et al., "Neuraminidase Sequence Analysis and Susceptibilities of Influenza Virus Clinical Isolates to Zanamivir and Oseltamivir," Antimicrobial Agents and Chemotherapy, vol. 47, No. 7, Jul. 2003, in 10 pages.
Meezan et al., "Comparative studies on the carbohydrate-containing membrane components of normal and virus-transformed mouse fibroblasts: II: Separation of glycoproteins and glycopeptides by Sephadex chromatography," *Biochemistry*, Jun. 1969, 8(6):2518-2524.
Medelson et al., NKp46 O-glycan Sequences that are involved in the interaction with Hemagglutinin Type 1 of Influenza Virus. J. Virol. Feb. 10, 2010, 84(8):3789-3797.
McLellan, J. S. et al. Structure of HIV-I gp120 V1/V2 domain with broadly neutralizing antibody PG9. Nature 480, 336-343, 2011.
Merck, MAB4304, Anti-Stage-Specific Embryonic Antigen-4 Antibody, Clone MC-813-70, 4 Pages, 2017.
Meyer, "Malignant gliomas in adults," *N. Engl. J. Med.*, Oct. 23, 2008, 359(17):1850.
Milstein, C & Cuello, AC, Hybrid Hydridomas and their use in immunohistochemistry, Nature 305, 537-540, Oct. 1993.
Mimura et al., "Role of oligosaccharide residues of IgG1-Fc in FcγRIIb binding," *J. Biol. Chem.*, Dec. 7, 2001, 276(49):45539-45547.
Mishima et al., "Growth suppression of intracranial xenografted glioblastomas overexpressing mutant epidermal growth factor receptors by systemic administration of monoclonal antibody (mAb) 806, a novel monoclonal antibody directed to the receptor," *Cancer Res.*, Jul. 15, 2001, 61(14):5349-5354.
Miyagi et al., "Mammalian sialidases: Physiological and pathological roles in cellular functions," *Glycobiology*, Jul. 2012, 22(7):880-896.
Miyagi et al., "Plasma membrane-associated sialidase as a crucial regulator of transmembrane signalling," *J. Biochem.*, Sep. 2008, 144(3):279-285.
Miyagi et al., "Sialidase and malignancy: a minireview," *Glycoconj. J.*, 2004, 20(3):189-198.
Miyagi, "Aberrant expression of sialidase and cancer progression," *Proc. Jpn. Acad. Ser. B. Phys. Biol. Sci.*, 2008(10), 84:407-418.
Miyaji, E. N. et al., Induction of Neutralizing Antibodies Against Diphtheria Toxin by Priming with Recombinant *Mycobacterium bovis* BCG Expressing CRM197, a Mutant Diphtheria Toxin, Infect. Immun. 2001, 69, 869.
Miyamoto et al., "A synthetic glycolipid prevents autoimmune encephalomyelitis by inducing $T_H2$ bias of natural killer T cells," *Nature*, Oct. 4, 2001, 413(6855):531-534.
Moal, E. Le et al., Enhanced Fluorescence Cell Imaging with Metal-Coated Slides, Biophysical Journal, vol. 92, 2150-2161, Mar. 2007.
Monti et al., "Sialidases in vertebrates: a family of enzymes tailored for several cell functions," *Adv. Carbohydr. Chem. Biochem.*, 2010, 64:403-479.
Moody, M. D. et al., Array-based ELISAs for High-Throughput Analysis of Human Cytokines. Biotechniques (2001), 31, 186-194.
Morelle, W. et al., "The Mass Spectrometric Analysis of Glycoproteins and their Glycan Structures", *Review in Current Analytical Chemistry*, vol. 1, No. 1 (2005), pp. 29-57.
Mori K, et al., "Non-fucosylated therapeutic antibodies: the next generation of therapeutic antibodies" *Cytotechnology*. Dec. 2007;55(2-3):109-14. Epub Oct. 31, 2007.
Morimoto et al., "Single-step purification of F(ab')$_2$ fragments of mouse monoclonal antibodies (immunoglobulins G1) by hydrophobic interaction high performance liquid chromatography using TSKgel Phenyl-5PW," *J. Biochem. Biophys. Meth.*, Mar. 1992, 24(1-2):107-117.
Morphy et al., Designed multiple ligands. An emerging drug discovery paradigm. J Med Chem. Oct. 20, 2005;48(21):6523-43.
Morphy et al., From magic bullets to designed multiple ligands. Drug Discov Today. Aug. 1, 2004;9(15):641-51.
Morrison et al., "Chimeric human antibody molecules: mouse antigen-binding domains with human constant region domains," *Proc. Natl. Acad. Sci. U.S.A.*, Nov. 1984, 81(21):6851-6855.
Morrison, "Immunology. Success in specification," *Nature*, Apr. 28, 1994, 368(6474):812-813.
Moscona, "Global transmission of oseltamivir-resistant influenza," N Engl. J Med, Mar. 5, 2009, 360(10):953-956.
Moscona, Oseltamivir Resistance—Disabling Our Influenza Defenses, The New England Journal of Medicine, 2005, vol. 353, pp. 2633-2636.
Mosmann et al., "The expanding universe of T-cell subsets: Th1, Th2 and more," *Immunol. Today*, Mar. 1996, 17(3):138-146.
Mossong et al., "Emergence of oseltamivir-resistant influenza A H1N1 virus during the 2007-2008 winter season in Luxembourg: clinical characteristics and epidemiology," Antiviral Res., Oct. 2009, 84(1):91-94.
Mouquet, H. et al. Complex-type N-glycan recognition by potent broadly neutralizing HIV antibodies. Proc. Natl. Acad. Sci. U. S. A 109, E3268-E3277, (2012).
Munson et al., "Ligand: a versatile computerized approach for characterization of ligand-binding systems," *Anal. Biochem.*, Sep. 1, 1980, 107(1):220-239.
Murphy, C. I. et al. Enhanced expression, secretion, and large-scale purification of recombinant HIV-I gp 120 in insect cell using the baculovirus egt and p67 signal peptides. Protein Expres. Purif. 4, 349-357 (1993).
Muthana, S., Yu, H., Huang, S., and Chen, X. Chemoenzymatic synthesis of size-defined polysaccharides by sialyltransferase-catalyzed block transfer of oligosaccharides. J. Am. Chem. Soc. 129, 11918-11919, (2007).
Natarajan et al, Caffeic acid phenethyl ester is a potent and specific inhibitor of activation of nuclear transcription factor NF-kappa B. Proc Natl Acad Sci USA Aug. 20, 1996;93(17):9090-5.
Neuberger et al., "Recombinant antibodies possessing novel effector functions," *Nature*, Dec. 13-19, 1984, 312(5995):604-608.
Neuberger, "Generating high-avidity human Mabs in mice," *Nature Biotechnol.*, Jul. 1996, 14(7):826.
Ni, Jing et al., Immunoassay Readout Method Using Extrinsic Raman Labels Adsorbed on Immunogold Colloids, Anal. Chem., 1999, 71(21), pp. 4903-4908.
Nicolaou et al., "Calicheamicin $\Theta^I_1$: A rationally designed molecule with extremely potent and selective DNA cleaving properties and apoptosis inducing activity," *Angew. Chem. Intl. Ed. Engl.*, Feb. 1, 1994, 33(2):183-186.
Niculescu-Duvaz et al., "Antibody-directed enzyme prodrug therapy (ADEPT): A review," *Adv. Drg. Del. Rev.*, Jul. 7, 1997, 26(2-3):151-172.
Nieuwenhuis et al., "CD1d-dependent macrophage-mediated clearance of *Pseudomonas aeruginosa* from lung," *Nat. Med.*, Jun. 2002, 8(6):588-593.
Nielsen, U. B. et al., Multiplexed Sandwich Assays in Microarray Format, Journal Immunol. Meth. (2004), 290, 107-120.

(56) References Cited

OTHER PUBLICATIONS

Ning, X. et al., Visualizing Metabolically-Labeled Glycoconjugates of Living Cells by Copper-Free and Fast Huisgen Cycloadditions, J. Angew. Chem. Int. Ed. 2008, 47, 2253-2255.

Noto et al., "CD44 and SSEA-4 positive cells in an oral cancer cell line HSC-4 possess cancer stem-like cell characteristics," *Oral Oncol.*, Aug. 2013, 49(8):787-795.

Nowak, MW et al., Nicotinic Receptor Binding Site Probed With Unnatural Amino Acid Incorporation in Intact Cells, Science 268:439, 1995.

Novotný et al., "Structural invariants of antigen binding: comparison of immunoglobulin $V_L$-$V_H$ and $V_L$-$V_L$ domain dimers," *Proc. Natl. Acad. Sci. USA*, Jul. 1985, 82(14):4592-4596.

Oberli, Matthias et al., A Possible Oligosaccharide-Conjugate Vaccine Candidate for Clostridium Difficile is Antigenic and Immunogenic, Chemistry & Biology, vol. 18, No. 5, May 2011, 580-588.

Office Action dated Dec. 3, 2013, from corresponding Chinese Patent Application No. 201180034218.3, 15 total pages.

Office Action dated Oct. 22, 2014, from corresponding Chinese Patent Application No. 201180034218.3, 16 total pages.

O'Garra, "Cytokines induce the development of functionally heterogeneous T helper cell subsets," *Immunity*, Mar. 1998, 8(3):275-283.

Okada, Yoshio et al. Changes in the Expression of Sialyl-Lewisx, a Hepatic Necroinflammation-Associated Carbohydrate Neoantigen, in Human Depatocellular Carcinomas, (1994) Cancer 73, 1811-1816.

Okamura et al., "Interleukin-18: a novel cytokine that augments both innate and acquired immunity," *Adv. Immunol.*, 1998, 70:281-312.

Olden, Kenneth et al., Carbohydrate Moieties of Glycoproteins: A Re-Evaluation of Their Function, Biochem et Biophys Acta 650:209-232 (1982).

Orlandi et al., "Cloning immunoglobulin variable domains for expression by the polymerase chain reaction," *Proc. Natl. Acad. Sci. U.S.A.*, May 1989, 86(10):3833-3837.

Ørum et al., "Efficient method for constructing comprehensive murine Fab antibody libraries displayed on phage." *Nucleic Acids Res.*, Sep. 25, 1993, 21(19):4491-4498.

Otsubo N, et al., An Efficient and Straightforward Synthesis of Sialyl Lex Glycolipid as a Potent Selectin Blocker[[1]], Carbohydr. Res. 1998, 306, 517-530.

Ottolini et al., Combination anti-inflammatory and antiviral therapy of influenza in a cotton rat model. Pediatr. Pulmonol. 2003:36;290-4.

Oyelaran, 0. & Gildersleeve, J. C. Glycan arrays: recent advances and future challenges. Curr. Opin. Chem. Biol. 13, 406-413, (2009).

Pabst, M. et al., Glycan profiles of the 27 Nglycosylation sites of the HIV envelope protein CN54gp140. Biol. Chem. 393, 719-730, (2012).

Pacino, G. et al., Purification and Characterization of a Breast-Cancer-Associated Glycoprotein Not Expressed in Normal Breast and Identified by Monoclonal Antibody 83D4, Br. J. Cancer, 1991, 63, 390-398.

Pan, Yanbin et al., Synthesis and Immunological Properties of N-Modified GM3 Antigens as Therapeutic Cancer Vaccines, J. Med. Chem., 48(3), 875-883, 2005.

Pancera, M. et al. Crystal structure of PG16 and chimeric dissection with somatically related PG9: structure-function analysis of two quaternary-specific antibodies that effectively neutralize HIV-I. J. Virol. 84, 8098-8110, (2010).

Pancera, M. et al. Structural basis for diverse N-glycan recognition by HIV-I-neutralizing V1-V2-directed antibody PG16. Nat. Struct. Mol. Biol. 20, 804-813, (2013).

Papanastassiou et al., "The potential for efficacy of the modified (ICP 34.5⁻) herpes simplex virus HSV1716 following intratumoural injection into human malignant glioma: a proof of principle study," Gene Therapy, Mar. 2002, 9(6):398-406.

Parker, C. A.; Rees, W. T., Correction of Fluorescence Spectra and Measurement of Fluorescence Quantum Efficiency, Analyst 1960, 85, 587-600.

Parrish, M. L. et al., A Microarray Platform Comparison for Neuroscience Applications, J. Neurosci. Methods, 2004, 132, 57-68.

Patricelli et al., "Functional interrogation of the kinome using nucleotide acyl phosphates," *Biochemistry*, Jan. 16, 2007, 46(2):350-358.

Paulson, J. C., Blixt, 0. & Collins, B. E. Sweet spots in functional glycomics. Nat. Chem. Biol. 2, 238-248, (2006).

Pearlman et al., *Peptide and Protein Drug Delivery, Chapter 6: Analysis of Protein Drugs*, Lee, ed., 1991, pp. 247-301, Marcel Dekker Publishing, New York.

Peelle et al., "Characterization and use of green fluorescent proteins from *Renilla mulleri* and *Ptilosarcus guernyi* for the human cell display of functional peptides," *J. Protein Chem.*, Aug. 2001, 20(6):507-519.

Peipp et al., "Antibody fucosylation differentially impacts cytotoxicity mediated by NK and PMN effector cells," *Blood*, 2008, 112(6):2390-2399.

Peiris et al., Re-emergence of fatal human influenza A subtype H5N1disease. Lancet. Feb. 21, 2004 ;363(9409):617-9.

Pejchal, R. et al. A potent and broad neutralizing antibody recognizes and penetrates the HIV glycan shield. Science 334, 1097-1103, (2011).

Pellicci et al., "Differential recognition of CD1d-α-galactosyl ceramide by the Vβ8.2 and Vβ7 semi-invariant NKT T-cell receptors," *Immunity*, Jul. 17, 2009, 31(1):47-59.

Perlmutter, R.M. et al., Subclass Restriction of Murine Anti-Carbohydrate Antibodies, Journal of Immunology 1978, 121, 566-572.

Pettit, George et al., Antineoplastic Agents. Part 189. The Absolute Configuration and Synthesis of Natural (−)-Dolastatin 10, J Am Chem Soc. 111:5463-5465 (1989).

Pettit, George et al., Dolastatins 23: Stereospecific Synthesis of Dolaisoleuine, J Chem Soc Perkin Trans. 15:853-858 (1996).

Pettit, George et al., Antineoplastic Agents 365. Dolastatin 10 SAR Probes, Anti-Cancer Drug Design 13:243-277 (1998).

Pettit, Robin et al., Specific Activities of Dolastatin 10 and Peptide Derivatives Against Cryptococcus Neoformans, Antimicrob Agents Chemother. 42:2961-2965 (1998).

Pettit, George et al., The Dolastatins; 18: Stereospecific Synthesis of Dolaproine, Synthesis, 719-725 (1996).

Piizi, G. and Hardinger, S., Stereochemistry: an Introduction, UCLA Chemistry 30A Presentation, Fall 2002, in 40 pages.

Plückthun, "Mono- and bivalent antibody fragments produced in *Escherichia coli*: Engineering, folding and antigen binding," *Immunol. Rev.*, Dec. 1992, 130:151-188.

Plückthun, *Handbook of Experimental Pharmacology*, vol. 113: The Pharacology of Monoclonal Antibodies, Chapter 11: Antibodies from *Escherichia coli*, Rosenberg et al., eds., 1994, pp. 269-315, Springer-Verlag, Berlin.

Poloukhtine et al., "Selective labeling of living cells by a photo-triggered click reaction," *J. Am. Chem. Soc.*, Nov. 4, 2009, 131(43):15769-15776.

Porcelli, S.A., "Preparation of α-galactosylceramide derivatives as modulators of immunity and autoimmunity," CAPLUS 147:440317 (2007).

Potier et al., "Fluorometric assay of neuraminidase with a sodium (4-methylumbelliferyl-alpha-D-N-acetylneuraminate) substrate," Anal. Biochem., Apr. 15, 1979, 94(2):287-296.

Pratt, M. R. & Bertozzi, C. R. Chemoselective ligation applied to the synthesis of a biantennary N-linked glycoform of CD52. J Am. Chem. Soc. 125, 6149-6159, (2003).

Prescher, J. A.; Bertozzi, C.R. "Chemistry in living systems." Nat. Chem. Biol. 2005, 1, 13-21.

Presta et al., "Humanization of an antibody directed against IgE," *J. Immunol.*, Sep. 1, 1993, 151(5):2623-2632.

Presta et al., "Humanization of an anti-vascular endothelial growth factor monoclonal antibody for the therapy of solid tumors and other disorders," *Cancer Res.*, Oct. 15, 1997, 57(20):4593-4599.

Presta, "Antibody engineering," *Curr. Opin. Biotechnol.*, Aug. 1992, 3(4):394-398.

(56) References Cited

OTHER PUBLICATIONS

Presta, "Antibody engineering," *Curr. Opin. Struct. Biol.*, Aug. 1992, 2(4):593-596.
Pritchard, L. K. et al. Structural Constraints Determine the Glycosylation of HIV-I Envelope Trimers. Cell Rep. 11, 1604-13, (2015).
Pritchard, Laura et al., Cell- and Protein-Directed Glycosylation of Native Cleaved HIV-I Envelope. J. Virol. 89, 8932-44, (2015).
Proba et al., "Functional antibody single-chain fragments from the cytoplasm of *Escherichia coli*: influence of thioredoxin reductase (TrxB)," *Gene*, Jul. 4, 1995, 159(2):203-207.
Pshezhetsky, M. Potier, J. Biol. Chem. 1996, 271, 28359-28365. Association of N-acetylgalactosamine-6-sulfate sulfatase with the multienzyme lysosomal complex of betagalactosidase, cathepsin A, and neuraminidase. Possible implication for intralysosomal catabolism of keratan sulfate.
Puigbò P, Guzmán E, Romeu A, Garcia-Vallvé S. Optimizer: a web server for optimizing the codon usage of DNA sequences. *Nucleic Acids Res.* Jul. 2007;35(Web Server issue):W126-31. Epub Apr. 16, 2007.
Qi, Jianjun et al., Developing visible fluorogenic 'clickon' dyes for cellular imaging, Bioconjugate Chem. 2011, 22, 1758-1762.
Rabbani, Said et al., Glycosyltransferases: An efficient tool for the enzymatic synthesis of oligosaccharides and derivatives as well as mimetics thereof Chimia 60, 23-27, (2006).
Raju et al., "Synthesis and evaluation of 3"- and 4"-deoxy and -fluoro analogs of the immunostimulatory glycolipid, KRN7000," *Bioorg. Med. Chem. Lett.*, 2009, 19:4122-4125.
Ramm et al., "The periplasmic *Escherichia coli* peptidylprolyl cis,trans-isomerase FkpA. II. Isomerase-independent chaperone activity in vitro," *J. Biol. Chem.*, Jun. 2, 2000, 275(22):17106-17113.
Rana, G. Kucukayan-Dogu, E. Bengu "Growth of vertically aligned carbon nanotubes over self-ordered nano-porous alumina films and their surface properties" Applied Surface Science, 2012, 258 7112-7117.
Raska, M. et al. Glycosylation patterns of HIV-I gp120 depend on the type of expressing cells and affect antibody recognition. J. Biol. Chem. 285, 20860-20869, (2010).
Ravetch et al., "Divergent roles for Fc receptors and complement in vivo," *Ann. Rev. Immunol.*, 1998, 16:421-432.
Ravetch et al., "Fc receptors," *Annu. Rev. Immunol.*, 1991, 9:457-492.
Reyes et al., "Expression of human β-interferon cDNA under the control of a thymidine kinase promoter from herpes simplex virus," *Nature*, Jun. 17, 1982, 297(5867):598-601.
Riechmann et al., "Reshaping human antibodies for therapy," *Nature*, Mar. 24, 1988, 332(6162):323-327.
Rillahan, C. D. & Paulson, J. C. Glycan microarrays for decoding the glycome. Annu. Rev. Biochem. 80, 797-823, (2011).
Ritamo, Ilja al., Comparison of the Glycosylation of in Vitro Generated Polyclonal Human IgG and Therapeutic Immunoglins, Mol Immunol. Feb. 2014; 57(2): 255-62.
Rogers, GN et al., Single Amino Acid Substitutions in Influenza Haemagglutinin Change Receptor Binding Specificity. Nature, 304:76, 1983.
Rogers, GN et al., Receptor Determinants of Human and Animal Influenza Virus Isolates: Differences in Receptor Specificity of the H3 Hemagglutinin Based on Species of Origin. Virology, 127:361, 1983.
Roguska et al., "Humanization of murine monoclonal antibodies through variable domain resurfacing," *Proc. Natl. Acad. Sci. U.S.A.*, Feb. 1, 1994, 91(3):969-973.
Romagnani, "Induction of $T_H1$ and $T_H2$ responses: a key role for the 'natural' immune response?" *Immunol. Today*, Oct. 1992, 13(10):379-381.
Roos et al., "Specific inhibition of the classical complement pathway by C1q-binding peptides," *J. Immunol.*, Dec. 15, 2001, 167(12):7052-7059.
Rosenstein, N.E. et al, Meningococcal Disease, N Engl J Med 2001, 344, 1378-1388.
Rostovtsev et al., "A stepwise Huisgen cycloaddition process catalyzed by copper(I) regioselective ligation of azides and terminal alkynes," *Angew. Chem. Int. Ed. Engl.*, Jul. 15, 2002, 41(41):2596-2599.
Roth, Jurgen et al., Reexpression of Poly(sialic Acid) Units of the Neural Cell Adhesion Molecule in Wilms Tumor, Proc. Natl. Acad. Sci. 85, 2999-3000, 1988.
Rowland et al, "Drug localisation and growth inhibition studies of vindesine-monoclonal anti-CEA conjugates in a human tumour xenograft," *Cancer Immunol. Immunother.*, 1986, 21(3):183-187.
Rudnick et al., Affinity and Avidity in Antibody-Based Tumor Targeting, Can Biotherp & Radoipharm, 24, 155-162 (2009).
Ruiz et al., "IMGT, the international ImMunoGeneTics database," *Nucl. Acids Res.*, Jan. 1, 2000, 28(1):219-221.
Russell et al., "The structure of H5N1 avian influenza neuraminidase suggests new opportunities for drug design," Nature, Sep. 7, 2006, 443(7107):45-49.
Saito, Seiichi et al., Haptoglobin-β Chain Defined by Monoclonal Antibody RM2 as a Novel Serum Marker for Prostate Cancer, Int. J Cancer, 2008, 123(3), 633-640.
Saito et al., "Expression of globo-series gangliosides in human renal cell carcinoma," *Jpn. J. Cancer Res.*, Jul. 1997, 88(7):652-659.
Saito et al., "Human α2,3-sialyltransferase (ST3Gal II) is a stage-specific embryonic antigen-4 synthase," *J. Biol. Chem.*, Jul. 18, 2003, 278(29):26474-26479.
Saitoh, Osamu et al., Differential Glycosylation and Cell Surface Expression of Lysosomal Membrane Glycoproteins in Sublines of a Human Colon Cancer Exhibiting Distinct Metastatic Potentials, J. Biol. Chem. 267, 5700-5711, 1992.
Salisbury et al., "Activity-based probes for proteomic profiling of histone deacetylase complexes," *Proc. Natl. Acad. Sci. USA*, Jan. 23, 2007, 104(4):1171-1176.
Salomon et al., Inhibition of the cytokine response does not protect against lethal H5N1 nfluenza infection. Proc Natl Acad Sci U S A Jul. 24, 2007;104(30): 12479-81.
Sanna, Peitro et al., Directed Selection of Recombinant Human Monoclonal Antibodies to Herpes Simplex Virus Glycoproteins From Phage Display Libraries, Proc. Natl. Acad. Sci., 92:6439 (1995).
Sarkar et al., "Disaccharide uptake and priming in animal cells: inhibition of sialyl Lewis X by acetylated Galβ1→4GlcNAcβ-O-naphthalenemethanol," *Proc. Natl. Acad. Sci. USA*, Apr. 11, 1995, 92(8):3323-3327.
Sastry et al., "Cloning of the immunological repertoire in *Escherichia coli* for generation of monoclonal catalytic antibodies: construction of a heavy chain variable region-specific cDNA library," *Proc. Natl. Acad. Sci. U.S.A.*, Aug. 1989, 86(15):5728-5732.
Sauter, NK et al., Binding of Influenza Virus Hemagglutinin to Analogs of Its Cell-Surface Receptor, Sialic Acid: Analysis by Proton Nuclear Magnetic Resonance Spectroscopy and X-Ray Crystallography. Biochemistry, 31 :9609, 1992.
Sawa, M.; Hsu, T.-L.; Itoh,T.; Sugiyama, M. ; Hanson, S. R. ; Vogt, P. K.; Wong, C.-H. "Glycoproteomic probes for fluorescent imaging of fucosylated glycans in vivo." Proc. Nat. Acad. Sci. US.A., 2006, 103, 12371-12376.
Sawada, Tetsuji et al., E-Selectin Binding by Pancreatic Tumor Cells is Inhibited by Cancer Sera, Int. J. Cancer 57, 901-907, 1994.
Sawada, Ritsuko et al., Differential E-Selectin-Dependent Adhesion Efficiency in Sublines of a Human Colon Cancer Exhibiting Distinct Metastatic Potentials, J. Biol. Chem. 269, 1425-1431, 1994.
Scanlan, C. N. et al., Exploiting the defensive sugars of HIV-I for drug and vaccine design. Nature 446, 1038-1045, (2007).
Schena, M. et al., Quantitative Monitoring of Gene Expression Patterns with a Complementary DNA Microarray, Science, 1995, 270:467-70.
Schengrund et al., "Localization of sialidase in the plasma membrane of rat liver cells," *J. Biol. Chem.*, May 10, 1972, 247(9):2742-2746.
Schenkel-Brunner, *Human Blood Groups, Chapter 8: P System*, 1995, pp. 211-234, Springer-Verlag, Vienna.
Schier et al., "Identification of functional and structural amino-acid residues by parsimonious mutagenesis," *Gene*, Mar. 9, 1996, 169(2):147-155.

(56) References Cited

OTHER PUBLICATIONS

Schmitz, U. et al., Phage Display: A Molecular Tool for the Generation of Antibodies—A Review, Placenta, 21 Suppl. A:S 106 (2000).
Schneider, M.C. et al., Interactions Between Neisseria Meningitidis and the Complement System, Trends Microbial 2007, 15, 233-240.
Schroder et al., The Peptides, vol. 1, p. 76-136, 1965.
Schug, Kevin et al., "Noncovalent binding between guanidinium and anionic groups: focus on biological- and synthetic-based arginine/guanidinium interactions with phosph[on]ate and sulf[on]ate residues," Chem. Rev., Jan. 2005, 105(1):67-113.
Schweitzer, Barry et al., Multiplexed Protein Profiling on Microarrays by Rolling-Circle Amplification, Nat. Biotechnol. (2002), 20, 359-365.
Scurr, D. J. et al. Surface characterization of carbohydrate microarrays. Langmuir 26, 17143-17155, (2010).
Sell, "Cancer-associated carbohydrates identified by monoclonal antibodies," Hum. Pathol., Oct. 1990, 21(10):1003-1019.
Serna, S. et al., Construction of N-Glycan Microarrays by Using Modular Synthesis and On-Chip Nanoscale Enzymatic Glycosylation. Chem. Eur. J 16, 13163-13175, (2010).
Severi et al., "Sialic acid utilization by bacterial pathogens," Microbiology, Sep. 2007, 153(Pt 9):2817-2822.
Seyrantepe et al., "Neu4, a novel human lysosomal lumen sialidase, confers normal phenotype to sialidosis and galactosialidosis cells," J. Biol. Chem., Aug. 27, 2004, 279(35):37021-37029.
Shalaby et al., "Development of humanized bispecific antibodies reactive with cytotoxic lymphocytes and tumor cells overexpressing the HER2 protooncogene," J. Exp. Med., Jan. 1, 1992, 175(1):217-225.
Sheu et al., "Surveillance for neuraminidase inhibitor resistance among human influenza A and B viruses circulating worldwide from 2004 to 2008," Antimicrob. Agents Chemother., Sep. 2008, 52(9):3284-3292.
Shie, Jiun-Jie et al., "A concise and flexible synthesis of the potent anti-influenza agents tamiflu and tamiphosphor," Angew. Chem. Int. Ed Engl., 2008, 47(31):5788-5791.
Shie, Jiun-Jie et al., An Azido-BODIPY Probe for Glycosylation: Initiation of Strong Fluorescence Upon Triazole Formation, J. Am. Chem. Soc. 2014, 136, 9953-9961.
Shieh, Peyton et al., Fluorogenic Azidofluoresceins for Biological Imaging, J. Am. Chem. Soc. 2012, 134, 17428-17431.
Shields et al., "High resolution mapping of the binding site on human IgG1 for FcγRI, FcγRII, FcγRIII, and FcRn and design of IgG1 variants with improved binding to the FcγR," J. Biol. Chem., Mar. 2, 2001, 276(9):6591-6604.
Shields et al., "Lack of fucose on human IgG1 N-linked oligosaccharide improves binding to human FcγRIII antibody-dependent cellular toxicity," J. Biol. Chem., Jul. 26, 2002, 277(30):26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J. Biol. Chem., Jan. 31, 2003, 278(5):3466-3473.
Shivatare, S. S. et al. Efficient convergent synthesis of bi-, tri-, and tetra-antennary complex type N-glycans and their HIV-1 antigenicity. J. Am. Chem. Soc. 135, 15382-15391, (2013).
Shivatare, S. S. et al., Modular Synthesis of N-Glycans and Arrays for the Hetero-Ligand Binding Analysis of HIV Antibodies, Nature Chemistry, Mar. 7, 2016, vol. 8(4), p. 338-346.
Shriver, Zachary et al., Glycomics: a Pathway to a Class of New and Improved Therapeutics, Nat Rev Drug Disc, 2004, 3, 863-873.
Sidhu et al., "Phage-displayed antibody libraries of synthetic heavy chain complementarity determining regions," J. Mol. Biol., Apr. 23, 2004, 338(2):299-310.
Siebenlist et al., "E. coli RNA polymerase interacts homologously with two different promoters," Cell, Jun. 1980, 20(2):269-281.

Sieber et al., "Proteomic profiling of metalloprotease activities with cocktails of active-site probes," Nat. Chem. Biol., May 2006, 2(5):274-281.
Simmons et al., "Expression of full-length immunoglobulins in Escherichia coli: Rapid and efficient production of aglycosylated antibodies," J. Immunol. Methods, May 1, 2002, 263(1-2):133-147.
Sims et al., "A humanized CD18 antibody can block function without cell destruction," J. Immunol., Aug. 15, 1993, 151(4):2296-2308.
Sivakumar, Krishnamoorthy et al., "A fluorogenic 1,3-dipolar cycloaddition reaction of 3-azidocoumarins and acetylenes." Org. Lett. 2004,24, 4603-4606.
Skehel, John et al., Receptor Binding and Membrane Fusion in Virus Entry: The Influenza Hemagglutinin, Ann. Rev Biochem, 69:531, 2000.
Skerra, "Bacterial expression of immunoglobulin fragments," Curr. Opinion in Immunol., Apr. 1993, 5(2):256-262.
Slamon DJ, et al., Human breast cancer: correlation of relapse and survival with amplification of the HER-2/neu oncogene, Science. Jan. 9, 1987; 235(4785):177-82.
Sletten et al., "Bioorthogonal Chemistry: Fishing for Selectivity in a Sea of Functionality," Angew. Che. Int. Ed. Engl., Aug. 27, 2009, 48(38):6974-6998.
Smith RA et al., "The active form of tumor necrosis factor is a trimer" J Biol Chem. May 25, 1987;262(15):6951-4.
Smyth MJ, et al., "CD4+CD25+ T regulatory cells suppress NK cell-mediated immunotherapy of cancer" J Immunol. Feb. 1, 2006;176(3):1582-7.
Sok, Devin et al., SnapShot: Broadly Neutralizing Antibodies. Cell 155, 728-728, (2013).
Solomons, G. and Fryhle, C., Chapter 5 Titled, Stereochemistry: Chiral Molecules, p. 184-228, in "Organic Chemistry," 7th Edition, Wiley, Jun. 18, 2001.
Soriano del Amo, David et al. Chemoenzymatic synthesis of the sialyl Lewis X glycan and its derivatives. Carbohydr. Res. 345, 1107-13, (2010).
Spinosa, Maria Rita et al., The Neisseria Meningitidis Capsule is Important for Intracellular Survival in Huamn Cells, Infect Immun 2001, 75, 3594-3603.
Srinivasan, Quantitative et al., Biochemical Rationale for Differences in Transmissibility of 1918 Pandemic Influenza A Viruses, Proc. Natl. Acad. Sci., 105, 2800-2805, 2008.
Stein, K.E. et al., The Immune Response to an Isomaltohexosyl-Protein Conjugate, a Thymus-Dependent Analogue of Alpha(1 Replaced by 6) Dextran., J Immunol 1982, 128, 1350-1354.
Stein, K.E., Thymus-Independent and Thymus-Dependent Responses to Polysaccharide Antigens, J Infect Dis 1992, 165 Suppl 1, S49-52.
Stephens, David, Conquering the Meningococcus, FEALS Microbial Rev 2007, 31, 3-14.
Stephens, D.S. et al., Epidemic Meningitis, Meningococcaemia, and Neisseria Meningitidis, Lancet 2007, 369, 2196-2210.
Stephenson et al., "Neuraminidase inhibitor resistance after oseltamivir treatment of acute influenza A and B in children," Clin. Infect. Dis., Feb. 15, 2009, 48(4):389-396.
Stevanovic, Stefan, Identification of Tumour-Associated T-Cell Epitopes for Vaccine Development, Nat. Rev. Cancer, 2002, 2, 514-520.
Stevens, James et al., Structure of the Uncleaved Human H1 Hemagglutinin From the Extinct 1918 Influenza Virus, Science, 303:1866, 2004.
Stevens, James et al., Structure and Receptor Specificity of the Hemagglutinin From an H5N1 Influenza Virus, Science, 312:404, 2006.
Stevens et al., Glycan Microarray Analysis of the Hemagglutinins From Modern and Pandemic Influenza Viruses Reveals Different Receptor Specificities. Journal of Molecular Biology 355.5 (2006): 1143-1155.
Stickings, P. et al., nfect. Immun. 2008, 76, 1766.
Stockmann, H. et al., Development and Evaluation of New Cyclootynes for Cell Surface Glycan Imaging in Cancer Cells, J. Chem. Sci. 2011, 2, 932-936.

(56) References Cited

OTHER PUBLICATIONS

Streicher et al., "Building a successful structural motif into sialylmimetics-cyclohexenephosphonate monoesters as pseudo-sialosides with promising inhibitory properties," Bioorg. Med Chem., Feb. 15, 2006, 14(4):1047-1057.

Stubbs et al., "Synthesis and use of mechanism-based protein-profiling probes for retaining β-D-glucosaminidases facilitate identification of Pseudomonas aeruginosa NagZ," J. Am. Chem. Soc., Jan. 9, 2008, 130(1):327-335.

Su, G. Hahner, W. Zhou "Investigation of the pore formation in anodic aluminum oxide" J Mater. Chem. 2008, 18 5787-5795.

Sun, B., Srinibasan, B., Huang, X., Pre-activation-based one-pot synthesis of an alpha-(2,3)-sialylated core-fucosylated complex type bi-antennary N-glycan dodecasaccharide. Chem. Eur. J 14 (23), 7072-81, (2008).

Supplementary European Search Report in European Application No. EP 13775664.9, dated Oct. 27, 2015, in 7 pages.

Suresh et al., "Bispecific monoclonal antibodies from hybrid hybridomas," Methods in Enzymology, 1986, 121:210-228.

Sutton, VR et al., Bcl-2 Prevents Apoptosis Induced by Perforin and Granzyme B, but Not That Mediated by Whole Cytotoxic Lymphocytes, J of Immunology 1997, 158(12), 5783.

Suzuki E, et al., "A nonfucosylated anti-HER2 antibody augments antibody-dependent cellular cytotoxicity in breast cancer patients" Clin Cancer Res. Mar. 15, 2007;13(6):1875-82.

Svennerholm et al., "Human brain gangliosides: Developmental changes from early fetal stage to advanced age," Biochim. Biophys. Acta, Sep. 25, 1989, 1005(2):109-117.

Syrigos et al., "Antibody directed enzyme prodrug therapy (ADEPT): a review of the experimental and clinical considerations," Anticancer Research, Jan.-Feb. 1999, 19(1A):605-614.

Tahir et al., "Loss of IFN-γ production by invariant NK T cells in advanced cancer," J. Immunol., Oct. 1, 2001, 167(7):4046-4050.

Takakura, Yoshimitsu et al., Molecular cloning, expression and properties of an alpha/beta-Galactoside alpha 2,3-sialyltransferase from Vibrio sp. JT-FAJ-16. J. Biochem. 142, 403-412, (2007).

Takano, Ryo et al., Sialylation and Malignant Potential in Tumour Cell Glycosylation Mutants, Glycobiology 4, 665-674 (1994).

Takeda et al., "Construction of chimaeric processed immunoglobulin genes containing mouse variable and human constant region sequences," Nature, Apr. 4-10, 1985, 314(6010):452-454.

Taki, Takao et al., Glycolipids of Metastatic Tissue in Liver From Colon Cancer: Appearance of Sialylated Lex and Lex Lipids, J. Biochem. 103, 998-1003, 1998.

Talmadge et al., Murine models to evaluate novel and conventional therapeutic strategies for cancer, Am. J. Pathol, 170(3): 793-804 (2007).

Tanaka, Hiroshi et al., An Efficient Convergent Synthesis of GP1c Ganglioside Epitope, J Am Chem Soc. 2008, 130, 17244.

Tanaka, Katsunori et al., Synthesis of a Sialic Acid Containing Complex-Type N-Glycan on a Solid Support, Chemistry—an Asian Journal, 2009, vol. 4 (4), p. 574-580.

Taton, T. Andrew et al., Scanometric DNA Array Detection with Nanoparticle Probes, Science 289 (2000) 1757-1760.

Taton, T. Andrew et al., Two-Color Labeling of Oligonucleotide Arrays via Size-Selective Scattering of Nanoparticle Probes, J. Am. Chem. Soc. (2001), 123, 5164-5165.

Taylor-Papadimitriou et al., "Exploiting altered glycosylation patterns in cancer: Progress and challenges in diagnosis and therapy," Trends Biotechnol., Jun. 1994, 12(6):227-233.

Telford et al., "The Aspergillus Fumigatus Sialidase is a 3'-Deoxy-D-galacto-2-nonulosonic Acid Hydrolase (KDNase)," The Journal of Biological Chemistry, 286(12), 10783-10792 (Mar. 25, 2011).

"The Human Protein Atlas", B3GALT5 URL:http://www.proteinatlas.org/ENSG00000183778-B3GALT5/cancer, Sep. 9, 2015.

Thorpe, (1985) "Antibody Carriers of Cytotoxic Agents in Cancer Therapy: A Review," in Monoclonal Antibodies '84: Biological and Clinical Applications, A. Pinchera et al. (ed.s), pp. 475-506.

Thurber, Greg et al., Antibody Tumor Penetration: Transport Opposed by Systemic and Antigen-Mediated Clearance, Adv Drug Deliv Rev, 60: 1421-1434, 2008.

Toba, et al., "Synthesis and biological evaluation of truncated α-glaactosylceramide derivatives focusing on cytokine induction profile," Bioorganic & Medicinal Chemistry 20(2012): 2850-2859.

Tomlinson et al., "The repertoire of human germline $V_H$ sequences reveals about fifty groups of $V_H$ segments with different hypervariable loops," J. Mol. Biol., Oct. 5, 1992, 227(3):776-798.

Torres-Sanchez et al., "Synthesis and Biological Evaluation of Phophono Analogues of Capsular Polysaccharide Fragments From Neisseria Meningtitidis A" Chem Eur J (2007) vol. 13, pp. 6623-6635.

Toshima, K. Glycosyl fluorides in glycosidations. Carbohydr. Res. 327, 15-26 (2000).

Traunecker et al., "Bispecific single chain molecules (Janusins) target cytotoxic lymphocytes on HIV infected cells," EMBO J., Dec. 1991, 10(12):3655-3659.

Traylor et al., "Gangliosides of human cerebral astrocytomas," J. Neurochem., Jan. 1980, 34(1):126-131.

Trinchieri, "Interleukin-12: a proinflammatory cytokine with immunoregulatory functions that bridge innate resistance and antigen-specific adaptive immunity," Annu. Rev. Immunol., 1995, 13:251-276.

Tsai et al., "Design and synthesis of activity probes for glycosidases," Org. Lett., Oct. 17, 2002, 4(21):3607-3610.

Tsai, Charng-sheng et al., Development of Trifunctional Probes for Glycoproteomic Analysis, Chem. Commun. 2010, 46, 5575-5577.

Tsai Ti, et al., "Effective sugar nucleotide regeneration for the large-scale enzymatic synthesis of Globo H and SSEA4" J Am Chem Soc. Oct. 2, 2013;135(39):14831-9, Epub Sep. 17, 2013.

Tseng, Susan Y. et al., Glycan Arrays on Aluminum Coated Glass Slides. Chem. Asian J, 2008, 3, 1395-1405.

Tsuji, et al., "Preparation of glycolipids and analogs as antigens for NKT cells for use in vaccines and immunotherapy," CAPLUS 149:492050 (2008).

Tsukamoto, Hiroshi et al., Photobacterium sp. JT-ISH-224 produces two sialyltransferases, alpha-/beta-galactoside alpha2,3-sialyltransferase and betagalactoside alpha2,6-sialyltransferase. J. Biochem. 143, 187-197, 2008.

Tumpey, Terrence et al., Characterization of the Reconstructed 1918 Spanish Influenza Pandemic Virus, Science, 310:77, 2005.

Tutt et al., "Trispecific F(ab')₃ derivatives that use cooperative signaling via the TCR/CD3 complex and CD2 to activate and redirect resting cytotoxic T cells," J. Immunol., Jul. 1, 1991, 147(1):60-69.

Tyagarajan K et al., "Exoglycosidase purity and linkage specificity: assessment using oligosaccharide substrates and high-pH anion-exchange chromatography with pulsed amperometric detection" Glycobiology. Jan. 1996;6(1):83-93.

Tzeng, Y. L. et al, Epidemiology and Pathogenesis of Neisseria Meningitidis, Microbes Infect 2000, 2, 687-700.

Uchida, Tsuyoshi et al., Diphtheria Toxin and Related Proteins, J Biol. Chem. 218; 3838-3844 (1973).

Udommaneethanakit et al., "Dynamic behavior of avain influenza A virus neuraminidase subtype H5N1 in complex with oseltamivir, zanamivir, peramivir, and their phosphonate analogues," J Chem. Inf Model, Oct. 2009, 49(10):2323-2332.

Ulevitch, RJ et al., Receptor-Dependent Mechanisms of Cell Stimulation by Bacterial Endotoxin, 1995, Annu. Rev. Immunol., 13: 437.

Ulrich, G.; Ziessel, R.; Harriman, A. "The chemistry of fluorescent bodipy dyes: Versatility unsurpassed." Angew. Chem. Int. Ed. 2008, 47, 1184-1201.

Urlaub et al., "Isolation of Chinese hamster cell mutants deficient in dihydrofolate reductasc activity." Proc. Natl. Acad. Sci. U.S.A., Jul. 1980, 77(7):4216-4220.

Valentine MA, et al., "Phosphorylation of the CD20 phosphoprotein in resting B lymphocytes. Regulation by protein kinase C" J Biol Chem. Jul. 5, 1989;264(19):11282-7.

Van Beek et al., "Increased sialic acid density in surface glycoprotein of transformed and malignant cells—a general phenomenon?" Cancer Res., Nov. 1973, 33(11):2913-2922.

(56) References Cited

OTHER PUBLICATIONS

Van der Horst et al., "Photoaffinity labeling of a bacterial sialidase with an aryl azide derivative of sialic acid," *J. Biol. Chem.*, Jul. 5, 1990, 265(19), 10801-10804.
Van Hest, Jan C.M. et al., Efficient Introduction of Alkene Functionality Into Proteins in Vivo (1998) FEES Lett. 428:68.
Vaki, Ajit et al., Symbols Nomenclatures for Glycan Representation, Proteomics. Dec. 2009, 9(24): 5398-5399.
Van Meir et al., "Exciting new advances in neuro-oncology: the avenue to a cure for malignant glioma," *CA Cancer J. Clin.*, May-Jun. 2010, 60(3):166-193.
Van Slambrouck et al., "Clustering of monosialyl-Gb5 initiates downstream signalling events leading to invasion of MCF-7 breast cancer cells," *Biochem. J.*, Feb. 1, 2007, 401(3):689-699.
Varghese et al., Three-dimensional structure of the complex of 4-guanidino-Neu5Ac2en and nfluenza virus neuraminidase. Protein Sci. Jun. 1995;4(6):1081-7.
Varki, "Glycan-based interactions involving vertebrate sialic-acid-recognizing proteins," *Nature*, Apr. 26, 2007, 446(7139):1023-1029.
Vasella et al., "Synthesis of a phosphonic acid analogue of N-Acetyl-2,3-didehydro-2-deoxyneuraminic acid, an inhibitor of Vibrio cholerae sialidase," Helv. Chim. Acta, Mar. 13, 1991, 74(2):451-463.
Vaswani et al., "Humanized antibodies as potential therapeutic drugs," *Ann. Allergy, Asthma Immunol.*, Aug. 1998, 81(2):105-116, 119.
Vavricka, Christopher et al., Influenza Neuraminidase Operates via a Nucleophilic Mechanism and Can Be Targeted by Covalent Inhibitors, Nature Communcations, 4:1491 (2013).
Verhoeyen et al., "Reshaping human antibodies: grafting an antilysozyme activity," *Science*, Mar. 25, 1988, 239(4847):1534-1536.
Vermeer AW et al., "The thermal stability of immunoglobulin: unfolding and aggregation of a multi-domain protein" *Biophys J.* Jan. 2000;78(1):394-404.
Vinogradova et al., "Molecular mechanism of lysosomal sialidase deficiency in galactosialidosis involves its rapid degradation," *Biochem. J.*, Mar. 1, 1998, 330(Pt 2.):641-650.
Vippagunta, Sudha et al., Crystalline Solids, Advanced Drug Delivery Reviews 48, 3-26 (2001).
Virji, Mumtaz et al., Pathogenic Neisseriae: Surface Modulation, Pathogenesis and Infection Control, Nat Rev, Microbiol 2009, 7, 274-286.
Vitetta, ES et al., Redesigning Nature's Poisons to Create Anti-Tumor Reagents, Science 23(8): 1098 (1987).
Vocadlo et al., "A strategy for functional proteomic analysis of glycosidase activity from cell lysates," *Angew. Chem. Int. Ed. Engl.*, Oct. 11, 2004, 43(40):5338-5342.
Von Itzstein et al., "Rational design of potent sialidase-based inhibitors of influenza virus replication," Nature, Jun. 3, 1993, 363(6428):418-423.
Voskoglou-Nomikos, Clinical predictive value of the in vitro cell line, human xenograft, and mouse allograft preclinical cancer models, Clin Can Res, 9: 4227-4239 (2003).
Wada et al., "A crucial role of plasma membrane-associated sialidase in the survival of human cancer cells," *Oncogene*, Apr. 12, 2007, 26(17):2483-2490.
Wagner, R et al., "Functional balance between haemagglutinin and neuraminidase in influenza virus infections," Rev. Med Viral., May-Jun. 2002, 12(3): 159-166.
Walls et al., "Activity-based protein profiling of protein tyrosine phosphatases," *Methods Mol. Biol.*, 2009, 519:417-429.
Walker, L. M. et al. Broad neutralization coverage of HIV by multiple highly potent antibodies. Nature 477, 466-470, (2011).
Wang, Chao et al., Tuning the Optical Properties of BODIPY Dye Through Cu(I) Catalyzed Azide-Alkyne Cycloaddition (CuAAC) Reaction, Sci. China Chemistry 2012, 55, 125-130.
Wang, Zhen et al., Multi-Component One-Pot Synthesis of the Tumor-Associated Carbohydrate Antigen Globo-H Based on Preactivation of Thioglycosyl Donors, J Org. Chem. 2007, 72, 6409.

Wang et al., "Glycan microarray of Globo H and related structures for quantitative analysis of breast cancer," *Proc. Natl. Acad. Sci. U.S.A.*, Aug. 19, 2008, 105(33):11661-11666.
Wang et al., "A continuous colorimetric assay for rhinovirus-14 3C protease using peptide p-nitroanilides as substrates," Anal. Biochem., Oct. 15, 1997, 252(2):238-245.
Wang et al., "Synthesis of Neisseria Meningitidis Serogroup W135 Capsular Oligosaccharides for Immunogenicity Comparison and Vaccine Development" Angew Chem Int Ed (2013) vol. 52, pp. 9157-9161.
Wang, Michael et al., "Mechanism by which mutations at his274 alter sensitivity of influenza A virus NI neuraminidase to oseltamivir carboxylate and zanamivir," Antimicrob. Agents Chemother., Dec. 2002, 46(12):3809-3816.
Wang, D., Liu, S., Trummer, B. J., Deng, C. & Wang, A. Carbohydrate microarrays for the recognition of cross-reactive molecular markers of microbes and host cells. Nat. Biotechnol . 20, 275-281, (2002).
Wang et al., Computational Studies of H5N1 Influenza Virus Resistance to Oseltamivir. Protein Sci. 2009, 18(4): 707-715; p. 713.
Wang, C. C. et al. Glycans on Influenza Hemagglutinin Affect Receptor Binding and Immune Response, Proc. Natl. Acad. Sci. 2009, 106, 18137-18142.
Wang, L. X. Carbohydrate-based vaccines against HIV/AIDS. Acs Sym. Ser. 932, 133-160 (2006).
Wang, L. X. Synthetic carbohydrate antigens for HIV vaccine design. Curr. Opin. Chem. Biol. 17, 997-1005, (2013).
Wang, W. et al. A systematic study of the N-glycosylation sites of HIV-I envelope protein on infectivity and antibody-mediated neutralization. Retrovirology, 10, 14, (2014).
Wang, Zhen et al. A general strategy for the chemoenzymatic synthesis of asymmetrically branched N-glycans. Science 341, 379-383, (2013).
Ward et al., "Binding activities of a repertoire of single immunoglobulin variable domains secreted from *Escherichia coli,*" *Nature*, Oct. 12, 1989, 341(6242):544-546.
Waterhouse et al., "Combinatorial infection and in vivo recombination: a strategy for making large phage antibody repertoires," *Nuc. Acids Res.*, May 11, 1993, 21(9):2265-2266.
Watts et al., "The Synthesis of Some Mechanistic Probes for Sialic Acid Processing Enzymes and the Labeling of a Sialidase from Trypanosoma Rangeli," Canadian Journal of Chemistry, 82(11), 1581-1588 (2004).
Watts et al., "*Trypanosoma cruzi* trans-sialidase operates through a covalent sialyl-enzyme intermediate: tyrosine is the catalytic nucleophile," *J. Am. Chem. Soc.*, Jun. 25, 2003, 125(25):7532-7533.
Weibel, Robert et al., Tumor-Associated Membrane Sialoglycoprotein on Human Small Cell Lung Carcinoma Identified by the lgG2a Monoclonal Antibody SWA20, (1988) Cancer Res. 48, 4318-4323.
Wen, Wen Hsien et al., "Synergistic effect of zanamivir-porphyrin conjugates on inhibition of neuraminidase and inactivation of influenza virus," J Med Chem., Aug. 13, 2009, 52(15):4903-4910.
White, Clinton et al., "A sialic acid-derived phosphonate analog inhibits different strains of influenza virus neuraminidase with different efficiencies," J Mol. Biol., Feb. 3, 1995, 245(5):623-634.
Wikstrand et al., "Monoclonal antibody therapy of human gliomas: Current status and future approaches," *Cancer Metastasis Rev.*, 1999, 18(4):451-464.
Wilen et al., "Strategies in optical resolutions," Tetrahedron, 1977, 33(21):2725-2736.
Williams et al., "Cloning and sequencing of human immunoglobulin V lambda gene segments." *Eur. J. Immunol.*, Jul. 1993, 23(7):1456-1461.
Wiltshire, S. et al. Proc. Natl. Acad. Sci. (2000) 97, 10113-10119.
Winter et al., "Making antibodies by phage display technology," *Annu. Rev. Immunol.*, 1994, 12:433-455.
Wiseman, GA et al., Phase I/II 90Y-Zevalin (yttrium-90 Ibritumomab Tiuxetan, IDEC-Y2B8) Radioimmunotherapy Dosimetry Results in Relapsed or Refractory Non-Hodgkin's Lymphoma, Eur Jour Nucl Med 27(7): 766-77 (2000).
Wiseman, Gregory et al., Ibritumomab Tiuxetan Radioimmunotherapy for Patients with Relapsed or Refractory Non-

(56) References Cited

OTHER PUBLICATIONS

Hodgkin Lymphoma and Mild Thrombocytopenia: a Phase II Multicenter Trial, Blood 99(12): 4336-42 (2002).
Witte et al., "Ultrasensitive in situ visualization of active glucocerebrosidase molecules," *Nat. Chem. Biol.*, Dec. 2010, 6(12):907-913.
Witzig, Thomas et al., Randomized Controlled Trial of Yttrium-90-Labeled Ibritumomab Tiuxetan Radioimmunotherpay Versus Rituximab Immunotherapy for Patients with Relapsed or Refractory Low-Grade, Follicular, or Transformed B-Cell Non-Hodgkin's Lymphoma, J Clin Oncol 20(10):2453-63 (2002).
Witzig, Thomas et al., Treatment with Ibritumomab Tiuxetan Radioimmunotherapy in Patients with Rituximab-Refractory Follicular Non-Hodgkin's Lymphoma, J Clin Oncol 20(15):3262-69 (2002).
Wong et al., α-Galactosyl Ceramide Analogs and Their use as Therapeutic, 2010:50988, 2 Pages.
Woo et al. Cytokine profiles induced by the novel swine-origin influenza A/HINI virus: mplications for treatment strategies. J Infect Dis. Feb. 1, 2010;201(3):346-53.
Woof et al., "Human antibody-Fc receptor interactions illuminated by crystal structures," *Nat. Rev. Immunol.*, Feb. 2004, 4(2):89-99.
Woyke, Tanja et al., Effect of Auristatin PHE on Microtubule Integrity and Nuclear Localization in Cryptococcus Neoformans, Antimicrob. Agents and Chemother. 45(12): 3580-3584 (2001).
Wright et al. Antibody variable region glycosylation: biochemical and clinical effects, Springer Semin Immunopathology, 15:259-273 (1993).
Wu et al., "Avidity of CD1d-ligand-receptor ternary complex contributes to T-helper 1 (Th1) polarization and anticancer efficacy," *Proc. Natl. Acad. Sci. USA*, Oct. 18, 2011, 108(42):17275-17280.
Wu, Xueling et al. Rational design of envelope identifies broadly neutralizing human monoclonal antibodies to HIV-I. Science 329, 856-861, (2010).
Wu, Liangxing et al., Fluorescent Cassettes for Monitoring Three-Component Interactions in Vitro and in Living Cells, Journal of the American Chemical Society (2009), 131(26), 9156-9157.
Wu et al., "Catalytic azide-alkyne cycloaddition: reactivity and applications," Aldrichimica Acta, 2007, 40(1):7-17.
Xie, F.; Sivakumar, K.; Zeng, Q. B.; Bruckman, M. A.; Hodges, B.; Wang, Q. "A fluorogenic 'click' reaction of azidoanthracene derivatives." Tetrahedron 2008, 64, 2906-2914.
Yamaguchi, Kazunori et al., "Evidence for mitochondrial localization of a novel human sialidase (NEU4)," *Biochem. J.*, Aug. 15, 2005, 390(Pt 1):85-93.
Yamane-Ohnuki, Naoko et al., Production of Therapeutic Antibodies with Controlled Fucosylation, mAbs 2009, 1;3:230-236.
Yamashita et al., CS-8958, a prodrug of the new neuraminidase inhibitor R-125489, shows ong-acting anti-influenza virus activity. Antimicrob Agents Chemother. Jan. 2009;53(1): 186-92.
Yamashita, Yoshito et al., Alterations in Gastric Mucin with Malignant Transformation: Novel Pathway for Mucin Synthesis, (1995) J. Natl. Cancer Inst. 87, 441-446.
Yang, JM et al., Alterations of )-Glycan Biosynthesis in Human Colon Cancer Tissues, (1994) Glycobiology 4, 873-884.
Yaniv, Nature 297: 17-18, 1982.
Yansura et al., "Nucleotide sequence selection for increased expression of heterologous genes in *Escherichia coli*," *Methods: A Companion to Methods in Enzymol.*, Aug. 1992, 4(2):151-158.
Yates AJ et al., Brain Tumors in Childhood. Childs Brain 5(1), 31-39 (1979).
Ye et al., "Stage-specific embryonic antigen 4 expression in epithelial ovarian carcinoma," *Int. J. Gynecol. Cancer*, Aug. 2010, 20(6):958-964.
Yelton et al., "Affinity maturation of the BR96 anti-carcinoma antibody by codon-based mutagenesis." *J. Immunol.*, Aug. 15, 1995, 155(4):1994-2004.
Yguerabide, Juan et al., Light-Scattering Submicroscopic Particles as Highly Fluorescent Analogs and Their Use as Tracer Labels in Clinical and Biological Applications: II. Experimental Characterization, Anal. Biochem. (1998), 262, 157-176.
Ying et al., One-bead-one-inhibitor-one-substrate screening of neuraminidase activity. Chembiochem. Oct. 2005;6(10):1857-65.
Yoshida M, et al. Glycoconjugate J. 1993, 10, 324.
Yoshimoto et al., "CD4$^{pos}$, NK1.1$^{pos}$ T cells promptly produce interleukin 4 in response to in vivo challenge with anti-CD3," *J. Exp. Med.*, Apr. 1, 1994, 179(4):1285-1295.
Yu et al., "Anti-GD2 antibody with GM-CSF, interleukin-2, and isotretinoin for neuroblastoma," *N. Engl. J. Med.*, Sep. 30, 2010, 363(14):1324-1334.
Yuen et al., Human infection by avian influenza A H5N1. Hong Kong Med J. Jun. 2005;1 1(3):189-99.
Zapata et al., "Engineering linear F(ab')$_2$ fragments for efficient production in *Escherichia coli* and enhanced antiproliferative activity," *Protein Eng.*, Oct. 1995, 8(10):1057-1062.
Zarei et al., "Separation and identification of GM1b pathway Neu5Ac- and Neu5Gc gangliosides by on-line nanoHPLC-QToF MS and tandem MS: toward glycolipidomics screening of animal cell lines," *Glycobiology*, Jan. 2010, 20(1):118-126.
Zhang et al., "New cerebrosides from Acanthopanax gracilistylus," CAPLUS 156:225776 (2011).
Zhang et al., "Selection of tumor antigens as targets for immune attack using immunohistochemistry: I. Focus on gangliosides," *Int. J. Cancer*, Sep. 26, 1997, 73(1):42-49.
Zhang, Hai-Long et al., A Novel Combined Conjugate Vaccine: Enhanced Immunogenicity of bFGF with CRM197 as a Carrier Protein, Molecular Medicine Reports, 4, 857-863, 2011.
Zheng et al., Delayed antiviral plus immunomodular treatment still reduces mortality in mice infected by high inoculum of influenza A/H5N1 virus. Proc Natl Acad Sci U S A. Jun. 10, 2008;105(23):8091-6.
Zhou et al., A fluorogenic probe for the copper(I)-catalyzed azide-alkyne ligation reaction: modulation of the fluorescence emission via $^3(n,\pi)$-$^1(\pi,\pi)$ inversion, *J. Am. Chem. Soc.*, Jul. 28, 2004, 126(29):8862-8863.
Zhu, X et al., Mass spectrometric characterization of the glycosylation pattern of HIV-gp120 expressed in CHO cells. Biochemistry 39, 11194-11204 (2000).
Zou, et al., Chemoenzymatic synthesis and Fc gamma receptor binding of homogenous glycoforms of antibody Fc to FcIIIa receptor. J Am Chem Soc. 2011, 133(46):18975-91.
Zimmermann et al., Multi-target therapeutics: when the whole is greater than the sum of the parts. Drug Discov Today. Jan. 2007;12(1-2):34-42. Epub Nov. 28, 2006.

\* cited by examiner

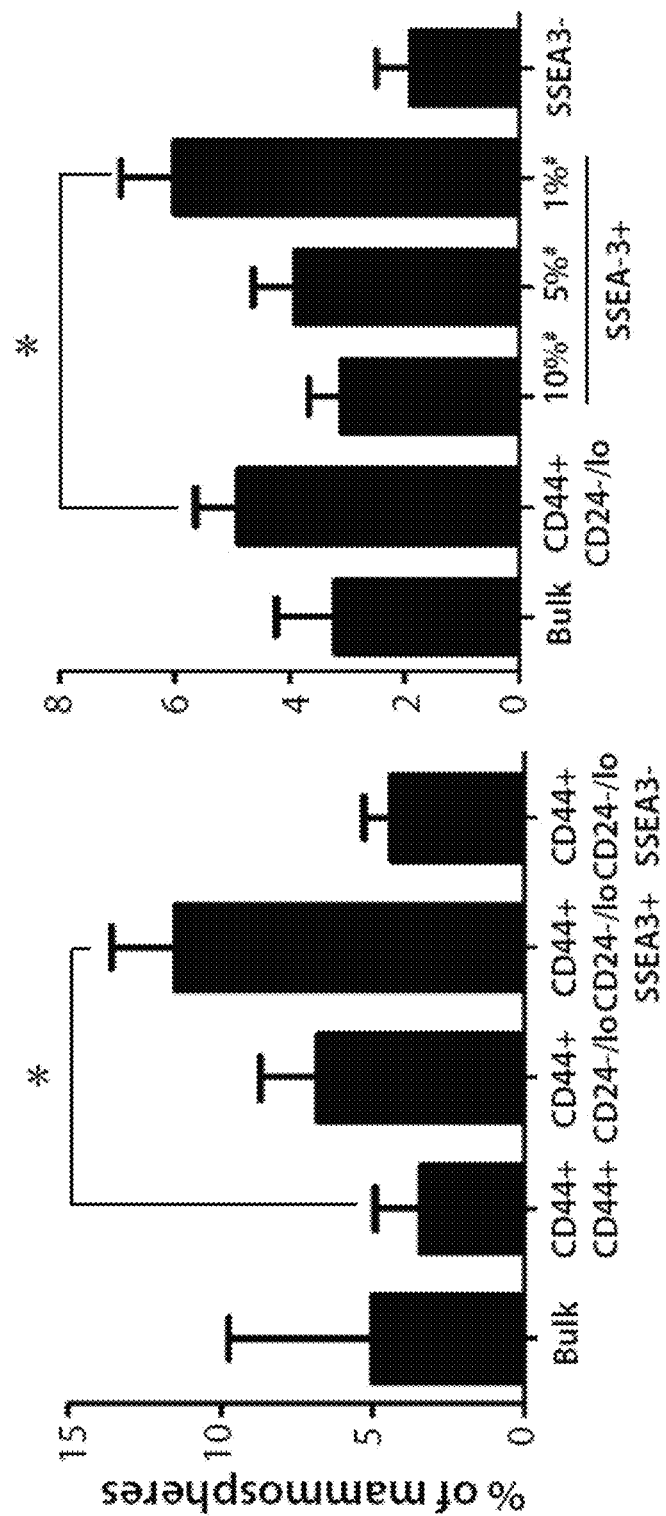

FIG. 1C

| Injected cell number | Marker Sets | | | | |
|---|---|---|---|---|---|
| | CD44+ CD24-/lo | CD44+ CD24-/lo SSEA-3+ | CD44+ CD24-/lo SSEA-3- | SSEA-3+ | SSEA-3- |
| 2500 | 4/4 | 8/8 | 5/8 | 7/8 | 5/8 |
| 500 | 3/4 | 7/8 | 6/8 | 7/8 | 4/8 |
| 100 | 2/4 | 7/7 | 3/7 | 3/8 | 0/8 |
| 50 | 1/4 | 7/8 | 3/8 | 0/4 | 0/4 |
| 10 | 0/4 | 1/8 | 0/8 | 0/4 | 0/4 |

FIG. 1D

| Injected cell number | Marker Sets | | | |
|---|---|---|---|---|
| | ESA$^{hi}$ PROCR$^{hi}$ | ESA$^{hi}$ PROCR$^{hi}$ SSEA-3$^+$ | ESA$^{hi}$ PROCR$^{hi}$ SSEA-3$^-$ | SSEA-3$^+$ | SSEA-3$^-$ |
| 2500 | 2/4 | 3/6 | 1/6 | 7/8 | 5/8 |
| 500 | 1/4 | 5/6 | 0/6 | 4/8 | 2/8 |
| 100 | 1/4 | 3/6 | 0/6 | 3/4 | 0/8 |

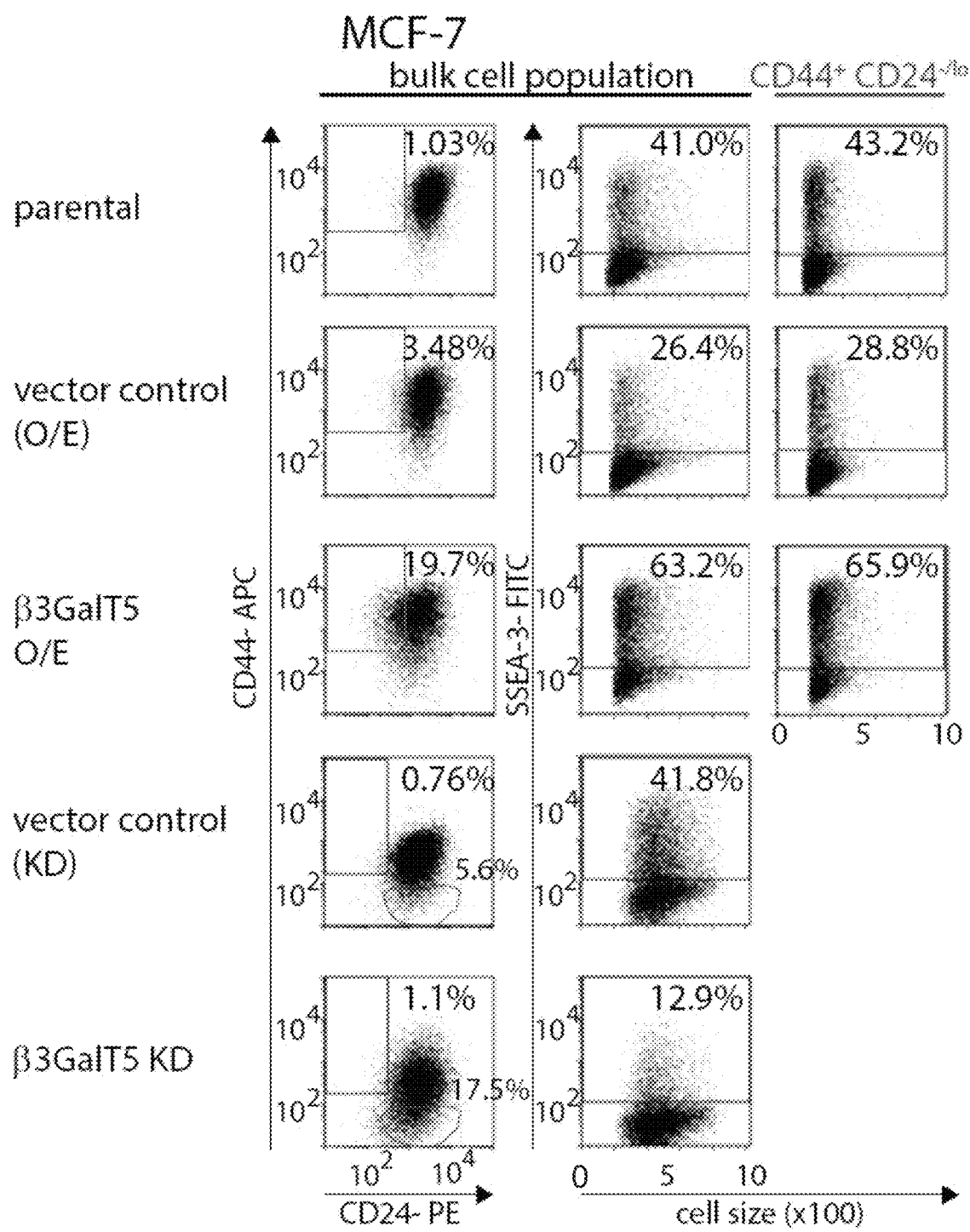

A MCF-7

<sorting 1>

<sorting 2>

B MDA-MB-231

<sorting 1>

<sorting 2>

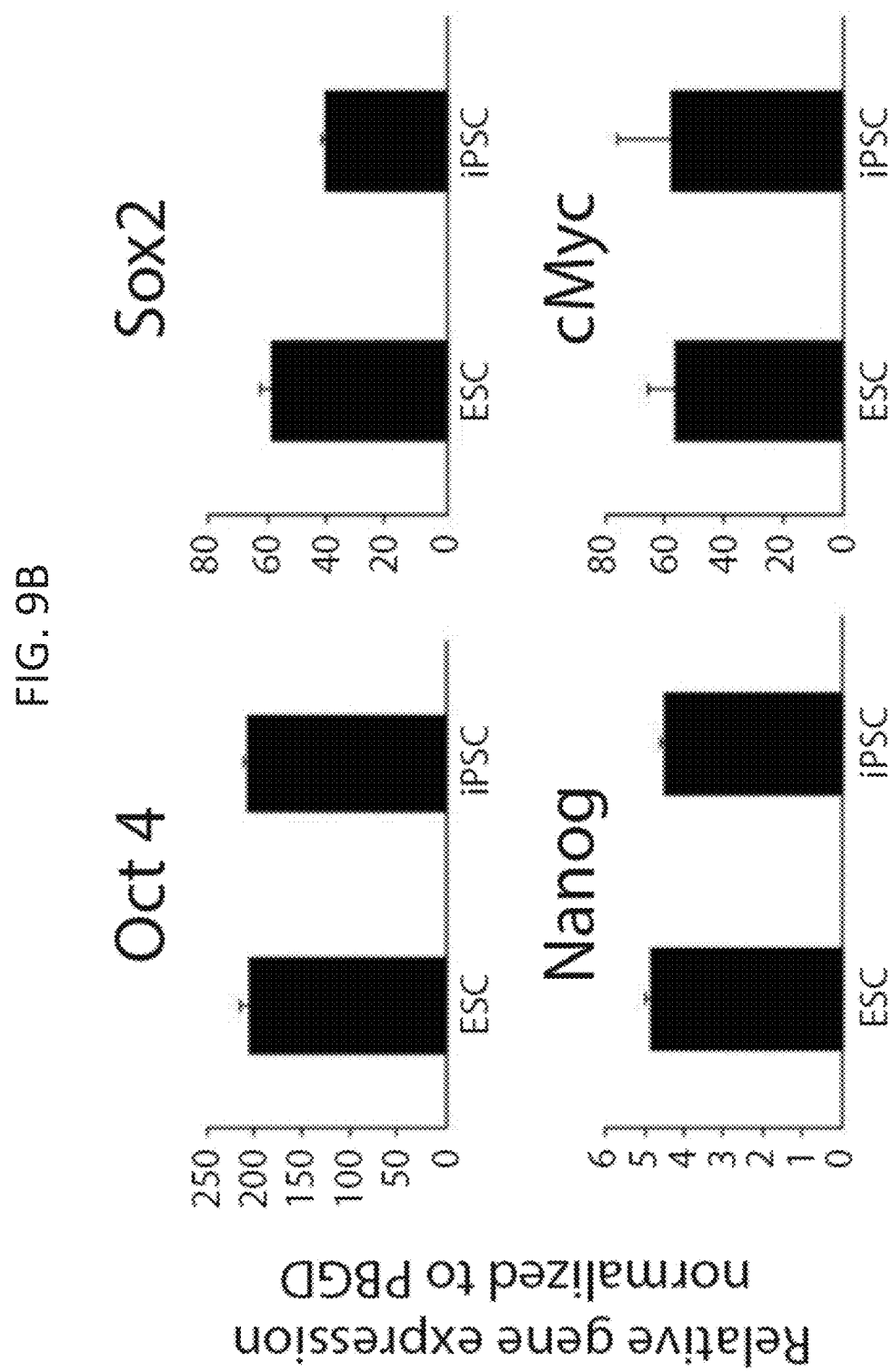

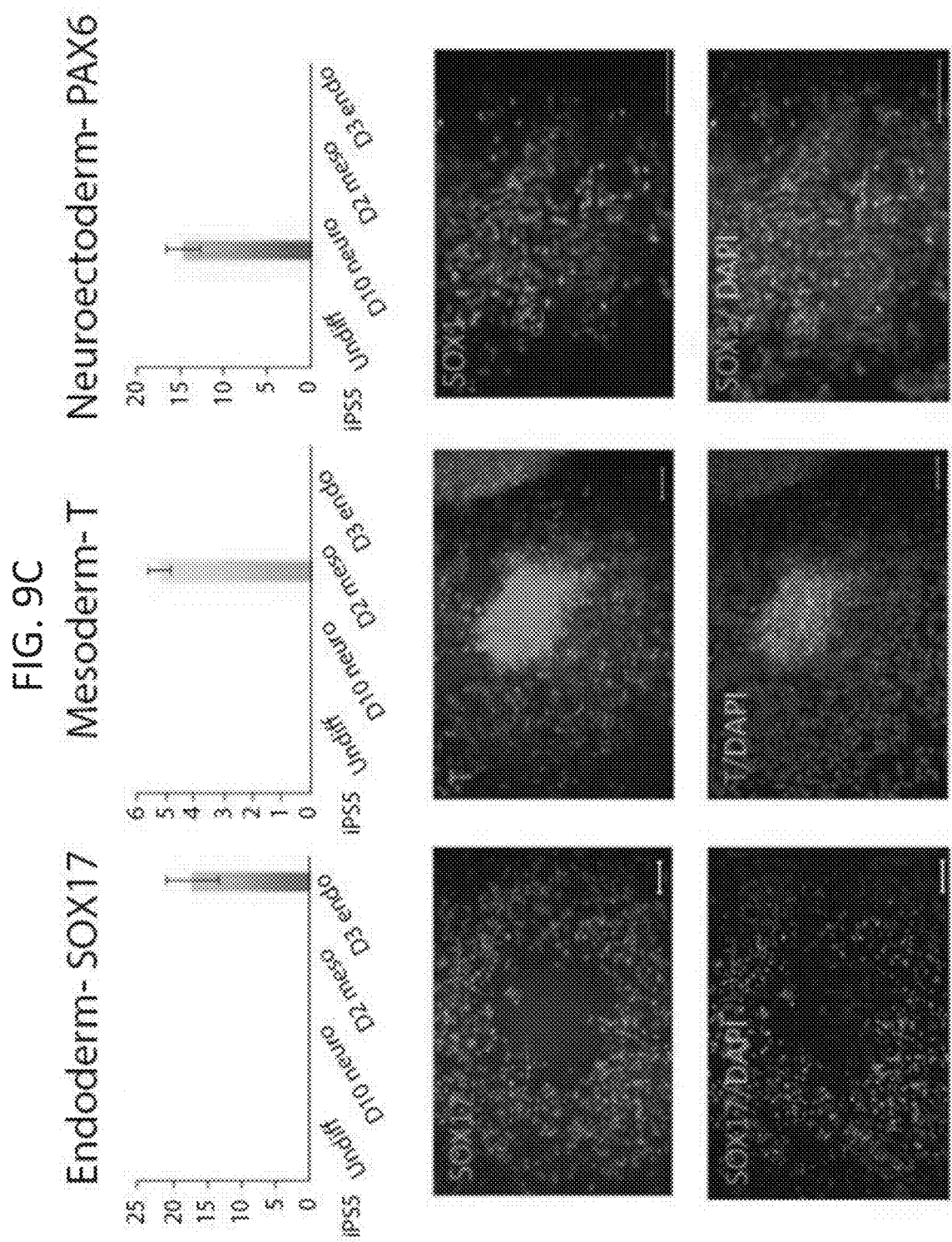

SEQUENCE LISTING

<160> NUMBER OF SEQ ID NOS: 5

<210> SEQ ID NO 1
<211> LENGTH: 26
<212> TYPE: DNA
<213> ORGANISM: Artificial Sequence
<220> FEATURE:
<223> OTHER INFORMATION: Description of artificial sequence: synthetic polynucleotide

<400> SEQUENCE: 1
gcagatctat ggctttcccg aagatg      26

```
<210> SEQ ID NO 2
<211> LENGTH: 25
<212> TYPE: DNA
<213> ORGANISM: Artificial Sequence
<220> FEATURE:
<223> OTHER INFORMATION: Description of artificial sequence: synthetic
      polynucleotide

<400> SEQUENCE: 2
gtctcgagtc agacaggcgg acaat                                          25

<210> SEQ ID NO 3
<211> LENGTH: 58
<212> TYPE: DNA
<213> ORGANISM: Artificial Sequence
<220> FEATURE:
<223> OTHER INFORMATION: Description of artificial sequence: synthetic
      polynucleotide

<400> SEQUENCE: 3
ccgggcaagt ggtttgtcag taaatctcga gatttactga caaaccactt gcttttg       58

<210> SEQ ID NO 4
<211> LENGTH: 22
<212> TYPE: DNA
<213> ORGANISM: Artificial Sequence
<220> FEATURE:
<223> OTHER INFORMATION: Description of artificial sequence: synthetic
      polynucleotide

<400> SEQUENCE: 4
agcggaaacg aaagaggtgg ac                                             22

<210> SEQ ID NO 5
<211> LENGTH: 22
<212> TYPE: DNA
<213> ORGANISM: Artificial Sequence
<220> FEATURE:
<223> OTHER INFORMATION: Description of artificial sequence: synthetic
      polynucleotide

<400> SEQUENCE: 5
cctgaggaca aaagcgatgg ac                                             22
```

CANCER MARKERS AND METHODS OF USE THEREOF

RELATED APPLICATIONS

This application claims the benefit of priority to U.S. Ser. No. 62/107,378 filed Jan. 24, 2015 and U.S. Ser. No. 62/266,514, filed Dec. 11, 2015, and claims the benefit of priority of, and is a continuation-in-part of U.S. Ser. No. 14/599,174, filed Jan. 16, 2015. The content of each of which is incorporated herein.

FIELD

The present disclosure relates to methods and compositions useful for modulating the globoseries glycosphingolipid synthesis as well as markers useful for selecting cancer stem cells. Particularly, the present disclosure is directed to glycoenzyme inhibitor compound and compositions and methods of use thereof that can modulate the synthesis of globoseries glycosphingolipid SSEA-3/SSEA-4/GloboH in the biosynthetic pathway; particularly, the glycoenzyme inhibitors target the alpha-4GalT; beta-4GalNAcT-I; or beta-3GalT-V enzymes in the globoseries synthetic pathway. Additionally, the present disclosure is also directed to vaccines, antibodies, and/or immunogenic conjugate compositions targeting the SSEA-3/SSEA-4/Globo H associated epitopes (natural and modified) which can elicit antibodies and/or binding fragment production useful for modulating the globoseries glycosphingolipid synthesis. Moreover, the present disclosure is also directed to the method of using the compositions described herein for the treatment or detection of hyperproliferative diseases and/or conditions. Furthermore the present disclosure is also directed to markers useful for selecting cancer stem cells in diagnostic and/or therapeutic applications.

BACKGROUND OF THE INVENTION

The carbohydrate antigens Globo H, stage-specific embryonic antigen-3 (SSEA-3), and stage-specific embryonic antigen-4 (SSEA-4) are closely related to one another in either structure or in function. Globo H, SSEA-3 and SSEA-4 are globoseries glycosphingolipids, with SSEA-3 being the non-fucosylated pentasaccharide precursor structure of Globo H, SSEA-4 is sialylated SSEA-3 with sialic acid α2-3 links to the non-reducing end of galactose of SSEA-3.

Stage specific embryonic antigen-3 (SSEA-3) was first identified and defined by the reactivity of an IgM monoclonal antibody generated in a rat immunized with 4-to 8-cell stage mouse embryos. This monoclonal antibody reacted with all mouse preimplantation embryos from oocytes up to the early blastocyst stage where its expression became more restricted, in the primitive endoderm after implantation. The SSEA-3 antigenic determinant was determined to be a carbohydrate present on glycolipids and glycoproteins; it was also found on human teratocarcinoma cells and human erythrocytes. In a panel of structures isolated from the 2102Ep human teratocarcinoma cell line, the SSEA-3 antibody had the highest affinity for Galβ(1-3)GalNAcβ(1-3)Galα(1-4)Galβ(1-94)Glcβ(1)Cer. This structure is also known as Gb5, galactosyl-globoside, or globopentaosylceramide.

Synthesis of SSEA-3 occurs when β1,3-galactosyltransferase V (β3GalT-V) transfers galactose to the GalNAc of globoside to form Gb5 or galactosyl-globoside. In more recent studies, attempts were made to determine if SSEA-3 could be used as a marker to identify stem cells in umbilical cord blood. It was determined that SSEA-3 was not expressed in hematopoietic or mesenchymal stem cells and therefore was not a good marker of multipotent cells. Schrump et al. immortalized lymph node lymphocytes from primary lung cancer patients, generated hybridomas, and selected for antibody secreting clones. Monoclonal antibodies were then generated from two of these clones—J309 and D579, which recognized the SSEA-3 antigenic determinant. The antibodies recognized SSEA-3 on several tumor cell lines including Jung and breast cancer cell lines, and a teratocarcinoma cell line; in an immune adherence assay, rodent monoclonal SSEA-3 antibody, also referred to as MC631, reacted against the same cell lines as the J309 and D579 antibodies. SSEA-3 has also been found on testicular germ cell tumors, as well as in breast cancer and in BCSCs (breast cancer stem cells).

Chang et al. looked at SSEA-3 expression on normal tissues using a tissue microarray because its location outside of cancer and development was largely unknown. The group found SSEA-3 to be expressed on normal epithelium of colon, esophagus, small intestine, kidney, prostate, rectum, skin, testis, thymus, and uterine cervix. Expression was located only on the apical surfaces of epithelial cells or in the cytoplasm, which are considered immune system restricted or inaccessible sites.[1] In an experiment using a KLH conjugated Globo H monovalent vaccine in mice, an antibody response was made to only the Globo H antigen. When α-GalCer was added as an adjuvant, the amount of overall antibody production increased and the mice made polyclonal antibodies to both the Globo H, the SSEA-3 and the SSEA-4 antigen structures, which vaccination was unable to generate in the absence of the adjuvant.[1] This result showed that SSEA-3, Globo H and SSEA-4 could make promising targets for cancer vaccines and could be targeted simultaneously.

However, most tumor associated carbohydrate antigens have poor immunogenicity and many approaches have been developed to increase the immune response of carbohydrate-based vaccines, including conjugation with a carrier protein administration with an immunologic adjuvant using unnatural glycosidic linkage, clustered antigens, unimolecular polyvalent vaccine or hetero-glycan multivalent vaccine. Using these strategies, a few carbohydrate-based vaccines that could elicit significant immune responses to target glycan structures were designed for cancer therapy and entered clinical trials. Among them, the clinical trials of Theratope and GMK with adjuvant QS-21 failed to produce statistically significant difference between time-to-disease and overall survival rate. Probably these two vaccines could not elicit robust T cell-dependent immune response in patients. Specifically, Theratope and GMK induced a higher level of IgM in patients but could not induce a strong immune IgG response, which is a major problem in carbohydrate-based vaccine development.

Previous studies showed that modification of carbohydrate antigen structures (MCAS) could effectively elicit a higher level of immune response. For example, in the modification study of the capsular polysaccharide of group B meningococci, the N-acetyl groups of α-(2,8)-linked polysialic acid (PSA) was replaced with the N-propinoyl group and such a modification elicited a high antibody response to recognize not only the N-propinoyl PSA, but also the nature N-acetyl PSA. Similar approaches were applied to STn and GM3 antigens to produce high antibody titers against modified and nature forms. The results indicated that N-phenylacetyl, N-fluoroacetyl or N-difluoroacetyl modifications on glycan antigens could improve the immunogenicity. Moreover, the Schultz group reported that incorporation of a p-nitrophenylalanine into the tumor necrosis factor-α(TNF-α) could break immune tolerance and induce more antibody response to TNF-α. Using glycans as antigens, although some progress has been achieved, most cases are the N-modification of disaccharide (STn). trisaccharide (GM3) and polysialic acid (PSA) and some are based on fluorinated MUC1glycopeptide antigens.

The discovery of cancer stem cells (CSCs), which are responsible for self-renewal and tumor-growth in heterogeneous cancer tissues, has stimulated interests in developing new cancer therapies and early diagnosis. The markers currently used for isolation of CSCs, however, are often not selective enough to enrich CSCs for the study of this special cell population.

SUMMARY OF THE INVENTION

The present disclosure relates to therapeutic methods which are based on the use of an agent that specifically targets tumor-associated carbohydrate antigen(s) and/or pathways regulating those targets, for the treatment of cancers comprising cancer stem cells and related diseases. Also provided are diagnostic and prognostic methods using one or more tumor-associated carbohydrate antigens as markers for cancer stem cells.

In one aspect, a binding agent is provided which specifically binds to one or more tumor-associated carbohydrate antigens for use in the treatment of cancers comprising cancer stem cells expressing said one or more tumor-associated carbohydrate antigens. Also provided is a pharmaceutical composition, comprising a respective binding agent for use in the treatment of cancers comprising cancer stem cells expressing said one or more tumor-associated carbohydrate antigens. Bindign agents include agents targeting SSEA3, SSEA4, and GloboH antigens, any combinations thereof and/or agents targeting related pathway targets.

In a second aspect, a method is provided for identifying a cancer comprising cancer stem cells that is susceptible to treatment with one or more binding agents each of which specifically binds to one or more tumor-associated carbohydrate antigens, wherein said treatment effects the cancer stem cells, the method comprising determining whether a cancer sample obtained from a patient comprises cancer stem cells that express one or more tumor-associated carbohydrate antigens the one or more binding agents is specific for, wherein the presence of said tumor-associated carbohydrate antigen(s) on cancer stem cells indicates that the cancer is susceptible to treatment with the binding agent(s) that specifically binds said tumor-associated carbohydrate antigen and wherein said treatment effects the cancer stem cells. In some embodiments, the tumor-associated carbohydrate antigens are selected from the list consisting of SSEA3, SSEA4, and GloboH antigens.

In a third aspect, a method is provided for identifying a population of cancer stem cells, the method comprising
a) providing a starting population of cancer cells,
b) determining the expression level of one or more tumor-associated carbohydrate antigens,
c) selecting a population of cells whose expression level of said one or more tumor-associated carbohydrate antigens as determined in step b) is increased when compared to control cells, wherein said selected population of cells are cancer stem cells and
d) optionally isolating and/or enriching for said population of cells selected in step c), wherein said control cells are cells from the same starting cancer cell population which do not express, or express lower levels of said one or more tumor-associated carbohydrate antigens.
In some embodiments, the tumor-associated carbohydrate antigens are selected from the list consisting of SSEA3, SSEA4, and GloboH antigens. In some embodiments, the determining step in b) further includes determining the expression level of one or more additional tumor associated antigens, and the selection and isolating steps in c) and d), respectively, also includes consideration of the expression level of said one or more additional tumor associated antigens. In some embodiments, the one or more tumor-associated antigens include, but are not limited by CD24, CD44, PROCR, ESA, CD176, CD175, CD175s, CD174, CD173 and CA19-9 antigens. In some embodiments, the determining step in b) and/or the isolation step in d) is carried out using FACS. In some embodiments, the level of expression of said one or more tumor-associated carbohydrate antigens is high or highly increased, when compared to control cells. In some embodiments, the level of expression of said one or more tumor-associated carbohydrate antigens is low or lowly increased, when compared to control cells.

In a fourth aspect, a method for diagnosing, staging and/or prognosing cancer and/or monitoring the susceptibility to treatment is provided, comprising the step of analyzing the expression of one or more tumor-associated carbohydrate antigens on cells in a sample isolated from a patient, wherein the presence of cells expressing the one or more tumor-associated carbohydrate antigens indicates the presence of cancer stem cells in said sample.

In another aspect, a kit for use in a method according to the present invention is provided, comprising a binding agent which specifically binds to one or more tumor-associated carbohydrate antigens and instructions for use in a method according to the present invention.

In another aspect, a method is provided for screening a candidate therapeutic agent, e.g. a chemotherapeutic agent or another anti-cancer drug, for effectiveness against a cancer comprising cells that express one or more tumor-associated carbohydrate antigens as described herein, the method comprising:
a. providing a cancer sample comprising cells that express one or more tumor-associated carbohydrate antigens,
b. contacting said agent with the cells, and
c. determining the effectiveness of said agent against said tumor-associated carbohydrate antigen positive cancer cells.

The present disclosure also relates to methods and compositions which can modulate the globoseries glycosphingolipid synthesis. Particularly, the present disclosure is directed to glycoenzyme inhibitor compound and compositions and methods of use thereof that can modulate the synthesis of globoseries glycosphingolipid SSEA-3/SSEA-4/GloboH in the biosynthetic pathway; particularly, the glycoenzyme inhibitors target the alpha-4GalT; beta-4Gal-NAcT-I; or beta-3GalT-V enzymes in the globoseries synthetic pathway. Additionally, the present disclosure is also directed to vaccines, antibodies, and/or immunogenic conjugate compositions targeting the SSEA-3/SSEA-4/Globo H associated epitopes (natural and modified) which can elicit antibodies and/or binding fragment production useful for modulating the globoseries glycosphingolipid synthesis. Moreover, the present disclosure is also directed to the method of using the compositions described herein for the treatment or detection of hyperproliferative diseases and/or conditions. In addition, the disclosure is also directed to cancer stem cell markers useful for selecting cancer stem cells (e.g. breast cancer) in diagnostic and/or therapeutic applications.

The present disclosure is also based on a surprising discovery is that the inhibition or silencing the galactosyl transferase (beta3GalT5) for the biosynthesis of SSEA3 abolishes the grow of cancer stem cell. This finding imply the stage-specific embryonic antigen SSEA-3 can serve as a target for development of therapeutics and vaccines. Moreover, the 3 enzymes alpha4GalT, beta4GalNAcT-I, and beta3GalT-V those involved in the biosynthesis of SSEA-3 can be targets for inhibitors development.

The present disclosure is also based on the discovery that the modification of the stage-specific embryonic antigens (SSEA3 and SSEA4) with certain groups disclosed herein elicited robust IgG antibody response to specifically recognize SSEA3 and SSEA4, respectively. The antibodies induced by an immunogenic composition comprising such unnatural glycan moiety are able to mediate the complement-dependent cell cytotoxicity against tumor cells.

Accordingly, the present invention features the design of antibodies against SSEA-3 for treating cancers. The present invention also features novel compounds consisting of the modified carbohydrate antigens (SSEA3, SSEA4), glycan conjugates comprising such, and immunogenic compositions and vaccines thereof.

Present disclosure provides inhibitor compound which modulates the globoseries synthetic pathway and optionally at least one pharmaceutically acceptable carrier for the treatment of a proliferative disease, especially a proliferative disease in which the globoseries pathway is concomitantly dysregulated; a pharmaceutical composition comprising such a composition; the use of such a composition for the preparation of a medicament for the treatment of a proliferative disease; a commercial package or product comprising such a preparation; and to a method of treatment of a warm-blooded animal, especially a human.

The present disclosure is based on a surprising discovery that the inhibition or silencing the glycoenzymes such as galactosyl transferase (β3GalT5), alpha-4GalT, and beta-4GalNAcT-I for the biosynthesis of SSEA3 abolishes the growth of cancer cells and cancer stem cell. This finding imply the stage-specific embryonic antigen SSEA-3 and/or SSEA4 and/or Globo-H can serve as a target for development of therapeutics and vaccines.

The present disclosure is also based on the discovery that the modification of the stage-specific embryonic antigens (SSEA3 and SSEA4) with certain groups disclosed herein elicited robust IgG antibody response to specifically recognize SSEA3 and SSEA4, respectively. The antibodies induced by an immunogenic composition comprising such unnatural glycan moiety are able to mediate the complement-dependent cell cytotoxicity against tumor cells.

Accordingly, the present invention features the design of antibodies against SSEA-3 and/or SSEA4 for treating cancers. The present invention also features novel compounds consisting of the modified carbohydrate antigens (SSEA3 and SSEA4), glycan conjugates comprising such, and immunogenic compositions and vaccines thereof.

In one aspect, the present invention provides a compound of formula (I):

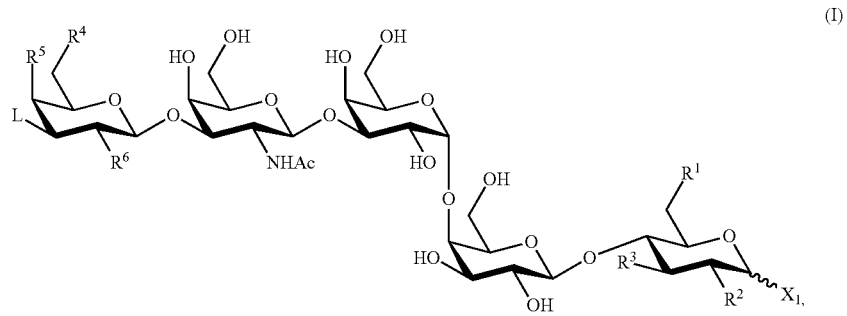

or a salt thereof, wherein $X_1$, $R^1$, $R^2$, $R^3$, $R^4$, $R^5$, $R^6$ and L are as described herein. In certain embodiments, a compound of Formula (I) is useful for making an immunogenic composition for treating cancers.

In another aspect, the present invention provides a compound of Formula (II):

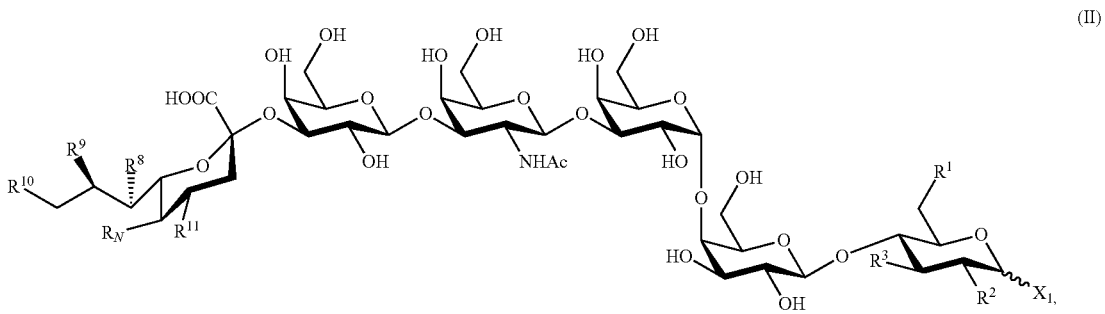

or a salt thereof, wherein $X_1$, $R^1$, $R^2$, $R^3$, $R^8$, $R^9$, $R^{10}$, $R^{11}$ and $R_N$ are as described herein. In certain embodiments, a compound of Formula (II) is useful for making an immunogenic composition for treating cancers.

In another aspect, the present invention provides an immunogenic composition, comprising (a) a glycan conjugate including a carrier and one or more glycans, and optionally (b) an adjuvant, wherein: each of the one or more glycans is conjugated with the carrier through a linker, having the formula (III) or (IV):

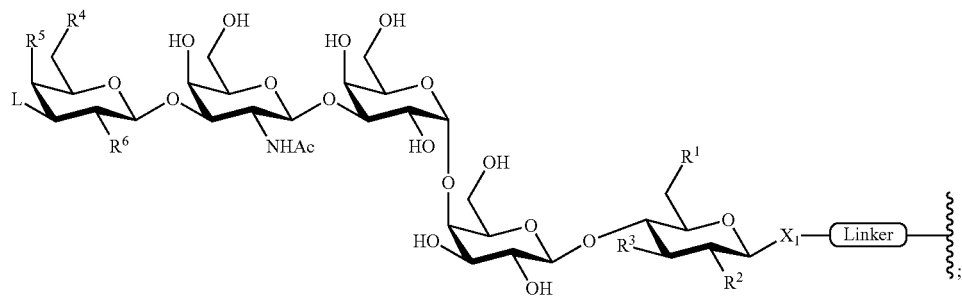

(III)

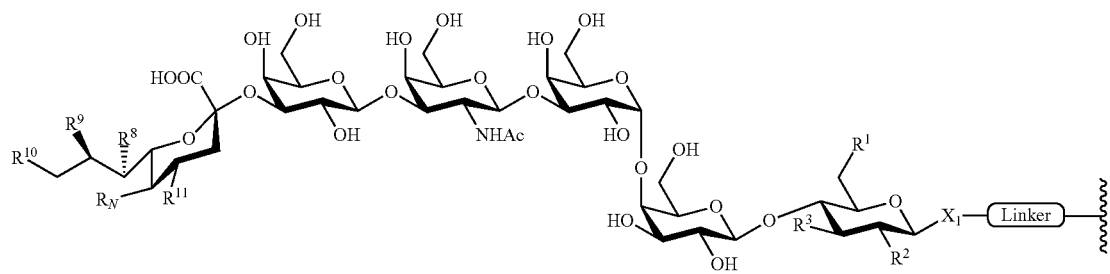

(IV)

wherein $X_1$, $R^1$, $R^2$, $R^3$, $R^4$, $R^5$, $R^6$, $R^8$, $R^9$, $R^{10}$, $R^{11}$, L and $R_N$ are as described herein.

In certain aspects, it is contemplated that any construct of vaccine containing a combination of any one or more of the three glycans (SSEA3, SSEA4 and Globo-H) and analogs thereof in any ratio can be linked to a carrier.

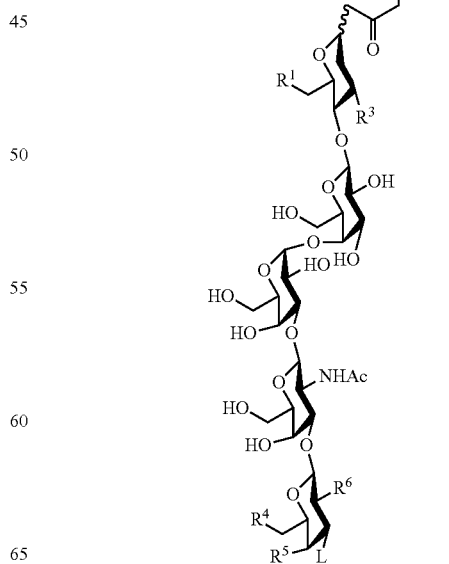

wherein n can be an integer from 1 to 10;

wherein Glycan can be selected from the group consisting of Formulas I, II, III, and IV;

wherein if n is 2 or more, each Glycan can be the same as another Glycan on the aspartyl peptide or a difference Glycan on the aspartyl peptide.

In some embodiments, Glycan can be selected from the group consisting of SSEA-3, SSEA-4, and Globo-5.

In some embodiments, the exemplary multivalent construct can be:

-continued

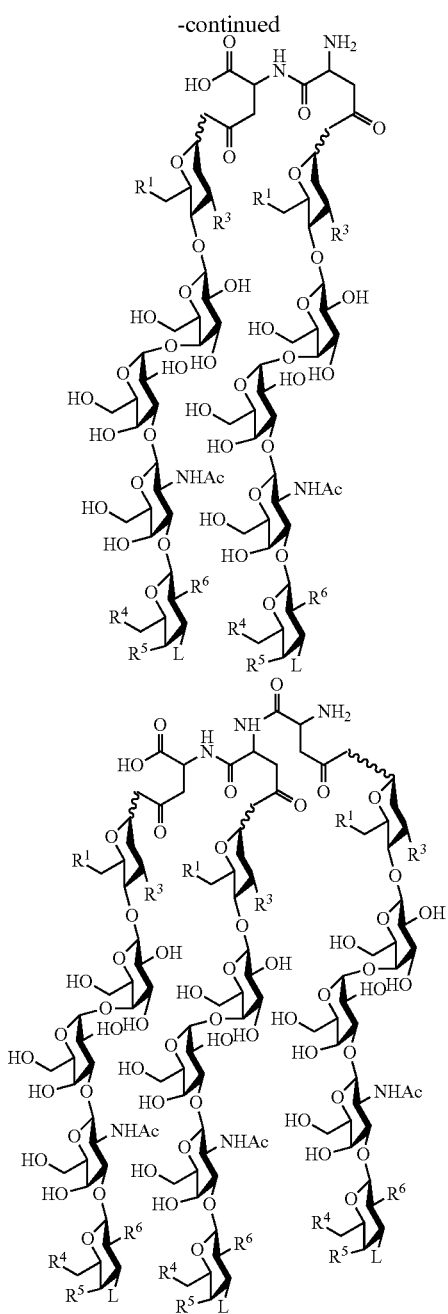

Wherein $R^1$, $R^2$, $R^3$, $R^4$, $R^5$, $R^6$, and L on each Glycan moiety can be the same or different.

In certain embodiments, the immunogenic composition of the invention comprises an adjuvant. Adjuvants suitable for the invention are as described herein.

In certain embodiments, the immunogenic composition is capable of eliciting an immune response against a cancer cell in a subject. In certain embodiments, the cancer cell is selected from the group consisting of a brain cancer cell, a lung cancer cell, a breast cancer cell, an oral cancer cell, an esophagus cancer cell, a stomach cancer cell, a liver cancer cell, a bile duct cancer cell, a pancreas cancer cell, a colon cancer cell, a kidney cancer cell, a bone cancer cell, a skin cancer cell, a cervix cancer cell, an ovary cancer cell, and a prostate cancer cell.

In certain embodiments, the immune response includes generation of antibodies that specifically bind to one or more of the antigens selected from the group consisting of Globo H, SSEA-3 and SSEA-4. In certain embodiments, the antibodies are developed to neutralize one or more of Globo H, SSEA-3 and SSEA-4 expressed on the surface of cancer cells or cancer stem cells. In certain embodiments, the antibodies predominantly include IgG antibodies. In certain embodiments, the immunogenic compositions provided herein mainly induce IgG1, IgG2b, IgG2c and IgG3.

Further, the present disclosure features monoclonal antibodies and binding fragments raised against the immunogenic composition described herein.

In one embodiment, the antibody is a human antibody.

In one embodiment, the antibody is a humanized antibody.

In one embodiment, the antibody is specifically targeted against one or more of SSEA4, SSEA3, or Globo-H.

In one embodiment, the antibody is specifically targeted against SSEA3.

In one embodiment, the antibody is specifically targeted against SSEA4.

In one embodiment, the antibody is a homogeneous antibody having the biantennary glycan terminated by two sialic acid in alpha-2,6-linkage.

In one aspect, the present disclosure provides a pharmaceutical composition comprising an effective amount of the antibody or antigen-binding fragment specifically targeted against one or more of SSEA4, SSEA3, or Globo-H and a pharmaceutically acceptable carrier In one embodiment, the pharmaceutical composition comprises a combination of antibodies and/or binding fragment thereof each independently targeting one or more of the SSEA4, SSEA3, or Globo-H glycans.

In one embodiment, the pharmaceutical composition is useful for the treatment of cancer, infectious diseases, and/or anti-inflammatory diseases, In one embodiment, the pharmaceutical composition comprises antibodies or binding fragments thereof having universal biantennary n-glycan terminated with sialic acid in alpha-2,6-linkage.

In another aspect, the present invention provides a cancer vaccine comprising an immunogenic composition described herein and a pharmaceutically acceptable excipient.

In another aspect, the present invention provides methods for treating and/or reducing the risk for cancer in a subject comprising administering to a subject in need thereof a therapeutically effective amount of an immunogenic composition or a cancer vaccine as described herein.

The treatment results in reduction of tumor size, elimination of malignant cells, prevention of metastasis, prevention of relapse, reduction or killing of disseminated cancer, prolongation of survival and/or prolongation of time to tumor cancer progression.

In some embodiments, the treatment further comprises administering an additional therapy to said subject prior to, during or subsequent to said administering of the immunogenic composition or the cancer vaccine described herein. In some embodiments, the additional therapy is treatment with a chemotherapeutic agent. In some embodiments, the additional therapy is radiation therapy.

Another aspect of the present disclosure features a method of vaccinating a mammal against cancers, comprising administering to the mammal a pharmacologically effective amount of an immunogenic composition or a cancer vaccine as described herein.

In some embodiments, the mammal is a human. In some embodiments, the immunogenic composition or the cancer vaccine described herein is administered subcutaneously.

Examples of the cancer include, but are not limited to, brain cancer, lung cancer, breast cancer, oral cancer, esophagus cancer, stomach cancer, liver cancer, bile duct cancer, pancreas cancer, colon cancer, kidney cancer, cervix cancer, ovary cancer and prostate cancer. In some embodiments, the cancer is brain cancer, lung cancer, breast cancer, ovarian cancer, prostate cancer, colon cancer, or pancreas cancer.

In another aspect, the present invention provides methods of synthesizing the compounds of the invention as described herein.

In yet another aspect, the present disclosure features the process for making an immunogenic composition or a cancer vaccine as described herein.

The details of certain embodiments of the invention are set forth herein. Other features, objects, and advantages of the invention will be apparent from the Detailed Description, the Figures, the Examples, and the Claims.

BRIEF DESCRIPTION OF THE DRAWINGS

FIG. 1A-F the tumorigenicity of cells carrying conventional markers and SSEA-3 was higher than other subpopulations. 1A, 1C Percentage of cell colony or mammosphere formation of the subpopulation isolated by selected marker (s) for suspension culture or soft agar assay in MCF-7 or MDA-MB-231 respectively. Graphs are the triple samples from one representative experiment. 1B, 1D The number of tumor formed in mammary gland of NS injected with selected marker-expressing cell subpopulations from breast cancer cell lines MDA-MB-231 and MCF-7. The corresponding limiting dilution assay was done in vivo. 1E, 1F The tumor volume from different subpopulations of MDA-MB-231 (2500 cells/injection), and MCF-7 (500 cells/injection) was monitored and compared (n=4 tumors per group). #the percentage of SSEA-3+ cells sorted in the total cell population. Data represent the mean and standard deviation (S.D.). Asterisks indicate statistical significance, $p<0.05$.

FIG. 2A-B Knockdown or overexpression of β3GalT5 in MCF-7 and MDA-MB-231 cell culture reduced or increased the level of SSEA-3 on cell surface and stemness properties by FACS analysis. The expression of cancer stem cell markers and SSEA-3 in parental cells. The level of SSEA-3 in subpopulations $CD44^+CD24^{-/lo}$ and $ESA^{hi} PROCR^{hi}$ gated in overexpressed β3GalT5 group was also determined. 2A The expression of CD24, CD44 and SSEA-3 in MCF-7 with overexpression, knocked down of β3GalT5 or their corresponding vector control. 2B The expression of ESA, PROCR and SSEA-3 in MDA-MB-231 with overexpression, knockdown down of beta-3GalT5 or their corresponding vector control. All of experiments are the representative sample from triplicate.

FIG. 9A-D (Fig. S4)—the characterization of iPSC5. 9A Immunofluorescent staining of stem cell proteins TRA1-60 and Nanog. Nuclei were stained with DAPI. 9B qPCR of stem genes OCT4, SOX2, NANOG and c-Myc. 9C in vitro differentiation capability of iPSC5 to three germ layer lineages. 9D H&E staining of iPSC5 to three germ layer lineages in teratoma.

DETAILED DESCRIPTIONS

Figure 1B:
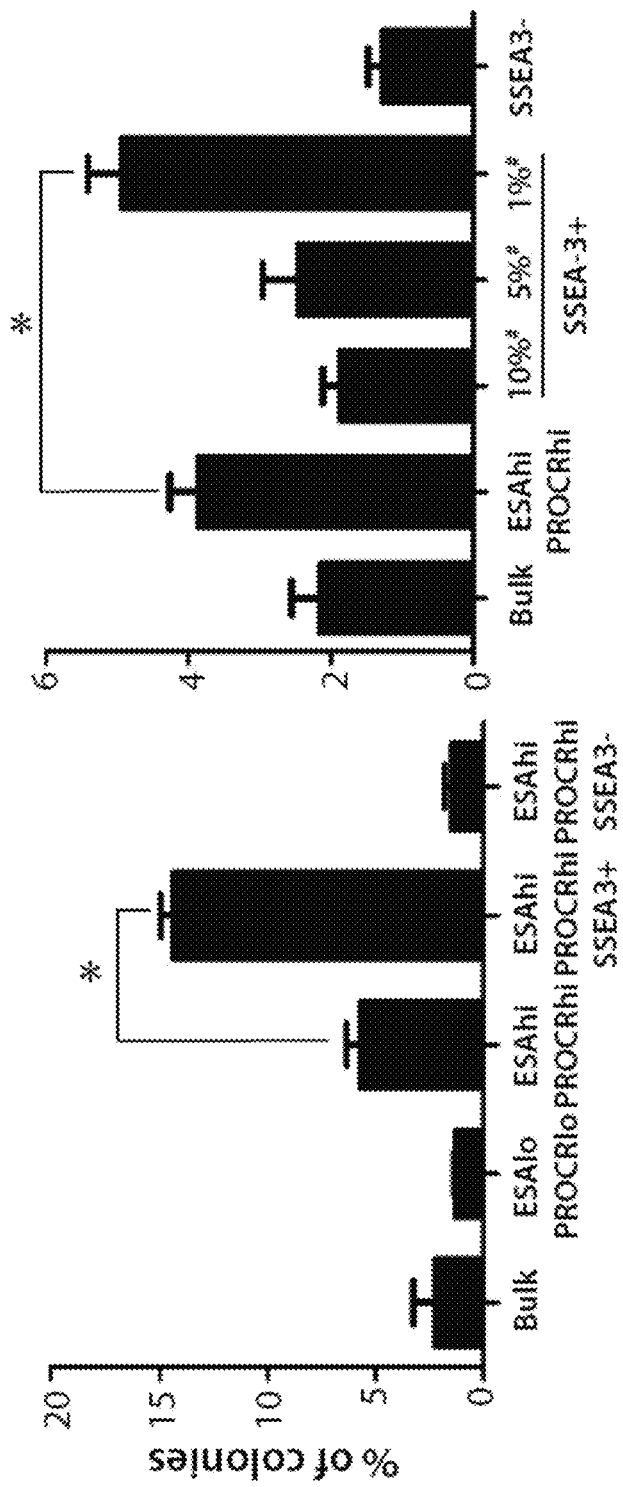

The present invention is based on the finding that tumor-associated carbohydrate antigens are suitable cancer stem cell markers.

The present disclosure is based on the surprising discovery that tumor-associated carbohydrate antigens are expressed on cancer stem cells. Thus, these tumor-associated carbohydrate antigens are suitable markers for cancer stem cells and furthermore, provide suitable therapeutic targets for a therapy that attacks cancer stem cells.

Both normal stem cells and tumorigenic cells have extensive proliferative potential and the ability to give rise to new (normal or abnormal) tissues. Tumorigenic cells can be thought of as cancer stem cells (CSC) or cancer initiating cells (CIC—the terms CSC and CIC are used as synonyms herein) that undergo an aberrant and poorly regulated process of organogenesis analogous to what normal stem cells do. Both tumors and normal tissues are composed of heterogeneous combinations of cells, with different phenotypic characteristics and different proliferative potentials.

Cancer stem cells are believed to be a certain fraction of tumor cells with stem cell-like properties, which initiate and maintain neoplastic clones. These cells have the ability to self-renew, but also give rise to progenitors that yield phenotypically diverse cancer cells but with lower tumorigenic potential. This subpopulation of stem cell-like cells are the ones that are efficient at tumor formation and metastatic tumor spread as compared to tumor cells that are not cancer stem cells.

Cancer stem cells (CSCs) have now been identified in a wide variety of cancers including leukemias, glioblastomas, medulloblastomas, and almost all types of epithelial tumors (carcinomas). Cancer stem cells can be characterized based on the investigation of distinct surface marker patterns within primary tumors. CD44 was reported as a robust marker of cancer stem cells. A single CD44+ cell from a colorectal tumor could form a sphere in vitro and was able to generate a xenograft tumor resembling the properties of the primary tumor. CD133 is also a marker of cancer stem cells.

The presence of cancer stem cells has profound implications for cancer therapy. Existing therapies have been developed largely against the bulk population of tumor cells, because the therapies are identified by their ability to shrink the tumor mass. However, cancer stem cells are often resistant to chemotherapy and can account for chemotherapy failure. To design novel therapeutic agents that (also) target cancer-initiating cells (also referred herein as cancer stem cells), it will be desirable to seek molecular targets of cancer stem cells that are preferably absent on benign tumors and/or normal non-tumor cells, and at the same time are specifically directed against cancer stem cells. Such agents are anticipated to result in more durable responses and cures of tumors, and especially of metastatic tumors. Therefore, new cancer stem cell markers are wanted to provide novel therapeutic targets to improve therapy. Most of the known stem-cell markers are proteins. Many of them have also been found to be normal stem cell markers and are thus expressed on non-tumor stem cells. This makes them not or at least less suitable as therapeutic target. At present, there is no clear cut distinction between normal and cancer stem cell markers.

A "binding agent" may be any compound or complex of compounds which is capable of binding a target substance such as a tumor-associated carbohydrate antigen and/or combination of carbohydrate and non-carbohydrate specific antigens, individually or in a combination (such as a panel). Preferably, the binding agent is capable of specifically binding the target substance. Suitable binding agents may be obtained by screening a binding agent library in order to identify/obtain binding agents that bind to the target substance. Examples for respective binding agent includes glycoantibodies. Such as antibodies against SSEA3, SSEA4, and/or globoH. The binding agents may have any structure, as long as they are able to specifically recognize and bind the target substance, here a tumor-associated carbohydrate antigen. Binding agents may be selected from the group consisting of antibodies, antigen-binding fragments or derivatives thereof or binding agents having a protein scaffold providing a binding function such as for example anticalins or lectins. Binding agents may also be peptides or fusion proteins providing a binding function. An overview of binding agents which have a similar binding function as antibodies is given in Hey, et al. (Hey et al. (2005) "Artificial, non-antibody binding proteins for pharmaceutical and industrial application", Trends in Biotechnology 23(10), 514-522). An antibody derivative also includes antibodies or antibody fragments having the same binding function but e.g. an altered amino acid sequence.

As used herein, exemplary binding agents targeting the SSEA3 marker is reported in U.S. Ser. No. 14/599,174, the contents of which is incorporated herein in its entirety.

According to the invention, "staging" of a cancer preferably refers to the classification of the progression and extent of a cancer. A preferred cancer staging system is the TNM classification of malignant tumors, wherein T describes the size of the tumor and whether it has invaded nearby tissue, N describes regional lymph nodes that are involved, and M describes distant metastasis. Each of these parameters is given a particular value depending on the situation in the patient, wherein generally a higher number indicates a more severe situation (T(0-4), N(0-3), M(0/1)). Additionally, for a more detailed classification further parameters can be determined and/or prefixes can be used. Furthermore, the TNM classification may be summarized in a cancer staging system according to the UICC, referring to cancer of from stage 0 to stage IV.

According to the invention, a "sample" in particular refers to but is not limited to a tissue sample, a body fluid and/or a cellular sample and may be obtained by conventional manners such as by tissue biopsy, including punch biopsy or by taking blood, bronchial aspirate, sputum, urine, feces or other body fluids or tissue sections, slides, etc. containing or suspected of containing cancer cells. According to the invention, the term "sample" also includes fractions or components of respective samples.

The terms "cell proliferation" and "to proliferate" as used herein in particular refer to the amplification of the cell by cell division. The term "cancer stem cells" in particular relates but is not limited to cells capable of generating aggregates of undifferentiated cells, so called tumor spheres, under suitable conditions in vitro. The cells that form spheres are capable of self-renewal; when they are dissociated and grown under the same conditions, they will form spheres again. In vivo, cancer stem cells are characterized by their potential to form metastases and the expression of stem cell markers such as, e.g., CD44. They may also provide drug resistance. The terms "cancer stem cells" and "cancer initiating cells" are used as synonyms herein.

The term "tumor-associated carbohydrate antigen" in particular refers to a carbohydrate antigen that is expressed on cancer and/or tumor cells, in particular on malignant cancer and/or malignant tumor cells.

The term "tumor-specific carbohydrate antigen" in particular refers to a carbohydrate antigen that is predominantly or even exclusively expressed on cancer and/or tumor cells and thus not or only to a low extent on non-cancer respectively non-tumor cells. Preferably, the term "tumor-specific carbohydrate antigen" refers to a carbohydrate antigen that is predominantly or preferably exclusively expressed on malignant cancer and/or malignant tumor cells and thus not or only to a low extent on non-cancer respectively non-tumor cells, on benign cancer and/or benign tumor cells and/or on healthy tissue of the same patient. Preferentially, the tumor-specific carbohydrate antigen is not expressed on most normal cells, even more preferred it is expressed only on few normal cells or cell types, even more preferred the expression on these normal cells has a special localization, e.g. strictly apical or in between the tight junctions, so that a binding molecule administered systemically, and especially i.v., can not or barely reach the antigen on these normal cells, even more preferred it is not expressed on normal epithelial cells, most preferred it is not expressed on normal cells. In certain embodiments, the tumor-specific carbohydrate antigen may be attached to a carrier molecule when expressed. Such carrier molecule may in particular be a protein, peptide or carbohydrate.

"CD44" is an adherence molecule (H-CAM, Pgp-1) of varying molecular weight. It is a cell surface hyaluronan receptor, interacts with matrix metalloproteinases, and plays a key role in cell migration. CD44 has been described as a cancer stem cell marker in breast, ovarian, pancreatic, prostate, colon, gastric, and other cancer types (see Li et al, 2007, and Takaishi et al, 2009). It is also a marker of normal pluripotent stem cells.

The present inventors have shown that several tumor-associated antigens such as CD24, CD44, SSEA3, PROCR, ESA are expressed on cancer stem cells and thus, are novel cancer stem cell markers. The identification of tumor-associated carbohydrate antigens as cancer stem cell markers provides novel therapeutic applications for agents specifically binding to one or more of said tumor-associated carbohydrate antigens. Agents specifically binding to one or more respective tumor-associated carbohydrate antigen can now be therapeutically used for targeting cancer stem cells that express said tumor-associated carbohydrate antigen. This provides the opportunity of therapeutic treatments that target and preferably kill cancer stem cells. The respective therapeutic agents can for example be used to target and thus destroy cancer stem cells which are resistant to regular chemotherapy. Thereby, improved cancer therapies are provided with the present invention. According to one embodiment, the tumor-associated carbohydrate antigen is expressed predominantly or even exclusively on breast cancer stem cells. According to another embodiment, the tumor-associated carbohydrate antigen is expressed on the cancer stem cells as well as on cancer cells that are not cancer stem cells. If the tumor-associated carbohydrate antigen is expressed on both cell populations, this has the advantage that treatment with the binding agent specifically binding the tumor-associated carbohydrate antigen targets both cell populations.

According to one embodiment, the binding agent specifically binding to the one or more tumor-associated carbohydrate antigens is therapeutically active. One example of a respective embodiment is the use of a therapeutically active antibody or antigen-binding fragment or derivative thereof as binding agent. A therapeutically active antibody or antigen-binding fragment or derivative thereof preferably is capable of inducing complement-dependent cytotoxicity (CDC) and/or antibody-dependent cellular cytotoxicity (ADCC), which preferably results in lysis of the target cell, in particular the cancer stem cell expressing the tumor-associated carbohydrate antigen. According to a further embodiment, the binding agent specifically binding the tumor-associated carbohydrate antigen functions as a targeting molecule and is coupled to at least one therapeutic agent. Coupling can be achieved by covalent or non-covalent means. When the binding agent specifically binding the tumor-associated carbohydrate antigen functions as a targeting molecule, it can be itself therapeutically active or it may not be therapeutically active. In case it is not therapeutically active, it basically functions as a molecular carrier which brings the actual therapeutic agent (e.g. a radiopharmaceutical, chemotherapeutic agent or a toxin) to the desired target side of action, namely the cancer stem cells expressing the tumor-associated carbohydrate antigen. The therapeutic agent coupled to the binding agent specifically binding the tumor-associated carbohydrate antigen can be for example a chemotherapeutic agent or other anti-cancer drug. Said coupled therapeutic agent preferably destroys or kills the targeted cancer stem cells or inhibits proliferation thereof. This can either be achieved directly by the coupled therapeutic agent or indirectly via induction of suitable biological mechanisms of the targeted cancer stem cells and/or of the subject to be treated.

In certain embodiments, the tumor-associated carbohydrate antigen as described herein can be further combined with any one or more of the markers selected from the group consisting of CD24, CD44, PROCR, ESA, CD176, CD175, CD175s, CD174, CD173 and CA19-9.

According to a further aspect of the present invention, a method is provided for identifying a cancer comprising cancer stem cells that is susceptible to treatment with a binding agent that specifically binds a tumor-associated carbohydrate antigen wherein said treatment effects the cancer stem cells, comprising determining whether a cancer sample obtained from a patient comprises cancer stem cells that express the tumor-associated carbohydrate antigen the binding agent is specific for, wherein the presence of said tumor-associated carbohydrate antigen on cancer stem cells indicates that the cancer is susceptible to treatment with the binding agent that specifically binds a tumor-associated carbohydrate antigen and wherein said treatment also effects the cancer stem cells.

This method according to the present invention allows to test whether the cancer stem cells of a cancer are susceptible to treatment with a binding agent that specifically binds a tumor-associated carbohydrate antigen. The results of the method provide valuable diagnostic information to the physician. E.g. in case the cancer would comprise cancer stem cells which do not express said tumor-associated carbohydrate antigen, treatment with a binding agent specifically binding said tumor-associated carbohydrate antigen would not affect the cancer stem cells and accordingly, would be useless against the cancer stem cells. However, in case it is shown by said method that the cancer stem cells express said tumor-associated carbohydrate antigen the binding agent is specific for, chances are good that treatment with said binding agent will also target and accordingly affect the cancer stem cells. Thus, the method according to the present invention provides valuable aid to the physician for choosing the best therapy for the patient and to estimate whether a certain treatment will affect the cancer stem cells of a cancer.

According to a related diagnostic aspect, a method is provided for diagnosing, staging and/or prognosing cancer and/or monitoring the susceptibility to treatment, comprising the step of analyzing the expression of a tumor-associated carbohydrate antigen on cells in a sample isolated from a patient, wherein the presence of cells expressing the tumor-associated carbohydrate antigen indicates the presence of cancer stem cells in said sample.

According to a further aspect of the present invention, a method is provided for identifying a population of cancer stem cells, the method comprising: a) providing a starting population of cancer cells, b) determining the expression level of one or more tumor-associated carbohydrate antigens, c) selecting a population of cells whose expression level of said one or more tumor-associated carbohydrate antigens as determined in step b) is increased when compared to control cells, wherein said selected population of cells are cancer stem cells and d) optionally isolating and/or enriching for said population of cells selected in step c), wherein said control cells are cells from the same starting cancer cell population which do not express, or express lower levels of said one or more tumor-associated carbohydrate antigens. In some embodiments, the tumor-associated carbohydrate antigens are selected from the list consisting of SSEA3, SSEA4, and GloboH antigens. In some embodiments, the determining step in b) further includes determining the expression level of one or more additional tumor associated antigens, and the selection and isolating steps in c) and d), respectively, also includes consideration of the expression level of said one or more additional tumor associated antigens. In some embodiments, the one or more tumor-associated antigens include, but are not limited by CD24, CD44, PROCR, ESA, CD176, CD175, CD175s, CD174, CD173 and CA19-9 antigens. In some embodiments, the determining step in b) and/or the isolation step in d) is carried out using FACS. In some embodiments, the level of expression of said one or more tumor-associated carbohydrate antigens is high or highly increased, when compared to control cells. In some embodiments, the level of expression of said one or more tumor-associated carbohydrate antigens is low or lowly increased, when compared to control cells.

The presence of cancer stem cells in a patient sample can be indicative of the stage of a cancer. In addition, detection of cancer stem cells can be used to monitor response to therapy and to aid in prognosis. The information obtained by the methods according to the present invention is useful in prognosis and diagnosis, including analysing the susceptibility to acceleration of the disease, the analysis by active monitoring of the disease wherein it is analysed whether the cancer progresses and e.g. needs treatment, the status of a disease state, the response to changes in the environment, such as the passage of time, the treatment with a chosen therapeutic agent, in particular a binding agent as described above, or other modalities. By analysing whether cells contained in the sample express a tumor-associated carbohydrate antigen and accordingly, the sample comprises cancer stem cells, the cells can also be classified as to their ability to respond to therapeutic agents and treatments. Furthermore, the information derived is useful in determining and/or predicting the metastatic behavior of a cancer.

According to one aspect of the diagnostic methods according to the present invention, the binding agents according to the present invention which specifically bind to one or more tumor-associated carbohydrate antigens expressed on cancer stem cells are used for in vivo diagnostic, in particular in vivo imaging. A respective method is also useful for diagnostic purposes. E.g. it can be determined, whether cancer cells expressing the tumor-associated carbohydrate antigen expressed on cancer stem cells can be identified and/or located in the patient. If this is the case, there is a risk that there are cancer stem cells. As is described above and below, it is preferred that a second stem cell marker is additionally detected to confirm and/or determine the nature of the cancer stem cells. Furthermore, the response to therapy can be monitored as it can be determined e.g. whether the tumor size decreases or whether metases develop. Furthermore, a respective method is advantageous to identify the suitable dosage for a patient. According to one embodiment, the binding agent is labelled, e.g. being a radiopharmaceutical comprising a radionuclide. However, the binding agent may also be coupled to other agents/compounds such as e.g. a PET tracer that allow in vivo imaging. Suitable compounds are known in the prior art and thus, do not need further description here. Details regarding the binding agents, the tumor-associated carbohydrate antigens, further cancer stem cell markers and cancer types are described above and below and also apply to the in vivo imaging embodiment. It is referred to the respective disclosure.

According to one embodiment, samples, containing or suspected of containing cancer cells, are contacted and preferably stained with at least one agent specifically binding the tumor-associated, preferably tumor-specific carbohydrate antigen and thus the carbohydrate cancer stem cell marker and optionally at least one further agent specifically binding at least one second cancer stem cell marker, such as CD44. This allows to detect the presence of cancer stem cells in the sample. According to one embodiment, binding of the binding agent against the tumor-associated carbohydrate antigen and preferably the binding of the binding agent against the second cancer stem cell marker is detected by appropriate detection methods as known in the art and as described herein. Suitable detection methods are for example ELISA, FACS, fluorescence microscopy and the like.

Samples to be analysed by the methods of the invention may be obtained from a variety of sources, particularly from a biopsy sample. Cells of such samples can be separated by centrifugation, elutriation, density gradient separation, apheresis, affinity selection, panning, FACS, centrifugation with Hypaque, etc. prior to analysis. Once a sample is obtained, it can be used directly, frozen, or maintained in appropriate culture medium for short periods of time, or fixed in a suited fixation solution, or fixed and embedded in a medium suited for histoligigal or immunohistological examination. Various media can be employed to maintain cells. The samples may be obtained by any convenient procedure, such as biopsy, or from surgical specimen. Usually a sample will comprise at least about $10^2$ cells, more usually at least about $10^3$ cells, and preferable $10^4$, $10^5$ or more cells. In one embodiment, the sample comprises 10 cells. In one embodiment, the sample comprises any number of cells between 10 and 100 cells. In one embodiment, the sample comprises any number of cells between 10 and 1000 cells. In one embodiment, the sample comprises any number of cells between 1 and 10 cells. Typically the samples will be from human patients, although animal models may find use, e.g. equine, bovine, porcine, canine, feline, rodent, e.g. mice, rats, hamster, primate, etc.

The samples may be frozen, embedded, fixed, present in a tissue microarray, and the like. The agents used for binding, detecting and in particular staining the tumor-associated carbohydrate antigen and, optionally, a further cancer stem cell marker can be e.g. binding agents specifically binding the cancer stem cell markers such as e.g. antibodies. Suitable examples are described above. These agents may be detectably labelled, or may be indirectly labelled in the staining procedure. According to one embodiment, the label can also be used for separating the tumor-associated carbohydrate antigen positive cells. Suitable labels as well as staining procedures are known in the prior art and accordingly, do not need further description here even though some examples are described herein. A standard procedure for analysis may include a histological fixation of the sample (e.g. by formalin) and subsequent staining as is e.g. described in the examples. The obtained data allows to determine the number and distribution of cancer stem cells in the sample.

Methods suitable for detecting and/or quantifying cells expressing the tumor-associated carbohydrate antigen include, for example, immunologic assays such ELISA, RIA, Western blot and immunohistochemistry, flow cytometry, immunohistochemistry or the like.

In screening assays for candidate therapeutic agents usually a culture comprising cancer stem cells expressing the tumor-associated carbohydrate antigen of interest is contacted with the binding agent of interest, and the effect of the agent assessed by monitoring output parameters, such as expression of markers, cell viability, and the like. The screening may also involve determining modulation of growth, proliferation, viability, and/or differentiation status of the cell in the presence of the candidate therapeutic agent as compared to the growth, proliferation, viability, and/or differentiation status of the cell in the absence of the candidate therapeutic agent.

Isolated cell populations that are highly enriched for cancer stem cells expressing one or more tumor-associated carbohydrate antigens can be isolated and enriched/purified using these markers. In some embodiments, said cancer stem cell populations are isolated from the circulation, such as from the blood. In some embodiments, said cancer stem cell populations are isolated from the a tumor sample, or from pleural effusions or other fluids obtained from a cancer patient.

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. Moreover, exemplary glycan and antibody methodologies are described in Wong et al, US20100136042, US20090317837, and US20140051127, the disclosures of each of which are hereby incorporated by reference.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In certain embodiments, the heteroatom is independently selected from nitrogen, sulfur, and oxygen. In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

Alkyl, alkenyl, alkynyl, carbocyclyl, heterocyclyl, aryl, and heteroaryl groups, as defined herein, which are divalent bridging groups are further referred to using the suffix—ene, e.g., alkylene, alkenylene, alkynylene, carbocyclylene, heterocyclylene, arylene, and heteroarylene.

The term "alkoxy" or "alkyloxy" refers to an —O-alkyl radical, wherein alkyl is optionally substituted alkyl as defined herein. Examples of alkoxy include, but are not limited to, methoxy, ethoxy, n-propoxy, isopropoxy, n-butoxy, iso-butoxy, sec-butoxy, and tert-butoxy.

The term "aryloxy" refers to an —O-aryl, wherein aryl is optionally substituted aryl as defined herein.

As used herein, the term "optionally substituted" refers to a substituted or unsubstituted moiety.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of —C(=O)$R^{aa}$, —CHO, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —C(=O)N$R^{bb}$SO$_2R^{aa}$, —C(=S)N($R^{bb}$)$_2$, —C(=O)S$R^{aa}$, and —C(=S)S$R^{aa}$, wherein $R^{aa}$ and $R^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on an oxygen atom is an oxygen protecting group (also referred to as a hydroxyl protecting group). Oxygen protecting groups include, but are not limited to, —$R^{aa}$, —N($R^{bb}$)$_2$, —C(=O) S$R^{aa}$, —C(=O)$R^{aa}$, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —SO$_2R^{aa}$, —Si($R^{aa}$)$_3$, —P($R^{cc}$)$_2$, —P($R^{cc}$)$_3$, —P(=O)$_2R^{aa}$, —P(=O)($R^{aa}$)$_2$, —P(=O) (O$R^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. Oxygen protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenyl selenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris (levulinoyloxyphenyl)methyl, 4,4',4''-tris (benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2- methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Other Definitions

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Antibodies: A Laboratory Manual, by Harlow and Lane s (Cold Spring Harbor Laboratory Press, 1988); and Handbook Of Experimental Immunology, Volumes I-IV (D. M. Weir and C. C. Blackwell, eds., 1986).

As used herein, the term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of O-glycosidic linkages between monosaccharides. For example, cellulose is a glycan (or more specifically a glucan) composed of β-1,4-linked D-glucose, and chitin is a glycan composed of β-1,4-linked N-acetyl-D-glucosamine. Glycans can be homo or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes. N-Linked glycans are found attached to the R-group nitrogen (N) of asparagine in the sequon. The sequon is a Asn-X-Ser or Asn-X-Thr sequence, where X is any amino acid except praline.

As used herein, the term "antigen" is defined as any substance capable of eliciting an immune response.

As used herein, the term "immunogenicity" refers to the ability of an immunogen, antigen, or vaccine to stimulate an immune response.

As used herein, the term "CD1d" refers to a member of the CD1 (cluster of differentiation 1) family of glycoproteins expressed on the surface of various human antigen-presenting cells. CD1d presented lipid antigens activate natural killer T cells. CD1d has a deep antigen-binding groove into which glycolipid antigens bind. CD1d molecules expressed on dendritic cells can bind and present glycolipids, including α-GalCer analogs such as C34.

As used herein, the term "epitope" is defined as the parts of an antigen molecule which contact the antigen binding site of an antibody or a T cell receptor.

As used herein, the term "vaccine" refers to a preparation that contains an antigen, consisting of whole disease-causing organisms (killed or weakened) or components of such organisms, such as proteins, peptides, or polysaccharides, that is used to confer immunity against the disease that the organisms cause. Vaccine preparations can be natural, synthetic or derived by recombinant DNA technology.

As used herein, the term "antigen specific" refers to a property of a cell population such that supply of a particular antigen, or a fragment of the antigen, results in specific cell proliferation.

As used herein, the term "specifically binding," refers to the interaction between binding pairs (e.g., an antibody and an antigen). In various instances, specifically binding can be embodied by an affinity constant of about $10^{-6}$ moles/liter, about $10^{-7}$ moles/liter, or about $10^{-8}$ moles/liter, or less.

As used herein, the term "Flow cytometry" or "FACS" means a technique for examining the physical and chemical properties of particles or cells suspended in a stream of fluid, through optical and electronic detection devices.

As used herein, the terms glycoenzymes refers to at least in part the enzymes in the globoseries biosynthetic pathway; exemplary glycoenzymes include alpha-4GalT; beta-4GalNAcT-I; or beta-3GalT-V enzymes.

Figure 1E:
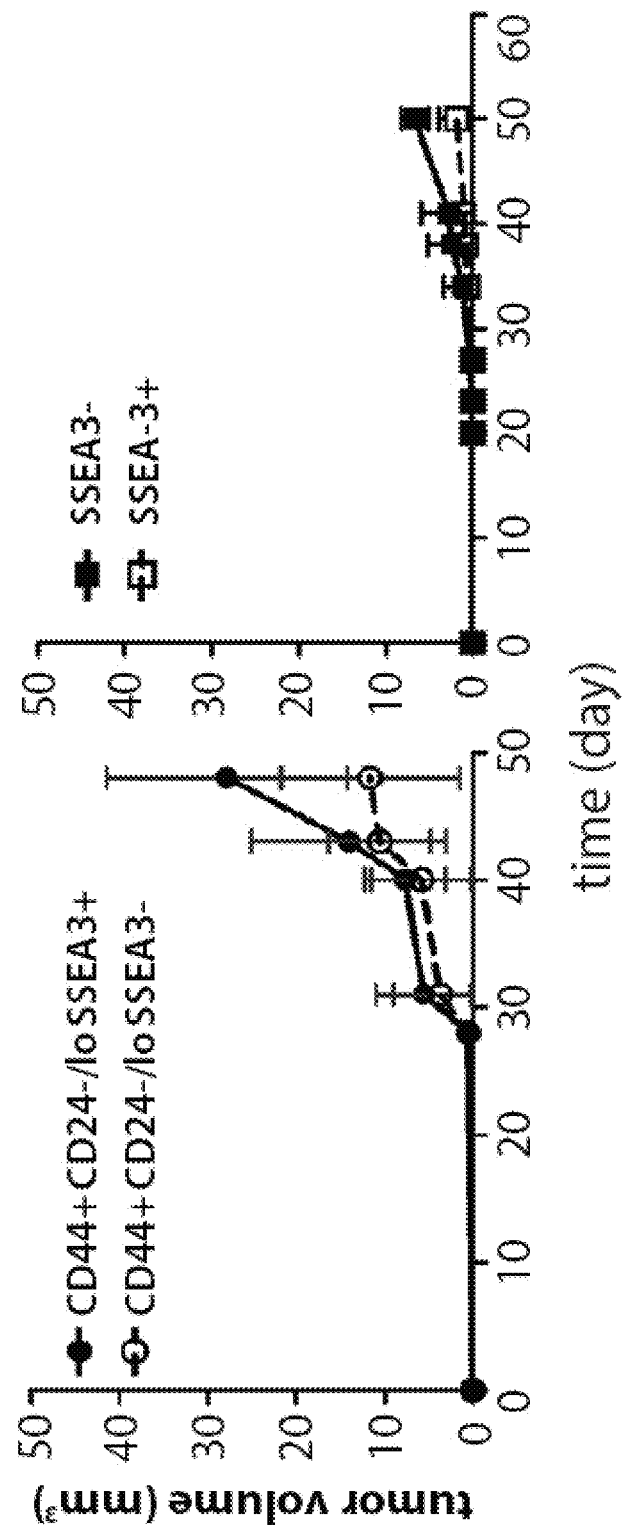
Figure 1F:
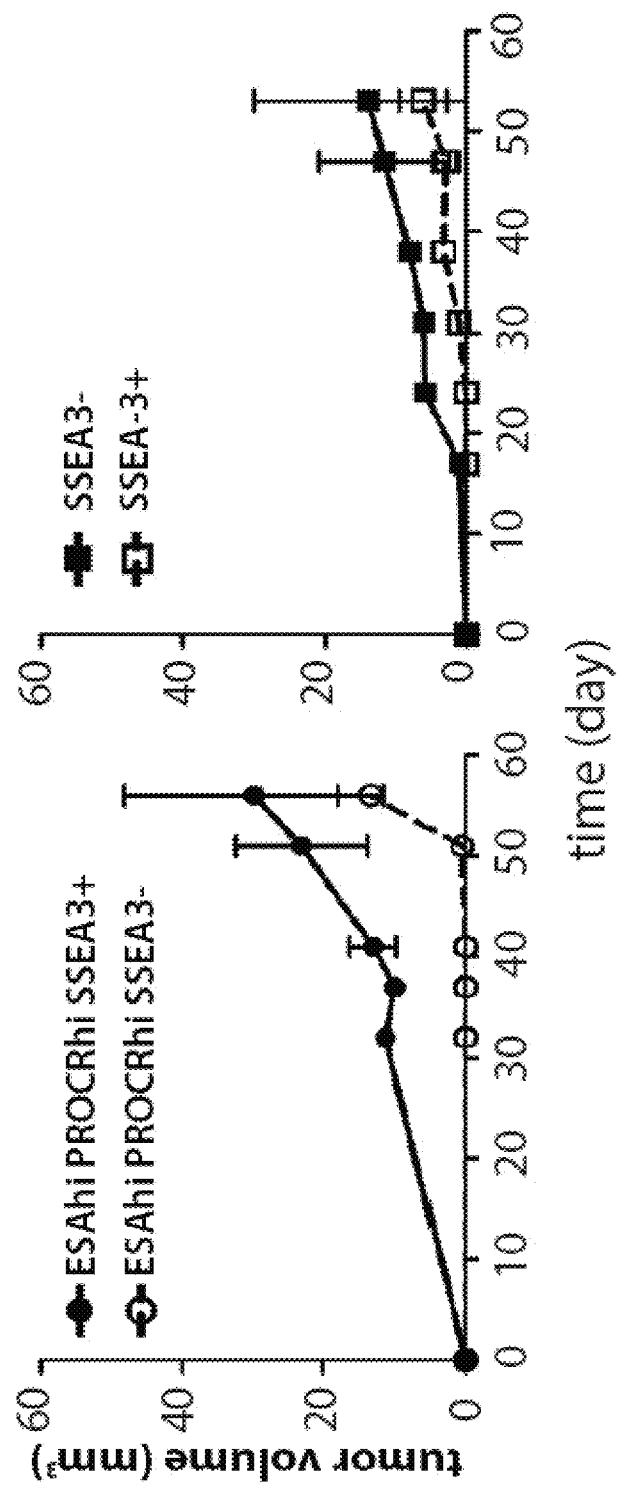

As used herein, the term "globoseries pathway" refers to a biochemical pathway described in FIG. 1.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In one embodiment, the antibody will be purified (1) to greater than 95% by weight of antibody as determined by, for example, the Lowry method, and in some embodiments more than 99% by weight, (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

The phrase "substantially similar," "substantially the same", "equivalent", or "substantially equivalent", as used herein, denotes a sufficiently high degree of similarity between two numeric values (for example, one associated with a molecule and the other associated with a reference/comparator molecule) such that one of skill in the art would consider the difference between the two values to be of little or no biological and/or statistical significance within the context of the biological characteristic measured by said values (e.g., Kd values, anti-viral effects, etc.). The difference between said two values is, for example, less than about 50%, less than about 40%, less than about 30%, less than about 20%, and/or less than about 10% as a function of the value for the reference/comparator molecule.

The phrase "substantially reduced," or "substantially different", as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of (125I)-labeled antigen in the presence of a titration series of unlabeled antigen, then capturing bound antigen with an anti-Fab antibody-coated plate (Chen, et al., (1999) J. Mol Biol 293:865-881). To establish conditions for the assay, microtiter plates (Dynex) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [125I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 µl/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. In each experiment, a spot was activated and ethanolamine blocked without immobilizing protein, to be used for reference subtraction. For kinetics measurements, two-fold serial dilutions of Fab (0.78 nM to 500 nM) are injected in PBS with 0.05% Tween 20 (PBST) at 25° C. at a flow rate of approximately 25 µl/min. Association rates (kon) and dissociation rates (koff) are calculated using a simple one-to-one Langmuir binding model (BIAcore Evaluation Software version 3.2) by simultaneously fitting the association and dissociation sensorgrams. The equilibrium dissociation constant (Kd) is calculated as the ratio koff/kon. See, e.g., Chen, Y., et al., (1999) J. Mol Biol 293:865-881. If the on-rate exceeds 106 M–1s–1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette.

An "on-rate" or "rate of association" or "association rate" or "kon" according to this invention can also be determined with the same surface plasmon resonance technique described above using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 µl/min. Association rates (kon) and dissociation rates (koff) are calculated using a simple one-to-one Langmuir binding model (BIAcore Evaluation Software version 3.2) by simultaneously fitting the association and dissociation sensorgram. The equilibrium dissociation constant (Kd) was calculated as the ratio koff/kon. See, e.g., Chen, Y., et al., (1999) J. Mol Biol 293:865-881. However, if the on-rate exceeds 106 M-1s-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent, multivalent antibodies, multi specific antibodies (e.g., bispecific antibodies so long as they exhibit the desired biological activity) and may also include certain antibody fragments (as described in greater detail herein). An antibody can be chimeric, human, humanized and/or affinity matured.

The "variable region" or "variable domain" of an antibody refers to the amino-terminal domains of heavy or light chain of the antibody. These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably, to refer to an antibody in its substantially intact form, not antibody fragments as defined below. The terms particularly refer to an antibody with heavy chains that contain the Fc region.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise an antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256: 495 (1975); Harlow et al., Antibodies: A Laboratory Manual, (Cold Spring Harbor Laboratory Press, 2nd ed. 1988); Hammerling et al., in: Monoclonal Antibodies and T-Cell hybridomas 563-681 (Elsevier, N.Y., 1981)), recombinant DNA methods (see, e.g., U.S. Pat. No. 4,816,567), phage display technologies (See, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996) and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

Loop Kabat AbM Chothia Contact
L1 L24-L34 L24-L34 L26-L32 L30-L36
L2 L50-L56 L50-L56 L50-L52 L46-L55
L3 L89-L97 L89-L97 L91-L96 L89-L96
H1 H31-H35B H26-H35B H26-H32 H30-H35B
(Kabat Numbering)
H1 H31-H35 H26-H35 H26-H32 H30-H35
(Chothia Numbering)
H2 H50-H65 H50-H58 H53-H55 H47-H58
H3 H95-H102 H95-H102 H96-H101 H93-H101

Hypervariable regions may comprise "extended hypervariable regions" as follows: 24-36 or 24-34 (L1), 46-56 or 50-56 or 49-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the hypervariable region residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO93/11161; and Hollinger et al., Proc. Natl. Acad. Sci. USA 90: 6444-6448 (1993).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

A "blocking" antibody or an "antagonist" antibody is one which inhibits or reduces biological activity of the antigen it binds. Certain blocking antibodies or antagonist antibodies substantially or completely inhibit the biological activity of the antigen.

An "agonist antibody", as used herein, is an antibody which mimics at least one of the functional activities of a polypeptide of interest.

A "disorder" is any condition that would benefit from treatment with an antibody of the invention. This includes chronic and acute disorders or diseases including those pathological conditions which predispose the mammal to the disorder in question. Non-limiting examples of disorders to be treated herein include cancer.

The terms "cell proliferative disorder" and "proliferative disorder" refer to disorders that are associated with some degree of abnormal cell proliferation. In one embodiment, the cell proliferative disorder is cancer.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "muscular disorder" refers to or describes the physiological condition in muscle-containing animals that is typically characterized by deterioration or weakening of skeletal and/or smooth muscle such that normal muscular function is significantly reduced. Examples of muscular disorders include, but are not limited to, muscular dystrophy, multiple sclerosis, amyotrophic lateral sclerosis, Isaac's syndrome; stiff-person syndrome; familiar periodic paralyses, myopathy, myotonia, rhabdomyolyses, muscle atrophy, and various types of muscle weakness and muscle rigidity.

The term "globoseries-related disorder" refers to or describes a disorder that is typically characterized by or contributed to by aberrant functioning or presentation of the pathway. Examples of such disorders include, but are not limited to, hyperproliferative diseases, including cancer.

The terms "neurological disorder" or "neurological disease" refer to or describe a disease or disorder of the central and/or peripheral nervous system in mammals that is typically characterized by deterioration of nervous tissue or deterioration of communication between cells in nervous tissue. Examples of neurological disorders include, but are not limited to, neurodegenerative diseases (including, but not limited to, Lewy body disease, postpoliomyelitis syndrome, Shy-Draeger syndrome, olivopontocerebellar atrophy, Parkinson's disease, multiple system atrophy, striatonigral degeneration, tauopathies (including, but not limited to, Alzheimer disease and supranuclear palsy), prion diseases (including, but not limited to, bovine spongiform encephalopathy, scrapie, Creutzfeldt-Jakob syndrome, kuru, Gerstmann-Straussler-Scheinker disease, chronic wasting disease, and fatal familial insomnia), bulbar palsy, motor neuron disease, and nervous system heterodegenerative disorders (including, but not limited to, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome), dementia (including, but not limited to, Pick's disease, and spinocerebellar ataxia.

The terms "inflammatory disorder" and "immune disorder" refer to or describe disorders caused by aberrant immunologic mechanisms and/or aberrant cytokine signaling. Examples of inflammatory and immune disorders include, but are not limited to, autoimmune diseases, immunologic deficiency syndromes, and hypersensitivity. An "autoimmune disease" herein is a non-malignant disease or disorder arising from and directed against an individual's own tissues. The autoimmune diseases herein specifically exclude malignant or cancerous diseases or conditions, especially excluding B cell lymphoma, acute lymphoblastic leukemia (ALL), chronic lymphocytic leukemia (CLL), Hairy cell leukemia and chronic myeloblastic leukemia. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE) (including but not limited to lupus nephritis, cutaneous lupus); diabetes mellitus (e.g. Type I diabetes mellitus or insulin dependent diabetes mellitus); multiple sclerosis; Reynaud's syndrome; autoimmune thyroiditis; Hashimoto's thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies;

Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia, etc.

Examples of immunologic deficiency syndromes include, but are not limited to, ataxia telangiectasia, leukocyte-adhesion deficiency syndrome, lymphopenia, dysgammaglobulinemia, HIV or deltaretrovirus infections, common variable immunodeficiency, severe combined immunodeficiency, phagocyte bactericidal dysfunction, agammaglobulinemia, DiGeorge syndrome, and Wiskott-Aldrich syndrome. Examples of hypersensitivity include, but are not limited to, allergies, asthma, dermatitis, hives, anaphylaxis, Wissler's syndrome, and thrombocytopenic purpura.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing or decreasing inflammation and/or tissue/organ damage, decreasing the rate of disease progression, amelioration or palliation of the disease state, and remission or improved prognosis. In some embodiments, antibodies of the invention are used to delay development of a disease or disorder.

An "individual" or a "subject" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, the vertebrate is a human.

"Mammal" for purposes of treatment refers to any animal classified as a mammal, including humans, domestic and farm animals, and zoo, sports, or pet animals, such as dogs, horses, cats, cows, etc. In certain embodiments, the mammal is human.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

The term "cytotoxic agent" as used herein refers to a substance that inhibits or prevents the function of cells and/or causes destruction of cells. The term is intended to include radioactive isotopes (e.g., At211, I131, I125, Y90, Re186, Re188, Sm153, Bi212, P32, Pb212 and radioactive isotopes of Lu), chemotherapeutic agents (e.g., methotrexate, adriamicin, *vinca* alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.);

razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Most recently, Wong et al 25 attempts to improve the immunogenicity of the vaccine, the research team synthesized a variety of GH-derivatives containing modifications at either the reducing end or at the non-reducing end of the carbohydrate, and found that vaccines containing GH modified with a fluoro, azido, or phenyl group at the reducing end or an azido group at the non-reducing end could stimulate the production of GH, SSEA3, and SSEA4-targeting antibodies, with the latter vaccine eliciting an especially favorable high ratio of IgG:IgM antibodies not usually achieved in anticancer vaccines. Encouragingly, the antibodies produced in response to these vaccines mediated complement-dependent cytotoxicity towards cultured GH-positive human breast cancer cells.

The present disclosure is based on the surprising discovery that the modification of the stage-specific embryonic antigens (SSEA3 and SSEA4) with certain groups elicited robust IgG antibody response to specifically recognize SSEA3 and SSEA4, respectively.

In some examples, the modification of SSEA-3 comprises a fluoro, an azido or an O-phenyl group at the one or more positions of the glucose of SSEA-3. In some examples, the modification of SSEA-3 comprises a fluoro, an azido or an O-phenyl group at the one or more positions of the non-reducing end galactose. In some examples, the modification of SSEA-4 comprises a fluoro, an azido or an O-phenyl group at one or more positions of the glucose of SSEA-4. In some examples, the modification of SSEA-4 comprises a fluoro, an azido or an O-phenyl group at one or more positions of the sialic acid residue.

Described herein are SSEA3 and SSEA4 derivatives having the modification at the reducing and/or non-reducing end. Such SSEA3 and SSEA4 derivatives can elicit a stronger immune response (e.g., induction of IgG antibodies against SSEA3 and/or SSEA4) as compared to the native SSEA3 and SSEA4. The antibodies induced by an immunogenic composition comprising such unnatural glycan moiety are able to mediate the complement-dependent cell cytotoxicity against tumor cells.

Compounds

Accordingly, the present invention also features novel compounds consisting of the modified carbohydrate antigens (SSEA3 and SSEA4), glycan conjugates comprising such, and immunogenic compositions and vaccines thereof.

In one aspect, the present invention provides a compound of formula (I):

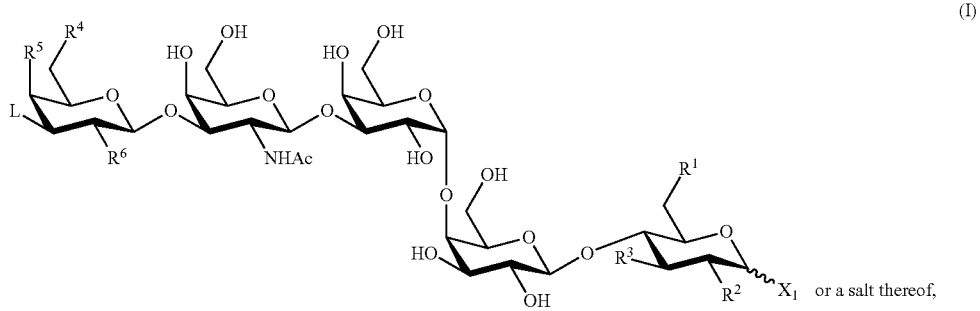

or a salt thereof, wherein:

$X_1$ is —OR or —SR, wherein R is hydrogen, a oxygen or sulfur protecting group, optionally substituted $C_{1-10}$ alkyl, optionally substituted aryl, optionally substituted acyl, or optionally substituted imidoyl;

each instance of $R^1$, $R^2$, $R^3$, $R^4$, $R^5$, $R^6$ and L is independently selected from hydrogen, halogen, optionally substituted alkyl, optionally substituted alkenyl, optionally substituted alkynyl, optionally substituted heterocyclyl, optionally substituted aryl, —$N_3$, —$NO_2$, —$N(R^B)_2$, —$N(R^A)C(O)R^A$, —$OR^A$, —$OC(O)R^A$, —$SR^A$, —$C(O)N(R^B)_2$, —CN, —$C(O)R^A$, —$C(O)OR^A$, —$S(O)R^A$, —$SO_2R^A$, —$SO_2N(R^B)_2$, and —$NHSO_2R^B$;

each instance of $R^A$ is independently selected from hydrogen, optionally substituted alkyl, optionally substituted alkenyl, optionally substituted alkynyl, optionally substituted heterocyclyl, and optionally substituted aryl;

each instance of $R^B$ is independently selected from hydrogen, optionally substituted alkyl, optionally substituted alkenyl, optionally substituted alkynyl, optionally substituted heterocyclyl, and optionally substituted aryl; and provided the compound is not of the formula:

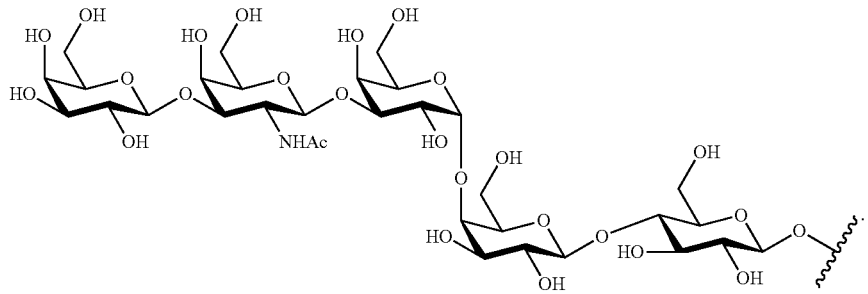

In certain embodiments, $X_1$ is in the alpha configuration. In certain embodiments, $X_1$ is in the beta configuration.

In some embodiments, $X_1$ is —$OR^A$. In some embodiments, $X_1$ is —OH. In some embodiments, $X_1$ is —O (protecting group). In some embodiments, $X_1$ is —$OR^A$, wherein $R^A$ is unsubstituted $C_{1-10}$ alkyl. In some embodiments, $X_1$ is —$OR^A$, wherein $R^A$ is substituted $C_{1-10}$ alkyl. In some embodiments, $X_1$ is —$OR^A$, wherein $R^A$ is unsubstituted aryl. In some embodiments, $X_1$ is —$OR^A$, wherein $R^A$ is substituted aryl. In some embodiments, $X_1$ is —$OR^A$, wherein $R^A$ is unsubstituted acyl. In some embodiments, $X_1$ is —$OR^A$, wherein $R^A$ is substituted acyl. In some embodiments, $X_1$ is —$OR^A$, wherein $R^A$ is unsubstituted imidoyl. In some embodiments, $X_1$ is —$OR^A$, wherein $R^A$ is substituted imidoyl.

In some embodiments, $X_1$ is —$SR^A$. In some embodiments, $X_1$ is —SH. In some embodiments, $X_1$ is —S (protecting group). In some embodiments, $X_1$ is —$SR^A$, wherein $R^A$ is unsubstituted $C_{1-10}$ alkyl. In some embodiments, $X_1$ is —$SR^A$, wherein $R^A$ is substituted $C_{1-10}$ alkyl. In certain embodiments, $X_1$ is —$SCH_3$. In some embodiments, $X_1$ is —$SR^A$, wherein $R^A$ is unsubstituted aryl. In some embodiments, $X_1$ is —$SR^A$, wherein $R^A$ is substituted aryl. In some embodiments, $X_1$ is —$SR^A$, wherein $R^A$ is unsubstituted acyl. In some embodiments, $X_1$ is —$SR^A$, wherein $R^A$ is substituted acyl. In some embodiments, $X_1$ is —$SR^A$, wherein $R^A$ is unsubstituted imidoyl. In some embodiments, $X_1$ is —$SR^A$, wherein $R^A$ is substituted imidoyl.

In some embodiments, $X_1$ is $C_{1-10}$ alkoxy. In some embodiments, $X_1$ is $C_{1-3}$ alkoxy. In certain embodiments, $X_1$ is methoxy. In certain embodiments, $X_1$ is alpha-methoxy.

In some embodiments, $X_1$ is selected from the group consisting of alpha-thiomethyl, beta-thiomethyl, alpha-thiocresyl, beta-thiocresyl, alpha-t-butyldiphenylsilyloxy, beta-t-butyldiphenylsilyloxy, and alpha-methoxy.

In some embodiments, $R^1$ is —$N_3$ or —$N(R^W)_2$, wherein each $R^W$ is independently hydrogen or a nitrogen protecting group. In certain embodiments, $R^1$ is —$N_3$. In certain embodiments, $R^1$ is —$N(R^W)_2$, wherein each $R^W$ is independently hydrogen or a nitrogen protecting group. In certain embodiments, $R^1$ is —$NH_2$. In certain embodiments, $R^1$ is —$NHR^W$, wherein $R^W$ is a nitrogen protecting group. In certain embodiments, $R^1$ is —$N(R^W)_2$, wherein each $R^W$ is a nitrogen protecting group. In certain embodiments, $R^1$ is selected from the group consisting of —$N_3$, —NH(Cbz), —NH(Boc), —NH(Fmoc), —NHC(O)CCl$_3$, —NHC(O)CH$_3$, and —N(C(O)CH$_3$)$_2$. In certain embodiments, R$^1$ is —NH(Cbz). In certain embodiments, R$^1$ is —NH(Fmoc). In certain embodiments, R$^1$ is —NHC(O)CCl$_3$. In certain embodiments, R$^1$ is —NHC(O)CH$_3$. In certain embodiments, R$^1$ is —N(C(O)CH$_3$)$_2$.

In some embodiments, R$^2$ is —N$_3$ or —N(R$^W$)$_2$, wherein each R$^W$ is independently hydrogen or a nitrogen protecting group. In certain embodiments, R$^2$ is —N$_3$. In certain embodiments, R$^2$ is —N(R$^W$)$_2$, wherein each R$^W$ is independently hydrogen or a nitrogen protecting group. In certain embodiments, R$^2$ is —NH$_2$. In certain embodiments, R$^2$ is —NHR$^W$, wherein R$^W$ is a nitrogen protecting group. In certain embodiments, R$^2$ is —N(R$^W$)$_2$, wherein each R$^W$ is a nitrogen protecting group. In certain embodiments, R$^2$ is selected from the group consisting of —N$_3$, —NH(Cbz), —NH(Boc), —NH(Fmoc), —NHC(O)CCl$_3$, —NHC(O)CH$_3$, and —N(C(O)CH$_3$)$_2$. In certain embodiments, R$^2$ is —NH(Cbz). In certain embodiments, R$^2$ is —NH(Fmoc). In certain embodiments, R$^2$ is —NHC(O)CCl$_3$. In certain embodiments, R$^2$ is —NHC(O)CH$_3$. In certain embodiments, R$^2$ is —N(C(O)CH$_3$)$_2$.

In some embodiments, R$^3$ is —N$_3$ or —N(R$^W$)$_2$, wherein each R$^W$ is independently hydrogen or a nitrogen protecting group. In certain embodiments, R$^3$ is —N$_3$. In certain embodiments, R$^3$ is —N(R$^W$)$_2$, wherein each R$^W$ is independently hydrogen or a nitrogen protecting group. In certain embodiments, R$^3$ is —NH$_2$. In certain embodiments, R$^3$ is —NHR$^W$, wherein R$^W$ is a nitrogen protecting group. In certain embodiments, R$^3$ is —N(R$^W$)$_2$, wherein each R$^W$ is a nitrogen protecting group. In certain embodiments, R$^3$ is selected from the group consisting of —N$_3$, —NH(Cbz), —NH(Boc), —NH(Fmoc), —NHC(O)CCl$_3$, —NHC(O)CH$_3$, and —N(C(O)CH$_3$)$_2$. In certain embodiments, R$^3$ is —NH(Cbz). In certain embodiments, R$^3$ is —NH(Fmoc). In certain embodiments, R$^3$ is —NHC(O)CCl$_3$. In certain embodiments, R$^3$ is —NHC(O)CH$_3$. In certain embodiments, R$^3$ is —N(C(O)CH$_3$)$_2$.

In some embodiments, R$^4$ is —N$_3$ or —N(R$^W$)$_2$, wherein each R$^W$ is independently hydrogen or a nitrogen protecting group. In certain embodiments, R$^4$ is —N$_3$. In certain embodiments, R$^4$ is —N(R$^W$)$_2$, wherein each R$^W$ is independently hydrogen or a nitrogen protecting group. In certain embodiments, R$^4$ is —NH$_2$. In certain embodiments, R$^4$ is —NHR$^W$, wherein R$^W$ is a nitrogen protecting group. In certain embodiments, R$^4$ is —N(R$^W$)$_2$, wherein each R$^W$ is a nitrogen protecting group. In certain embodiments, R$^4$ is selected from the group consisting of —N$_3$, —NH(Cbz), —NH(Boc), —NH(Fmoc), —NHC(O)CCl$_3$, —NHC(O)CH$_3$, and —N(C(O)CH$_3$)$_2$. In certain embodiments, R$^4$ is —NH(Cbz). In certain embodiments, R$^4$ is —NH(Fmoc). In certain embodiments, R$^4$ is —NHC(O)CCl$_3$. In certain embodiments, R$^4$ is —NHC(O)CH$_3$. In certain embodiments, R$^4$ is —N(C(O)CH$_3$)$_2$.

In some embodiments, R$^5$ is —N$_3$ or —N(R$^W$)$_2$, wherein each R$^W$ is independently hydrogen or a nitrogen protecting group. In certain embodiments, R$^5$ is —N$_3$. In certain embodiments, R$^5$ is —N(R$^W$)$_2$, wherein each R$^W$ is independently hydrogen or a nitrogen protecting group. In certain embodiments, R$^5$ is —NH$_2$. In certain embodiments, R$^5$ is —NHR$^W$, wherein R$^W$ is a nitrogen protecting group. In certain embodiments, R$^5$ is —N(R$^W$)$_2$, wherein each R$^W$ is a nitrogen protecting group. In certain embodiments, R$^5$ is selected from the group consisting of —N$_3$, —NH(Cbz), —NH(Boc), —NH(Fmoc), —NHC(O)CCl$_3$, —NHC(O)CH$_3$, and —N(C(O)CH$_3$)$_2$. In certain embodiments, R$^5$ is —NH(Cbz). In certain embodiments, R$^5$ is —NH(Fmoc). In certain embodiments, R$^5$ is —NHC(O)CCl$_3$. In certain embodiments, R$^5$ is —NHC(O)CH$_3$. In certain embodiments, R$^5$ is —N(C(O)CH$_3$)$_2$.

In some embodiments, R$^6$ is —N$_3$ or —N(R$^W$)$_2$, wherein each R$^W$ is independently hydrogen or a nitrogen protecting group. In certain embodiments, R$^6$ is —N$_3$. In certain embodiments, R$^6$ is —N(R$^W$)$_2$, wherein each R$^W$ is independently hydrogen or a nitrogen protecting group. In certain embodiments, R$^6$ is —NH$_2$. In certain embodiments, R$^6$ is —NHR$^W$, wherein R$^W$ is a nitrogen protecting group. In certain embodiments, R$^6$ is —N(R$^W$)$_2$, wherein each R$^W$ is a nitrogen protecting group. In certain embodiments, R$^6$ is selected from the group consisting of —N$_3$, —NH(Cbz), —NH(Boc), —NH(Fmoc), —NHC(O)CCl$_3$, —NHC(O)CH$_3$, and —N(C(O)CH$_3$)$_2$. In certain embodiments, R$^6$ is —NH(Cbz). In certain embodiments, R$^6$ is —NH(Fmoc). In certain embodiments, R$^6$ is —NHC(O)CCl$_3$. In certain embodiments, R$^6$ is —NHC(O)CH$_3$. In certain embodiments, R$^6$ is —N(C(O)CH$_3$)$_2$.

In some embodiments, R$^1$, R$^2$ and R$^3$ are the same. In some embodiments, R$^1$, R$^2$ and R$^3$ are —OH. In some embodiments, R$^4$, R$^5$ and R$^6$ are the same. In some embodiments, R$^4$, R$^5$ and R$^6$ are —OH.

In certain embodiments, L is —OH.
In certain embodiments, L is —OH and R$^1$ is —N$_3$. In certain embodiments, L is —OH, R$^1$ is —N$_3$, and each instance of R$^2$, R$^3$, R$^4$, R$^5$ and R$^6$ is —OH.
In certain embodiments, L is —OH and R$^2$ is —N$_3$. In certain embodiments, L is —OH, R$^2$ is —N$_3$, and each instance of R$^1$, R$^3$, R$^4$, R$^5$ and R$^6$ is —OH.
In certain embodiments, L is —OH and R$^3$ is —N$_3$. In certain embodiments, L is —OH, R$^3$ is —N$_3$, and each instance of R$^1$, R$^2$, R$^4$, R$^5$ and R$^6$ is —OH.
In certain embodiments, L is —OH and R$^4$ is —N$_3$. In certain embodiments, L is —OH, R$^4$ is —N$_3$, and each instance of R$^1$, R$^2$, R$^3$, R$^5$ and R$^6$ is —OH.
In certain embodiments, L is —OH and R$^5$ is —N$_3$. In certain embodiments, L is —OH, R$^5$ is —N$_3$, and each instance of R$^1$, R$^2$, R$^3$, R$^4$ and R$^6$ is —OH.
In certain embodiments, L is —OH and R$^6$ is —N$_3$. In certain embodiments, L is —OH, R$^6$ is —N$_3$, and each instance of R$^1$, R$^2$, R$^3$, R$^4$ and R$^5$ is —OH.

In certain embodiments, each instance of R$^1$, R$^2$, R$^3$, R$^4$, R$^5$, R$^6$ and L is —F. In certain embodiments, R$^1$ is —F. In certain embodiments, R$^2$ is —F. In certain embodiments, R$^3$ is —F. In certain embodiments, R$^4$ is —F. In certain embodiments, R$^5$ is —F. In certain embodiments, R$^6$ is —F. In certain embodiments, L is —F.

In certain embodiments, L is of the following structure:

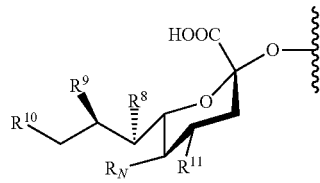

wherein:
each instance of R$^8$, R$^9$, R$^{10}$ and R$^{11}$ is independently selected from hydrogen, halogen, optionally substituted alkyl, optionally substituted alkenyl, optionally substituted alkynyl, optionally substituted heterocyclyl, optionally substituted aryl, —N$_3$, —NO$_2$, —N(R$^B$)$_2$, —N(R$^A$)C(O)R$^A$, —OR$^A$, —OC(O)R$^A$, —SR$^A$, —C(O)N(R$^B$)$_2$, —CN, —C(O)R$^A$, —C(O)OR$^A$, —S(O)R$^A$, —SO$_2$R$^A$, —SO$_2$N(R$^B$)$_2$, and —NHSO$_2$R$^B$;

R$_N$ is selected from —N$_3$, —NO$_2$, —N(R$^B$)$_2$, —N(R$^A$)C(O)R$^A$, —OR$^A$, —OC(O)R$^A$, —SR$^A$, —C(O)N(R$^B$)$_2$, —CN, —C(O)R$^A$, —C(O)OR$^A$, —S(O)R$^A$, —SO$_2$R$^A$, —SO$_2$N(R$^B$)$_2$, and —NHSO$_2$R$^B$;

each instance of R$^A$ is independently selected from hydrogen, optionally substituted alkyl, optionally substituted alkenyl, optionally substituted alkynyl, optionally substituted heterocyclyl, and optionally substituted aryl; and each instance of R$^B$ is independently selected from hydrogen, optionally substituted alkyl, optionally substituted alkenyl, optionally substituted alkynyl, optionally substituted heterocyclyl, and optionally substituted aryl.

In some embodiments, the compound is of Formula (II)

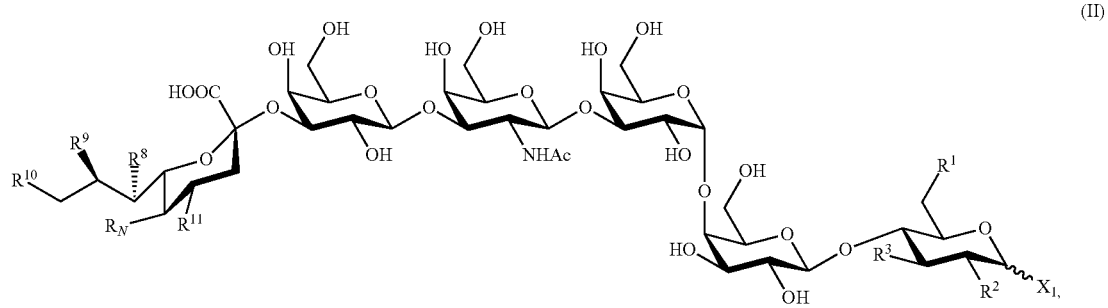

(II)

wherein: R$^1$, R$^2$, R$^3$, R$^8$, R$^9$, R$^{10}$, R$^{11}$ and R$_N$ and X$_1$ are as described herein, and provided the compound is not of the formula:

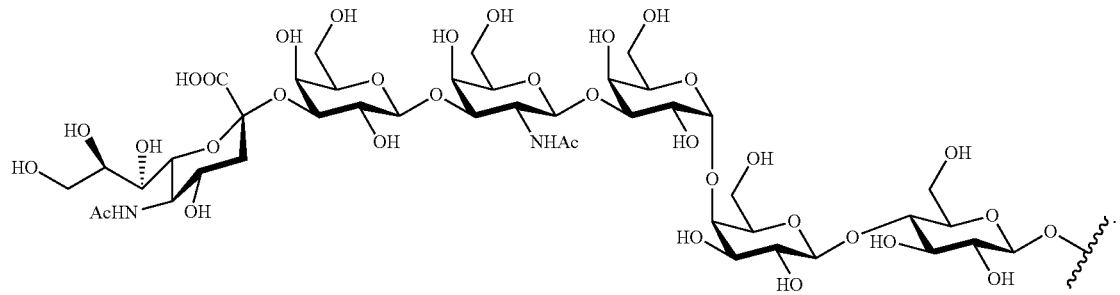

In some embodiments, R$^8$ is —N$_3$ or —N(R$^W$)$_2$, wherein each R$^W$ is independently hydrogen or a nitrogen protecting group. In certain embodiments, R$^8$ is —N$_3$. In certain embodiments, R$^8$ is —N(R$^W$)$_2$, wherein each R$^W$ is independently hydrogen or a nitrogen protecting group. In certain embodiments, R$^8$ is —NH$_2$. In certain embodiments, R$^8$ is —NHR$^W$, wherein R$^W$ is a nitrogen protecting group. In certain embodiments, R$^8$ is —N(R$^W$)$_2$, wherein each R$^W$ is a nitrogen protecting group. In certain embodiments, R$^8$ is selected from the group consisting of —N$_3$, —NH(Cbz), —NH(Boc), —NH(Fmoc), —NHC(O)CCl$_3$, —NHC(O)CH$_3$, and —N(C(O)CH$_3$)$_2$. In certain embodiments, R$^8$ is —NH(Cbz). In certain embodiments, R$^8$ is —NH(Fmoc). In certain embodiments, R$^8$ is —NHC(O)CCl$_3$. In certain embodiments, R$^8$ is —NHC(O)CH$_3$. In certain embodiments, R$^8$ is —N(C(O)CH$_3$)$_2$.

In some embodiments, R$^9$ is —N$_3$ or —N(R$^W$)$_2$, wherein each R$^W$ is independently hydrogen or a nitrogen protecting group. In certain embodiments, R$^9$ is —N$_3$. In certain embodiments, R$^9$ is —N(R$^W$)$_2$, wherein each R$^W$ is independently hydrogen or a nitrogen protecting group. In certain embodiments, R$^9$ is —NH$_2$. In certain embodiments, R$^9$ is —NHR$^W$, wherein R$^W$ is a nitrogen protecting group. In certain embodiments, R$^9$ is —N(R$^W$)$_2$, wherein each R$^W$ is a nitrogen protecting group. In certain embodiments, R$^9$ is selected from the group consisting of —N$_3$, —NH(Cbz), —NH(Boc), —NH(Fmoc), —NHC(O)CCl$_3$, —NHC(O)CH$_3$, and —N(C(O)CH$_3$)$_2$. In certain embodiments, R$^9$ is —NH(Cbz). In certain embodiments, R$^9$ is —NH(Fmoc). In certain embodiments, R$^9$ is —NHC(O)CCl$_3$. In certain embodiments, R$^9$ is —NHC(O)CH$_3$. In certain embodiments, R$^9$ is —N(C(O)CH$_3$)$_2$.

In some embodiments, R$^{10}$ is —N$_3$ or —N(R$^W$)$_2$, wherein each R$^W$ is independently hydrogen or a nitrogen protecting group. In certain embodiments, R$^{10}$ is —N$_3$. In certain embodiments, R$^{10}$ is —N(R$^W$)$_2$, wherein each R$^W$ is independently hydrogen or a nitrogen protecting group. In certain embodiments, R$^{10}$ is —NH$_2$. In certain embodiments, R$^{10}$ is —NHR$^W$, wherein R$^W$ is a nitrogen protecting group. In certain embodiments, R$^{10}$ is —N(R$^W$)$_2$, wherein each R$^W$ is a nitrogen protecting group. In certain embodiments, R$^{10}$ is selected from the group consisting of —N$_3$, —NH(Cbz), —NH(Boc), —NH(Fmoc), —NHC(O)CCl$_3$, —NHC(O)CH$_3$, and —N(C(O)CH$_3$)$_2$. In certain embodiments, R$^{10}$ is —NH(Cbz). In certain embodiments, R$^{10}$ is —NH(Fmoc). In certain embodiments, R$^{10}$ is —NHC(O)CCl$_3$. In certain embodiments, R$^{10}$ is —NHC(O)CH$_3$. In certain embodiments, R$^{10}$ is —N(C(O)CH$_3$)$_2$.

In some embodiments, R$^{11}$ is —N$_3$ or —N(R$^W$)$_2$, wherein each R$^W$ is independently hydrogen or a nitrogen protecting group. In certain embodiments, R$^{11}$ is —N$_3$. In certain embodiments, R$^{11}$ is —N(R$^W$)$_2$, wherein each R$^W$ is independently hydrogen or a nitrogen protecting group. In certain embodiments, R$^{11}$ is —NH$_2$. In certain embodiments, $R^{11}$ is —NHR$^W$, wherein R$^W$ is a nitrogen protecting group. In certain embodiments, $R^{11}$ is —N(R$^W$)$_2$, wherein each R$^W$ is a nitrogen protecting group. In certain embodiments, $R^{11}$ is selected from the group consisting of —N$_3$, —NH(Cbz), —NH(Boc), —NH(Fmoc), —NHC(O)CCl$_3$, —NHC(O)CH$_3$, and —N(C(O)CH$_3$)$_2$. In certain embodiments, $R^{11}$ is —NH(Cbz). In certain embodiments, $R^{11}$ is —NH(Fmoc). In certain embodiments, is —NHC(O)CCl$_3$. In certain embodiments, $R^{11}$ is —NHC(O)CH$_3$. In certain embodiments, $R^{11}$ is —N(C(O)CH$_3$)$_2$.

certain embodiments, $R_N$ is —NHC(O)CCl$_3$. In certain embodiments, $R_N$ is —NHC(O)CH$_3$. In certain embodiments, $R_N$ is —N(C(O)CH$_3$)$_2$.

Immunogenic Compositions

In another aspect, the present invention provides an immunogenic composition, comprising (a) a glycan conjugate including a carrier and one or more glycans, and optionally (b) an adjuvant, wherein: each of the one or more glycans is conjugated with the carrier through a linker, having the formula (III) or (IV):

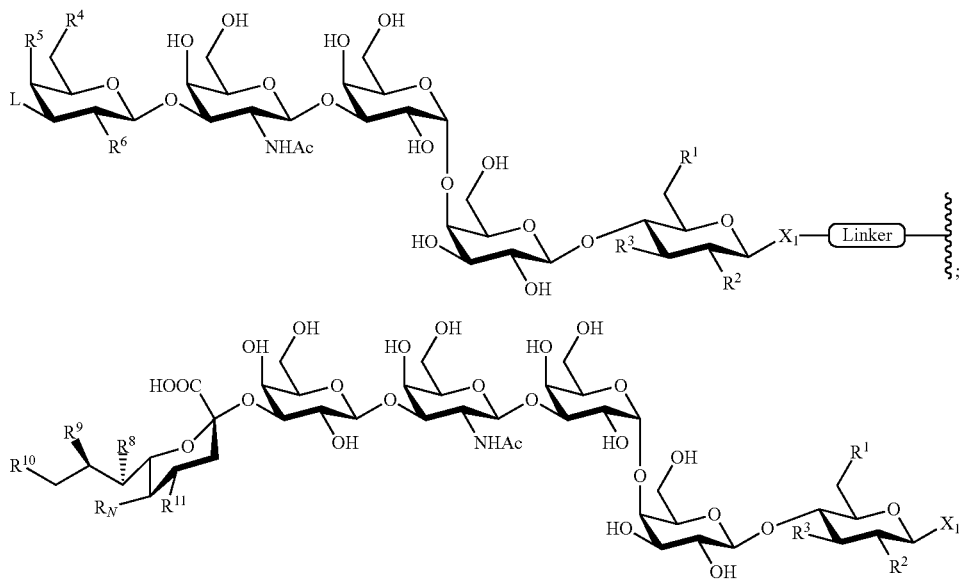

wherein $X_1$, $R^1$, $R^2$, $R^3$, $R^4$, $R^5$, $R^6$, $R^8$, $R^9$, $R^{10}$, $R^{11}$, and $R_N$ are as described herein.

In certain embodiments, the linker is a hetero- or homo-bifunctional linker.

In certain embodiments, the linker includes at least one sulfur atom, carboxylate group, amide group, carbamate group, carbonate group, thiocarbamate group, thiocarbonate group, thioether group, succinamide group, n-hydroxy succinamide group, or any combination thereof.

In some embodiments, $R^{12}$ is —N$_3$ or —N(R$^W$)$_2$, wherein each R$^W$ is independently hydrogen or a nitrogen protecting group. In certain embodiments, $R^{12}$ is —N$_3$. In certain embodiments, $R^{12}$ is —N(R$^W$)$_2$, wherein each R$^W$ is independently hydrogen or a nitrogen protecting group. In certain embodiments, $R^{12}$ is —NH$_2$. In certain embodiments, $R^{12}$ is —NHR$^W$, wherein R$^W$ is a nitrogen protecting group. In certain embodiments, $R^{12}$ is —N(R$^W$)$_2$, wherein each R$^W$ is a nitrogen protecting group. In certain embodiments, $R^{12}$ is selected from the group consisting of —N$_3$, —NH(Cbz), —NH(Boc), —NH(Fmoc), —NHC(O)CCl$_3$, —NHC(O)CH$_3$, and —N(C(O)CH$_3$)$_2$. In certain embodiments, $R^{12}$ is —NH(Cbz). In certain embodiments, $R^{12}$ is —NH(Fmoc). In certain embodiments, $R^{12}$ is —NHC(O)CCl$_3$. In certain embodiments, $R^{12}$ is —NHC(O)CH$_3$. In certain embodiments, $R^{12}$ is —N(C(O)CH$_3$)$_2$.

In some embodiments, $R_N$ is —N$_3$ or —N(R$^W$)$_2$, wherein each R$^W$ is independently hydrogen or a nitrogen protecting group. In certain embodiments, $R_N$ is —N$_3$. In certain embodiments, $R_N$ is —N(R$^W$)$_2$, wherein each R$^W$ is independently hydrogen or a nitrogen protecting group. In certain embodiments, $R_N$ is —NH$_2$. In certain embodiments, $R_N$ is —NHR$^W$, wherein R$^W$ is a nitrogen protecting group. In certain embodiments, $R_N$ is —N(R$^W$)$_2$, wherein each R$^W$ is a nitrogen protecting group. In certain embodiments, $R_N$ is selected from the group consisting of —N$_3$, —NH(Cbz), —NH(Boc), —NH(Fmoc), —NHC(O)CCl$_3$, —NHC(O)CH$_3$, and —N(C(O)CH$_3$)$_2$. In certain embodiments, $R_N$ is —NH(Cbz). In certain embodiments, $R_N$ is —NH(Fmoc). In In certain embodiments, the linker is -L$^1$-L$^2$-, wherein L$^1$ is a bond, —O—, —S—, —NR$^{L1a}$—, —C(=O)—, —NR$^{L1a}$C(=O)—, —NR$^{L1a}$C(=O)O—, —C(=O)NR$^{L1a}$—, —OC(=O)NR$^{L1a}$—, —SC(=O)—, —C(=O)S—, —OC(=O)—, —C(=O)O—, —NR$^{L1a}$C(=S)—, —C(=S)NR$^{L1a}$—, trans-CR$^{L1b}$=CR$^{L1b}$—, cis-CR$^{L1b}$=CR$^{L1b}$—, —C≡C—, —OC(R$^{L1b}$)$_2$—, —C(R$^{L1b}$)$_2$O—, —NR$^{L1a}$C(R$^{L1b}$)$_2$—, —C(R$^{L1b}$)$_2$NR$^{L1a}$—, —SC(R$^{L1b}$)$_2$—, —C(R$^{L1b}$)$_2$S—, —S(=O)$_2$O—, —OS(=O)$_2$—, —S(=O)$_2$NR$^{L1a}$—, —NR$^{L1a}$S(=O)$_2$—, or an optionally substituted C$_{1-20}$ hydrocarbon chain, optionally wherein one or more carbon units of the hydrocarbon chain is replaced with —O—, —S—, —NR$^{L1a}$—, —C(=O)—, NR$^{L1a}$C(=O)—, —NR$^{L1a}$C(=O)O—, —C(=O)NR$^{L1a}$—, —OC(=O)NR$^{L1a}$—, —SC(=O)—, —C(=O)S—, —OC(=O)—, —C(=O)O—, —NR$^{L1a}$C(=S)—, —C(=S)NR$^{L1a}$—, trans-CR$^{L1b}$=CR$^{L1b}$—, cis-CR$^{L1b}$=CR$^{L1b}$—, —C≡C—, —S(=O)$_2$O—, —OS(=O)$_2$—, —S(=O)$_2$NR$^{L1a}$—, or —NR$^{L1a}$S(=O)$_2$—, wherein R$^{L1a}$ is hydrogen, optionally substituted C$_{1-6}$ alkyl, or a nitrogen protecting group, or $R^{L1a}$ is joined with the adjacent carbon atom to form an optionally substituted heterocyclic ring, and wherein each occurrence of $R^{L1b}$ is independently selected from the group consisting of hydrogen, halogen, optionally substituted $C_{1-10}$ alkyl, optionally substituted alkenyl, optionally substituted alkynyl, optionally substituted carbocyclyl, optionally substituted heterocyclyl, optionally substituted aryl, and optionally substituted heteroaryl, or $R^{L1b}$ is joined with the adjacent carbon or nitrogen or oxygen atom to form an optionally substituted carbocyclic or heterocyclic ring, or two $R^{L1b}$ groups are joined to form an optionally substituted carbocyclic or optionally substituted heterocyclic ring; and $L^2$ is a moiety derived from a crosslinking reagent capable of crosslinking the carrier and $L^1$.

The carrier can be a protein, a lipid, a lipolized protein, a virus, a peptide, or a dendrimer of glycopeptides. In certain embodiments, the carrier is a peptide comprising a T cell epitope.

Examples of carrier proteins which may be used in the present invention are tetanus toxoid (TT), diphtheria toxoid (DT), diphtheria toxin cross-reacting material 197 (CRM197), fragment C of TT, Keyhole limpet hemocyanin (KLH), bovine serum albumin (BSA), protein D, outer-membrane protein (OMP) and pneumolysin, diphtheria toxin cross-reacting material 197 (CRM197) or other DT point mutants, such as CRM176, CRM228, CRM 45 (Uchida et al J. Biol. Chem. 218; 3838-3844, 1973); CRM 9, CRM 45, CRM102, CRM 103 and CRM107 and other mutations described in the art.

In certain embodiments, the glycan conjugate is of the formula (IV-a) or (IV-b):

m is 15. In certain embodiments, m is 20. In certain embodiments, m is 30. In certain embodiments, m is 40.

In another aspect, the present invention provides a glycan conjugate mixture comprising at least two of the glycan conjugates as described herein. In certain embodiments, the average value of w in the glycan mixture is from about 1.0 to about 40.0. In certain embodiments, the average value of w in the glycan mixture is from about 1.0 to 10.0. In certain embodiments, the average value of w in the glycan mixture is about 5.7, 4.9, 2.9, 2.8, or 3.1. In certain embodiments, the average value of w in the glycan mixture is about 4.9, 2.9, 2.8, or 3.1.

In certain embodiments, the immunogenic compositions described herein include an immunogenically effective amount of a glycan conjugate of the invention.

The compounds of the invention can be synthesized using procedures known in the art or described herein. Also see US20140051127.

The immunogenic conjugate of the invention may include one or more molecules (e.g., 1-40, 1-20, 1-25, 1-30, 5-20, 5-25, 5-30, or 5-35) of the same or different SSEA-33 and/or SSEA-4 derivatives. Procedures for generating glycan conjugates are known in the art and described below. Also see U.S. Pat. No. 8,268,969.

In certain embodiments, the immunogenic composition of the invention may include one or more adjuvants. Suitable adjuvants are known in the art (e.g., C34, 7DW8-5, C17, C23, Gluco-C34, Aluminum salt, Squalene, MF59, and QS-21).

As used herein, the term "alum adjuvant" refers to an aluminum salt with immune adjuvant activity. This agent

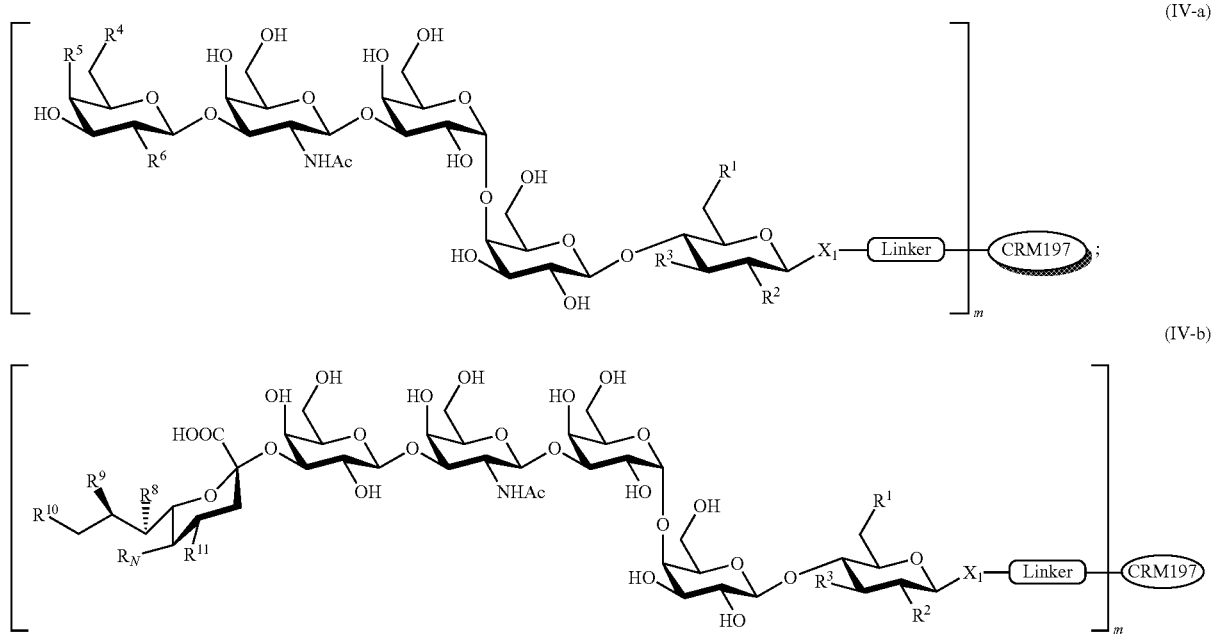

wherein m is an integer of 1 to 40, inclusive.

In certain embodiments, m is an integer of 1 to 30, inclusive. As generally defined herein, m is an integer of 1 to 20 inclusive. In certain embodiments, m is 1. In certain embodiments, m is 2. In certain embodiments, m is 4. In certain embodiments, m is 6. In certain embodiments, m is 8. In certain embodiments, m is 10. In certain embodiments, adsorbs and precipitates protein antigens in solution; the resulting precipitate improves vaccine immunogenicity by facilitating the slow release of antigen from the vaccine depot formed at the site of inoculation.

As used herein, the term "immunologic adjuvant" refers to a substance used in conjunction with an immunogen which enhances or modifies the immune response to the immunogen. The α-GalCer analogs of the present disclosure are used as immunologic adjuvants to modify or augment the effects of a vaccine by stimulating the immune system of a patient who is administered the vaccine to respond to the vaccine more vigorously. In an exemplary implementation, the analog C34 is used as an adjuvant. The structures of C34 and other alpha-galactosyl ceramide analogs and their use as adjuvants are disclosed in detail in U.S. Pat. No. 7,928,077.

As used herein, the term "glycolipid" refers to a carbohydrate-attached lipid that serves as a marker for cellular recognition.

The glycolipids C34, Gluco-C34, C23 and 7DW8-5 have the following structures:

ments, the immunogenic compositions described herein include an pharmaceutically effective amount of a glycan conjugate of the invention.

In another aspect, the present invention provides a cancer vaccine comprising an immunogenic composition described herein and a pharmaceutically acceptable excipient.

The cancer vaccines of the invention may include a single dose or multiple doses of the inventive glycan conjugates, a glycan conjugate mixture thereof, or immunogenic compositions thereof. The provided cancer vaccines may be useful for treating or reducing the risk of cancers. The cancer vaccines may also include packaging information describing

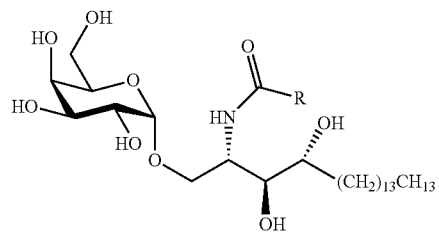

C1, R = (CH$_2$)$_{24}$CH$_3$
C23, R = (CH$_2$)$_7$PhF
C34, R = (CH$_2$)$_{10}$PhOPhF
7DW8-5, R = (CH$_2$)$_{10}$PhF

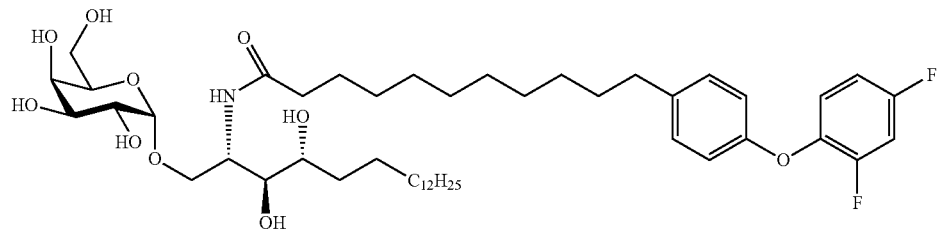

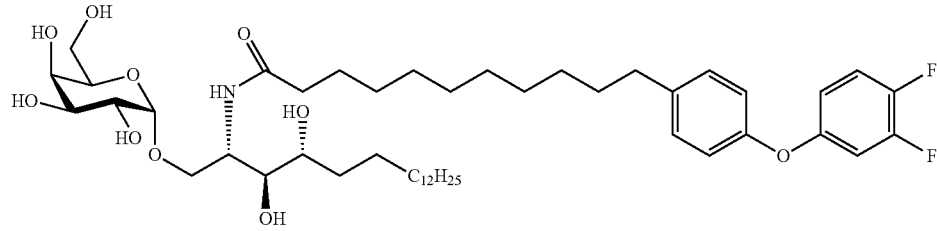

C34

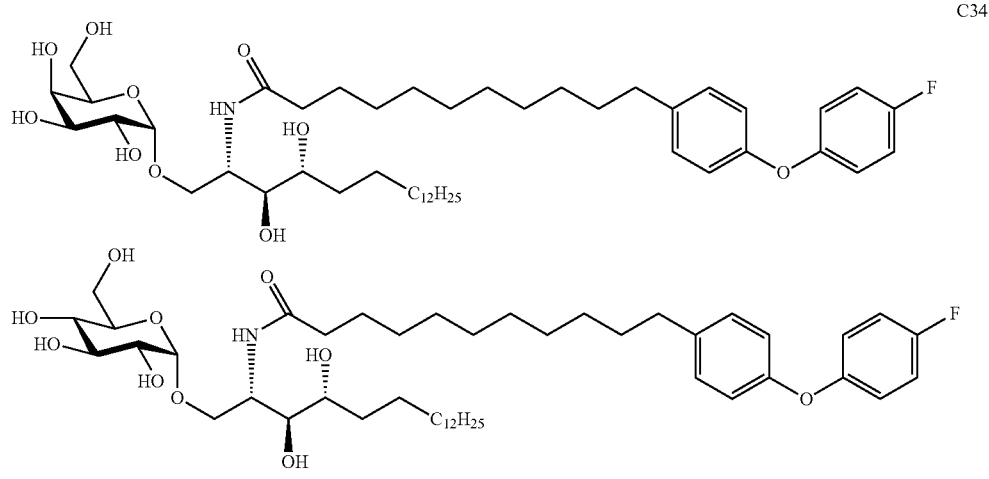

Gluco-C34

The immunogenic composition can further include a pharmaceutically acceptable excipient. In certain embodithe use or prescribing information for the subject or a health care professional. Such information may be required by a regulatory agency such as the U.S. Food and Drug Administration (FDA). The cancer vaccine may also optionally include a device for administration of the compound or composition, for example, a syringe for parenteral administration.

Pharmaceutical Formulations

The immune composition is administered in a manner compatible with the dosage formulation, and in an amount that is therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art. Suitable regimes for initial administration and booster doses are also variable, but may include an initial administration followed by subsequent administrations. The dosage of the vaccine may also depend on the route of administration and varies according to the size of the host.

The immune composition of this invention can also be used to generate antibodies in animals for production of antibodies, which can be used in both cancer treatment and diagnosis. Methods of making monoclonal and polyclonal antibodies and fragments thereof in animals (e.g., mouse, rabbit, goat, sheep, or horse) are well known in the art. See, for example, Harlow and Lane, (1988) *Antibodies: A Laboratory Manual*, Cold Spring Harbor Laboratory, New York. The term "antibody" includes intact immunoglobulin molecules as well as fragments thereof, such as Fab, F(ab')$_2$, Fv, scFv (single chain antibody), and dAb (domain antibody; Ward, et. al. (1989) *Nature*, 341, 544).

The compositions disclosed herein can be included in a pharmaceutical composition together with additional active agents, carriers, vehicles, excipients, or auxiliary agents identifiable by a person skilled in the art upon reading of the present disclosure.

The pharmaceutical compositions preferably comprise at least one pharmaceutically acceptable carrier. In such pharmaceutical compositions, the compositions disclosed herein form the "active compound," also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Clinical Applications

The present invention provides glycan conjugates, immunogenic compositions or vaccines useful for the treatment of a proliferative disease such as cancer (e.g. lung cancer, large bowel cancer, pancreas cancer, biliary tract cancer, or endometrial cancer), benign neoplasm, or angiogenesis in a subject.

The immunogenic compositions or vaccines described herein can also be used to generate antibodies in human or animals for production of antibodies, which can be used in both cancer treatment and diagnosis. In some embodiments, the immunogenic compositions or vaccines described herein can also be used to generate antibodies for production of Globo H, SSEA-3 and/or SSEA-4 antibodies. Methods of making monoclonal and polyclonal antibodies and fragments thereof in human and/or animals (e.g., mouse, rabbit, goat, sheep, or horse) are well known in the art. See, for example, Harlow and Lane, (1988) Antibodies: A Laboratory Manual, Cold Spring Harbor Laboratory, New York. The term "antibody" includes intact immunoglobulin molecules as well as fragments thereof, such as Fab, F(ab').sub.2, Fv, scFv (single chain antibody), and dAb (domain antibody; Ward, et. al. (1989) Nature, 341, 544).

Compositions comprising at least one anti-SSEA-3/SSEA-4/GLOBO H antibody or at least one polynucleotide comprising sequences encoding an anti-SSEA-3/SSEA-4/GLOBO H antibody are provided. In certain embodiments, a composition may be a pharmaceutical composition. As used herein, compositions comprise one or more antibodies that bind to one or more SSEA-3/SSEA-4/GLOBO H and/or one or more polynucleotides comprising sequences encoding one or more antibodies that bind to one or more SSEA-3/SSEA-4/GLOBO H. These compositions may further comprise suitable carriers, such as pharmaceutically acceptable excipients including buffers, which are well known in the art.

Isolated antibodies and polynucleotides are also provided. In certain embodiments, the isolated antibodies and polynucleotides are substantially pure.

In one embodiment, anti-SSEA-3/SSEA-4/GLOBO H antibodies are monoclonal. In another embodiment, fragments of the anti-SSEA-3/SSEA-4/GLOBO H antibodies (e.g., Fab, Fab'-SH and F(ab')2 fragments) are provided. These antibody fragments can be created by traditional means, such as enzymatic digestion, or may be generated by recombinant techniques. Such antibody fragments may be chimeric, humanized, or human. These fragments are useful for the diagnostic and therapeutic purposes set forth below.

Example of Generation of Anti-SSEA-3/SSEA-4/GLOBO H Antibodies Using a Phage Display Library A variety of methods are known in the art for generating phage display libraries from which an antibody of interest can be obtained. One method of generating antibodies of interest is through the use of a phage antibody library as described in Lee et al., J. Mol. Biol. (2004), 340(5): 1073-93.

The anti-SSEA-3/SSEA-4/GLOBO H antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-SSEA-3/SSEA-4/GLOBO H antibodies of the invention can be obtained by designing a suitable antigen screening procedure to select for the phage clone of interest followed by construction of a full length anti-SSEA-3/SSEA-4/GLOBO H antibody clone using the Fv sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

The antigen-binding domain of an antibody is formed from two variable (V) regions of about 110 amino acids, one each from the light (VL) and heavy (VH) chains, that both present three hypervariable loops or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., Ann. Rev. Immunol., 12: 433-455 (1994). As used herein, scFv encoding phage clones and Fab encoding phage clones are collectively referred to as "Fv phage clones" or "Fv clones".

Repertoires of VH and VL genes can be separately cloned by polymerase chain reaction (PCR) and recombined randomly in phage libraries, which can then be searched for antigen-binding clones as described in Winter et al., Ann. Rev. Immunol., 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., EMBO J, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, J. Mol. Biol., 227: 381-388 (1992).

Filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., J. Mol. Biol., 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., Nucl. Acids Res., 19: 4133-4137 (1991).

In general, nucleic acids encoding antibody gene fragments are obtained from immune cells harvested from humans or animals. If a library biased in favor of anti-SSEA-3/SSEA-4/GLOBO H clones is desired, the subject is immunized with SSEA-3/SSEA-4/GLOBO H to generate an antibody response, and spleen cells and/or circulating B cells or other peripheral blood lymphocytes (PBLs) are recovered for library construction. In one embodiment, a human antibody gene fragment library biased in favor of anti-human SSEA-3/SSEA-4/GLOBO H clones is obtained by generating an anti-human SSEA-3/SSEA-4/GLOBO H antibody response in transgenic mice carrying a functional human immunoglobulin gene array (and lacking a functional endogenous antibody production system) such that SSEA-3/SSEA-4/GLOBO H immunization gives rise to B cells producing human antibodies against SSEA-3/SSEA-4/GLOBO H. The generation of human antibody-producing transgenic mice is described below.

Additional enrichment for anti-SSEA-3/SSEA-4/GLOBO H reactive cell populations can be obtained by using a suitable screening procedure to isolate B cells expressing SSEA-3/SSEA-4/GLOBO H-specific antibody, e.g., by cell separation with SSEA-3/SSEA-4/GLOBO H affinity chromatography or adsorption of cells to fluorochrome-labeled SSEA-3/SSEA-4/GLOBO H followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which SSEA-3/SSEA-4/GLOBO H is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., Proc. Natl. Acad. Sci. (USA), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., Nature, 341: 544-546 (1989). However, for amplifying from cDNA, back primers can also be based in the leader exon as described in Jones et al., Biotechnol., 9: 88-89 (1991), and forward primers within the constant region as described in Sastry et al., Proc. Natl. Acad. Sci. (USA), 86: 5728-5732 (1989). To maximize complementarity, degeneracy can be incorporated in the primers as described in Orlandi et al. (1989) or Sastry et al. (1989). In certain embodiments, the library diversity is maximized by using PCR primers targeted to each V-gene family in order to amplify all available VH and VL arrangements present in the immune cell nucleic acid sample, e.g. as described in the method of Marks et al., J. Mol. Biol., 222: 581-597 (1991) or as described in the method of Orum et al., Nucleic Acids Res., 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., Nature, 352: 624-628 (1991).

Repertoires of synthetically rearranged V genes can be derived in vitro from V gene segments. Most of the human VH-gene segments have been cloned and sequenced (reported in Tomlinson et al., J. Mol. Biol., 227: 776-798 (1992)), and mapped (reported in Matsuda et al., Nature Genet., 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, J. Mol. Biol., 227: 381-388 (1992). VH repertoires can also be made with all the sequence diversity focused in a long H3 loop of a single length as described in Barbas et al., Proc. Natl. Acad. Sci. USA, 89: 4457-4461 (1992). Human Vκ and Vλ segments have been cloned and sequenced (reported in Williams and Winter, Eur. J. Immunol., 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, J. Mol. Biol., 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., Gene, 128: 119-126 (1993), or in vivo by combinatorial infection, e.g., the loxP system described in Waterhouse et al., Nucl. Acids Res., 21: 2265-2266 (1993). The in vivo recombination approach exploits the two-chain nature of Fab fragments to overcome the limit on library size imposed by E. coli transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about 1012 clones). Both vectors contain in vivo recombination signals so that the VH and VL genes are recombined onto a single replicon and are co-packaged into phage virions. These huge libraries provide large numbers of diverse antibodies of good affinity (Kd−1 of about 10−8 M).

Alternatively, the repertoires may be cloned sequentially into the same vector, e.g. as described in Barbas et al., Proc. Natl. Acad. Sci. USA, 88: 7978-7982 (1991), or assembled together by PCR and then cloned, e.g. as described in Clackson et al., Nature, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., Nucl. Acids Res., 20: 3831-3837 (1992).

Screening of the libraries can be accomplished by any art-known technique. For example, SSEA-3/SSEA-4/GLOBO H targets can be used to coat the wells of adsorption plates, expressed on host cells affixed to adsorption plates or used in cell sorting, or conjugated to biotin for capture with streptavidin-coated beads, or used in any other art-known method for panning phage display libraries.

The phage library samples are contacted with immobilized SSEA-3/SSEA-4/GLOBO H under conditions suitable for binding of at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., Proc. Natl. Acad. Sci. USA, 88: 7978-7982 (1991), or by alkali, e.g. as described in Marks et al., J. Mol. Biol., 222: 581-597 (1991), or by SSEA-3/SSEA-4/GLOBO H antigen competition, e.g. in a procedure similar to the antigen competition method of Clackson et al., Nature, 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., Proteins, 8: 309-314 (1990) and in WO 92/09690, and a low coating density of antigen as described in Marks et al., Biotechnol., 10: 779-783 (1992).

It is possible to select between phage antibodies of different affinities, even with affinities that differ slightly, for SSEA-3/SSEA-4/GLOBO H. However, random mutation of a selected antibody (e.g. as performed in some of the affinity maturation techniques described above) is likely to give rise to many mutants, most binding to antigen, and a few with higher affinity. With limiting SSEA-3/SSEA-4/GLOBO H, rare high affinity phage could be competed out. To retain all the higher affinity mutants, phages can be incubated with excess biotinylated SSEA-3/SSEA-4/GLOBO H, but with the biotinylated SSEA-3/SSEA-4/GLOBO H at a concentration of lower molarity than the target molar affinity constant for SSEA-3/SSEA-4/GLOBO H. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-SSEA-3/SSEA-4/GLOBO H clones may be activity selected. In one embodiment, the invention provides anti-SSEA-3/SSEA-4/GLOBO H antibodies that block the binding between a SSEA-3/SSEA-4/GLOBO H ligand and SSEA-3/SSEA-4/GLOBO H, but do not block the binding between a SSEA-3/SSEA-4/GLOBO H ligand and a second protein. Fv clones corresponding to such anti-SSEA-3/SSEA-4/GLOBO H antibodies can be selected by (1) isolating anti-SSEA-3/SSEA-4/GLOBO H clones from a phage library as described in Section B(I)(2) above, and optionally amplifying the isolated population of phage clones by growing up the population in a suitable bacterial host; (2) selecting SSEA-3/SSEA-4/GLOBO H and a second protein against which blocking and non-blocking activity, respectively, is desired; (3) adsorbing the anti-SSEA-3/SSEA-4/GLOBO H phage clones to immobilized SSEA-3/SSEA-4/GLOBO H; (4) using an excess of the second protein to elute any undesired clones that recognize SSEA-3/SSEA-4/GLOBO H-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding the Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., Curr. Opinion in Immunol., 5: 256 (1993) and Pluckthun, Immunol. Revs, 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. A Fv clone derived from the variable domain DNA of one animal (such as human) species and then fused to constant region DNA of another animal species to form coding sequence(s) for "hybrid", full length heavy chain and/or light chain is included in the definition of "chimeric" and "hybrid" antibody as used herein. In one embodiment, a Fv clone derived from human variable DNA is fused to human constant region DNA to form coding sequence(s) for all human, full or partial length heavy and/or light chains.

The antibodies produced by naive libraries (either natural or synthetic) can be of moderate affinity (Kd−1 of about 106 to 107 M−1), but affinity maturation can also be mimicked in vitro by constructing and reselecting from secondary libraries as described in Winter et al. (1994), supra. For example, mutation can be introduced at random in vitro by using error-prone polymerase (reported in Leung et al., Technique, 1: 11-15 (1989)) in the method of Hawkins et al., J. Mol. Biol., 226: 889-896 (1992) or in the method of Gram et al., Proc. Natl. Acad. Sci. USA, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., Biotechnol., 10: 779-783 (1992). This technique allows the production of antibodies and antibody fragments with affinities in the 10-9 M range.

Other Methods of Generating Anti-SSEA-3/SSEA-4/ GLOBO H Antibodies

Other methods of generating and assessing the affinity of antibodies are well known in the art and are described, e.g., in Kohler et al., Nature 256: 495 (1975); U.S. Pat. No. 4,816,567; Goding, Monoclonal Antibodies: Principles and Practice, pp. 59-103 (Academic Press, 1986; Kozbor, J. Immunol., 133:3001 (1984); Brodeur et al., Monoclonal Antibody Production Techniques and Applications, pp. 51-63 (Marcel Dekker, Inc., New York, 1987; Munson et al., Anal. Biochem., 107:220 (1980); Engels et al., Agnew. Chem. Int. Ed. Engl., 28: 716-734 (1989); Abrahmsen et al., EMBO J., 4: 3901 (1985); Methods in Enzymology, vol. 44 (1976); Morrison et al., Proc. Natl. Acad. Sci. USA, 81: 6851-6855 (1984).

General Methods

In general, the invention provides affinity-matured SSEA-3/SSEA-4/GLOBO H antibodies. These antibodies have increased affinity and specificity for SSEA-3/SSEA-4/ GLOBO H. This increase in affinity and sensitivity permits the molecules of the invention to be used for applications and methods that are benefited by (a) the increased sensitivity of the molecules of the invention and/or (b) the tight binding of SSEA-3/SSEA-4/GLOBO H by the molecules of the invention.

In one embodiment, SSEA-3/SSEA-4/GLOBO H antibodies that are useful for treatment of SSEA-3/SSEA-4/ GLOBO H-mediated disorders in which a partial or total blockade of one or more SSEA-3/SSEA-4/GLOBO H activities is desired. In one embodiment, the anti SSEA-3/SSEA-4/GLOBO H antibodies of the invention are used to treat cancer.

The anti-SSEA-3/SSEA-4/GLOBO H antibodies of the invention permit the sensitive and specific detection of the epitopes in straightforward and routine biomolecular assays such as immunoprecipitations, ELISAs, or immunomicroscopy without the need for mass spectrometry or genetic manipulation. In turn, this provides a significant advantage in both observing and elucidating the normal functioning of these pathways and in detecting when the pathways are functioning aberrantly.

The SSEA-3/SSEA-4/GLOBO H antibodies of the invention can also be used to determine the role in the development and pathogenesis of disease. For example, as described above, the SSEA-3/SSEA-4/GLOBO H antibodies of the invention can be used to determine whether the TACAs are normally temporally expressed which can be correlated with one or more disease states.

The SSEA-3/SSEA-4/GLOBO H antibodies of the invention can further be used to treat diseases in which one or more SSEA-3/SSEA-4/GLOBO Hs are aberrantly regulated or aberrantly functioning without interfering with the normal activity of SSEA-3/SSEA-4/GLOBO Hs for which the anti-SSEA-3/SSEA-4/GLOBO H antibodies of the invention are not specific.

In another aspect, the anti-SSEA-3/SSEA-4/GLOBO H antibodies of the invention find utility as reagents for detection of cancer states in various cell types and tissues.

In yet another aspect, the present anti-SSEA-3/SSEA-4/ GLOBO H antibodies are useful for the development of SSEA-3/SSEA-4/GLOBO H antagonists with blocking activity patterns similar to those of the subject antibodies of the invention. For example, anti-SSEA-3/SSEA-4/GLOBO H antibodies of the invention can be used to determine and identify other antibodies that have the same SSEA-3/SSEA-4/GLOBO H binding characteristics and/or capabilities of blocking SSEA-3/SSEA-4/GLOBO H-pathways.

As a further example, anti-SSEA-3/SSEA-4/GLOBO H antibodies of the invention can be used to identify other anti-SSEA-3/SSEA-4/GLOBO H antibodies that bind substantially the same antigenic determinant(s) of SSEA-3/ SSEA-4/GLOBO H as the antibodies exemplified herein, including linear and conformational epitopes.

The anti-SSEA-3/SSEA-4/GLOBO H antibodies of the invention can be used in assays based on the physiological pathways in which SSEA-3/SSEA-4/GLOBO H is involved to screen for small molecule antagonists of SSEA-3/SSEA-4/GLOBO H which will exhibit similar pharmacological effects in blocking the binding of one or more binding partners to SSEA-3/SSEA-4/GLOBO H as the antibody does.

Generation of antibodies can be achieved using routine skills in the art, including those described herein, such as the hybridoma technique and screening of phage displayed libraries of binder molecules. These methods are well-established in the art.

Briefly, the anti-SSEA-3/SSEA-4/GLOBO H antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-SSEA-3/SSEA-4/GLOBO H antibodies of the invention can be obtained by designing a suitable antigen screening procedure to select for the phage clone of interest followed by construction of a full length anti-SSEA-3/SSEA-4/GLOBO H antibody clone using the Fv sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

In one embodiment, anti-SSEA-3/SSEA-4/GLOBO H antibodies of the invention are monoclonal. Also encompassed within the scope of the invention are antibody fragments such as Fab, Fab', Fab'-SH and F(ab')2 fragments, and variations thereof, of the anti-SSEA-3/SSEA-4/GLOBO H antibodies provided herein. These antibody fragments can be created by traditional means, such as enzymatic digestion, or may be generated by recombinant techniques. Such antibody fragments may be chimeric, human or humanized. These fragments are useful for the experimental, diagnostic, and therapeutic purposes set forth herein.

Monoclonal antibodies can be obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

The anti-SSEA-3/SSEA-4/GLOBO H monoclonal antibodies of the invention can be made using a variety of methods known in the art, including the hybridoma method first described by Kohler et al., Nature, 256:495 (1975), or alternatively they may be made by recombinant DNA methods (e.g., U.S. Pat. No. 4,816,567).

Vectors, Host Cells and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Host cells include, but are not limited to, cells of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Generating Antibodies Using Prokaryotic Host Cells

Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention.

Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB- strains) provide cytoplasm conditions that are favorable for disulfide bond formation, thereby permitting proper folding and assembly of expressed protein subunits. Proba and Pluckthun Gene, 159:203 (1995).

Antibodies of the invention can also be produced by using an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence. In certain embodiments, changes in the nucleotide sequence are silent. Alterations in the TIR can include, for example, alterations in the number or spacing of Shine-Dalgarno sequences, along with alterations in the signal sequence.

One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) METHODS: A Companion to Methods in Enzymol. 4:151-158.

In one embodiment, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, E. coli cells are used as hosts for the invention. Examples of E. coli strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as E. coli 294 (ATCC 31,446), E. coli B, E. coli λ1776 (ATCC 31,537) and E. coli RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, E. coli, Serratia, or Salmonella species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, growth occurs at a temperature range including, but not limited to, about 20° C. to about 39° C., about 25° C. to about 37° C., and at about 30° C. The pH of the medium may be any pH ranging from about 5 to about 9, depending mainly on the host organism. For *E. coli*, the pH can be from about 6.8 to about 7.4, or about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. In one embodiment, the phosphate-limiting medium is the C.R.A.P medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, for example about 1,000 to 100,000 liters of capacity. These fermentors use agitator impellers to distribute oxygen and nutrients, especially glucose (a common carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J Bio Chem 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention.

Antibody Purification

In one embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the invention. Protein A is a 41 kD cell wall protein from *Staphylococcus aureas* which binds with a high affinity to the Fc region of antibodies. Lindmark et al (1983) J. Immunol. Meth. 62:1-13. The solid phase to which Protein A is immobilized can be a column comprising a glass or silica surface, or a controlled pore glass column or a silicic acid column. In some applications, the column is coated with a reagent, such as glycerol, to possibly prevent non-specific adherence of contaminants.

As the first step of purification, the preparation derived from the cell culture as described above can be applied onto a Protein A immobilized solid phase to allow specific binding of the antibody of interest to Protein A. The solid phase would then be washed to remove contaminants non-specifically bound to the solid phase. Finally the antibody of interest is recovered from the solid phase by elution.

Generating Antibodies Using Eukaryotic Host Cells

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected generally is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II (e.g., primate metallothionein genes), adenosine deaminase, ornithine decarboxylase, etc.

For example, cells transformed with the DHFR selection gene may first be identified by culturing all of the transformants in a culture medium that contains methotrexate (Mtx), a competitive antagonist of DHFR. Appropriate host cells when wild-type DHFR is employed include, for example, the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to nucleic acid encoding a polypeptide of interest (e.g., an antibody). Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(v) Enhancer Element Component

Transcription of DNA encoding an antibody polypeptide of the invention by higher eukaryotes can often be increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody polypeptide-encoding sequence, but is generally located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are generally removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a generally acceptable purification technique. The suitability of affinity reagents such as protein A as an affinity ligand depends on the species and isotype of any immunoglobulin Fc domain that is present in the antibody. Protein A can be used to purify antibodies that are based on human $\gamma 1$, $\gamma 2$, or $\gamma 4$ heavy chains (Lindmark et al., J. Immunol. Meth. 62:1-13 (1983)). Protein G is recommended for all mouse isotypes and for human $\gamma 3$ (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to further purification steps, as necessary, for example by low pH hydrophobic interaction chromatography using an elution buffer at a pH between about 2.5-4.5, generally performed at low salt concentrations (e.g., from about 0-0.25M salt).

It should be noted that, in general, techniques and methodologies for preparing antibodies for use in research, testing and clinical use are well-established in the art, consistent with the above and/or as deemed appropriate by one skilled in the art for the particular antibody of interest.

Activity Assays

Antibodies of the invention can be characterized for their physical/chemical properties and biological functions by various assays known in the art.

Purified antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

Where necessary, antibodies are analyzed for their biological activity. In some embodiments, antibodies of the invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays.

In one embodiment, the invention contemplates an altered antibody that possesses some but not all effector functions, which make it a desirable candidate for many applications in which the half life of the antibody in vivo is important yet certain effector functions (such as complement and ADCC)

are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). An example of an in vitro assay to assess ADCC activity of a molecule of interest is described in U.S. Pat. Nos. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998). C1q binding assays may also be carried out to confirm that the antibody is unable to bind C1q and hence lacks CDC activity. To assess complement activation, a CDC assay, e.g. as described in Gazzano-Santoro et al., J. Immunol. Methods 202:163 (1996), may be performed. FcRn binding and in vivo clearance/half life determinations can also be performed using methods known in the art.

Antibody Fragments

The present invention encompasses antibody fragments. In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')2 fragments (Carter et al., Bio/Technology 10: 163-167 (1992)). According to another approach, F(ab')2 fragments can be isolated directly from recombinant host cell culture. Fab and F(ab')2 fragment with increased in vivo half-life comprising salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) J. Immunol. 151:2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

Human anti-SSEA-3/SSEA-4/GLOBO H antibodies of the invention can be constructed by combining Fv clone variable domain sequence(s) selected from human-derived phage display libraries with known human constant domain sequences(s) as described above. Alternatively, human monoclonal anti-SSEA-3/SSEA-4/GLOBO H antibodies of the invention can be made by the hybridoma method. Human myeloma and mouse-human heteromyeloma cell lines for the production of human monoclonal antibodies have been described, for example, by Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90: 2551 (1993); Jakobovits et al., Nature, 362: 255 (1993); Bruggermann et al., Year in Immunol., 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for SSEA-3/SSEA-4/GLOBO H including a specific lysine linkage and the other is for any other antigen. In certain embodiments, bispecific antibodies may bind to two different SSEA-3/SSEA-4/GLOBO Hs having two different lysine linkages. Bispecific antibodies can be prepared as full length antibodies or antibody fragments (e.g. F(ab')2 bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., EMBO J., 10: 3655 (1991).

According to a different embodiment, antibody variable domains with the desired binding specificities (antibody-antigen combining sites) are fused to immunoglobulin constant domain sequences. The fusion, for example, is with an immunoglobulin heavy chain constant domain, comprising at least part of the hinge, CH2, and CH3 regions. In certain embodiments, the first heavy-chain constant region (CH1), containing the site necessary for light chain binding, is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach, the interface between a pair of antibody molecules can be engineered to maximize the percentage of heterodimers which are recovered from recombinant cell culture. The interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985)

describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F(ab')2 molecule. Each Fab' fragment was separately secreted from E. coli and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The dimerization domain comprises (or consists of), for example, an Fc region or a hinge region. In this scenario, the antibody will comprise an Fc region and three or more antigen binding sites amino-terminal to the Fc region. In one embodiment, a multivalent antibody comprises (or consists of), for example, three to about eight, or four antigen binding sites. The multivalent antibody comprises at least one polypeptide chain (for example, two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (for example, four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Antibody Variants

In some embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table A under the heading of "preferred substitutions". If such substitutions result in a change in biological activity, then more substantial changes, denominated "exemplary substitutions" in Table A, or as further described below in reference to amino acid classes, may be introduced and the products screened.

TABLE A

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Leu Phe; Norleucine | |
| Leu (L) | Norleucine; Ile; Val; Ile Met; Ala; Phe | |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Leu Ala; Norleucine | |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):
  (1) non-polar: Ala (A), Val (V), Leu (L), Ile (I), Pro (P), Phe (F), Trp (W), Met (M)
  (2) uncharged polar: Gly (G), Ser (S), Thr (T), Cys (C), Tyr (Y), Asn (N), Gln (O)
  (3) acidic: Asp (D), Glu (E)
  (4) basic: Lys (K), Arg (R), His (H)
Alternatively, naturally occurring residues may be divided into groups based on common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.
Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g. a humanized or human antibody). Generally, the resulting variant(s) selected for further development will have modified (e.g., improved) biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g. binding affinity) as herein disclosed. In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter Nature 322:738-40 (1988); U.S. Pat. Nos. 5,648,260; 5,624,821; and WO94/29351 concerning other examples of Fc region variants.

In one aspect, the invention provides antibodies comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, e.g., as described in U.S. Pat. No. 5,731,168.

Immunoconjugates

In another aspect, the invention provides immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986): 603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubutin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and 111In or 90Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10): 2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is tested for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is tested for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784) and are under therapeutic development.

Chemotherapeutic agents useful in the generation of immunoconjugates are described herein (above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include 212Bi, 131I, 131In, 90Y, and 186Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis-(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolostatins, aurostatins, a trichothecene, and CC1065, and the derivatives of these toxins that have toxin activity, are also contemplated herein.

Maytansine and Maytansinoids

In some embodiments, the immunoconjugate comprises an antibody of the invention conjugated to one or more maytansinoid molecules.

Maytansinoids are mitotic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307, 016; 4,308,268; 4,308,269; 4,309,428; 4,313,946; 4,315, 929; 4,317,821; 4,322,348; 4,331,598; 4,361,650; 4,364, 866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Exemplary embodiments of maytansinoid drug moieties include: DM1; DM3; and DM4. Immunoconjugates containing maytansinoids, methods of making same, and their therapeutic use are disclosed, for example, in U.S. Pat. Nos. 5,208,020, 5,416,064 and European Patent EP 0 425 235 B1, Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses 3×105 HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates can be prepared by chemically linking an antibody to a maytansinoid molecule without significantly diminishing the biological activity of either the antibody or the maytansinoid molecule. See, e.g., U.S. Pat. No. 5,208,020. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Maytansinoids include, but are not limited to, maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis-(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Coupling agents include, but are not limited to, N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In one embodiment, the linkage is formed at the C-3 position of maytansinol or a maytansinol analogue.

Auristatins and Dolostatins

In some embodiments, the immunoconjugate comprises an antibody of the invention conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands", U.S. Ser. No. 10/983,340, filed Nov. 5, 2004, the disclosure of which is expressly incorporated by reference in its entirety.

Exemplary auristatin embodiments include MMAE and MMAF. Additional exemplary embodiments comprising MMAE or MMAF and various linker components (described further herein) include Ab-MC-vc-PAB-MMAF, Ab-MC-vc-PAB-MMAE, Ab-MC-MMAE and Ab-MC-MMAF.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. Nos. 5,635,483; 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; and Pettit et al (1996) J. Chem. Soc. Perkin Trans. 1 5:859-863. See also Doronina (2003) Nat Biotechnol 21(7):778-784; "Monomethylvaline Compounds Capable of Conjugation to Ligands", U.S. Ser. No. 10/983,340, filed Nov. 5, 2004, hereby incorporated by reference in its entirety (disclosing, e.g., linkers and methods of preparing monomethylvaline compounds such as MMAE and MMAF conjugated to linkers).

Calicheamicin

In other embodiments, the immunoconjugate comprises an antibody of the invention conjugated to one or more calicheamicin molecules. The calicheamicin family of antibiotics is capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, and 5,877,296 (all to American Cyanamid Company). Structural analogues of calicheamicin which may be used include, but are not limited to, γ1 I, α2 I, α3 I, N-acetyl-γ1 I, PSAG and θI 1 (Hinman et al., Cancer Research 53:3336-3342 (1993), Lode et al., Cancer Research 58:2925-2928 (1998) and the aforementioned U.S. patents to American Cyanamid). Another anti-tumor drug to which the antibody can be conjugated is QFA, which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include At211, I131, I125, Y90, Re186, Re188, Sm153, Bi212, P32, Pb212 and radioactive isotopes of Lu. When the conjugate is used for detection, it may comprise a radioactive atom for scintigraphic studies, for example Tc99m or I123, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as Tc99m or I123, Re186, Re188 and In111 can be attached via a cysteine residue in the peptide. Yttrium-90 can be attached via a lysine residue. The IODOGEN method (Fraker et al (1978) Biochem. Biophys. Res. Commun. 80: 49-57) can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis-(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab-(L-D)p \qquad\qquad I$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl)cyclohexane-1 carboxylate ("SMCC"), and N-Succinimidyl (4-iodo-acetyl) aminobenzoate ("STAB"). Additional linker components are known in the art and some are described herein.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzyme, for example, a tumor-associated protease, cathepsin B, C and D, or a plasmin protease.

Exemplary linker component structures are shown below (wherein the wavy line indicates sites of covalent attachment to other components of the ADC):

Figure US08133488-20120313-000006

Additional exemplary linker components and abbreviations include (wherein the antibody (Ab) and linker are depicted, and p is 1 to about 8):

Figure US08133488-20120313-000007

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates of the invention may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent to one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Antibody (Ab)-MC-MMAE may be prepared by conjugation of any of the antibodies provided herein with MC-MMAE as follows. Antibody, dissolved in 500 mM sodium borate and 500 mM sodium chloride at pH 8.0 is treated with an excess of 100 mM dithiothreitol (DTT). After incubation at 37° C. for about 30 minutes, the buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm. The reduced antibody dissolved in PBS is chilled on ice. The drug linker reagent, maleimidocaproyl-monomethyl auristatin E (MMAE), i.e. MC-MMAE, dissolved in DMSO, is diluted in acetonitrile and water at known concentration, and added to the chilled reduced antibody 2H9 in PBS. After about one hour, an excess of maleimide is added to quench the reaction and cap any unreacted antibody thiol groups. The reaction mixture is concentrated by centrifugal ultrafiltration and 2H9-MC-MMAE is purified and desalted by elution through G25 resin in PBS, filtered through 0.2 μm filters under sterile conditions, and frozen for storage.

Antibody-MC-MMAF may be prepared by conjugation of any of the antibodies provided herein with MC-MMAF following the protocol provided for preparation of Ab-MC-MMAE.

Antibody-MC-val-cit-PAB-MMAE is prepared by conjugation of any of the antibodies provided herein with MC-val-cit-PAB-MMAE following the protocol provided for preparation of Ab-MC-MMAE.

Antibody-MC-val-cit-PAB-MMAF is prepared by conjugation of any of the antibodies provided herein with MC-val-cit-PAB-MMAF following the protocol provided for preparation of Ab-MC-MMAE.

Antibody-SMCC-DM1 is prepared by conjugation of any of the antibodies provided herein with SMCC-DM1 as follows. Purified antibody is derivatized with (Succinimidyl 4-(N-maleimidomethyl)cyclohexane-1-carboxylate (SMCC, Pierce Biotechnology, Inc) to introduce the SMCC linker. Specifically, antibody is treated at 20 mg/mL in 50 mM potassium phosphate/50 mM sodium chloride/2 mM EDTA, pH 6.5 with 7.5 molar equivalents of SMCC (20 mM in DMSO, 6.7 mg/mL). After stirring for 2 hours under argon at ambient temperature, the reaction mixture is filtered through a Sephadex G25 column equilibrated with 50 mM potassium phosphate/50 mM sodium chloride/2 mM EDTA, pH 6.5. Antibody-containing fractions are pooled and assayed.

Antibody-SMCC prepared thusly is diluted with 50 mM potassium phosphate/50 mM sodium chloride/2 mM EDTA, pH 6.5, to a final concentration of about 10 mg/ml, and reacted with a 10 mM solution of DM1 in dimethylacetamide. The reaction is stirred at ambient temperature under argon for 16.5 hours. The conjugation reaction mixture is filtered through a Sephadex G25 gel filtration column (1.5× 4.9 cm) with 1×PBS at pH 6.5. The DM1 drug to antibody ratio (p) may be about 2 to 5, as measured by the absorbance at 252 nm and at 280 nm.

Ab-SPP-DM1 is prepared by conjugation of any of the antibodies provided herein with SPP-DM1 as follows. Purified antibody is derivatized with N-succinimidyl-4-(2-pyridylthio)pentanoate to introduce dithiopyridyl groups. Antibody (376.0 mg, 8 mg/mL) in 44.7 mL of 50 mM potassium phosphate buffer (pH 6.5) containing NaCl (50 mM) and EDTA (1 mM) is treated with SPP (5.3 molar equivalents in 2.3 mL ethanol). After incubation for 90 minutes under argon at ambient temperature, the reaction mixture is gel filtered through a Sephadex G25 column equilibrated with a 35 mM sodium citrate, 154 mM NaCl, 2 mM EDTA buffer. Antibody-containing fractions were pooled and assayed. The degree of modification of the antibody is determined as described above.

Antibody-SPP-Py (about 10 μmoles of releasable 2-thio-pyridine groups) is diluted with the above 35 mM sodium citrate buffer, pH 6.5, to a final concentration of about 2.5 mg/mL. DM1 (1.7 equivalents, 17 μmoles) in 3.0 mM dimethylacetamide (DMA, 3% v/v in the final reaction mixture) is then added to the antibody solution. The reaction proceeds at ambient temperature under argon for about 20 hours. The reaction is loaded on a Sephacryl S300 gel filtration column (5.0 cm×90.0 cm, 1.77 L) equilibrated with 35 mM sodium citrate, 154 mM NaCl, pH 6.5. The flow rate may be about 5.0 mL/min and 65 fractions (20.0 mL each) are collected. The number of DM1 drug molecules linked per antibody molecule (p') is determined by measuring the absorbance at 252 nm and 280 nm, and may be about 2 to 4 DM1 drug moieties per 2H9 antibody.

Antibody-BMPEO-DM1 is prepared by conjugation of any of the antibodies provided herein with BMPEO-DM1 as follows. The antibody is modified by the bis-maleimido reagent BM(PEO)4 (Pierce Chemical), leaving an unreacted maleimido group on the surface of the antibody. This may be accomplished by dissolving BM(PEO)4 in a 50% ethanol/water mixture to a concentration of 10 mM and adding a tenfold molar excess to a solution containing antibody in phosphate buffered saline at a concentration of approximately 1.6 mg/ml (10 micromolar) and allowing it to react for 1 hour to form an antibody-linker intermediate, 2H9-BMPEO. Excess BM(PEO)4 is removed by gel filtration (HiTrap column, Pharmacia) in 30 mM citrate, pH 6 with 150 mM NaCl buffer. An approximate 10 fold molar excess DM1 is dissolved in dimethyl acetamide (DMA) and added to the 2H9-BMPEO intermediate. Dimethyl formamide (DMF) may also be employed to dissolve the drug moiety reagent. The reaction mixture is allowed to react overnight before gel filtration or dialysis into PBS to remove unreacted DM1. Gel filtration on S200 columns in PBS is used to remove high molecular weight aggregates and to furnish purified 2H9-BMPEO-DM1.

Antibody Derivatives

Antibodies of the invention can be further modified to contain additional nonproteinaceous moieties that are known in the art and readily available. In one embodiment, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, the polymers can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Pharmaceutical Formulations

Therapeutic formulations comprising an antibody of the invention are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, including, but not limited to those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Uses

An antibody of the invention may be used in, for example, in vitro, ex vivo and in vivo therapeutic methods. Antibodies of the invention can be used as an antagonist to partially or fully block the specific antigen activity in vitro, ex vivo and/or in vivo. Moreover, at least some of the antibodies of the invention can neutralize antigen activity from other species. Accordingly, antibodies of the invention can be used to inhibit a specific antigen activity, e.g., in a cell culture containing the antigen, in human subjects or in other mammalian subjects having the antigen with which an antibody of the invention cross-reacts (e.g. chimpanzee, baboon, marmoset, cynomolgus and rhesus, pig or mouse). In one embodiment, an antibody of the invention can be used for inhibiting antigen activities by contacting the antibody with the antigen such that antigen activity is inhibited. In one embodiment, the antigen is a human protein molecule.

In one embodiment, an antibody of the invention can be used in a method for inhibiting an antigen in a subject suffering from a disorder in which the antigen activity is detrimental, comprising administering to the subject an antibody of the invention such that the antigen activity in the subject is inhibited. In one embodiment, the antigen is a human protein molecule and the subject is a human subject. Alternatively, the subject can be a mammal expressing the antigen with which an antibody of the invention binds. Still further the subject can be a mammal into which the antigen has been introduced (e.g., by administration of the antigen or by expression of an antigen transgene). An antibody of the invention can be administered to a human subject for therapeutic purposes. Moreover, an antibody of the invention can be administered to a non-human mammal expressing an antigen with which the antibody cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration). Antibodies of the invention can be used to treat, inhibit, delay progression of, prevent/delay recurrence of, ameliorate, or prevent diseases, disorders or conditions associated with abnormal expression and/or activity of SSEA-3/SSEA-4/GLOBO Hs and SSEA-3/SSEA-4/GLOBO Hated proteins, including but not limited to cancer, muscular disorders, ubiquitin-pathway-related genetic disorders, immune/inflammatory disorders, neurological disorders, and other ubiquitin pathway-related disorders.

In one aspect, a blocking antibody of the invention is specific for a SSEA-3/S SEA-4/GLOBO H.

In certain embodiments, an immunoconjugate comprising an antibody of the invention conjugated with a cytotoxic agent is administered to the patient. In some embodiments, the immunoconjugate and/or antigen to which it is bound is/are internalized by cells expressing one or more proteins on their cell surface which are associated with SSEA-3/SSEA-4/GLOBO H, resulting in increased therapeutic efficacy of the immunoconjugate in killing the target cell with which it is associated. In one embodiment, the cytotoxic agent targets or interferes with nucleic acid in the target cell. Examples of such cytotoxic agents include any of the chemotherapeutic agents noted herein (such as a maytansinoid or a calicheamicin), a radioactive isotope, or a ribonuclease or a DNA endonuclease.

Antibodies of the invention can be used either alone or in combination with other compositions in a therapy. For instance, an antibody of the invention may be co-administered with another antibody, and/or adjuvant/therapeutic agents (e.g., steroids). For instance, an antibody of the invention may be combined with an anti-inflammatory and/or antiseptic in a treatment scheme, e.g. in treating any of the diseases described herein, including cancer, muscular disorders, ubiquitin-pathway-related genetic disorders, immune/inflammatory disorders, neurological disorders, and other ubiquitin pathway-related disorders. Such combined therapies noted above include combined administration (where the two or more agents are included in the same or separate formulations), and separate administration, in which case, administration of the antibody of the invention can occur prior to, and/or following, administration of the adjunct therapy or therapies.

An antibody of the invention (and adjunct therapeutic agent) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Dosing can be by any suitable route, e.g. by injections, such as intravenous or subcutaneous injections, depending in part on whether the administration is brief or chronic.

The location of the binding target of an antibody of the invention may be taken into consideration in preparation and administration of the antibody. When the binding target is an intracellular molecule, certain embodiments of the invention provide for the antibody or antigen-binding fragment thereof to be introduced into the cell where the binding target is located. In one embodiment, an antibody of the invention can be expressed intracellularly as an intrabody. The term "intrabody," as used herein, refers to an antibody or antigen-binding portion thereof that is expressed intracellularly and that is capable of selectively binding to a target molecule, as described in Marasco, Gene Therapy 4: 11-15 (1997); Kontermann, Methods 34: 163-170 (2004); U.S. Pat. Nos. 6,004,940 and 6,329,173; U.S. Patent Application Publication No. 2003/0104402, and PCT Publication No. WO2003/077945. Intracellular expression of an intrabody is effected by introducing a nucleic acid encoding the desired antibody or antigen-binding portion thereof (lacking the wild-type leader sequence and secretory signals normally associated with the gene encoding that antibody or antigen-binding fragment) into a target cell. Any standard method of introducing nucleic acids into a cell may be used, including, but not limited to, microinjection, ballistic injection, electroporation, calcium phosphate precipitation, liposomes, and transfection with retroviral, adenoviral, adeno-associated viral and vaccinia vectors carrying the nucleic acid of interest. One or more nucleic acids encoding all or a portion of an anti-SSEA-3/SSEA-4/GLOBO H antibody of the invention can be delivered to a target cell, such that one or more intrabodies are expressed which are capable of intracellular binding to a SSEA-3/SSEA-4/GLOBO H and modulation of one or more SSEA-3/SSEA-4/GLOBO H-mediated cellular pathways.

In another embodiment, internalizing antibodies are provided. Antibodies can possess certain characteristics that enhance delivery of antibodies into cells, or can be modified to possess such characteristics. Techniques for achieving this are known in the art. For example, cationization of an antibody is known to facilitate its uptake into cells (see, e.g., U.S. Pat. No. 6,703,019). Lipofections or liposomes can also be used to deliver the antibody into cells. Where antibody fragments are used, the smallest inhibitory fragment that specifically binds to the binding domain of the target protein is generally advantageous. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA, 90: 7889-7893 (1993).

Entry of modulator polypeptides into target cells can be enhanced by methods known in the art. For example, certain sequences, such as those derived from HIV Tat or the Antennapedia homeodomain protein are able to direct efficient uptake of heterologous proteins across cell membranes. See, e.g., Chen et al., Proc. Natl. Acad. Sci. USA (1999), 96:4325-4329.

When the binding target is located in the brain, certain embodiments of the invention provide for the antibody or antigen-binding fragment thereof to traverse the blood-brain barrier. Certain neurodegenerative diseases are associated with an increase in permeability of the blood-brain barrier, such that the antibody or antigen-binding fragment can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the antibody or antigen-binding fragment across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9: 398-406 (2002)), interstitial infusion/convection-enhanced delivery (see, e.g., Bobo et al., Proc. Natl. Acad. Sci. USA 91: 2076-2080 (1994)), and implanting a delivery device in the brain (see, e.g., Gill et al., Nature Med. 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Vols 1 & 2, Plenum Press, N.Y. (1989))), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the antibody or antigen-binding fragment (see, e.g., U.S. Patent Publication No. 2003/0083299).

Lipid-based methods of transporting the antibody or antigen-binding fragment across the blood-brain barrier include, but are not limited to, encapsulating the antibody or antigen-binding fragment in liposomes that are coupled to antibody binding fragments that bind to receptors on the vascular endothelium of the blood-brain barrier (see, e.g., U.S. Patent Application Publication No. 20020025313), and coating the antibody or antigen-binding fragment in low-density lipoprotein particles (see, e.g., U.S. Patent Application Publication No. 20040204354) or apolipoprotein E (see, e.g., U.S. Patent Application Publication No. 20040131692).

Receptor and channel-based methods of transporting the antibody or antigen-binding fragment across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

The antibody composition of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibodies of the invention present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with other agents such as chemotherapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following are examples of the methods and compositions of the invention. It is understood that various other embodiments may be practiced, given the general description provided above.

In some embodiments, the provided glycan conjugates, immunogenic compositions or vaccines are useful in treating, or diagnosing a cancer, including, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM), a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva). In certain embodiments, the provided glycan conjugates, immunogenic compositions or vaccines are useful for treating brain cancer, lung cancer, breast cancer, oral cancer, esophagus cancer, stomach cancer, liver cancer, bile duct cancer, pancreas cancer, colon cancer, kidney cancer, bone cancer, skin cancer, cervix cancer, ovary cancer, and prostate cancer.

To perform the treatment methods described herein, an effective amount of any of the glycan conjugates or immunogenic compositions or vaccines described herein may be administered to a subject in need of the treatment via a suitable route, as described above. The subject, such as a human subject, can be a patient having cancer, suspected of having cancer, or susceptible to cancer. The amount of the glycan conjugate or immunogenic composition administered to the subject may be effective in eliciting immune responses specific to the glycan moiety in the conjugate or composition. In some embodiments, the amount of the glycan conjugate or immunogenic composition is sufficient to elicit immune responses leading to the inhibition of cancer growth and/or reduction of tumor mass. In other embodiments, the amount of the glycan conjugate or immunogenic composition may be effective in delaying the onset of the target cancer or reducing the risk for developing the cancer. The exact amount of the provided glycan conjugates, immunogenic compositions or vaccines required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount, of the provided glycan conjugates, immunogenic compositions or vaccines for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the provided glycan conjugates, immunogenic compositions or vaccines may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of the provided glycan conjugates, immunogenic compositions or vaccines to an adult. The amount to be administered to, for example, a child or an adolescent can be determined by a medical practitioner or person skilled in the art and can be lower or the same as that administered to an adult.

It will be also appreciated that the provided glycan conjugates, immunogenic compositions or vaccines can be administered in combination with one or more additional therapeutically active agents. The provided glycan conjugates, immunogenic compositions or vaccines can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The provided glycan conjugates, immunogenic compositions or vaccines can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

In certain embodiments, the provided glycan conjugate, immunogenic composition or vaccine is administered in combination with one or more additional pharmaceutical agents described herein. In certain embodiments, the additional pharmaceutical agent is an anti-cancer agent. Anti-cancer agents encompass biotherapeutic anti-cancer agents as well as chemotherapeutic agents.

Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. Herceptin (trastuzumab), T-DM1, AVASTIN (bevacizumab), ERBITUX (cetuximab), Vectibix (panitumumab), Rituxan (rituximab), Bexxar (tositumomab)).

Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), *vinca* alkaloids (e.g. vincristine, vinblastine, vindesine, and vinorelbine), taxoids (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), Ca2+ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIM 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

Cancer Stem Cell Biomarkers

The discovery of cancer stem cells (CSCs), which are responsible for self-renewal and tumor-growth in heterogeneous cancer tissues, has stimulated interests in developing new cancer therapies and early diagnosis. The markers currently used for isolation of CSCs, however, are often not selective enough to enrich CSCs for the study of this special cell population. Here we show that the breast cancer stem cells (BCSCs) isolated with CD44+CD24−/loSSEA-3+ or ESAhiPROCRhiSSEA-3+ markers had higher tumorigenicity than those with conventional markers in vitro and in vivo. As few as 10 cells with CD44+CD24−/loSSEA-3+ formed tumor in mice, compared to more than 100 cells with CD44+CD24−/lo. Suppression of SSEA-3 expression by knockdown of the gene encoding β1,3-galactosyltransferase 5 (βGalT5) in the globo-series pathway, led to apoptosis in cancer cells specifically but had no effect on normal cells. This finding is further supported by the analysis of SSEA-3 and the two related globo-series epitopes SSEA4 and globo-H in stem cells (ESCs and iPSCs) and various normal and cancer cells, and by the antibody approach to target the globo-series glycans and the late-stage clinical trials of a breast cancer vaccine.

Cancer stem cells are a special population of cancer cells with self-renewal and tumor-growth properties and are important targets for the development of anti-cancer therapy. We have found a glycolipid called stage-specific embryonic antigen 3 (SSEA-3) exclusively expressed on the surface of breast cancer stem cells, and when combined with the known protein markers (CD24 and CD44), breast cancer stem cells can be significantly enriched and as few as 10 such enriched cells can be used to grow tumor. In addition, the enzyme galactosyltransferase (β3GalT5) involved in the synthesis of SSEA3 is specifically expressed in breast cancer stem cells and cancer cells but not in normal cells, and both SSEA3 and β3GalT5 are found to be essential for cancer cell survival. These findings have led to the development of a new anti-cancer strategy.

Cancer stem cells (CSCs), which are rare cells with the ability of self-renewal and tumor initiation, are closely related to cancer progression and specific targets for effective therapy and early diagnosis. To date, many cancer stem cells have been identified and characterized by protein markers. Breast cancer stem cells (BCSCs) were first discovered in 2003 by Clarke et al.; it was demonstrated that breast cancer cells with CD44+CD24−/lo expression have higher level of tumorigenicity than others and can form tumor in animals with ~100 of such cells. In addition, other proteins such as ALDH-1 CD133, CD326 (ESA), CD201 (PROCR), and their combinations, are also reported as BCSCs biomarkers. However, the BCSCs obtained from the enrichment process based on these markers still contain a large number of non-cancer stem cells, and study of such cells would provide nonspecific characteristics of cancer stem cells. Therefore, new markers are required to enrich and obtain better-defined BCSCs for analysis and study.

Glycolipids are known to be altered during cancer development. In our previous study, the globo-series glycans SSEA-3 (Gb5), SSEA-4 (sialyl-Gb5) and globo-H (fucosyl-Gb5) are found exclusively on the cell surface of many cancers, including breast cancer and BCSCs. We also reported that BCSCs carrying either ESAhiPROCRhi or CD44+CD24−/lo showed high expression of these globo-series epitopes. SSEA-3 is synthesized from Gb4 by β3GalT5, and globo-H and SSEA-4 are synthesized from SSEA-3 by fucosyltransferases 1, 2 (FUT1, FUT2) and ST3 β-galactoside α-2,3-sialyltransferase 2 (ST3Gal2), respectively.

We report herein regarding SSEA-3 and the related glycans and enzymes in the globo-series pathway are cancer specific and are BCSC markers.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Exemplary Syntheses of SSEA3 Analogues

Scheme 1.

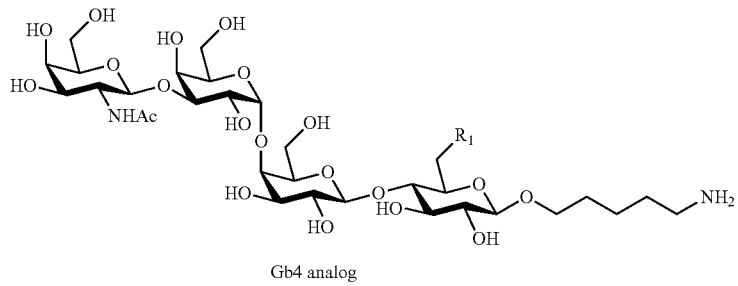

Gb4 analog

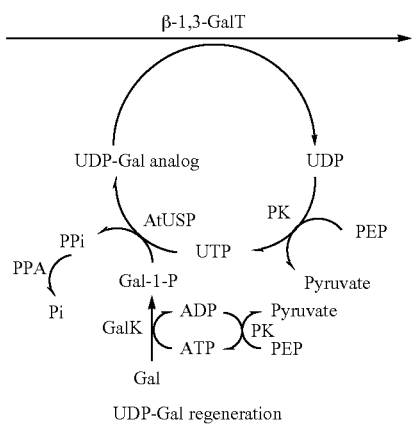

UDP-Gal regeneration

-continued

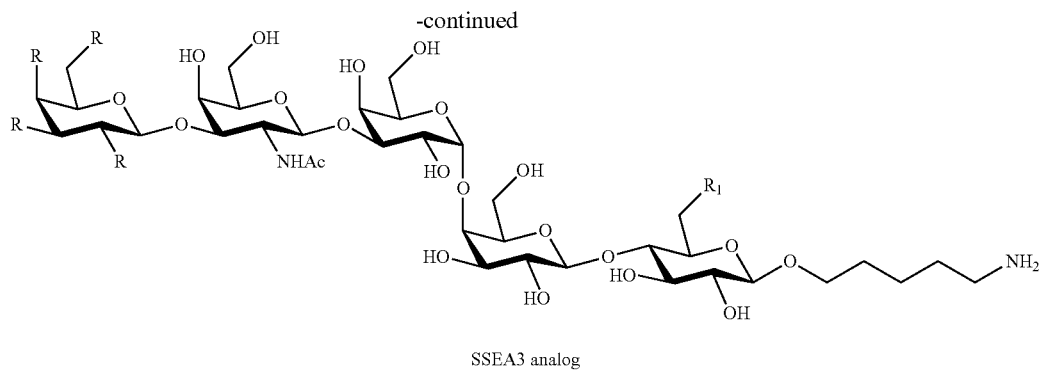

SSEA3 analog

The combined compounds Gb4 analog, ATP, UTP, galactose analog, phosphoenolpyruvate, MgCl2 with enzymes galactokinase (GalK), UDP-sugar pyrophosphorylase (AtUSP), β-1,3-galactosyltransferase (LgtD), pyruvate kinase (PK), and inorganic pyrophosphatase (PPA) in the solution, and the reaction was initiated at room temperature with the pH controlled at 7.0, and the reaction was monitored by TLC until no more product could be observed. After completion of the reaction, the proteins in the reaction mixture were removed by heating for 30 min followed by centrifugation and filtration with 0.22 μM filter. The filtrate was then purified by C-18 gel chromatography. Fractions were collected and monitored by TLC.

Example 2

Exemplary Syntheses of SSEA4 Analogues

Method 1: Chemical Synthesis of SSEA4-Gc

Compound 1-6 were prepared by literature reported methods. To a solution of acceptor 3 (93 mg, 0.045 mmol) and imidates 6 (76 mg, 0.068 mmol) in 6 mL of dichloromethane (CH2Cl2) was added powdered molecular sieves (4 A, 0.5 g). The mixture was stirred at room temperature for 2 h. After cooled to −10° C., TMSOTf (5 μL, 0.03 mmol) was added, and the mixture was stirred at 5° C. (cold room) overnight. The reaction mixture was quenched by the addition of triethylamine (0.5 mL), diluted with CH2Cl2 and filtered through a pad of celite. The filtrate was washed with saturated sodium bicarbonate (NaHCO3) aqueous solution, dried over sodium sulfate (Na2SO4), filtered, and concentrated. The residue was purified by flash silica get chromatography (50-100% EtOAc in Hexane) to afford hexasaccharide 7 contaminated with impurities from disaccharide imidates 6. The yield is estimated by NMR (90 mg, 68%).

To a solution of hexasaccharide 7 (90 mg, 0.03 mmol) in glacial acetic acid (5.0 mL) was added Zinc dust (1 g), and the mixture was stirred for 1-2 h, until compound 7 was consumed by TLC analysis. The reaction mixture was diluted with CH2Cl2, filtered through a pad of celite, and concentrated under reduced pressure. The residue was dissolved in pyridine/Ac2O (1:1, 2.0 mL), stirred for 1 h, and concentrated. The residue was purified by flash silica get chromatography. The acylated material was dissolved in anhydrous CH2Cl2 and MeOH (2:8, 10 mL) and treated with NaOMe (45 mg). After stirring at room temperature for 4 h, water (0.2 mL) was added, and the resulting mixture was stirred for 16 h. The reaction mixture was neutralized with amberlyst IR-120, filtered, and concentrated. The residue was purified by reverse phase chromatography (RP-18).

To the adduct in a mixture of methanol/water/Acetic acid (10:10:0.5, 6 mL) was added palladium hydroxide (20% in Charcoal, 50 mg), and the reaction mixture was stirred at room temperature under a positive pressure of hydrogen for 16 h. The reaction mixture was filtered through a pad of celite and concentrated. The residue was purified by reverse phase chromatography to afford 8 (17 mg, 43%).

Scheme 2:

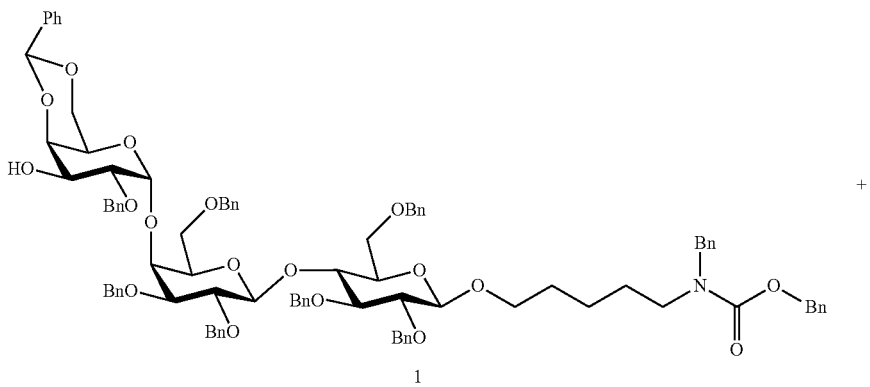

1

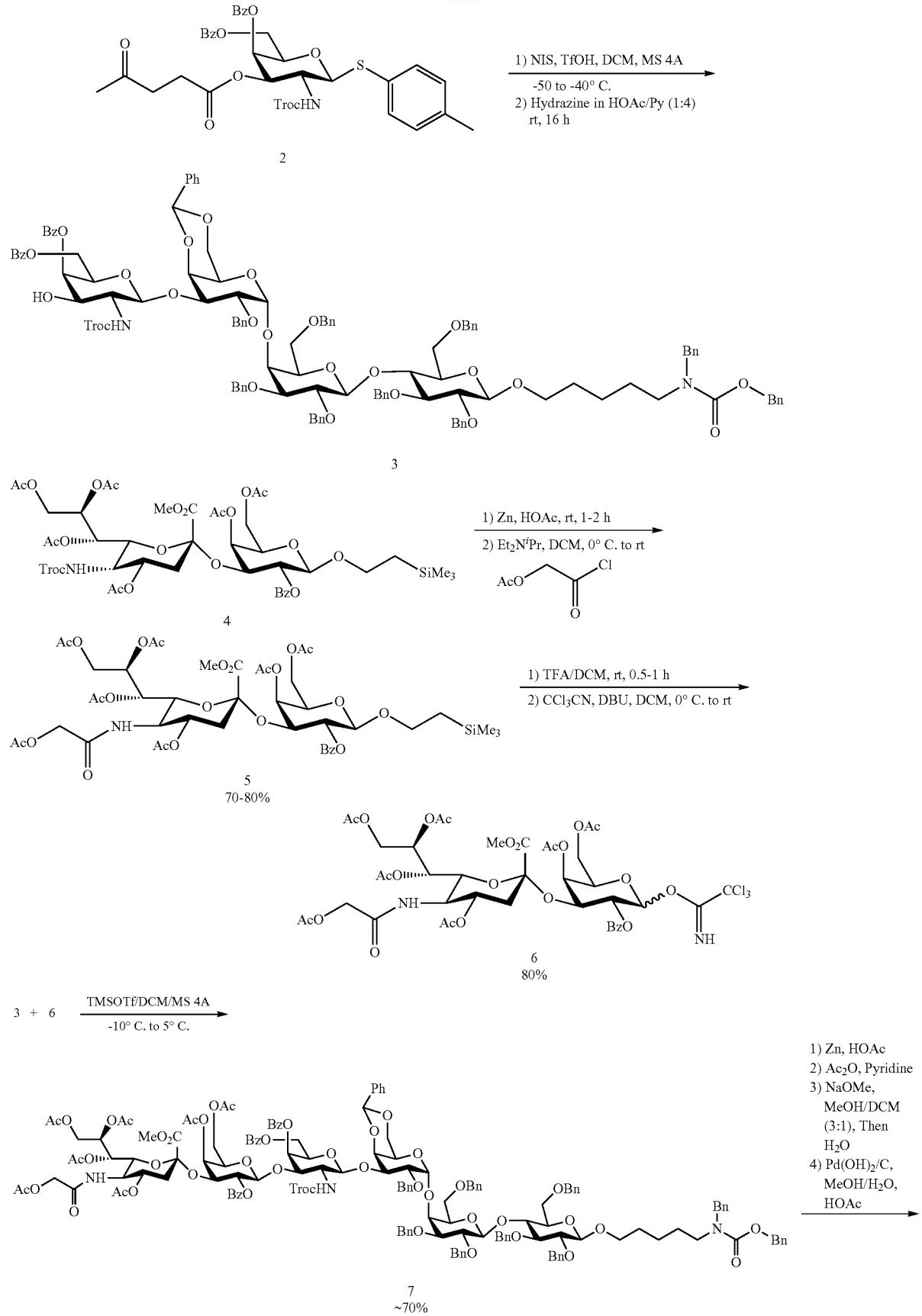

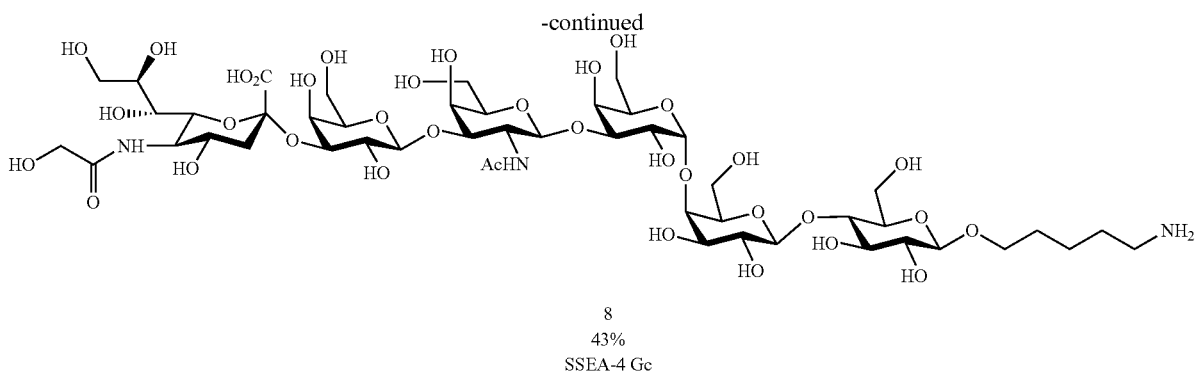

8
43%
SSEA-4 Gc

Method 2: General Strategy of Chemoenzymatic Synthesis of SSEA4 Analog

The CMP-sialic acid analog was synthesized by 3 enzymatic (ManNAc-6-kinase, NeuAc-9-P-synthase, and NeuAc-9-P-phosphase) reaction by using ManNAc as a starting material. The CMP-sialic acid analog reacted with Gb5 analog under α2,3-sialyltransferase reaction combined with CMP-Neu5AC regeneration can obtained the SSEA4 analog.ref2

Scheme 3

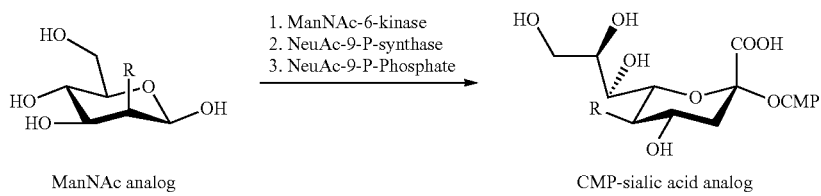

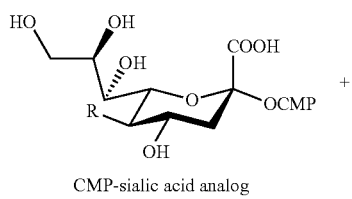

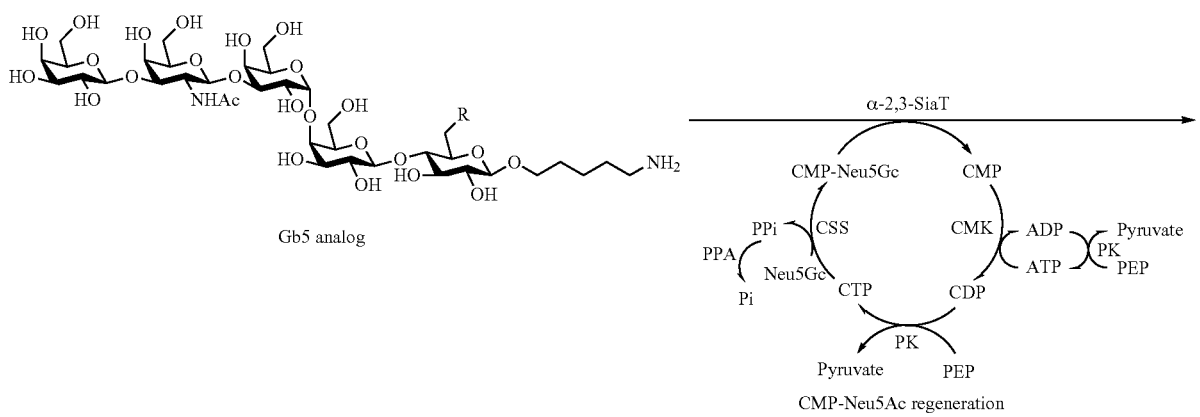

-continued

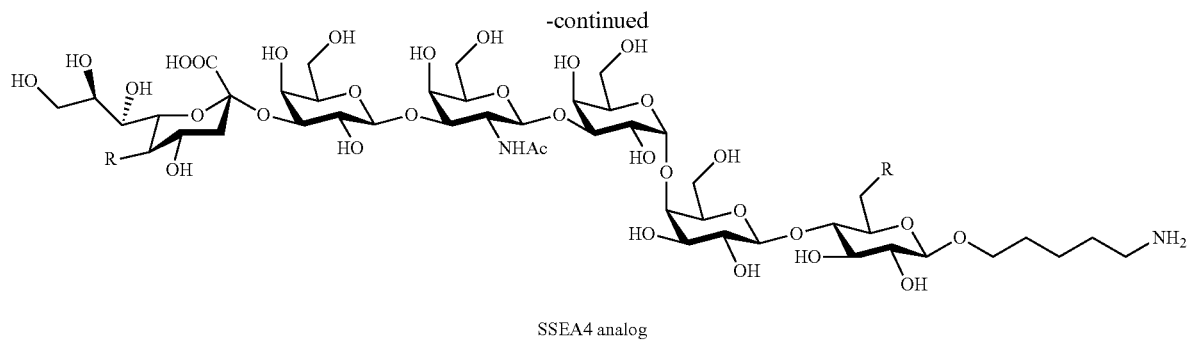

SSEA4 analog

Example 3

Synthesis of SSEA-3/SSEA-4 Derivatives DT-Conjugates

General Methods:

Step A. To Modify SSEA3 Analog-NH2 or SSEA4 Analog-NH2 into SSEA3 Analog-SH or SSEA4-Analog-SH To synthesize SSEA3/4 analog DT-conjugates, the amine-terminated SSEA3/4analog were reacted with the DTSSP linker in PBS buffer (pH 7.4) at room temperature. To monitor the pH value of solution by pH paper, and add some NaOH solution to the solution when the solution became neuter or acid. After the reaction was stirred at room temperature for 12 hours. DTT was added to the solution at room temperature. The solution was kept stirring at 40 C. and then the solvent was removed under reduced pressure. The residue was purified by LH-20 column chromatography to give SSEA3/4 analog-SH.

Step B: To Modify CRM197 into CRM197-Maleimide.

After the salt of commercial CRM197 (1.0 mg) was removed via alternate dissolving in water and dialyzing (Amicon Ultra-0.5, 10 kDa), the residue was dissolved in PBS buffer (pH 6.5, 1.0 mL) and transferred into a sample vial. Sulfo-EMCS (1.0 mg, 8.22×10−6 mol) was added to the solution, and then the reaction was kept stirring at room temperature for 2 hours. The mixture was purified by Amicon Ultra-0.5 (10 kDa). After using MALDI-TOF to check the molecular weight and BCA assay to calculate the amount of protein, the CRM197-maleimid was stored in PBS buffer (pH 7.2, 1.0 mg/mL) for next step. According to the data of MALDI-TOF, the amount of maleimid function groups could be calculated. For example, when the molecular weight of CRM197-maleimid was 61841, the numbers of maleimide function groups on CRM197-maleimid were (61841−58326)/193=18.2.

Step C: The Synthesis of SSEA3/4 Analog-CRM197 Conjugates

The CRM197-maleimids were dissolved in PBS buffer (pH 7.2, the concentration was 1.0 mg/mL) and then different amount of SSEA3/4 analog-SH (5.0 mg/mL in PBS buffer, pH 7.2) were added into the solution. The mixtures were stirred at room temperature for 2 hours. The SSEA3/4 analog-CRM197 conjugates were purified by using Amicon Ultra-0.5 (10 kDa) to remove the nonreactive SSEA3/4 analog-SH and sodium phosphate salt via dialysis. The obtained SSEA3/4 analog-CRM197 conjugates could be characterized by MALDI-TOF analysis to determine the carbohydrate incorporation rate. The nonreactive SSEA3/4 analog-SH could be recovered after reacting with DTT and purifying by LH-20 column chromatography.

Example 4

Syntheses of SSEA4-Gc CRM197 Conjugates

Step A: To Modify SSEA4-Gc-NH2 into SSEA4-Gc-SH

DTSSP (5.0 mg, 8.22×10−6 mol) was added to a flask of SSEA4-Gc-NH2 (5.0 mg, 4.01×10−6 mol) in PBS buffer (pH 7.4, 1.0 mL) at room temperature. To monitor the pH value of solution by pH paper, and add some NaOH (1 M/water) to the solution when the solution became neuter or acid. After the reaction was stirred at room temperature for 12 hours, DTT (5.0 mg, 32.41×10−6 mol) was added to the solution at room temperature. The solution was kept stirring at 40□ for 1 hour, and then the solvent was removed under reduced pressure. The residue was purified by LH-20 column chromatography to give SSEA4-Gc-SH (5.0 mg, 93%).

Step B: To Modify CRM197 into CRM197-Maleimide.

After the salt of commercial CRM197 (1.0 mg) was removed via alternate dissolving in water and dialyzing (Amicon Ultra-0.5, 10 kDa), the residue was dissolved in PBS buffer (pH 6.5, 1.0 mL) and transferred into a sample vial. Sulfo-EMCS (1.0 mg, 8.22×10−6 mol) was added to the solution, and then the reaction was kept stirring at room temperature for 2 hours. The mixture was purified by Amicon Ultra-0.5 (10 kDa). After using MALDI-TOF to check the molecular weight and BCA assay to calculate the amount of protein, the CRM197-maleimid was stored in PBS buffer (pH 7.2, 1.0 mg/mL) for next step. According to the data of MALDI-TOF, the amount of maleimid function groups could be calculated. For example, when the molecular weight of CRM197-maleimid was 61841, the numbers of maleimide function groups on CRM197-maleimid were (61841−58326)/193=18.2.

As following the Table 1, the CRM197-maleimids were dissolved in PBS buffer (pH 7.2, the concentration was 1.0 mg/mL) and then different amount of SSE4Gc-SH (5.0 mg/mL in PBS buffer, pH 7.2) were added into the solution. The mixtures were stirred at room temperature for 2 hours. The SSEA4-Gc-CRM197 conjugates were purified by using Amicon Ultra-0.5 (10 kDa) to remove the nonreactive SSEA4-Gc-SH and sodium phosphate salt via dialysis. The obtained SSEA4-Gc-CRM197 conjugates could be characterized by MALDI-TOF analysis to determine the carbohydrate incorporation rate as showing in Table 1. The nonreactive SSEA4-Gc-SH could be recovered after reacting with DTT and purifying by LH-20 column chromatography.

Step C: To Trap the Nonreactive Maleimides of CRM197-Maleimide

The SSEA4-Gc-CRM197 conjugates were dissolved in PBS buffer (pH 7.2, the concentration was 1.0 mg/mL) and 10.0 equivalent of 2-mercaptoethanol (5 mg/mL, PBS buffer, pH 7.2) were added to the solution. The mixtures were stirred at room temperature for 2 hours. The SSEA4-Gc-CRM197 conjugates were purified by using Amicon Ultra-0.5 (10 kDa) to remove the nonreactive 2-mercaptoethanol and sodium phosphate salt via dialysis and then lyphophilized to a white powder.

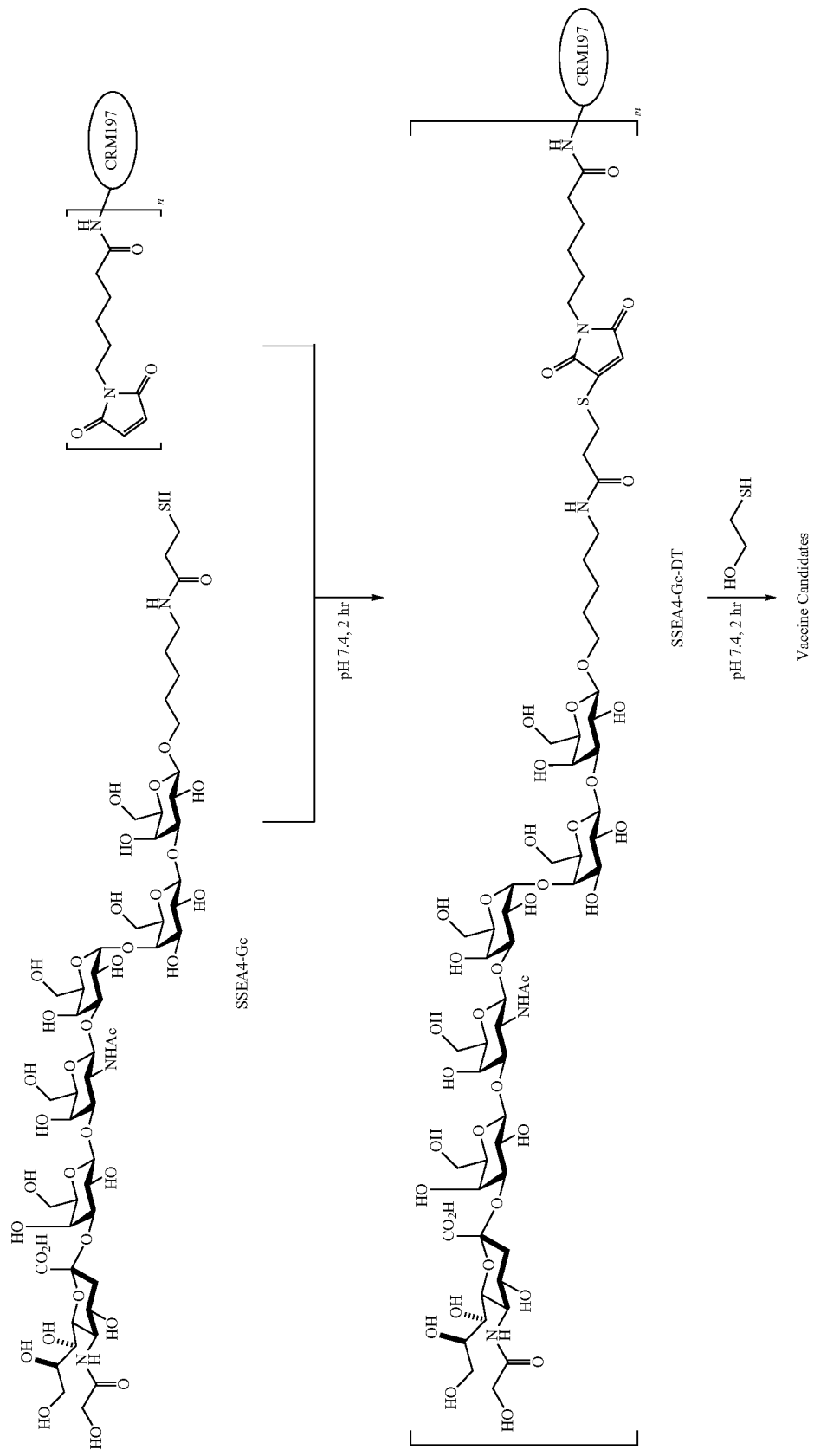

TABLE 1

MALDI-TOF analysis of average carbohydrate incorporation.
Conjugation of CRM197 with SSEA4-Gc

| | CRM197 (μg) | Number of Linkers | Amount of Linkers (mol) | PBS Buffer (pH 7.4, μL) | SSEA4-Gc (5 mg/mL) | Reaction Time | Number of Sugars | HSC$_2$H$_4$OH (5 mg/mL) 10.0 eq. | CRM197 (μg) |
|---|---|---|---|---|---|---|---|---|---|
| 1 | 1388 | 21.9 | 5.21 × 10$^{-7}$ | 1000 | 28.1 μL (0.2 eq.) | 2 hr | 2.0 | 81.4 μL | 1550.4 |
| 2 | 694 | 21.9 | 2.61 × 10$^{-7}$ | 500 | 28.2 μL (0.4 eq.) | 2 hr | 4.2 | 40.8 μL | 657.4 |
| 3 | 694 | 21.9 | 2.61 × 10$^{-7}$ | 500 | 56.4 μL (0.8 eq.) | 2 hr | 6.5 | 40.8 μL | 665.0 |
| 4 | 694 | 21.9 | 2.61 × 10$^{-7}$ | 500 | 84.5 μL (1.2 eq.) | 2 hr | 6.9 | 40.8 μL | 627.0 |
| 5 | 694 | 21.9 | 2.61 × 10$^{-7}$ | 500 | 140.9 μL (2.0 eq.) | 2 hr | 7.1 | 40.8 μL | 615.6 |
| 6 | 694 | 21.9 | 2.61 × 10$^{-7}$ | 500 | 281.8 μL (4.0 eq.) | 2 hr | 7.0 | 40.8 μL | 665.0 |
| 7 | 694 | 21.9 | 2.61 × 10$^{-7}$ | 500 | 704.4 μL (10.0 eq.) | 2 hr | 6.8 | 40.8 μL | 695.4 | a) M.W. of CRM197 = 58326 → 1000 μg = 0.1715 × 10$^{-7}$ mol
b) M.W. of SSEA4-Gc-SH = 1349.479 → 5 mg/mL = 37.051 × 10$^{-7}$ mol
c) M.W. of 2-Mercaptoethanol = 78.13 → 5 mg/mL 639.91 × 10$^{-7}$ mol Example 5

Immunogenicity Study of the SSEA-4 Derivatives DT-Conjugates

To investigate the immunogenicity of the SSEA4 analog DT-conjugates (1-DT to 10-DT), five female BALB/c mice were immunized intramuscularly with 2 μg of SSEA4 analog DT-conjugates and 2 μg of the glycolipid adjuvant C34 three times at biweekly intervals. In the previous study, the anti-GH antibodies titer was low with SSEA4 analog-protein conjugates alone without any adjuvants. The antisera from each immunogen were obtained ten days after the third immunization and were tested on the glycan microarray containing 94 chemically synthesized glycans, including globo series glycans and other tumor-associated carbohydrate antigens. Because some chemical modifications were carried out on the glycan, some functional linkers were also included in the glycan array to check the cross reactivity.

Figure 12:
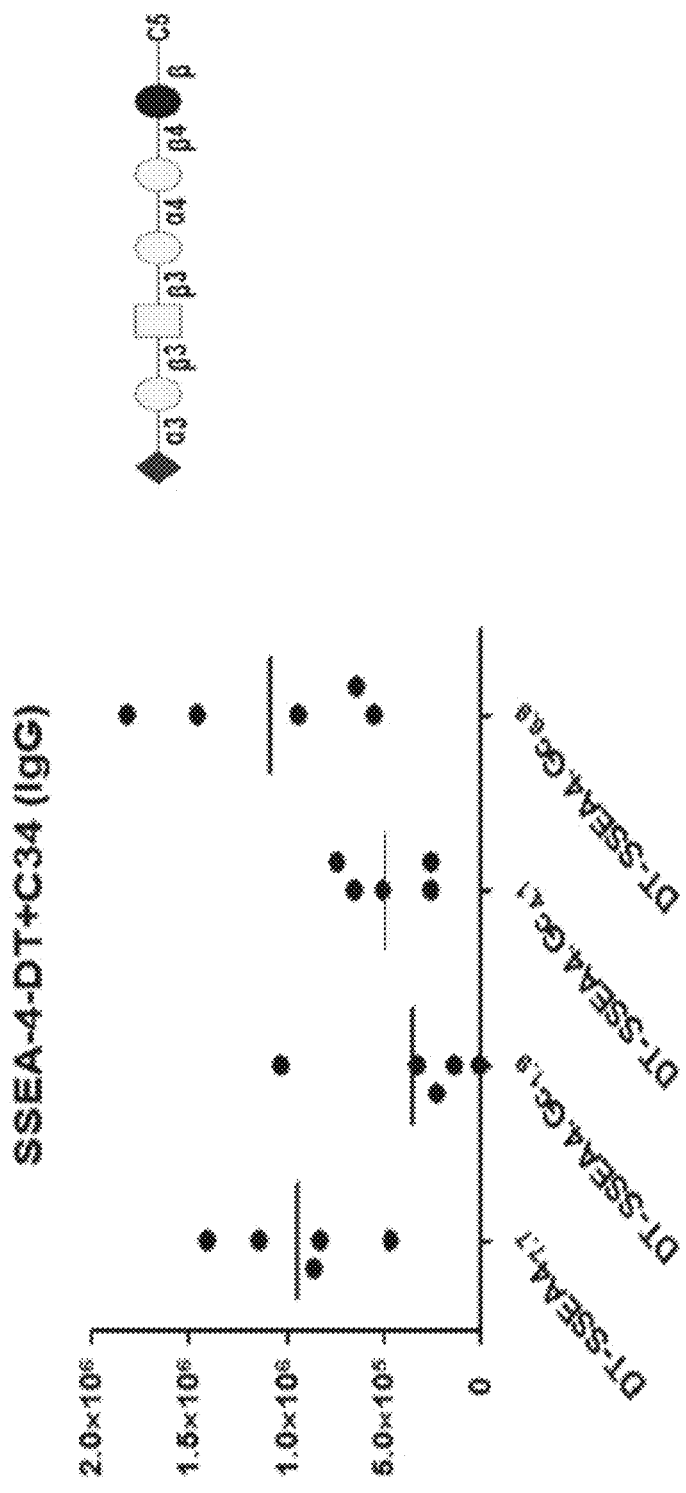
FIG. 12. The induced GH-IgG collected from different epitope ratios of SSE4-DT or SSEA4-Gc-DT immunization

Antibodies induced by the SSEA4-Gc CRM197-conjugates were specifically recognized by SSEA4-Gc, native SSEA4 or SSEA4 tetrasaccharide fragments but not by other TACAs and functional linkers. The sera obtained from the glycoconjugates induced high IgG antibody titers, indicating a T-cell-dependent immune response. Interestingly, no significant IgM production was observed for SSEA4-Gc or native SSEA4. Regarding the IgG level against GH, the titers of antibodies induced by SSEA4-Gc CRM197 was much higher than the nature form native SSEA-CRM197 conjugate. Among them the 6.9 molecule of SSEA4-Gc conjugated with one molecule of CRM197 can induce the highest antibody titers (also see FIG. 12).

Mice Dosage and Immunization Schedule

For comparing the immunogenicity of SSEA4 analog CRM197, ten groups of five mice (8-week-old female Balb/c mice, BioLASCO, Taiwan) were immunized intramuscularly with glycolipid C34. Three immunizations were given at 2-week intervals. Each vaccination contained 2 μg SSEA4 analog and 2 μg C34. Control mice were injected with phosphate buffer saline (PBS). Mice were bled before the first immunization (preimmune) and 10 d after the third immunization. All of the sera were obtained by centrifugation at 4,000×g for 10 min. The serologic responses were analyzed by glycan microarray.

Serologic Assay with Glycan Array

Mouse sera were diluted with 1% BSA/PBST buffer (PBST buffer: PBS and 0.05% Tween-20, pH 7.4). The glycan microarray was blocked with Superblock blocking buffer (Pierce) for 1 h at 4° C. and washed three times with PBST buffer before use. The serum dilutions were then introduced to the glycan microarray and incubated at 4° C. for 1 h. Excess serum antibodies were washed out and the microarrays were incubated individually with Alexa Fluor 647-conjugated goat anti-mouse IgG antibody or DyLight 649-conjugated goat anti-mouse IgM antibody as the 2nd antibody at 4° C. in dark for 1 h. The slides were then washed three times with PBST and scanned at 635 nm wavelength with a microarray fluorescence chip reader (GenePix 4300A; Molecular Devices Corporation) and scanned images were analyzed with GenePix Pro-6.0 analysis software (Axon Instruments, Union City, Calif., USA).

Example 6

Stage-Specific Embryonic Antigen-3 (SSEA-3) and β3GalT5 are Cancer Specific and Significant Markers for Breast Cancer Stem Cells Example: Cell Culture Breast cancer cell lines MDA-MB-231, MCF-7 and human breast cancer associated fibroblast (CAF) were obtained from American Type Culture Collection (ATCC). The culture of MDA-MB-231 was in DMEM supplemented with 10% of heat-inactivated FBS and antibiotic-antimycotic whereas that of MCF-7 culture was in RPMI supplemented with 10% of heat-inactivated FBS, non-essential amino acids and antibiotic-antimycotic. For the culture of CAF, it was in DMEM/F12 supplemented with 10% of heat-inactivated FBS, non-essential amino acids, sodium pyruvate, glutamine, penicillin and streptomycin. They were incubated at 37° C. incubator with 5% of CO2 and humidified atmosphere control. All the cell culture media and supplements were purchased from Life Technologies. Human ESC H9 and induced pluripotent stem cell 5 (iPSC5) were maintained and cultured on mitomycin C treated-mouse embryonic fibroblasts (MEFs) in human ES medium (Knockout DMEM with Knockout Serum Replacement, GlutaMAX, non-essential amino acids, 2-Mercaptoethanol, Penicillin/Streptomycin and bFGF) and were passaged weekly using collagenase IV.

Example: Derivation of iPSCs from Dermal Fibroblasts

Fibroblasts derived from dermal biopsies were reprogrammed into pluripotent stem cells using the CytoTune-iPS Sendai Reprogramming Kit (Life Technologies). Briefly, 5×104 fibroblasts were seeded per well in a 6-well dish at passage 3 for recovery overnight. The next day, Sendai viruses expressing human transcription factors OCT4, SOX2, Klf4, and c-Myc were mixed in fibroblast medium to infect fibroblast cells according to the manufacturer's instructions. After 2 days, the medium was exchanged with human ES medium supplemented with the ALK5 inhibitor SB431542 (2 µM; Stemgent), the MEK inhibitor PD0325901 (0.5 µM; Stemgent), and thiazovivin (0.5 µM; Stemgent). Day 7-10 after infection, cells were detached using TrypLE (Life Technologies) and passaged onto feeder cells. Individual colonies of iPSCs were picked between days 21 and 28 after infection, and each iPSC line was expanded from a single colony. All iPSCs lines were cultured on mouse embryonic fibroblast cells in human ES medium.

Karyotyping was performed by Cell Line Genetics Inc. In teratoma analysis, 1-2×107 from each iPSC line were detached and collected after TrypLE treatment. They were suspended in 0.5 mL human ES media. Followed by mixing with 0.5 mL Matrigel (BD Biosciences), cells were injected subcutaneously into dorsal flanks of an immunodeficient mouse (NOD.Cg-Prkdcscid Il2rgtm1Wjl/SzJ, stock no. 005557, The Jackson Laboratory). Eight weeks after injection, teratomas were harvested, fixed overnight with 4% paraformaldehyde, and processed according to standard procedures for paraffin embedding. The samples were then sectioned and H&E stained.

Example: Overexpression and Knockdown of β3GalT5

To establish human β3GalT5 overexpression stable lines, full-length cDNA that encodes human β3GalT5 was PCR amplified (forward primer—GCAGATCTATGGCTTTC-CCGAAGATG; reverse primer—GTCTCGACTCAGACA GGCGGACAAT), and subcloned into BglII/XhoI cut pMSCVpuro vector (Clontech). Murine stem cell virus (MSCV)-control and MSCV-β3GalT5 vesicular stomatitis virus G glycoprotein (VSV-G) pseudotyped retrovirus were then generated in GP2-293 cells (Clontech) and used to infect MCF-7 and MDA-MB-231 cells, Two days after viral infection. control and βGalT5 stable pools were selected with puromycin (2 µg/mL). To establish β3GalT5 knockdown cells, the lentivirus-shRNA systems for human β3ΓαλT5 were purchased from National RNAi Core Facility Platform, Academia Sinica, and the β3GalT5-short hairpin sequence is 5' CCGGGCAAGTGGTTTGTCAG-TAAATCTCGAGATTTACTGACAAACCACTTGCTT TTTG-3'. Briefly, shβ3GalT5 and shControl lentiviruses were incubated with MCF7 and MDA-MB-231 cells according to the manufacturer's instructions. Infected cells were harvested 48 h post-infection or selected with puromycin (2 µg/mL) and the knockdown efficiency was determined by quantitative RT-PCR (qPCR).

Example: Cell Proliferation Assay

Cell proliferation was analysed using a cell permeable tetrazolium salt, WST-1 (4-[3-(4-iodophenyl)-2-(4-nitrophenyl)-2H-5-tetrazolio]-1,3-benzene disulfonate), according to the manufacturer's instruction (Roche). 2×103 cells/well were cultured in 96-well plates. At different time points as indicated, WST-1 (20 µL per well for 200 µL culture medium) was added and incubated for 3 h at 37° C. incubator. Signaling detection of absorbance at 450 nm and 690 nm (as reference) were read by a SpectraMax M5 microplate spectrum reader (Molecular Devices).

Example: Apoptosis Assay

Cells were treated with or without 3β3GalT5 shRNA lentivirus (MOI: 5). Z-DEVD-FMK (caspase-3 inhibitor) (50 µM and 100 µM; R&D Systems), Z-IEFD-FMK (caspase-8 inhibitor), Z-LEHD-FMK (caspase-9 inhibitor), or Z-ATAD-FMK (caspase-12 inhibitor) (100 µM; R&D Systems) at 105 cells/mL as previously described. Three days later, cells were washed with PBS and incubated with allophycocyanin (APC)-conjugated armexin V (1:40 dilution; BD Biosciences) in binding buffer (0.01 M HEPES, 0.14 M NaCl, 2.5 mM CaCl2) for 15 min on ice and then subjected to flow cytometric analysis.

Exarmple: Western Blot Analysis

Protein lysates of MCF-7 and MDA-MB-231 cells were prepared using lysis buffer (150 mM NaCl2, 100 mM phosphate buffer at pH 7.4, 1% NP40, 10% glycerol) supplied with protease inhibitors (Roche). The proteins from cell lysate were denatured in sample buffer at 95° C. for 5 min before being applied to 4-12% gradient SDS/PAGE and were transferred onto methanol-rinsed PVDF membranes using transfer device (Bio-Rad). Membrane was blocked with 5% nonfat milk-supplied TBST for 30 min before probing with the anti-caspase-3 antibody that recognizes either procaspase-3 or cleaved/active form of caspase-3 (1:1,000 dilution; Abcam), followed by incubation with HRP-conjugated anti-rabbit antibody (1:5,000 dilution; Jackson ImmunoResearch) for 90 min. The signals were developed using the ECL Substrate Kit (Millipore) and detected by Fujifilm LAS-4000 imaging system.

Example: qPCR

Total mRNA from cell lines was extracted using GeneJET RNA Purification Kit (Thermo Scientific) and 2 ug of it was reverse transcribed to cDNA by High Capacity cDNA Reverse Transcription Kits (Life Technologies). qPCR reactions were prepared in a total volume of 20 µl containing 2 µl of cDNA of the test sample or control sample with 2×SYBR Green master mix (Thermo Scientific) optimized by the manufacturer's protocol. cDNA was examined the expression of B3GalT5 (Forward primer: 5'AGCGGA AAC-GAA AGAGGTGGAC 3'(SEQ ID NO: 4); Reversed primer: 5' CCTGAGGACAAA AGCGATGGAC 3' (SEQ ID NO: 5)) by Applied Biosystems 7300 Real-Time PCR system (Life Technologies). The relative gene expression was normalized as the ratio of the B3GalT5 gene to the internal GAPDH gene expression according to the Ct values using 7300 software.

Example: Extraction of Glycosphingolipids

Cells were harvested, washed with PBS, and homogenized in water. Methanol and chloroform were added to the homogenate at a ratio of 8:4:3 (vol/vol/vol), and the sample was incubated in a bath sonicator for 30 min. After centrifugation at 3,000×g for 15 min, the pellet was repeatedly extracted with 4:8:3 (vol/vol/vol) chloroform/methanol/water, and the combined supernatant was dried under a stream of nitrogen.

Example: Release of Glycans from Glycosphingolipids (GSLs) (26)

Cell were collected and quantified for the amount of total protein for normalization, and 1-3×106 cells were homogenized. In a typical procedure for the release of free glycans from GSLs, the GSLs were treated with ozone in chloroform/methanol (2:1; 1.0 mg/mL) in a glass tube until blue color occurs (10 min). The resulting solution was dried in a SpeedVac and treated by base for release of glycans from GSLs; briefly, aqueous sodium hydroxide solution (20-50 mM) was added, and the mixture was incubated for 16 h at room temperature. The resulting aqueous solution is lyophilized for labeling with NAIM tag.

Example: Labeling Glycans with NAIM Tag and LC-MS Analysis

After release from GSLs, the glycan mixture was lyophilized and labeled by following literature procedures (27, 28). Briefly, the glycan mixture was added 2,3-naphthalenediamine (NAIM, 1.0 mg) and iodine (1.0 mg) in AcOH (1.0 mL) at room temperature and stirred for 4 h. The completion of reaction was checked by TLC analysis. The reaction mixture was then triturated with EtOAc (10.0 mL×2) to give precipitates (globo-H-NAIM, SSEA-4-NAIM and SSEA-3-NAIM), which were collected by filtration using nylon membrane filter. The NAIM-labeled glycans, which showed enhanced ionization ability in MS (29), were analysed by high resolution and high mass accuracy nanoflow LC-MS/MS. Samples were injected at 10 μL/min into a precolumn (150 μm I.D.×30 mm, 5 μm, 200 Å) and then separated in a reversed phase C18 nano-column (75 μm I.D.×200 mm, 2.5 μm, 100 Å) for analysis in an LTQ FT Ultra mass spectrometer (Thermo Fisher Scientific) was equipped with a nanoelectrospry ion source (New Objective). Separation was performed at 300 nL/min using 0.1% formic acid in water as mobile phase A and 0.1% formic acid in 80% acetonitrile as mobile phase B. Survey full scan MS spectra (from m/z 320 to 2,000) were acquired in the FT with a mass resolution of 100,000 at m/z 400.

Example 9

Demonstration that Stage-Specific Embryonic Antigen-3 (SSEA-3) and β3GalT5 are Cancer Specific and Significant Markers for Breast Cancer Stem Cells To demonstrate the tumorigenic ability of cells, cancer cells were stained with corresponding antibodies against the glycolipid molecules SSEA-3, SSEA-4 and globo-H and the known marker sets CD44/CD24 and ESA/PROCR, in breast cancer cell lines MCF-7 and MDA-MB-231, respectively, for the cell sorting (Fig. S1, sorting 1). The isolated cell populations were next analyzed by both in vitro and in vivo assays (FIG. 1). In MCF-7, cancer cells expressing CD44+CD24−/loSSEA-3+ formed a higher percentage of mammospheres than those expressing CD44+CD24−/loSSEA-3− or CD44+CD24−/lo (FIG. 1A, left panel). Similarly, in MDA-MB-231, the ESAhiPROCRhiSSEA-3+ subpopulation formed a higher percentage of cell colonies than ESAhiPROCRhiSSEA-3− or ESANPROCRhi cells in the soft agar assay (FIG. 1C, left panel). However, there were no significant differences in the formation of cell colony and mamtnosphere using the cells isolated by the known marker sets along with the glycolipid epitopes SSEA-4 or globo-H (FIG. S2). In order to show the tumorigenicity in cells carrying known BCSC markers and SSEA-3, different subpopulations were inoculated into the mammary glands of NOD-SCID mice for tumor-growth. The result showed that both CD44+CD24−/loSSEA-3+ and ESAhiPROCRhiSSEA-3− effectively generated tumor in vivo with a low cell number, compared with other corresponding subpopulations (FIG. 1 B, D). Particularly for cells expressing CD44+CD24−/loSSEA-3+, as few as 10 cells were able to form tumor in mice (FIG. 1B). In terms of tumor-growth, the tumor volume of CD44+CD24−/loSSEA-3+cells was twice larger than that of CD44+CD24−/loSSEA-3− cells (FIG. 1E, left panel). In addition, ESAhiPROCRhiSSEA-3+ cells developed tumor earlier, and formed tumor in a greater average volume than ESAhiPROCRhiSSEA-3− cells. These results indicate that SSEA-3 is a specific marker for the enrichment of BCSCs in different breast cancer cell models. Among these glycan molecules, cells carrying SSEA-3 and known BCSC markers had a higher tumorigenicity than other subpopulations.

We next compared the stem-like properties of cancer cells with highly expressed SSEA-3 and those without SSEA-3 (Fig S1, sorting 2). In SSEA-3+ MCF-7 cells, the top 1% of cells expressing a high level of SSEA-3 within the total population, formed a higher percentage of mammosphere than the bulk population and those without SSEA-3 and CD44+CD24−/lo (FIG. 1A, right panel). In addition, the top 1% of MDA-MB 231 cells with the highest SSEA-3 expression within the bulk population also formed more cell colonies than the bulk population and other subpopulations (FIG. 1c, right panel). In the animal study, results showed that the cells with top 1% SSEA-3 expression had a higher potential to form tumor than SSEA-3− cells (FIGS. 1B and D), and the average tumor volume of SSEA-3+ cells was greater than that of SSEA-3− cells (FIG. 1E, F, right panel). Thus, cancer cells expressing a high level of SSEA-3 had a higher tumorigencity than those without SSEA-3 on cell surface, indicating that SSEA-3 is also an independent CSCs marker for breast cancer.

Figure 2B:
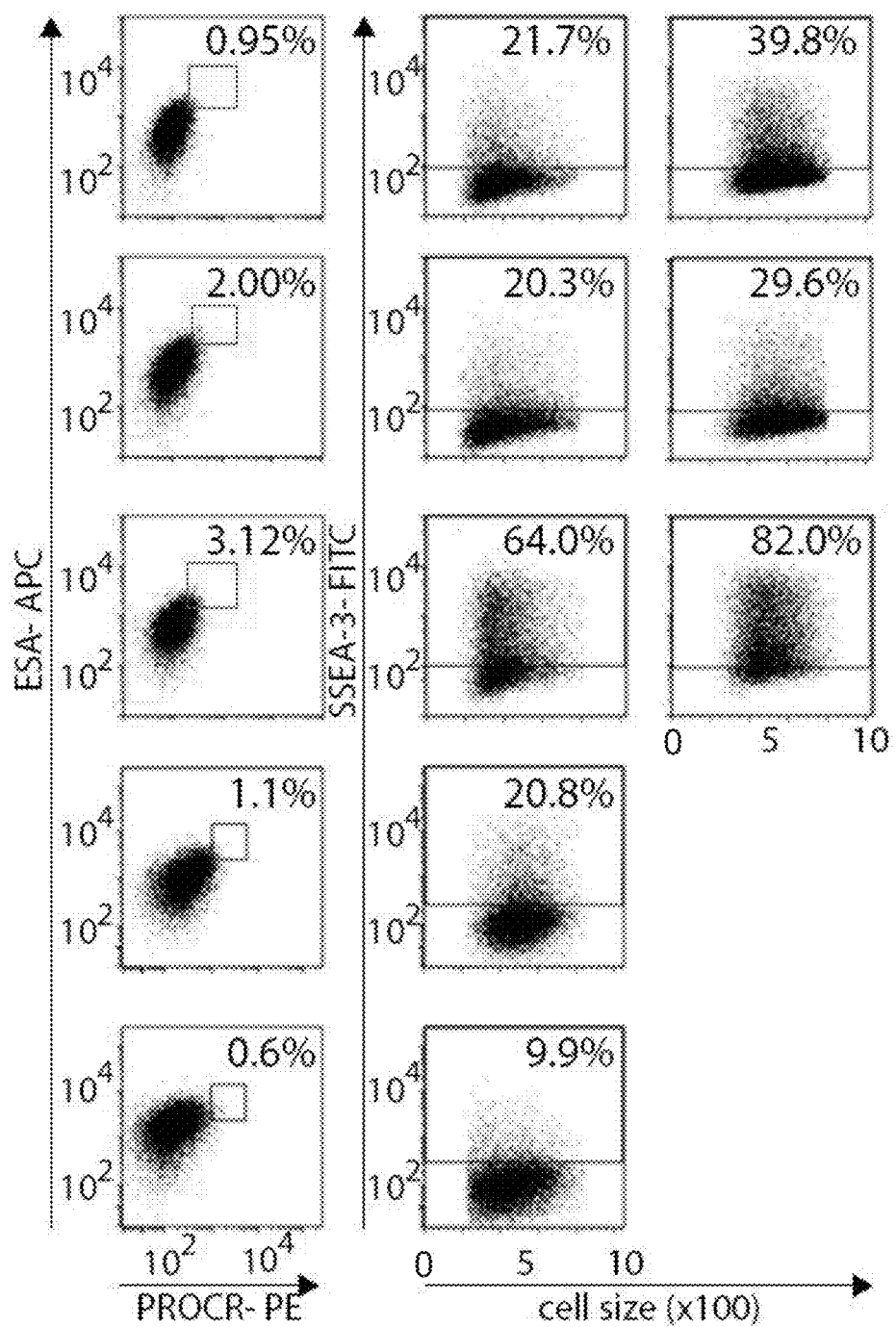

To understand the function of SSEA-3, the gene of β3GalT5 responsible for SSEA-3 biosynthesis (FIG. S3) was overexpressed or knocked down for further study. Overexpression of β3GalT5 increased the expression level of surface SSEA-3 in both MCF-7 and MDA-MB-231 cells (FIG. 2). Notably, in MCF-7 cells, the percentage of CD44+CD24−/lo cell population showed five-fold increase comparing to control (FIG. 2A); in MDA-MB-231 cells, there was no change in the percentage of ESAhiPROCRhi when β3GalT5 was overexpressed (FIG. 2B). In MCF-7 cells with β3GalT5 knockdown, comparing with control cells, the expression level of surface CD44 was reduced, and therefore the CD44-CD24+ cell population increased 10 folds (FIG. 2A). In MDA-MB-231 cells with β3GalT5 knockdown, the level of surface PROCR decreased and the ESAhiPROCRhi BCSC subpopulation reduced (FIG. 2B). These findings demonstrate that SSEA-3 is a critical glycan molecule associated with BCSCs.

Figure 3A:
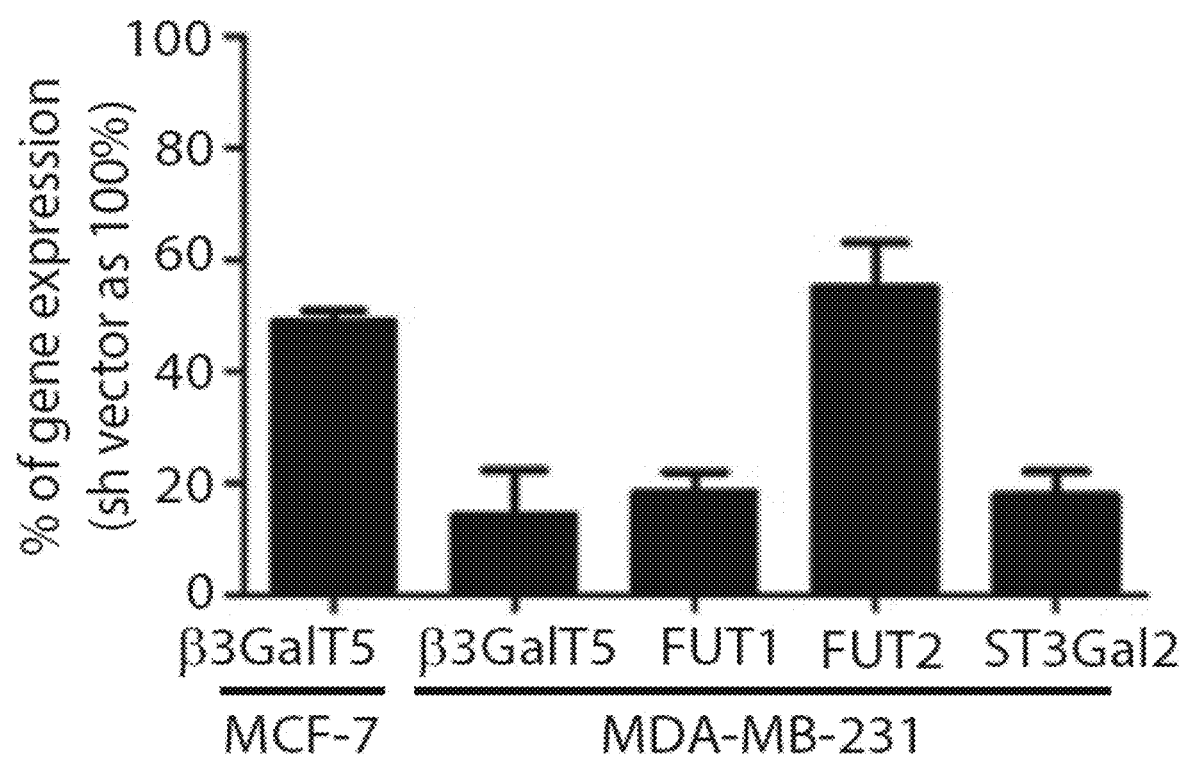
FIG. 3A-D—the induction of apoptosis in β3GalT5 knockdown cell lines. 3A The relative percentage of gene expression (β3GalT5 in MCF-7, 133GalT5, FUT1, FUT2 and ST3Gal2 in MDA-MB-231) after knocking down the respective genes. The percentage of gene expression in vector control cells were normalized to 100. 3B. The mean percentage of apoptosis in breast normal (hTERT-HME1, MCF-10A) and cancer (MCF-7, MDA-MB-231) cell lines from three experiments. 3C Flow cytometric analysis of the apoptosis percentage in breast cancer cell lines MDA-MB-231, MCF-7, and breast non-cancer lines hTERT-HME1 and MCF-10A was examined after knockdown of beta3GalT5 for 4 days. The apoptotic cells were compared with unstained cells and gated. 3D The percentage of apoptosis in MDA-MB-231 cells with knockdown of gene FUT1, FUT2, ST3Gal2 or beta3GalT5 and vector control. The mean of apoptotic cells is from three experiments. Asterisks indicate statistical significance, $p<0.05$; n.s. not significant.
Figure 3B:
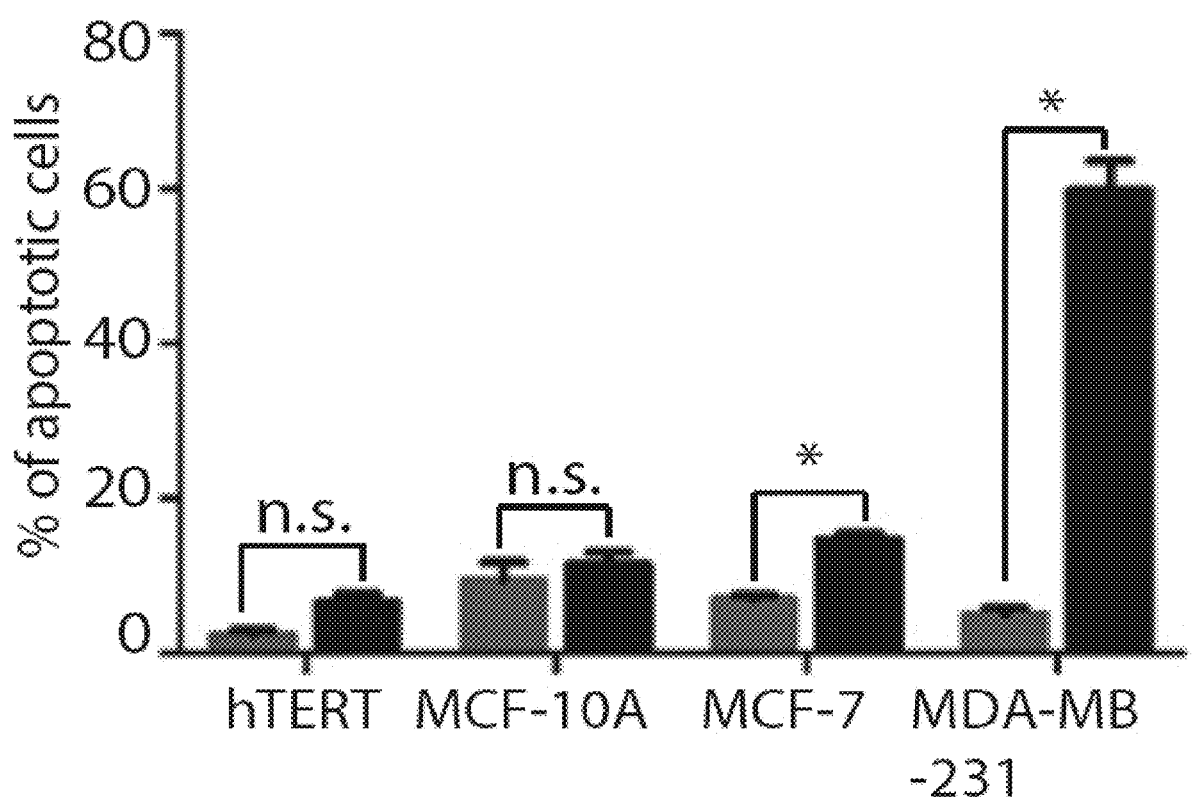
Figure 3C:
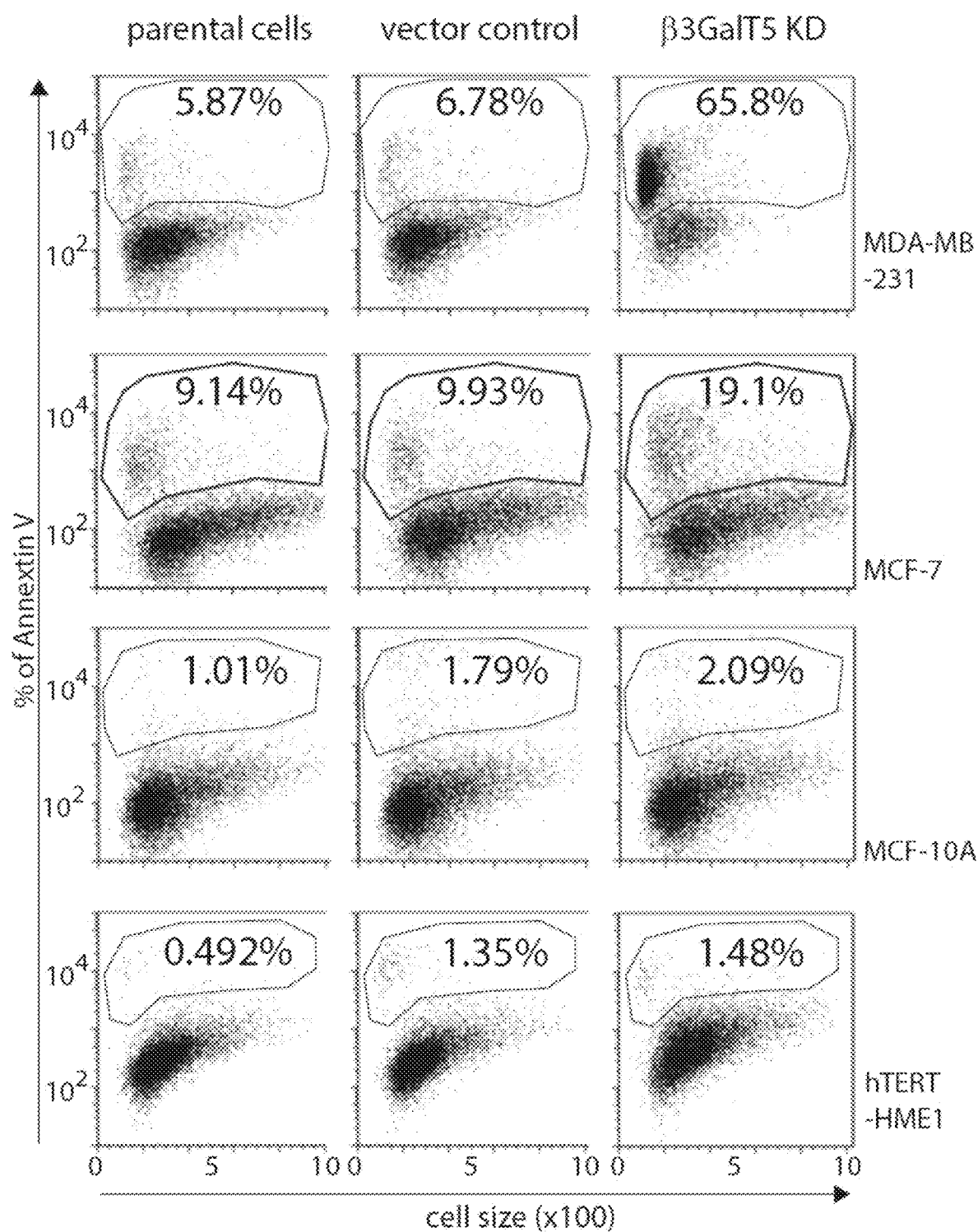
Figure 3D:
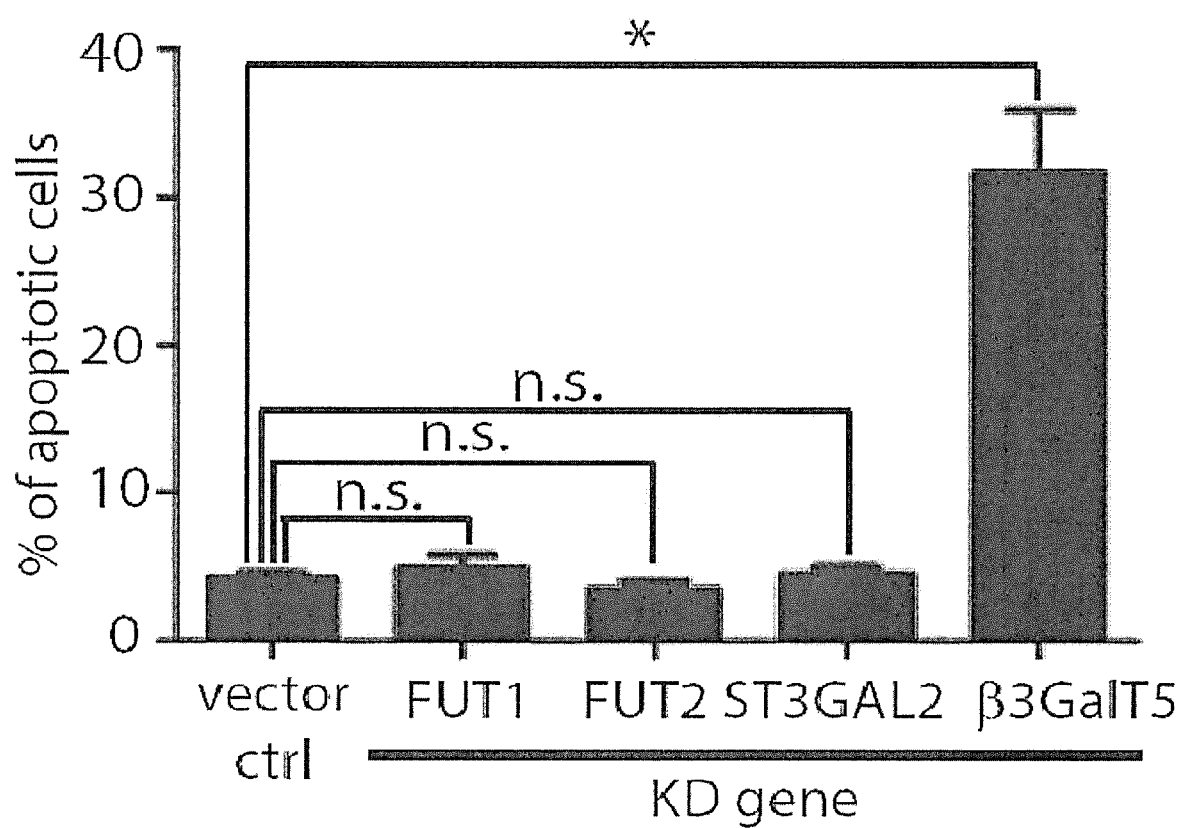
Figure 4A:
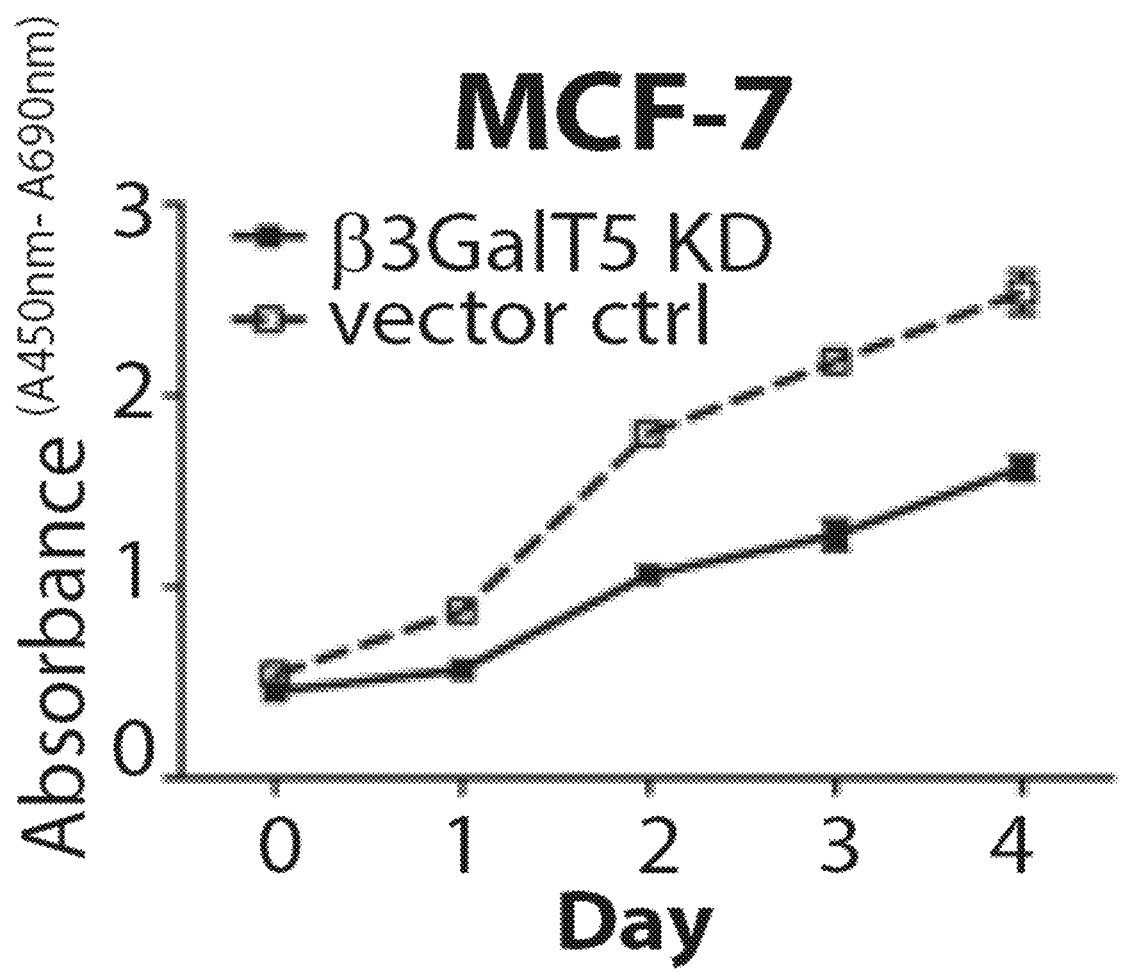
FIG. 4A-G—Knockdown of β3GalT5 caused reduced proliferation rate and increased apoptosis in cancer cell culture but no effect on normal breast cell culture. 4A-4D The rate of proliferation in cancer cell culture MCF-7 and MDA-231, as well as breast normal cell culture MCF-10A and hTERT-HME1. Proliferation rate, in terms of absorbance $^{(A450\ nm - A690\ nm)}$, is the triplicate from a representative sample. 4E MDA-MB-231 cells infected with shRNA beta3GalT5 or shRNA vector were lysed and whole-cell extract, cytoplasmic and nuclear fractions were prepared. Top, western-blot analysis of anti-caspase-3 antibody; middle, that of cleaved caspase-3 antibody; bottom, that of β-actin (served as a loading control) 4F, 4G The percentage of apoptotic MDA-MB-231 cells with β3GalT5 knockdown. MDA-MB-231 cells were treated with caspase-3 inhibitors Z-DEVD in different concentrations or the inhibitors for caspase-8, 9 or 12. Data represent here is the mean and standard deviation (S.D.) from triplicated sample. Asterisks indicate statistical significance, $p<0.05$; n.s. not significant.
Figure 4B:
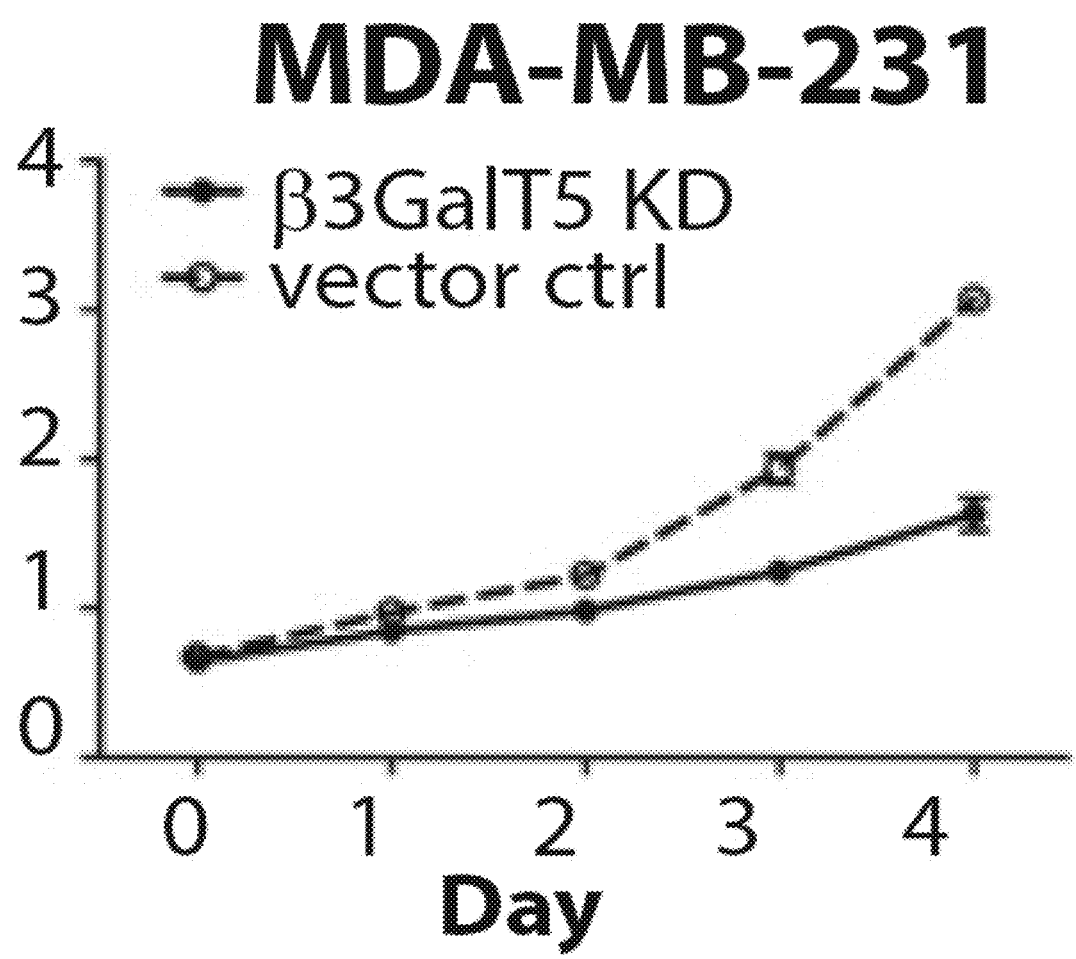
Figure 4C:
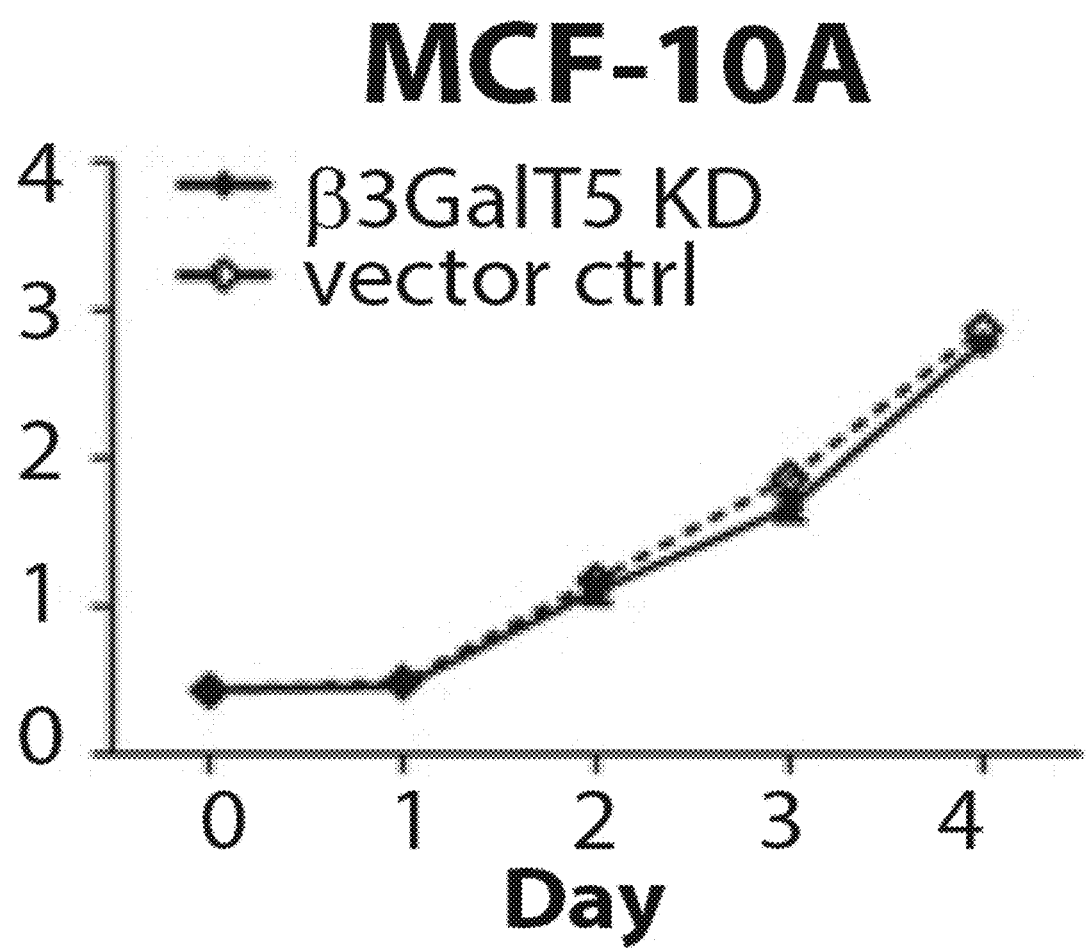
Figure 4D:
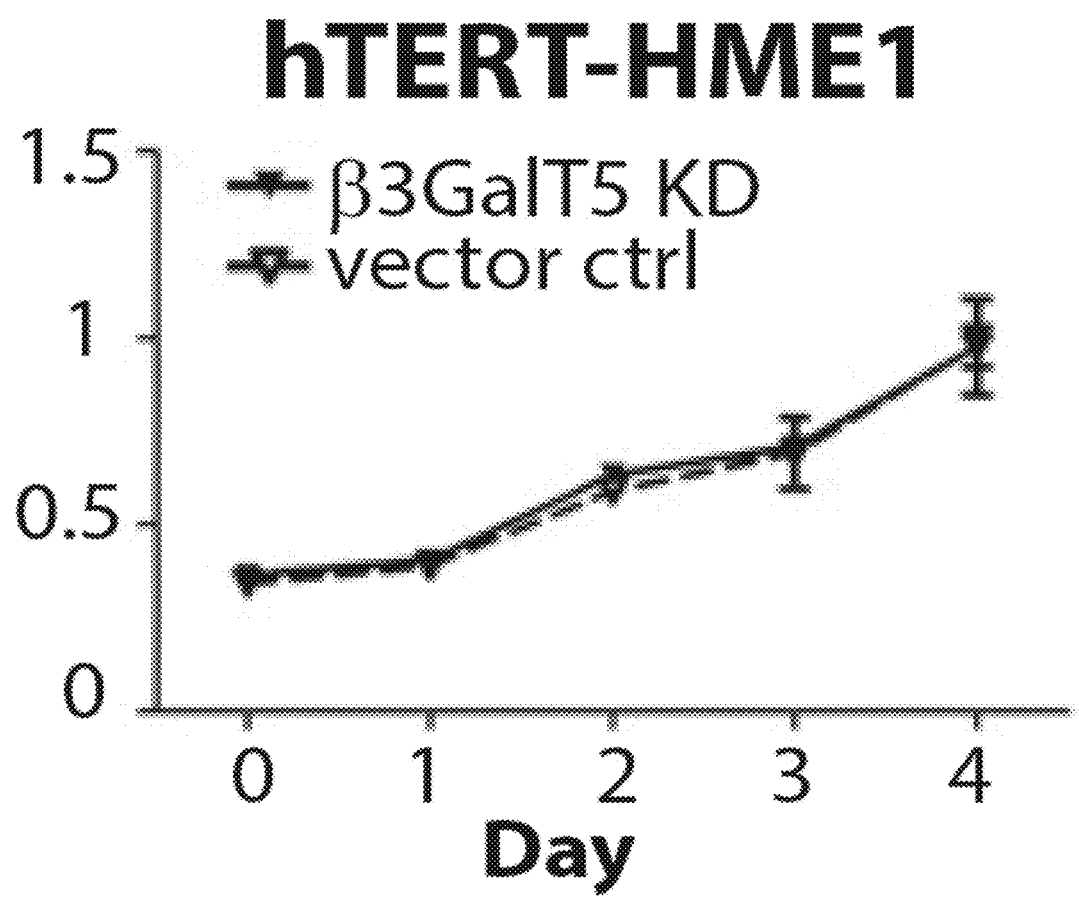

To demonstrate the role of SSEA-3 in breast cancer and normal cells, the cellular phenotypes were examined in the β3GalT5 knockdown cells. In both MDA-MB-231 and MCF-7 cells, knockdown of β3GalT5 suppressed cell growth (FIGS. 4A and B), along with the appearance of cell apoptosis, especially in MDA-MB-231 cells that >60% of cells underwent apoptosis on day 4 (FIGS. 3B and C). In contrast, in normal breast cells MCF-10A and human telomerase reverse transcriptase (hTERT)-immortalized human mammary epithelial cells, hTERT-HME1, the same growth rate and no apoptosis was observed with knockdown of β3GalT5 (FIGS. 3B, 3C, 4C and 4D). However, knockdown of FUT1 and FUT2 for the synthesis of globo-H from SSEA-3 or ST3Gal2 for the synthesis of SSEA-4 from SSEA-3 did not induce cell apoptosis in MDA-MB-231 cells (FIG. 3A, D).

Figure 4E:
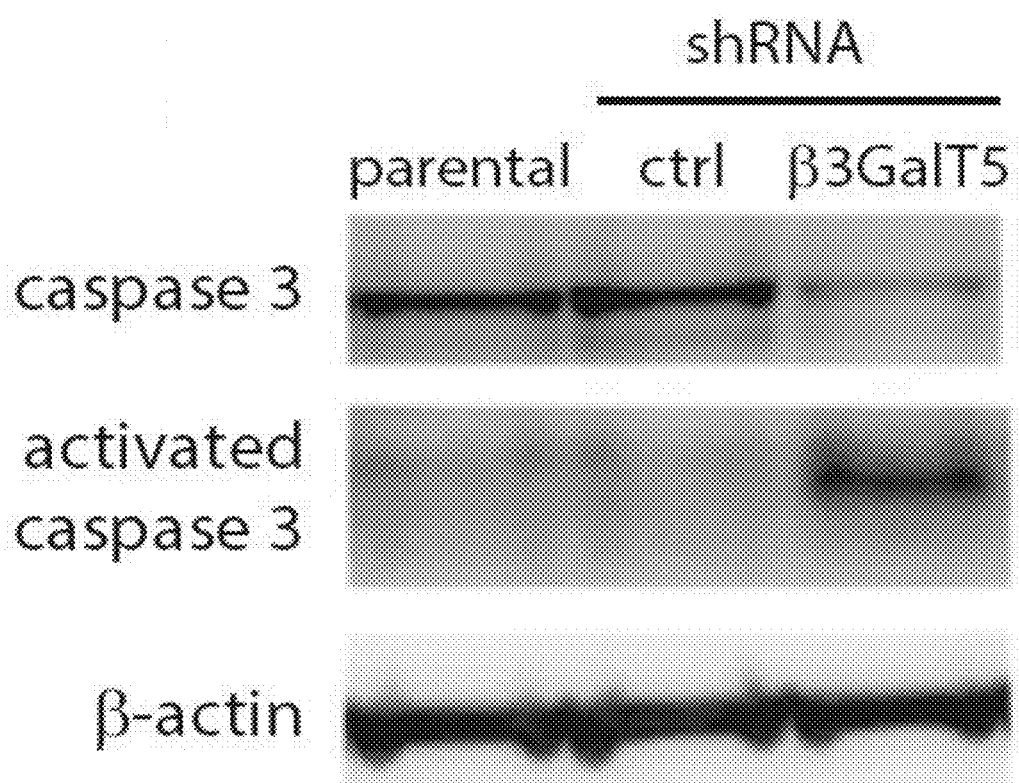
Figure 4F:
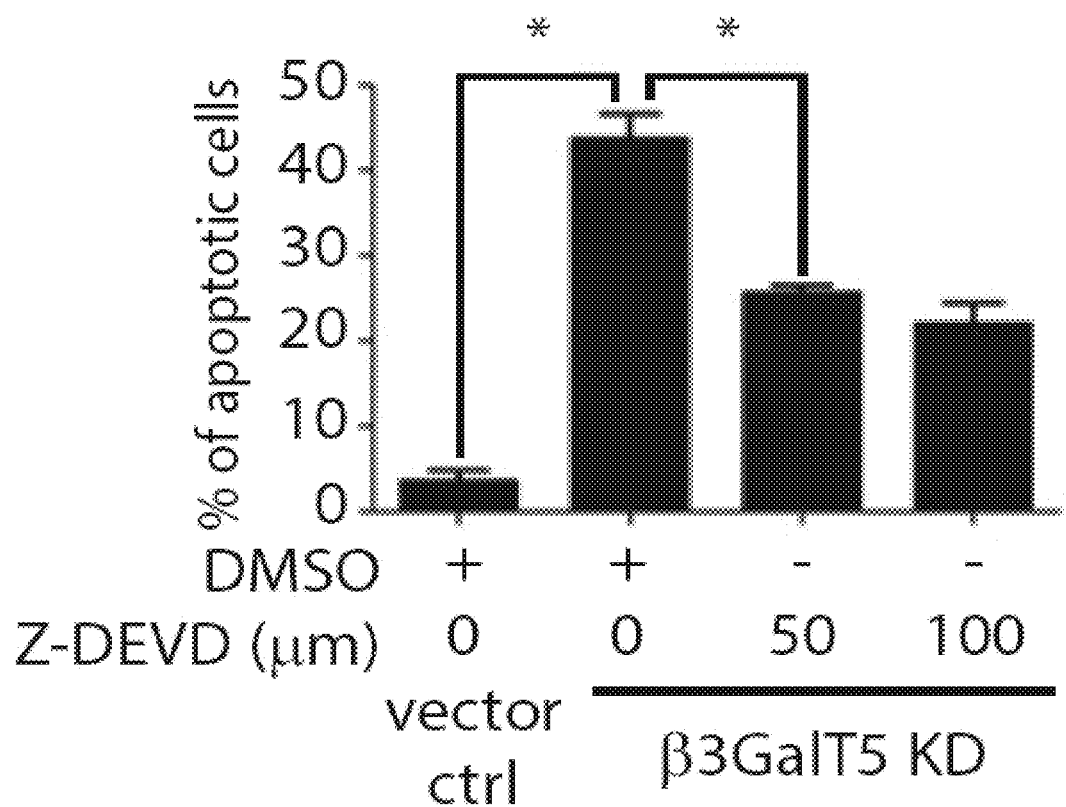
Figure 4G:
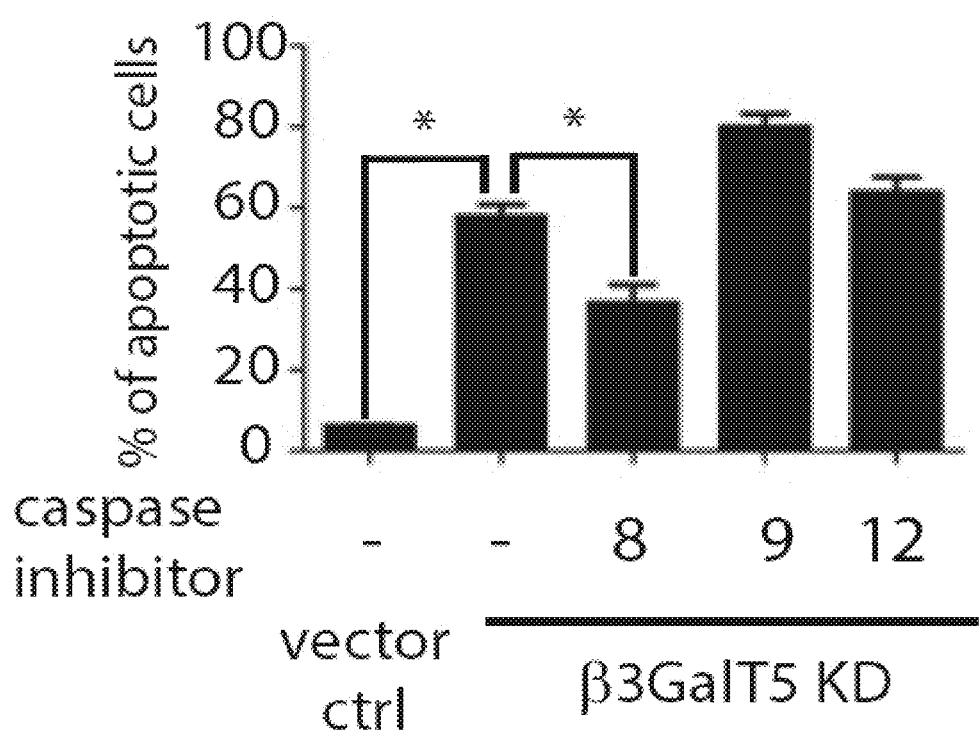

To further investigate if the apoptosis induced by β3GalT5 knockdown is associated with the activation of caspase-3, the most effector caspase for the downstream execution of apoptosis. Results showed that caspase-3 was activated in MDA-MB-231 cells with knockdown of β3GalT5 (FIG. 4E). When the inhibitor for caspase 3, Z-DEVD was added, the percentage of apoptosis induced by β3GalT5 knockdown reduced (FIG. 4F). The involvement of caspase-3 in the apoptosis induced by β3GalT5 knockdown was also confirmed in MCF-7, a caspase-3-deficient cell line. Although the growth rate of MCF-7 was significantly reduced by knockdown of β3GalT5, only a low level of apoptosis was shown when the expression of SSEA-3 was suppressed (FIGS. 3B and C). Further investigation of the upstream caspases (caspase-8, -9, and -12) was then studied by testing with specific inhibitors, and the result illustrated that caspase-8 also reduced the percentage of cell apoptosis in MDA-MB-231 cells with β3GalT5 knockdown (FIG. 3G). These results suggest that SSEA-3, the immediate enzymatic product of β3GalT5, is an important glycolipid for growth and survival in cancer.

Figure 5A:
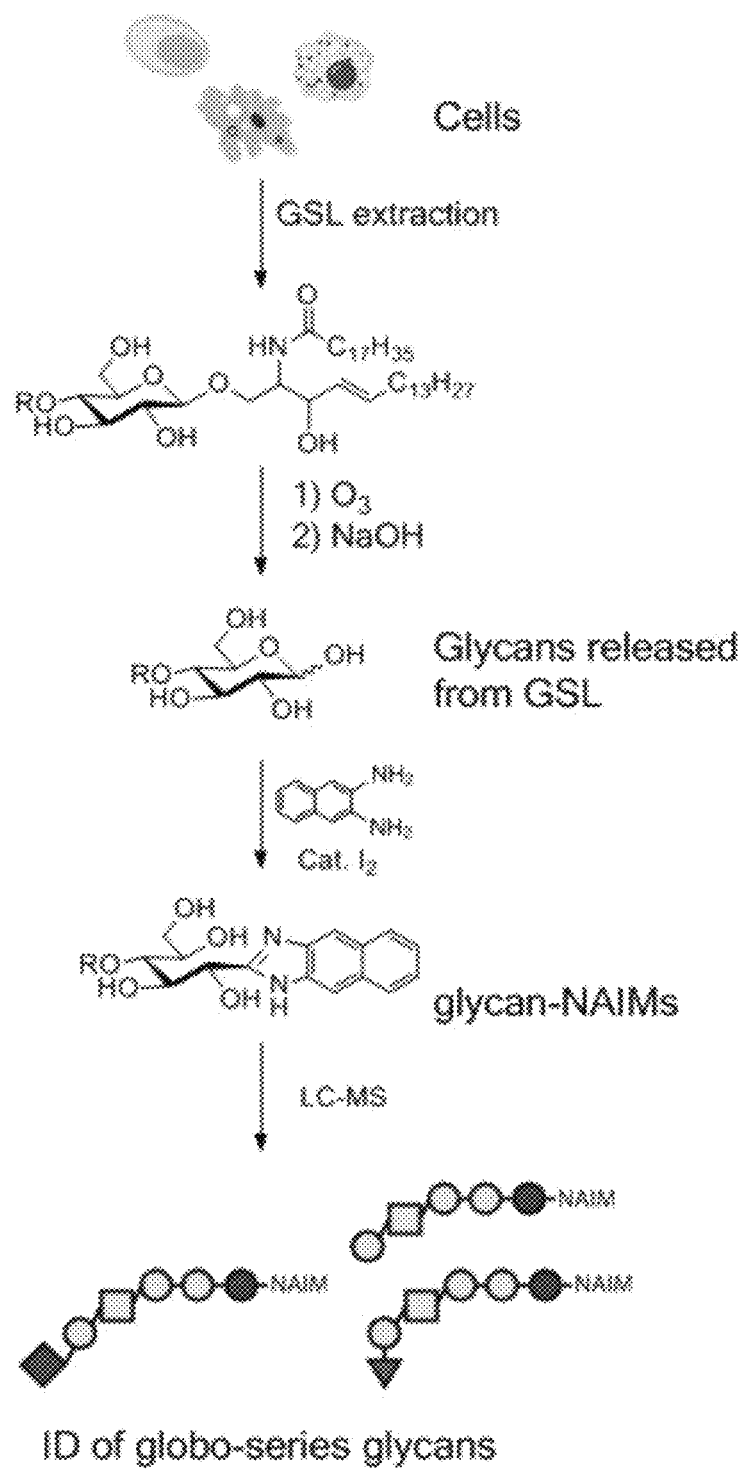
FIG. 5A-G—the comparison of the abundance of globo-series epitopes in cell lines by flow cytometry and mass spectrometry. 5A The scheme of extraction of glycan from glycolipid on cells for fluorescent labeling and LC-MS analysis. 5B-5G The relative abundance of globo-series epitopes SSEA-3, SSEA-4 and globo-H in breast cancer cell lines MCF-7 and MDA-MB-231, normal cell lines hTERT-HME1 and MCF-10A, embryonic stem cells (ESC) as well as induced pluripotent stem cells (iPSC) was detected by FACS and mass spectrometry. For figures of flow cytometry, histograms of cells stained with anti-glycan antibodies (in red, blue or green) and their corresponding antibody isotype controls (in gray) were shown. Geometric mean of fluorescence was shown in the bracket. For MS, the retention times of m/z (SSEA-3=1008.3667, SSEA-4=1299.4621 and globo-H=1154.4246) were shown in graphs.
Figure 5B:
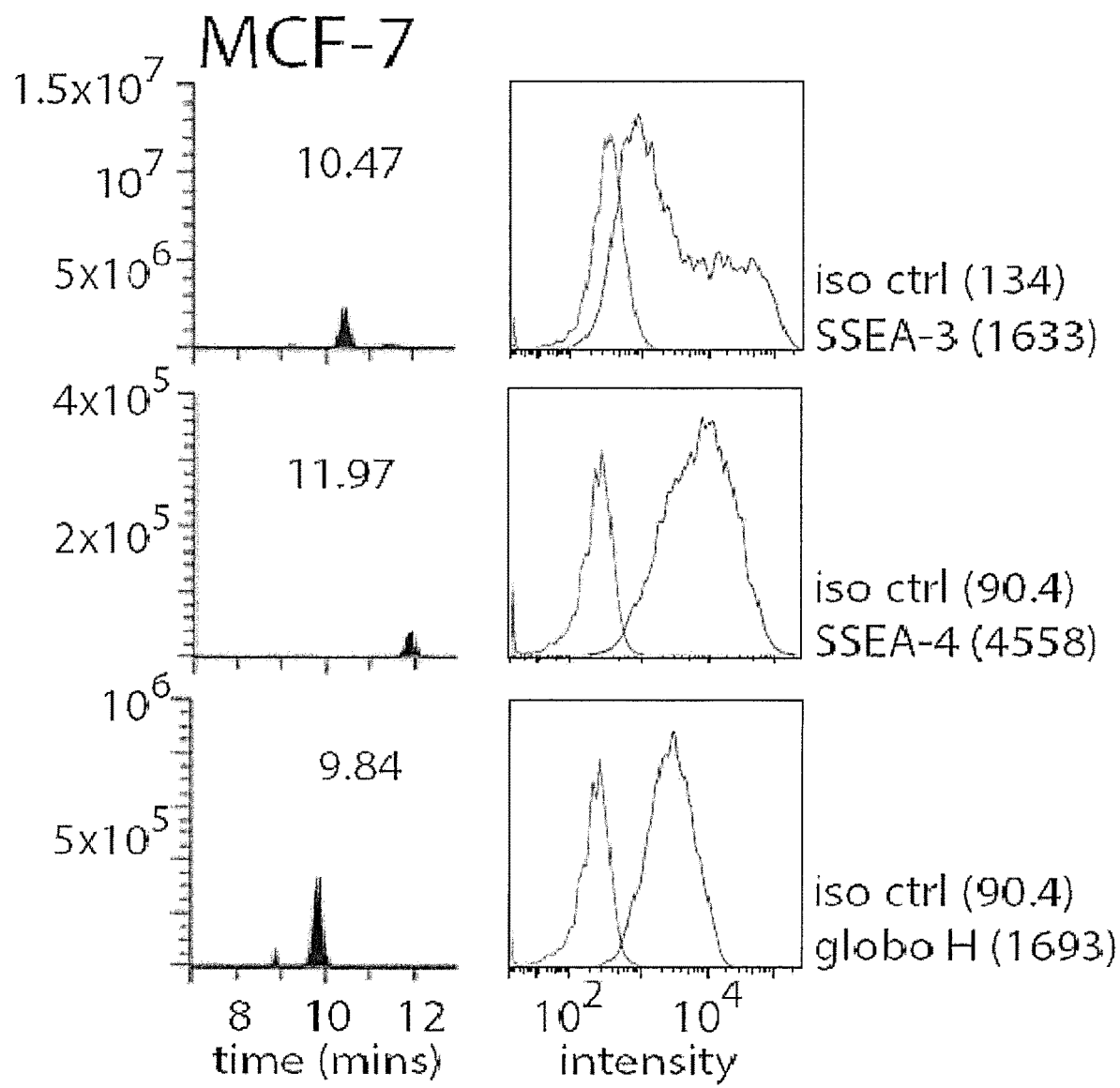
Figure 5C:
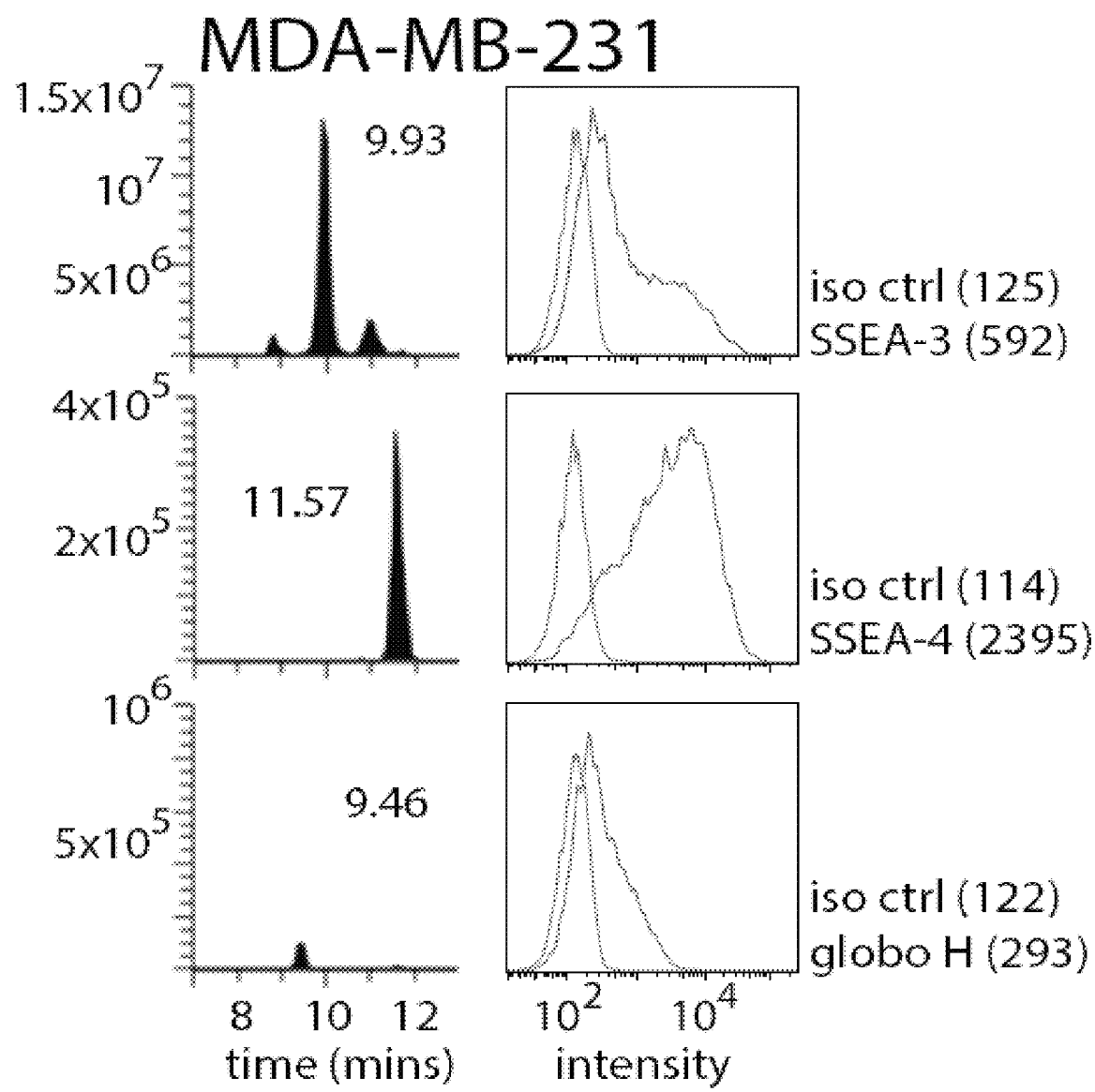
Figure 5D:
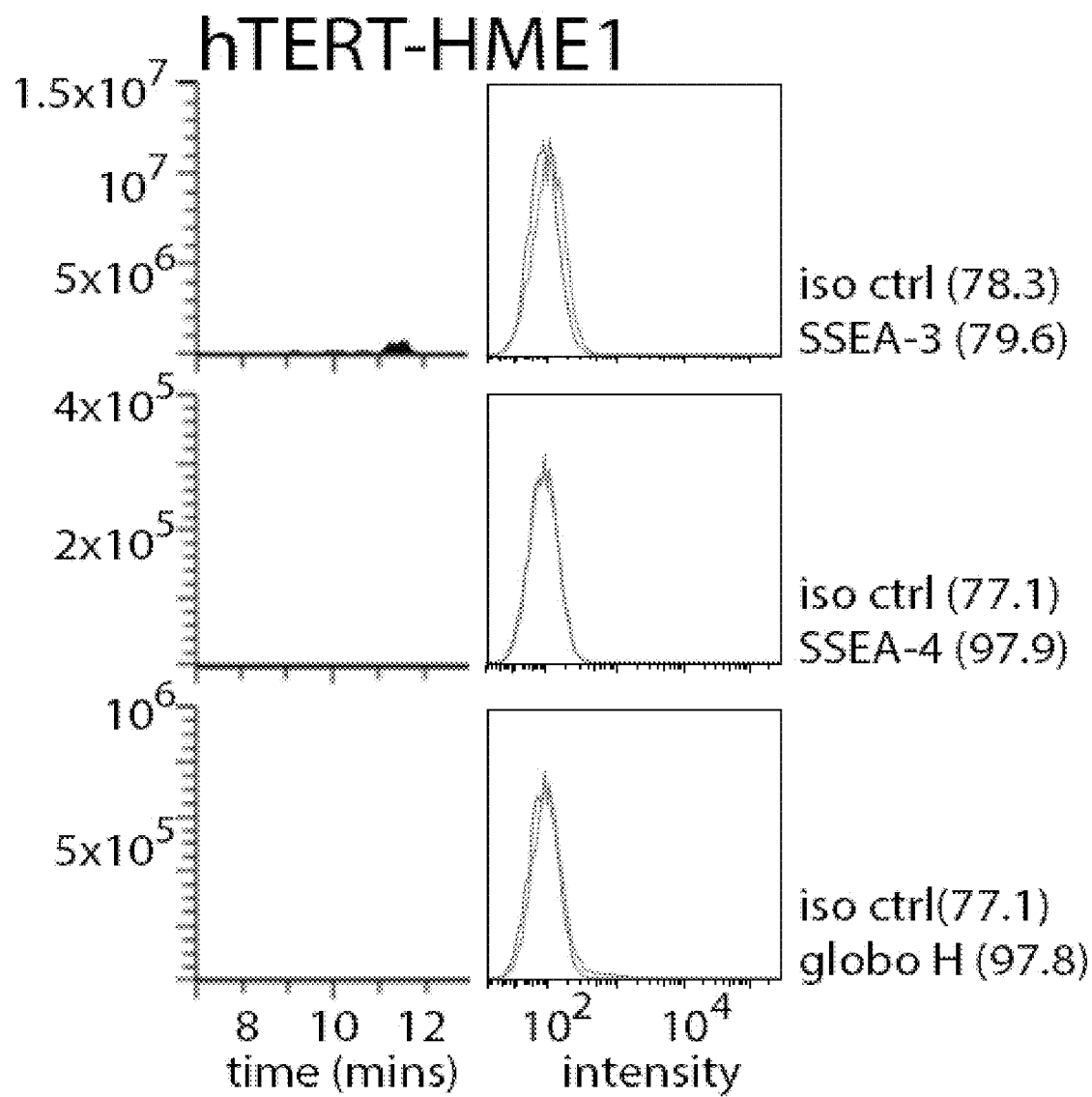
Figure 5E:
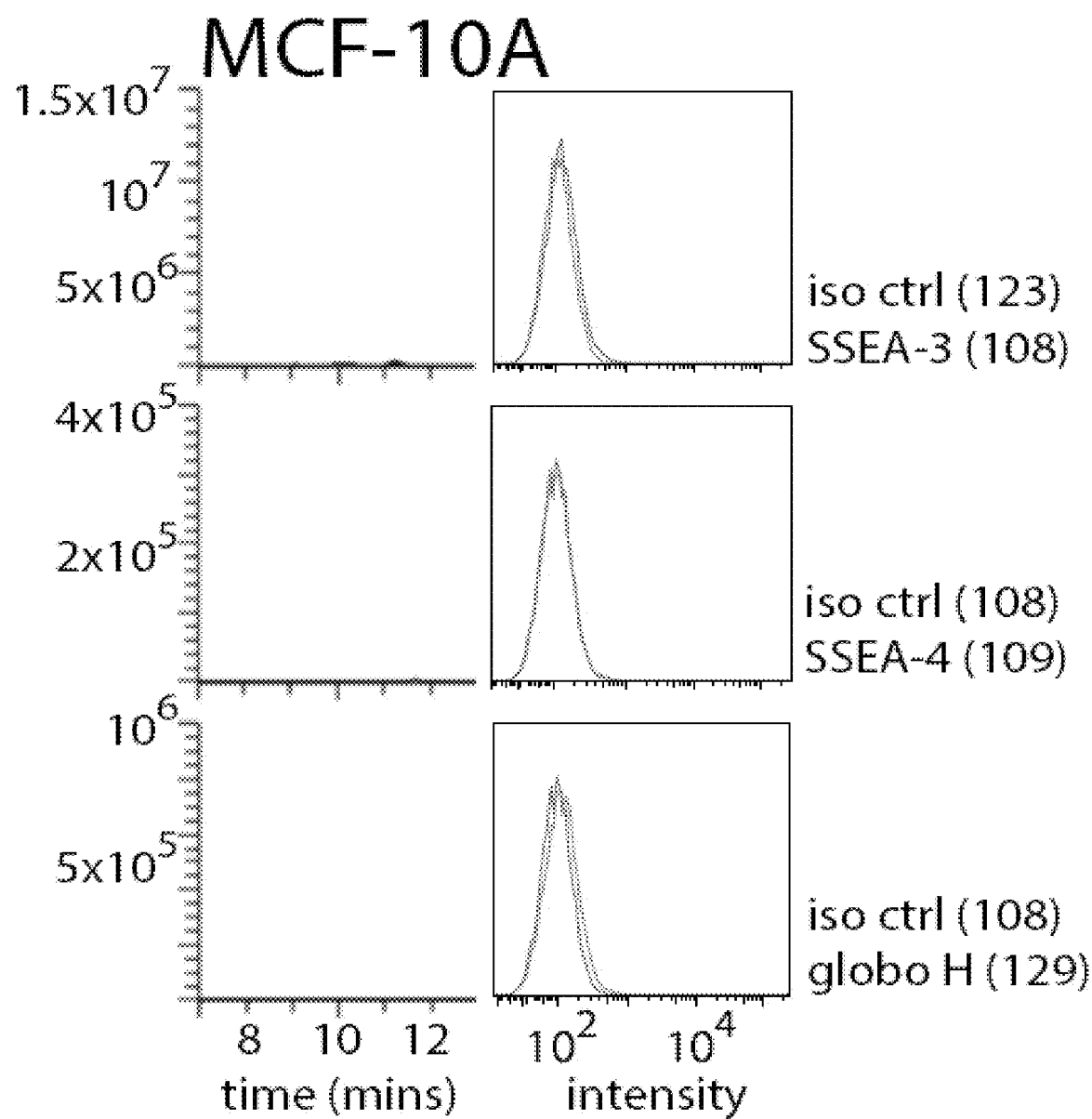
Figure 5F:
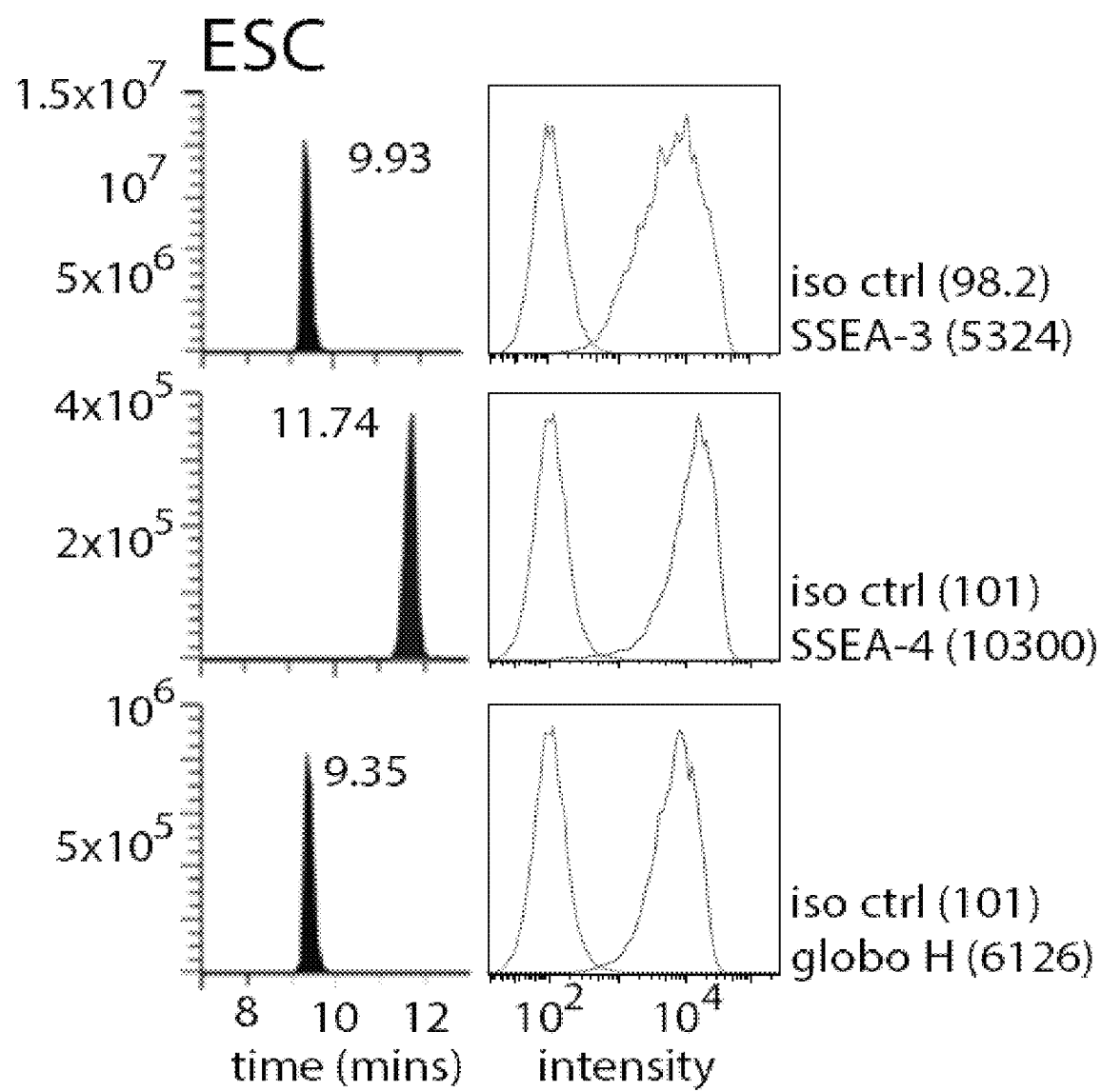
Figure 5G:
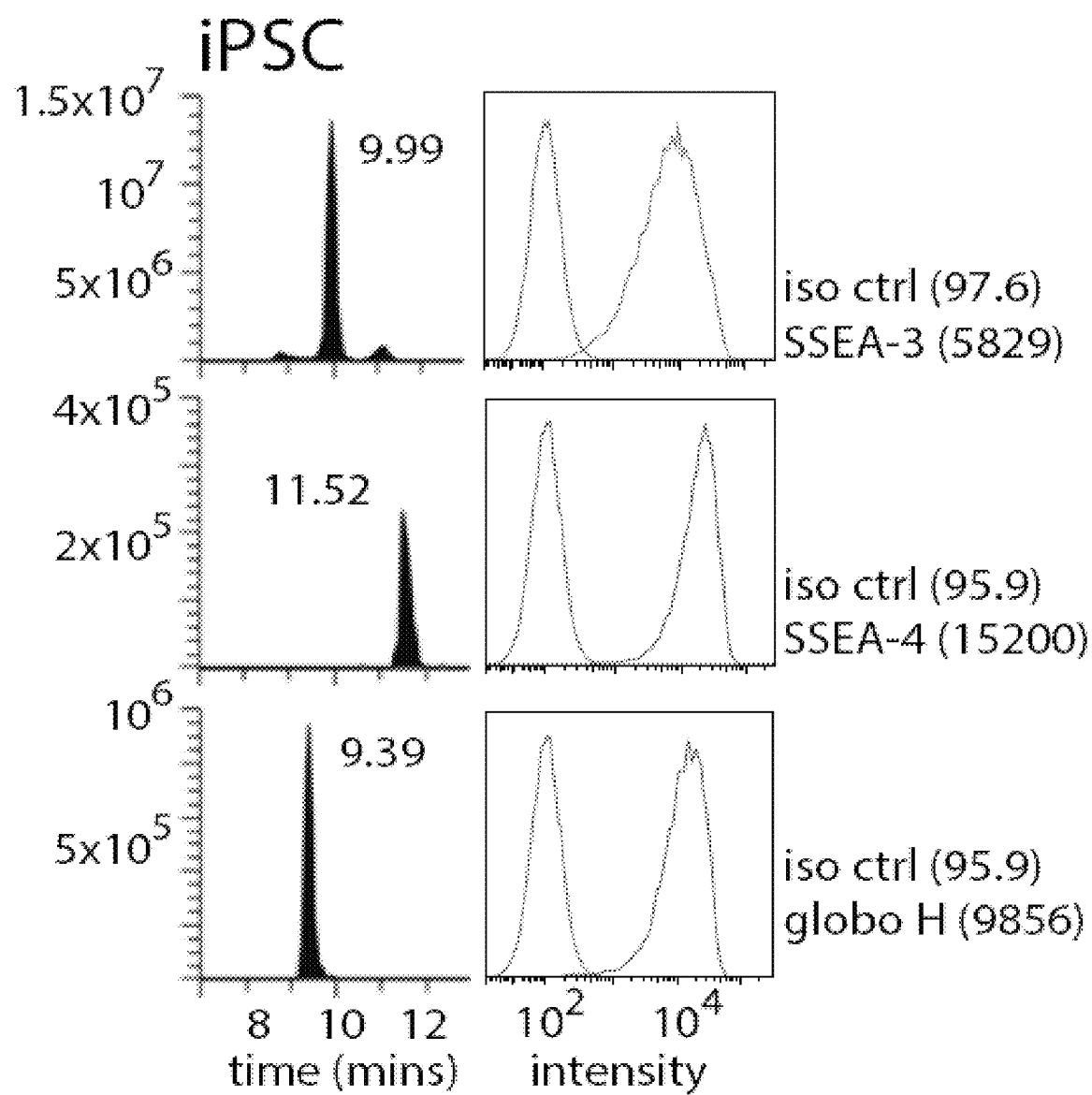
Figure 6:
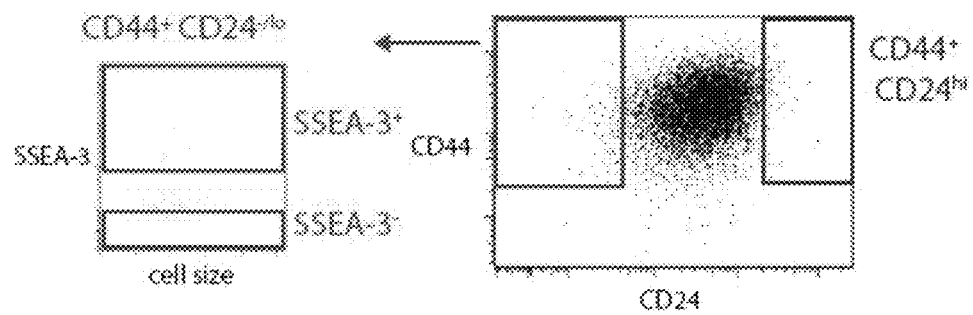
FIG. 6A-B. (Fig. S1)—the subpopulations in cell lines obtained by sorting for in vitro and in vivo assays. Subpopulations including 6A $CD44^+ CD24^{hi}$, $CD44^+ CD24^{-/lo}$, $CD44^+ CD24^{-/lo} SSEA-3^+$, $CD44^+ CD24^{-/lo} SSEA-3^-$, various percentages of SSEA-3+ (top 1, 5, 10%), and SSEA-3- in MCF-7, as well as 6B $ESA^{lo}PROCR^{lo}$, $ESA^{hi}PROCR^{hi}$, $ESA^{hi}PROCR^{hi}SSEA-3^+$, $ESA^{hi}PROCR^{hi}SSEA-3^-$, various percentages of SSEA-3+ (top 1, 5, 10%), and SSEA-3- in MDA-MB-231 were enriched by cell staining (as the methods and materials) and flow cytometry for the further analysis.
Figure 6:
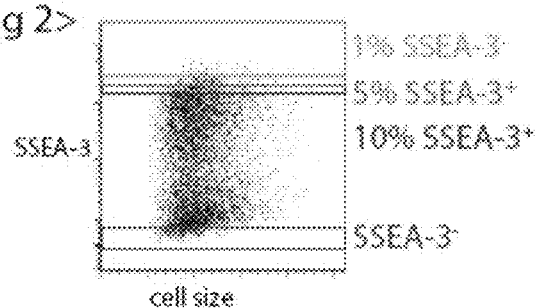
Figure 6:
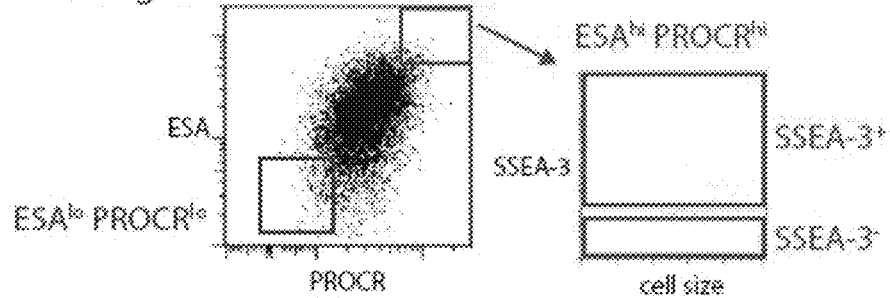
Figure 6:
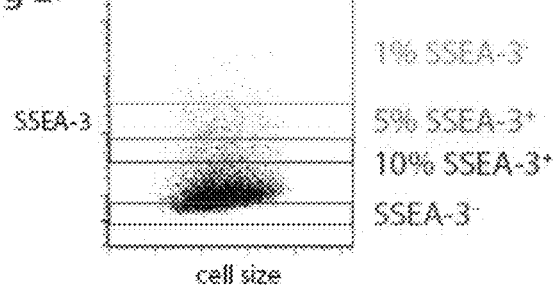
Figure 7:
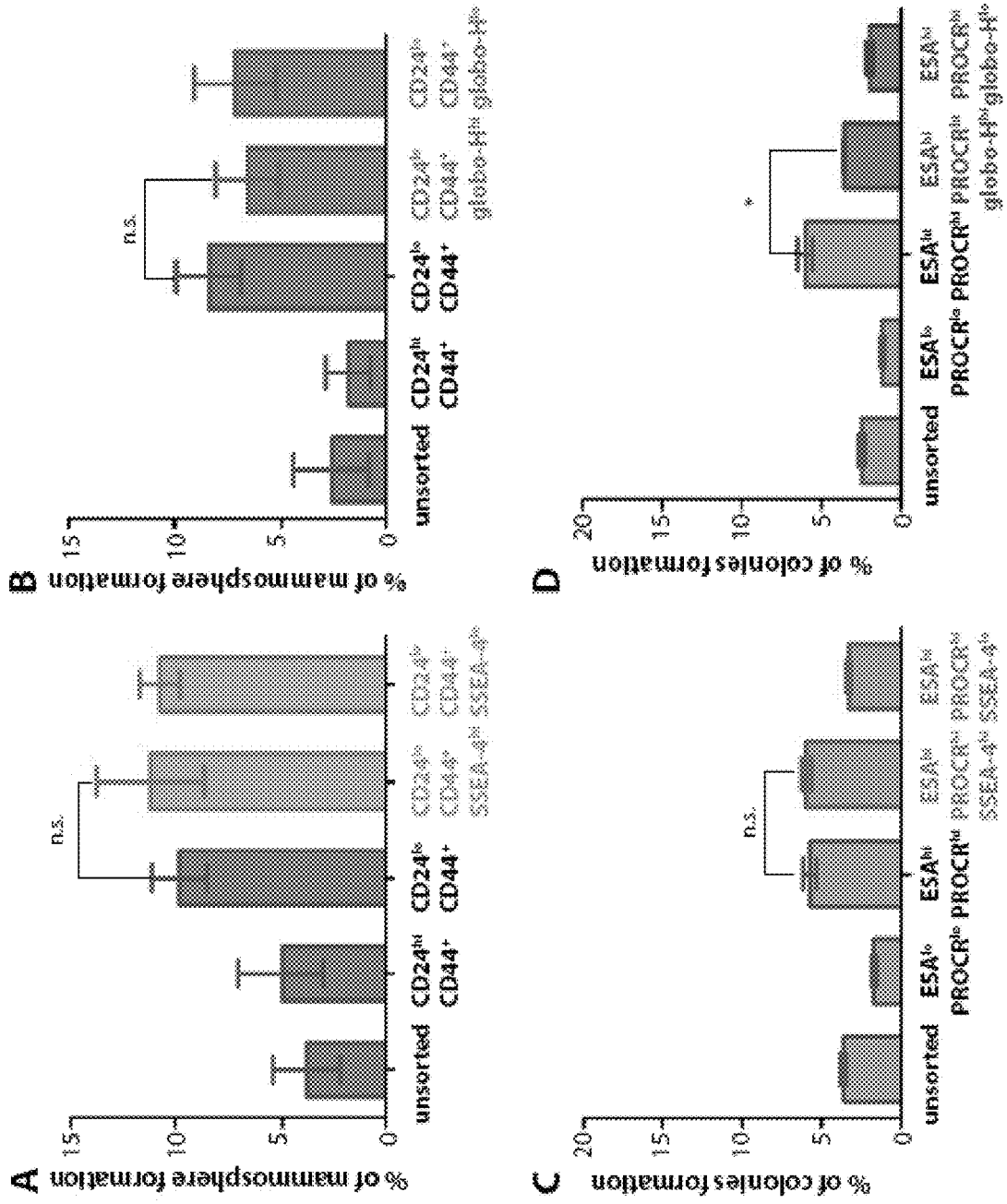
FIG. 7A-D (Fig. S2)—BCSCs were not enriched with globo-series epitopes SSEA-4 and globo-H by in vitro assays. 7A-7D Percentage of cell colony formation of unsorted cells or selected marker (known marker set CD24/CD44, or ESA/PROCR, along with SSEA-4 or globo-H) expressing cell subpopulation from breast cancer cell lines MCF-7 and MDA-MB-231. Graphs are the triple samples from one representative experiment. Data represent the mean and standard deviation (S.D.). Asterisks indicate statistical significance, $p<0.05$; n.s. not significant.
Figure 8:
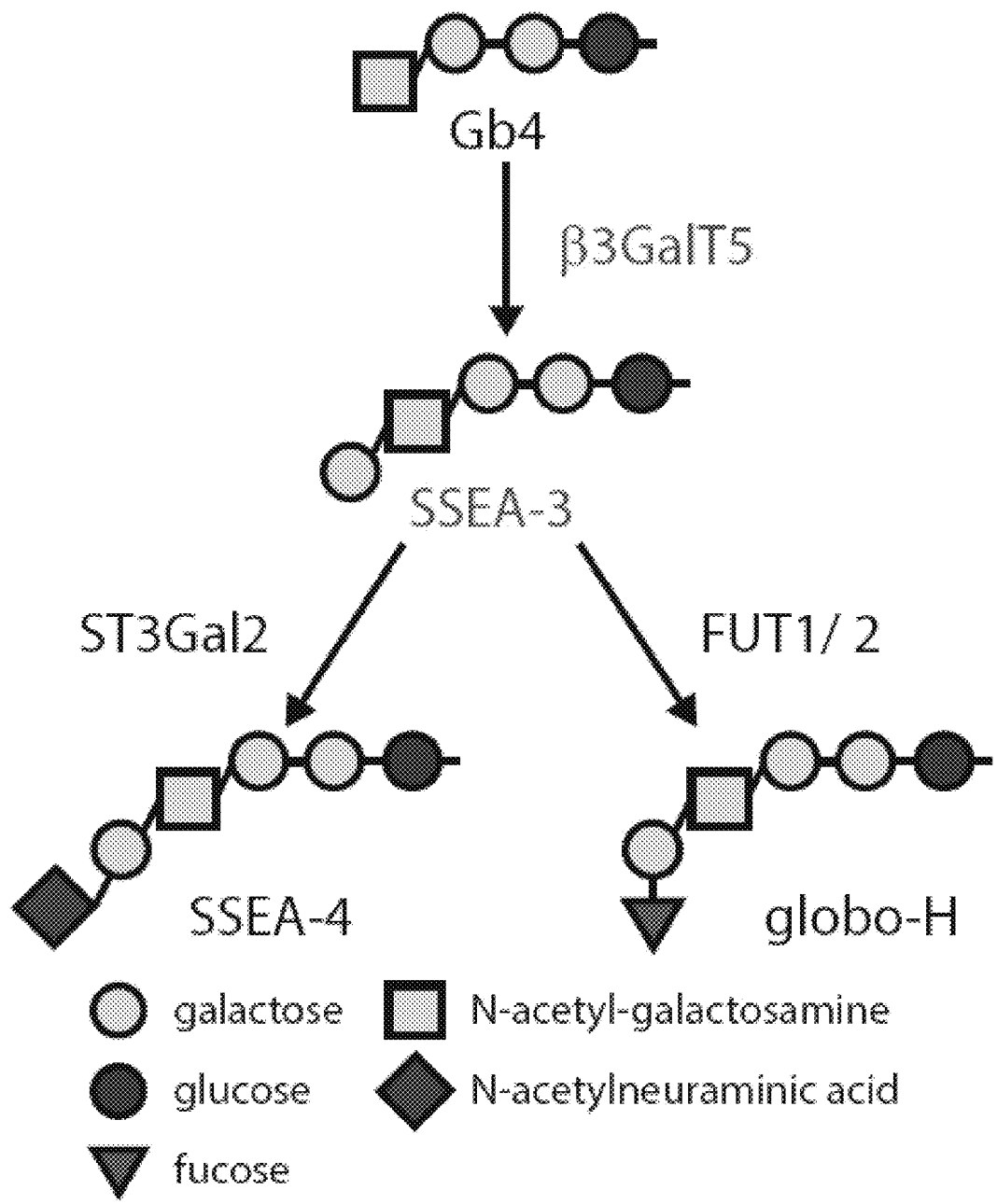
FIG. 8 (Fig. S3)—the globo-series pathway in human. The biosynthetic pathway of globo-series epitopes SSEA-3, SSEA-4 and globo-H from Gb4 with corresponding glycotransferases.
Figure 9A:
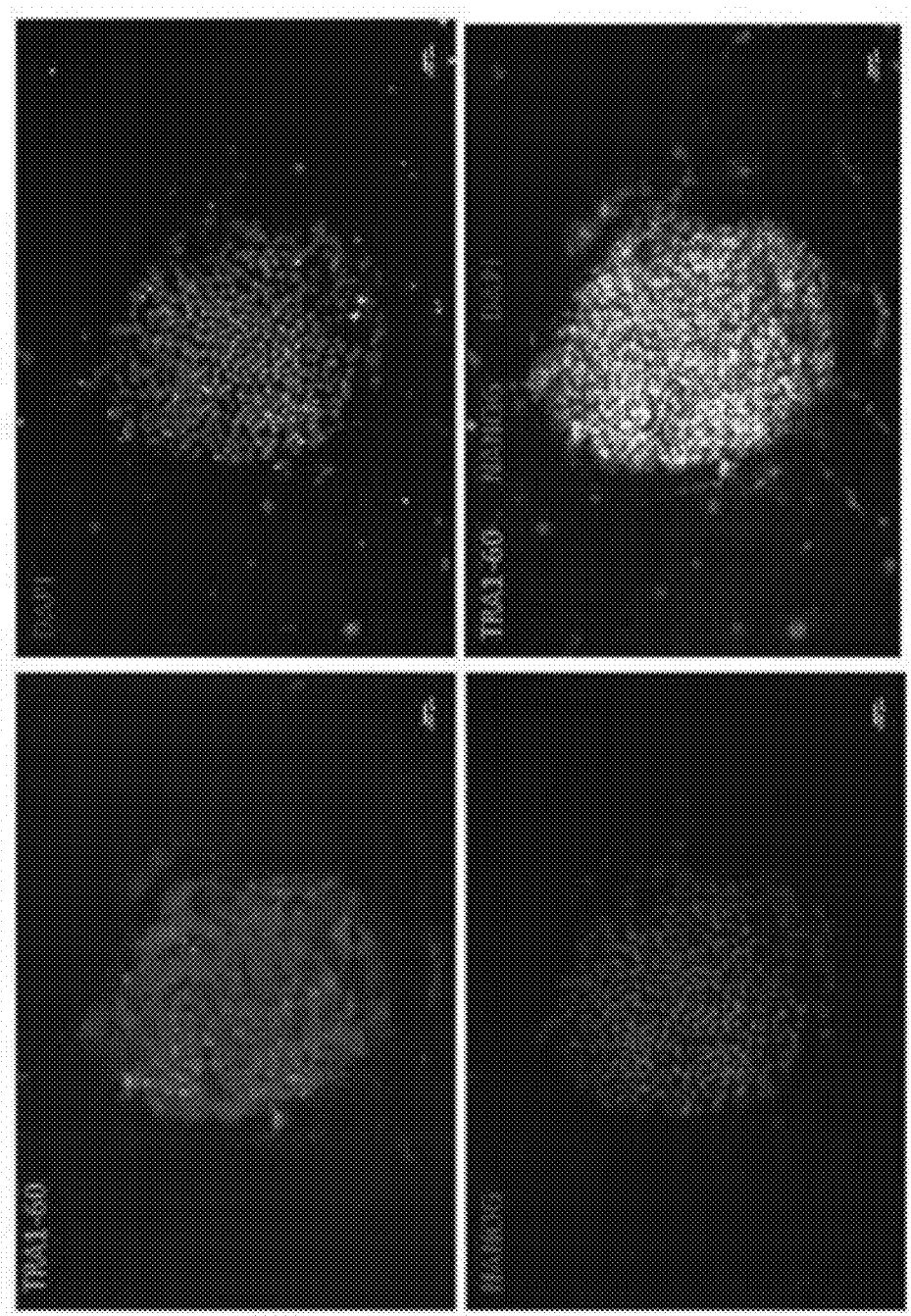
Figure 9D:
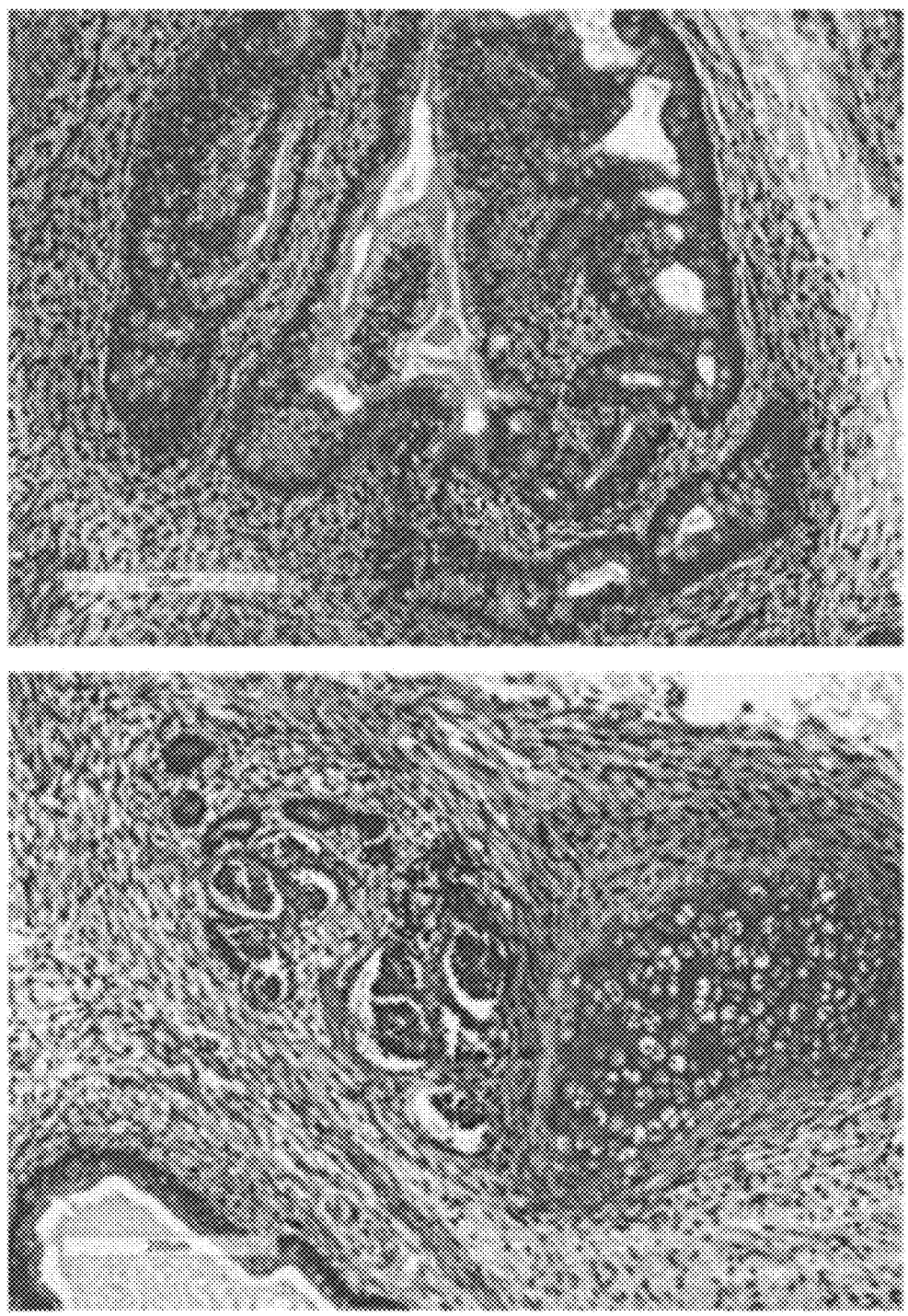
Figure 10:
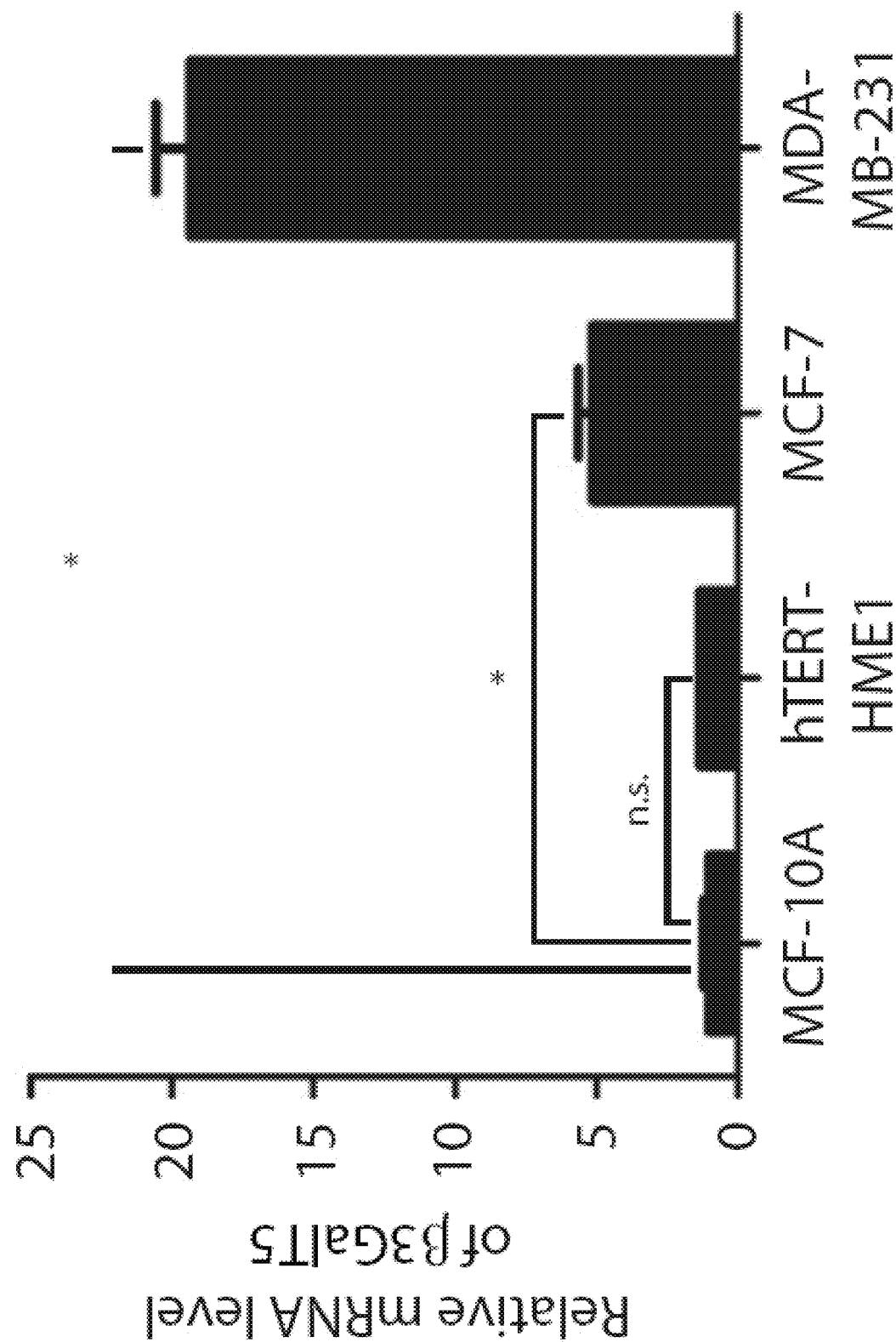
FIG. 10 (Fig S5)—the mRNA level of beta3GalT5 in breast cancer cell culture is higher than that of normal cell culture. GAPDH-normalized qPCR level of beta3GalT5 gene in normal cell culture MCF-10A and hTERT-HME1, as well as in breast cancer cell culture MCF-7 and MDA-MB-231. Triplicated samples from one representative experiment are shown. Data represent the mean and standard deviation (S.D.). Asterisks indicate statistical significance, $p<0.05$; n.s. not significant.
Figure 11:
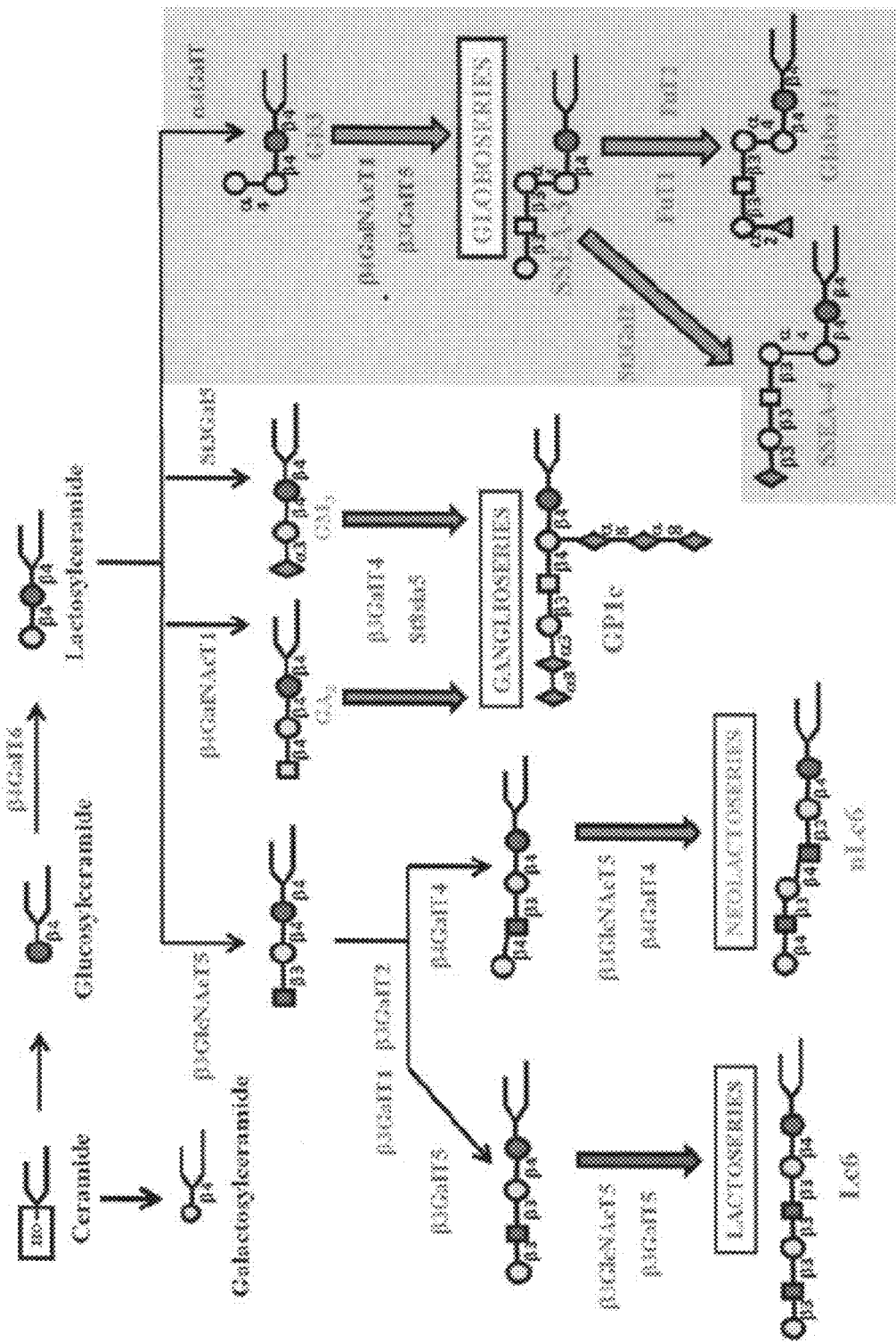
FIG. 11. Biosynthetic Pathway of Globo Series of Glycosphingolipids.

To confirm if SSEA-3 or any of the three globo-series glycans was only found in cancer cells, the glycolipids from embryonic stem cells (ESCs), induced pluripotent stem cells (iPSCs, FIG. S4), MCF-7 and MDA-MB-231 cells, and normal cell lines, including MCF-10A and hTERT-HME1, were extracted and the glycans were released, tagged and examined by LC-MS analysis (FIG. 5A). The data was compared with the results of flow cytometric analysis, in which same antibodies used for cell sorting were used to detect the expression levels of SSEA-3, SSEA-4, and globo-H (FIG. 5). It was found that ESCs, iPSCs and cancer cell lines but not normal cell lines expressed SSEA-3, SSEA-4 and globo-H. The result from this study was also supported by qPCR of β3GalT5 gene expression in normal and cancer cell lines (FIG. S5). Further analysis of the glycol-series glycans on different normal and cancer cell lines will be carried out.

The expression level of SSEA-3 in MCF-7 cells detected by flow cytometry was relatively higher than that by the LC-MS analysis, while the level of SSEA-3 in MDA-MB-231 detected by LC-MS was much higher than that by flow cytometry. The variation between the LC-MS and flow cytometry data could be due to the specificity of antibody and the distribution of the glycans on the cell surface. Due to the cross-reaction of anti-SSEA-3 antibody (MC-631) toward SSEA-4 and to a lesser extent, Gb4 (14), it is possible to overestimate the level of SSEA-3 detected by flow cytometry when there is a high expression level of SSEA-4. On the other hand, the level of SSEA-3 could be underestimated because of hindrance caused by other biomolecules on cell surface and thus SSEA-3 on the cells may not be reached in antibody staining. Therefore, we believe that the ,LC-MS result, which is supported by the qPCR detection of β3GalT5 gene expression (Fig. S5), more accurately reflects the expression of these glycolipids.

In the process of BCSC isolation, it is possible that some cells with a high level of SSEA-4 expression but carry no SSEA-3 are enriched when sorted based on MC-631 staining. Since we proved that both SSEA-3 and its synthetic enzyme 1 GalT5 are BCSCs markers, SSEA-3 negative cells are low tumorigenic. The cell population is not purified enough and thus the tumorigenicity of the cells sorted based on anti-SSEA-3 staining may be underestimated. We consider an antibody or molecule, which is highly specific to SSEA-3, can be generated for the enrichment of BCSC. On the other hand, if SSEA-3 on the cell surface can be specifically detected and sorted by flow cytometry, the results of both antibody staining and LC-MS analysis should be consistent.

SSEA-3 is a BCSC marker that plays a major role in cancer progression. From the experiments, we showed that manipulating the expression of β3GalT5 in cancer cells controlled the cell surface level of SSEA-3, SSEA-4 and globo-H, as well as the cellular survival and tumorigenicity. Interestingly, knockdown of β3GalT5 in cancer cells could trigger both apoptosis and inhibition of cell proliferation through different mechanisms, as MCF-7, a caspase-3 null cell line, underwent a limited level of apoptosis and profound suppression of cell growth after knockdown of β3GalT5. In contrast, in normal mammary epithelial cells, which lack SSEA-3 expression, knockdown of β3GalT5 did not affect these phenotypes.

In summary, this report demonstrated that SSEA-3 is a novel glycan marker useful for the enrichment of BCSCs, and both SSEA-3 and β3GalT5 are potential new targets for the development of breast cancer therapeutics. In addition to their specific expression on most cancer stem cells and cancer cells, the globo-series glycolipids SSEA-3, SSEA-4 and globo-H are also highly expressed on the surface of ESCs and iPSCs, but they disappear after differentiation of ESCs. It would be interesting to understand the fate of the globo-series glycolipids after differentiation of iPSCs for use in regenerative medicine.

Example Materials and Methods
Cell Culture

Breast cancer cell lines MDA-MB-231, MCF-7 and human breast cancer associated fibroblast (CAF) were obtained from American Type Culture Collection (ATCC). The culture of MDA-MB-231 was in DMEM supplemented with 10% of heat-inactivated FBS and antibiotic-antimycotic whereas that of MCF-7 culture was in RPMI supplemented with 10% of heat-inactivated FBS, non-essential amino acids and antibiotic-antimycotic. For the culture of CAF, it was in DMEM/F12 supplemented with 10% of heat-inactivated FBS, non-essential amino acids, sodium pyruvate, glutamine, penicillin and streptomycin. They were incubated at 37° C. incubator with 5% of CO2 and humidified atmosphere control. All the cell culture media and supplements were purchased from Life Technologies. Human ESC H9 and induced pluripotent stem cell 5 (iPSC5) were maintained and cultured on mitomycin C treated-mouse embryonic fibroblasts (MEFs) in human ES medium (Knockout DMEM with Knockout Serum Replacement, GlutaMAX, non-essential amino acids, 2-Mercaptoethanol, Penicillin/Streptomycin and bFGF) and were passaged weekly using collagenase IV.

Example
Derivation of iPSCs from Dermal Fibroblasts

Fibroblasts derived from dermal biopsies were reprogrammed into pluripotent stem cells using the CytoTune-iPS Sendai Reprogramming Kit (Life Technologies). Briefly, 5×104 fibroblasts were seeded per well in a 6-well dish at passage 3 for recovery overnight. The next day, Sendai viruses expressing human transcription factors OCT4, SOX2, Klf4, and c-Myc were mixed in fibroblast medium to infect fibroblast cells according to the manufacturer's instructions. After 2 days, the medium was exchanged with human ES medium supplemented with the ALK5 inhibitor SB431542 (2 μM; Stemgent), the MEK inhibitor PD0325901 (0.5 μM; Stemgent), and thiazovivin (0.5 μM; Stemgent). Day 7-10 after infection, cells were detached using TrypLE (Life Technologies) and passaged onto feeder cells. Individual colonies of iPSCs were picked between days 21 and 28 after infection, and each iPSC line was expanded from a single colony. All iPSCs lines were cultured on mouse embryonic fibroblast cells in human ES medium.

Karyotyping was performed by Cell Line Genetics Inc. In teratoma analysis, 1-2×107 from each iPSC line were detached and collected after TrypLE treatment. They were suspended in 0.5 mL human ES media. Followed by mixing with 0.5 mL Matrigel (BD Biosciences), cells were injected subcutaneously into dorsal flanks of an immunodeficient mouse (NOD.Cg-Prkdcscid Il2rgtm1Wjl/SzJ, stock no. 005557, The Jackson Laboratory). Eight weeks after injection, teratomas were harvested, fixed overnight with 4% paraformaldehyde, and processed according to standard procedures for paraffin embedding. The samples were then sectioned and H&E stained.

Example
Flow Cytometry and Cell Sorting

Cell labeling was done by staining with antibodies in buffer composed of PBS supplemented with 1% FBS. Accutase (eBioscience, San Diego, Calif.) detached cells were incubated with antibodies (using antibody titration suggested by the supplier) for 30 min on ice in the dark. Antibodies used in this study were PE-conjugated anti-PROCR (RCR-252; BD Biosciences, San Jose, Calif.), APC-conjugated anti-ESA (1B7; eBioscience), PE-conjugated anti-CD24 (SN3 A5-2H10, eBioscience), APC-conjugated anti-CD44 (IM-7, eBioscience) along with biotinylated anti-SSEA-3 (MC-631; eBioscience) at 4° C. for 30 min in the dark. After washing twice, the cells were stained with Alexa Fluor 488-conjugated streptavidin at 4° C. for 30 min in the dark. Proper isotype controls were used for each cell labeling experiment. The same antibodies were used in all staining and sorting experiments in this study. Live cell sorting was done using a BD FACSAriaU with a 100 βm nozzle following the manufacturer's instructions. For MDA-MB-231 cells, the sorted cells were incubated with DMEM/10% FBS/antibiotics/antimycotics to recover in ultra-low attachment surface plates overnight in a humidified 37° C. incubator before further analyses. For MCF-7 cells, they were subject to further experiments readily after sorting. The percentage of cells in different marker populations was evaluated using the software FlowJo.

Example
Soft Agar Assay

Soft agar colony formation assay was performed by seeding cells in a layer of 0.35% SeaPlaque agarose (Lonza, Switzland) with DMEM/FBS over a basal layer of 0.5% SeaPlaque agarose/DMEM/FBS. Cultures were maintained in a humidified 37° C. incubator. Additional media was added every 2-3 days to continuously supply growth supplements to the cells. On day 21 after seeding, cells were fixed with pure ethanol containing 0.05% crystal violet and colony forming efficiency quantified by light microscopy.

Example
Mammosphere Formation

In the mammosphere formation assay, cells were incubated in DMEM/F12 with supplement B27 (Life Technologies) and 10 ng/ml EGF on 96-well low-attachment plates in the density of 100 cells/well. Culture was maintained in a humidified 37° C. incubator. After 14 days, the number of mammospheres was counted under a light microscope.

Example
Mouse Tumorigenicity Assay

NOD-SCID (NS) mice were used to evaluate the stem cell properties of sorted cells expressing potential stem cell markers from the human breast cancer cell lines. Animal care and experiments were approved by the Institutional Animal Care and Utilization Committee of Academia *Sinica* (IACUC#130-09-575). Four-week old NS mice were injected with sorted cancer cells mixed with CAF (1:1) and Matrigel (BD bioscience) (1:1) in fat pads. For MCF-7, mice were additionally injected with estrogen pellets (0.18 mg/pellet, 90 days release, Innovative Research of America) before the day of experiment. Tumor volumes were evaluated every five days after initial detection. The tumor formation efficiency was determined on day 50 after cell injection.

Example
Overexpression and Knockdown of β3GalT5

To establish human β3GalT5 overexpression stable lines, full-length cDNA that encodes human β3GalT5 was PCR amplified (forward primer-GCAGATCTATGGCTTTC-CCGAAGATG (SEQ ID NO: 1); reverse primer-GTCTC-GAGTCAGACA GGCGGACAAT (SEQ ID NO: 2)), and subcloned into BglII/XhoI cut pMSCVpuro vector (Clontech). Murine stem cell virus (MSCV)-control and MSCV-β3GalT5 vesicular stomatitis virus G glycoprotein (VSV-G) pseudotyped retrovirus were then generated in GP2-293 cells (Clontech) and used to infect MCF-7 and MDA-MB-231 cells. Two days after viral infection, control and β3GalT5 stable pools were selected with puromycin (2 μg/mL). To establish β3GalT5 knockdown cells, the lentivirus-shRNA systems for human β3GalT5 were purchased from National RNAi Core Facility Platform, Academia *Sinica*, and the β3GalT5-short hairpin sequence is 5'CCGGGCAAGTGGTTTGTCAGTAAATCTCGAGATT-TACTGACAAACCACTTGCTT TTTG-3' (SEQ ID NO: 3). Briefly, shβ3GalT5 and shControl lentiviruses were incubated with MCF7 and MDA-MB-231 cells according to the manufacturer's instructions. Infected cells were harvested 48 h post-infection or selected with puromycin (2 μg/mL) and the knockdown efficiency was determined by quantitative RT-PCR (qPCR).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

---

What is claimed is:

1. A method of detecting a SSEA3hi/ESAhi/PROCRhi or SSEA3hi/CD44 hi/CD24lo/− breast cancer stem cell in a patient, the method comprising
   a) obtaining a biological sample from the patient;
   b) labeling the breast cancer stem cell in the biological sample by contacting the biological sample with antibodies that separately bind to tumor antigens SSEA3 ESA and PROCR and tumor cell antigens CD44 and CD24 on the breast cancer stem cell;
   c) detecting the specific binding of the antibodies in step b) and the level of expression of SSEA3, ESA and PROCOR or the level of expression of SSEA3, CD44, and CD24 using flow cytometry and cell sorting; wherein if the detected cells are SSEA3hi/ESAhi/PROCRhi or SSEA3hi/CD44 hi/CD24lo/−, the sample contains a breast cancer stem cell.

2. The method of claim 1, wherein the biological sample is a bodily fluid sample.

3. The method of claim 2, wherein the bodily fluid sample is a blood sample.

* * * * *